(12) United States Patent
Spangenberg et al.

(10) Patent No.: US 8,952,216 B2
(45) Date of Patent: Feb. 10, 2015

(54) PLANT PROMOTER OPERABLE IN BASAL ENDOSPERM TRANSFER LAYER OF ENDOSPERM AND USES THEREOF

(75) Inventors: German Spangenberg, Bundoora (AU); Ulrik John, Westgarth (AU); Carl Ramage, Mitcham (AU); Huihua Fu, Cary, NC (US)

(73) Assignee: BASF Plant Science Company GmbH, Ludwigshafen (DE)

( * ) Notice: Subject to any disclaimer, the term of this patent is extended or adjusted under 35 U.S.C. 154(b) by 451 days.

(21) Appl. No.: 13/320,122

(22) PCT Filed: May 12, 2010

(86) PCT No.: PCT/AU2010/000553
§ 371 (c)(1),
(2), (4) Date: Nov. 30, 2011

(87) PCT Pub. No.: WO2010/129999
PCT Pub. Date: Nov. 18, 2010

(65) Prior Publication Data
US 2012/0066795 A1    Mar. 15, 2012

Related U.S. Application Data

(60) Provisional application No. 61/251,635, filed on Oct. 14, 2009, provisional application No. 61/177,898, filed on May 13, 2009.

(51) Int. Cl.
| | | |
|---|---|---|
| *C12N 15/00* | (2006.01) | |
| *C12N 5/10* | (2006.01) | |
| *C12N 15/82* | (2006.01) | |
| *A01H 5/00* | (2006.01) | |
| *C07H 21/04* | (2006.01) | |

(52) U.S. Cl.
CPC .................................. *C12N 15/8234* (2013.01)
USPC ....... 800/287; 536/24.1; 435/320.1; 435/419; 435/468; 800/298

(58) Field of Classification Search
None
See application file for complete search history.

(56) References Cited

U.S. PATENT DOCUMENTS

| | | | |
|---|---|---|---|
| 6,528,704 B1 * | 3/2003 | Linnestad et al. ............. | 800/287 |
| 2007/0044171 A1 | 2/2007 | Kovalic et al. | |
| 2008/0313778 A1 * | 12/2008 | Perez et al. .................... | 800/290 |
| 2012/0036593 A1 | 2/2012 | Spangenberg et al. | |

FOREIGN PATENT DOCUMENTS

| | | |
|---|---|---|
| EP | 1528104 A1 | 5/2005 |
| WO | WO-98/08961 A2 | 3/1998 |
| WO | WO 99/50427 * | 10/1999 |
| WO | WO-2007/057402 A1 | 5/2007 |
| WO | WO-2007/093623 A1 | 8/2007 |
| WO | WO-2009/033229 A1 | 3/2009 |
| WO | WO-2010/069950 A1 | 6/2010 |
| WO | WO-2010/118477 A1 | 10/2010 |
| WO | WO-2010/122110 A1 | 10/2010 |
| WO | WO-2011/003901 A1 | 1/2011 |
| WO | WO-2011/067712 A1 | 6/2011 |

OTHER PUBLICATIONS

Gomez et al., FN400766 (2009).*
BLAST BETL-9 to SEQ ID No. 1 instant_2014.*
BLAST LOC100286270_2014.*
BLAST SIN-1 Linnestad to nucleic acid DB_2014.*
LOC100286270 precursor *Zea mays*_2009.*
Potenza_In Vitro Cell Dev Biol Plant_40_1_2004.*
Meinkoth Wahl_Anal Biochem_138_267_1984.*
Donald_EMBO J_9_1717_1990.*
Kim_Plant Mol Biol_24_105_1994.*
Dolferus_Plant Phys_105_1075_1994.*
European Search Report for EP 10774428, dated Sep. 13, 2012.
Hueros, G., et al., "Evidence for factors regulating transfer cell-specific expression in maize endosperm", Plant Molecular Biology, vol. 41, (1999), p. 403-414.
Hueros, G., et al., "Identification of a Promoter Sequence from the BETL1 Gene Cluster Able to Confer Transfer-Cell-Specific Expression in Transgenic Maize", Plant Physiology, vol. 121, No. 4, (1999), p. 1143-1152.
"Maize BETL9 promoter SEQ ID No. 32", Geneseq Database, Accession No. AGB10350, Jul. 26, 2007.
"Maize BETL9 promoter fragment nucleotide sequence, SEQ ID 18", Geneseq Database, Accession No. AJF57552, dated Nov. 1, 2007.
"Triticum durum PR60 (TdPR60) promoter DNA sequence, SEQ ID 3", Geneseq Database, Accession No. AWI81698, dated May 14, 2009.
"Wheat recombinant polynucleotide SEQ ID No. 16718", Accession No. AOG73912, dated Feb. 3, 2011.
Ming et al., "Spatial and Temporal Expression of Endosperm Transfer Cell-Specific Promoters in Transgenic Rice and Barley", Plant Biotechnology Journal, 2008, vol. 6, pp. 465-476.

(Continued)

*Primary Examiner* — Medina A Ibrahim
*Assistant Examiner* — Russell Boggs
(74) *Attorney, Agent, or Firm* — Drinker Biddle & Reath LLP

(57) ABSTRACT

The present invention provides an isolated promoter or an active fragment or derivative thereof capable of conferring selective expression on a gene to which it is operably connected in the endosperm of a developing plant seed and preferably in the basal endosperm transfer layer (BETL) of endosperm. The present invention also provides expression vectors and constructs and transgenic plant cells, plant parts and whole plants comprising the promoter, active fragments and derivatives, and well as methods of modulating one or more plant phenotypes employing the promoter, active fragments and derivatives.

15 Claims, 19 Drawing Sheets

(56) References Cited

OTHER PUBLICATIONS

Brink, R.A., et al., "Effect of the DE17 Allele on Development of the Maize Caryopsis", Genetics, 1947, vol. 32, pp. 350-368.

Charlton, W.L., et al., "Endosperm Development in *Zea mays*; Implication of Gametic Imprinting and Paternal Excess in Regulation of Transfer Layer Development", Development, 1995, vol. 121, pp. 3089-3097.

Higo, K., et al., "Plant cis-acting Regulatory DNA Elements (PLACE) Database: 1999", Nucleic Acids Research, 1999, vol. 27, No. 1, pp. 297-300.

Lamacchia, C., et al., "Endosperm-Specific Activity of a Storage Protein Gene Promoter in Transgenic Wheat Seed", Journal of Experimental Botany, 2001, vol. 52, No. 355, pp. 243-250.

Pate, J.S. et al., "Transfer Cells", Ann. Rev. Plant Physiol., 1972, vol. 23, pp. 173-196.

Schernthaner, J.P., et al., "Endosperm-specific Activity of a Zein Gene Promoter in Transgenic Tobacco Plants", The EMBO Journal, 1988, vol. 7, No. 5, pp. 1249-1255.

Shahmuradov, I.A., et al., "PlantProm: A Database of Plant Promoter Sequences", Nucleic Acids Research, 2003, vol. 31, No. 1, pp. 114-117.

Stoger, E., et al., "Sowing the Seeds of Success: Pharmaceutical Proteins from Plants", Current Opinion in Biotechnology, 2005, vol. 16, pp. 167-173.

Thijs, G., et al., "A Gibbs Sampling Method to Detect Overrepresented Motifs in the Upstream Regions of Coexpressed Genes", Journal of Computational Biology, 2002, vol. 9, No. 2, pp. 447-464.

"*Triticum aestivum* partial mRNA for 5a2 protein (5a2 gene), cultivar Wyuna, from endosperm tissue", May 31, 2005, EMBL Database, Accession No. AJ890018.1.

"*Triticum aestivum* endosperm transfer cell specific PR60 precursor (PR60) mRNA, complete cds", Apr. 1, 2008, GenBank Database, Accession No. EU264062.

"LTPL36—Protease inhibitor/seed storage/LTP family protein precursor, expressed", Ensembl Database, Accession No. LOC_Os03g25350.1.

"*H. vulgare* mRNA (clone END1)", Nov. 19, 1996, BioRS Database, Accession No. Z69631.

International Search Report for PCT/AU2010/000553, mailed Jul. 20, 2010.

International Preliminary Report on Patentability for PCT/AU2010/000553, issued Nov. 15, 2011.

* cited by examiner

```
Query= LOC_Os03g25350.1 (345 letters)

Database: Zm_gen_assembly.txt (294,427 sequences; 503,497,445 total letters)

Score      E
Sequences producing significant alignments:                   (bits)   Value ZmGSStuc11-12-04.13411.1                                        64     9e-09

LOC_Os03g25350.1         232  gagaaggtgtggtgcatggagaaggtcgtctatgtcgccaagttctgcaagaagccgttc  291
ZmGSStuc11-12-04.13411.1 1378 ..........a.................t..g..c........c.at..t....g......t 1437

LOC_Os03g25350.1         292  cagcctggctaccagtgcgg  311
ZmGSStuc11-12-04.13411.1 1438 ..a.........a.......  1457
```

Figure 17

```
Sel=0                           -----------------------------------------CCATAGTCATGGCAAAA---CTCATGTGCA---------------
rc_GW-WP04.r1        2116       ---------------------------------------------------------------------------------------
WP04                            TAGAGAAGGCTCTAGTGTAGCAGATACAAAAGCCATAGTC------------------------------------------------
PUT-153a-Triticum_ae            TAGAGAAGGCTCTAGTGTAGCAGATACAAAAGCCATAGTCATGGCAAAA---CTCATGTGCTTAT
affy_gb_BQ805508.1              TAGAGAAGGCTCTAGTGTAGCAGATACAAAAGCCATAGTCATGGCAAAA---CTCATGTGCTTAT
gi_66840997                     ---------------------------------------------------------------------------------------
ZmGSStuc11-12-04.134            CTTCGCCAAAAAAATTTCGTCAACAGTTGAAGTTATACCCATGGCAAAA---CTACTCTTGGGTT
PUT-157a-Zea_mays-01            CTTCGCCAAAAAAATTTCGTCAACAGTTGAAGTTATACCCATGGCAAAA---CTACTCTTGGGTT
LOC_Os03g25350.1_345             -------------------------------------------------ATGGCGAGACAACAACTCCTAGGTT
gi|57015217|gb|CM000            CATCTGAGAGAAACCAGGGAGATACACACAAGCAATAGCCATG
LOC_Os03g25350.1|120            CATCTGAGAGAAACCAGGGAGATACACACAAGCAATAGCCATG
```

PLANT PROMOTER OPERABLE IN BASAL ENDOSPERM TRANSFER LAYER OF ENDOSPERM AND USES THEREOF

RELATED APPLICATIONS

This application is a national stage application (under 35 U.S.C. §371) of PCT/AU2010/000553, filed May 12, 2010 which claims the benefit of priority from U.S. Provisional Application No. 61/177,898 filed May 13, 2009 and U.S. Patent Provisional Application No. 61/251,635 filed Oct. 14, 2009, the contents of which are both incorporated herein by reference in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074021_0156. The size of the text file is 81 KB, and the text file was created on Jun. 11, 2014.

BACKGROUND OF INVENTION

1. Field of the Invention

The present invention relates to compositions of matter comprising plant-operable promoter sequences and regulatory sequences derived therefrom and to uses of such compositions to confer gene expression, especially in developing endosperm cells such as in basal endosperm transfer layer cells of the endosperm.

2. Description of the Related Art

To date plants have been genetically modified for a variety of reasons, including to confer pest resistance, e.g., by expressing antifungal or antibacterial proteins, or improving an agronomic trait, e.g., by modulating fruit ripening, or inducing sterility in a hybrid plant or for the large-scale production of proteins for industrial, pharmaceutical, veterinary and agricultural use. In this respect, advances in biotechnological research have produced an explosion of information in relation to the number of nucleic acids identified which, if appropriately expressed, are useful to produce improved plants, for example, plants resistant to pre-harvest sprouting, plants having an improved nutritional quality, plants having a pharmaceutical quality, plants in which reproductive development is controlled, plants having altered shape or size characteristics, plants capable of rapid regeneration following harvest, or plants having improved resistance to pathogens, amongst others.

However, a problem associated with the genetic improvement of agriculturally-important plants, for example, crops, is the manipulation of gene expression to produce plants which exhibit novel characteristics. In this respect, it is often desirable that a nucleic acid to be expressed in a plant is expressed preferentially, selectively, or specifically, in one or more specific cell types, tissues or organs of the plant, or under specific environmental or developmental conditions, rather than being expressed constitutively.

Moreover, as more genes having desirable agronomic or pharmaceutical value become available, the need for transformed plants with multiple genes will increase exponentially. These multiple exogenous genes must typically be controlled by separate regulatory sequences, to provide appropriate levels and patterns of expression which may not be the same for each structural gene or other transgene to be expressed. For example, some genes may need to be expressed constitutively whereas other genes will need to be expressed at certain developmental stages or locations in the transgenic organism. Accordingly, a variety of regulatory sequences having diverse effects is needed.

By "preferentially" as used throughout the specification and claims is meant that a promoter confers expression on a nucleic acid to which it is operably linked to a greater extent or higher level in one or more specific cell types, tissues or organs of a plant, or under specific environmental or developmental conditions than it does in one or more other cells, tissues or organs or under another condition. However, the term "preferentially" does not limit the expression of the nucleic acid to the one or more specific cell types, tissues or organs of a plant, or under specific environmental or developmental conditions. Rather, the level of expression need only be increased to a higher level, and preferably significantly increased. For example, preferential expression may comprise gene expression in BETL that is at least about 1.5-fold the expression detected in endosperm cells other than the BETL layer or in silk tissue, leaves or roots. In another example, preferential expression may comprise gene expression in BETL that is at least about 2-fold the expression detected in endosperm cells other than the BETL layer or in silk tissue, leaves or roots. In another example, preferential expression may comprise gene expression in BETL that is at least about 3-fold the expression detected in endosperm cells other than the BETL layer or in silk tissue, leaves or roots. In anther example, preferential expression may comprise gene expression in BETL that is at least about 4-fold the expression detected in endosperm cells other than the BETL layer or in silk tissue, leaves or roots. In another example, preferential expression may comprise gene expression in BETL that is at least about 5-fold the expression detected in endosperm cells other than the BETL layer or in silk tissue, leaves or roots. In another example, preferential expression may comprise gene expression in BETL that is at least about 10-fold the expression detected in endosperm cells other than the BETL layer or in silk tissue, leaves or roots.

By "selectively" is meant that a promoter confers expression on a nucleic acid to which it is operably linked to in one or more specific cell types, tissues or organs of a plant, or under specific environmental or developmental conditions.

By "specifically" is meant exclusively.

As used throughout this specification and in the claims that follow, and unless the context requires otherwise, the word "confer" and variations thereof such as "conferring" shall be taken to mean the ability of a promoter or an active fragment or derivative thereof, for example in the context of other factors such as DNA conformation and/or cis-acting DNA sequence(s) and/or trans-acting factor(s) and/or signalling pathway(s) and/or transcript structure and/or transcript processing, to produce expression or a pattern of expression of nucleic acid to which the promoter or active fragment or derivative is operably-connected in response to one or more developmental and/or environmental and/or hormonal and/or other stimuli that would normally elicit the expression or pattern of expression for nucleic acid to which the promoter is operably-connected in its native context.

As used throughout this specification and in the claims that follow, the term "promoter" is to be taken in its broadest context and includes transcriptional regulatory sequences of a classical genomic gene, including a basal promoter regulatory region comprising a TATA box which is required for transcription initiation with or without a CCAAT box sequence, and optional additional regulatory elements (e.g., upstream activating sequences, enhancers and silencers) which alter gene expression in response to developmental and/or hormonal and/or environmental stimuli, or in a tissue-specific or cell-type-specific manner. A promoter is usually, but not necessarily, positioned upstream, or 5', of a structural gene, upon which it confers expression. Furthermore, the regulatory elements comprising a promoter are usually positioned within 2 kb of the start site of transcription of a plant gene.

As used throughout this specification and in the claims that follow, and unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used throughout this specification and in the claims that follow, the term "active fragment" in the context of a promoter shall be taken to mean a fragment or region or portion of a promoter that retains the ability of the promoter from which it is derived to initiate transcription. Such an active fragment need not necessarily confer expression or a pattern of expression on a nucleic acid to which it is operably connected in the same manner as the promoter from which it is derived. For example, an active fragment of a promoter induces the level of expression of a nucleic acid to a higher or lower degree than a promoter from which it is derived. Alternatively, or in addition, an active fragment of a promoter confers expression in a different cell, tissue or organ, or in fewer tissues or in an additional cell, tissue or organ to that in which a promoter from which it is derived confers expression. Methods for identifying such an active fragment will be apparent to the skilled artisan and/or described herein.

As used throughout this specification and in the claims that follow, the term "derivative" in the context of a promoter shall be taken to mean a promoter derived from a promoter as described according to any example hereof, e.g., a promoter comprising one or more additional regulatory elements, e.g., to increase or reduce or otherwise control expression of a nucleic acid operably connected thereto. The present invention also encompasses a derivative comprising a promoter as described according to any example hereof linked to another promoter, e.g., a bi-directional promoter. In this respect, the other promoter may also be a promoter as described according to any example hereof. The term "derivative" also encompasses a promoter comprising a variation in its sequence relative to a promoter as described according to any example hereof. For example, the sequence of such a derivative may include one or more of the following variations: a deletion, an insertion, a single or multiple point mutation or an alteration at a particular restriction enzyme site, provided that the derivative promoter retains its ability to initiate and/or suppress transcription of a nucleic acid linked thereto.

As used throughout this specification and in the claims that follow, the term "expression" or similar term such as "express" shall be taken to refer de minimis to transcription of a nucleic acid to produce RNA and to optionally encompass such transcription and subsequent translation of transcribed RNA to produce a peptide, polypeptide or protein. This definition is not to be limited to any specific cellular context and includes e.g., such expression obtained using in vitro expression systems or in isolated cells, tissues or organs.

Similarly, a "pattern of expression" refers to one or more of the timing, level, cellular location, sub-cellular location, tissue-selectivity or organ-selectivity of expression as hereinbefore defined, including the relative expression in one cell, tissue or organ compared to another cell, tissue or organ, and including the relative level or relative timing of expression such as at different developmental stages or in response to different environmental or hormonal stimuli.

As used throughout this specification and in the claims that follow, the term "operable" will be understood to mean the ability of a stated integer, to function in a particular context albeit not necessarily only in that stated context.

As used throughout this specification and in the claims that follow, the terms "operably connected" and "in operable connection with" mean the positioning of a promoter of the present invention or active fragment or derivative thereof in spatial relation to another nucleic acid, (e.g., a transgene including a structural gene, open reading frame, reporter gene, or nucleic acid encoding a ribozyme, minizyme, RNAi molecule or other RNA) to thereby confer expression on said other nucleic acid by the promoter, active fragment or derivative. Thus, the relative positioning of the promoter, active fragment or derivative to the other nucleic acid produces a structure that confer a functional expression pattern on the other nucleic acid. A promoter is generally positioned 5' (upstream) to the nucleic acid, the expression of which it controls. To construct heterologous promoter/nucleic acid combinations (e.g., promoter/transgene and/or promoter/selectable marker gene combinations), it is generally preferred to position the promoter at a distance from the gene transcription start site that is approximately the same as the distance between that promoter and the nucleic acid it controls in its natural setting, i.e., the gene from which the promoter is derived. As is known in the art, some variation in this distance can be accommodated without loss of promoter function.

As used throughout this specification and in the claims that follow, the term "native context" in the present context shall be taken to mean a genomic gene in which a promoter naturally occurs in the genome of a plant, i.e., from which the promoter is isolated. The genomic gene in which a promoter is located in nature may be identified and/or subjected to sequence comparison using sequence analysis software available from, for example National Center for Biotechnology Information (NCBI) at the National Library of Medicine at the National Institutes of Health of the Government of the United States of America, Bethesda, Md., 20894, United States of America.

In angiosperms, the seed endosperm forms a nutritive tissue for the embryo. For example, the endosperm of cereals originates with a series of free-nuclear divisions, followed by cellularisation and the subsequent formation of a range of functional cellular domains. This tissue is complex in its structure and development, particularly in cereals. The uptake of assimilates by the growing endosperm is a critical process in seed development. The central area of the endosperm consists of large vacuolated cells that store the reserves of starch and highly-abundant storage proteins.

The Basal Endosperm Transfer Layer (BETL) of the endosperm comprises highly specialized transfer cells that facilitate uptake of solutes from maternal pedicel tissue, and translocate the solutes to the developing endosperm and embryo. There is no symplastic connection between maternal and embryonic tissues, and phloem unloading releases nutrients into an apoplastic space. The uptake of nutrients by the endosperm from the apoplast is facilitated by the basal transfer cells, which possess extensive cell wall ingrowths to increase the membrane surface area and transport capacity (Pate et al., *Ann. Rev. Plant Physiol.* 23 (1972), 173-196). The absence of a basal endosperm cell transfer layer is correlated with reduced rates of grain filling and eventual abortion of seed in maize (Brink and Cooper, *Genetics* 32, (1947), 350-368; Charlton et al., *Development* 121 (1995), 3089-3097).

BETL genes may be expressed during the period of maximum grain filling and storage protein deposition in the endosperm e.g., between about 8 to about 20 days after pollination (DAP) in wheat. To date a limited number of BETL-expressed genes have been identified, and these include genes encoding cysteine-rich proteins that contain extensin-like motifs e.g., SPPPP, proteins related at the amino acid sequence level to plant defensins and proteins related at the amino acid sequence level to Bowman-Birk proteases/alpha-amylase inhibitors.

The ability to express a recombinant nucleic acid in endosperm is desirable for the production of heterologous proteins, e.g., for pharmaceutical or industrial purposes. For example, endosperm has evolved to permit the accumulation of large amounts of storage proteins in a small volume and a stable environment. Moreover, the small size of the endosperm permits recombinant proteins to reach a relatively high concentration in a small biomass, which is beneficial for extraction and downstream processing. Such downstream processing is also simplified as a result of low levels of compounds known to interfere with downstream processing steps, such as phenolics and alkaloids present in tobacco leaves and oxalic acid present in alfalfa. Furthermore, because seed is generally suitable for human and animal consumption, accumulation of proteins in developing seed is an attractive means for producing recombinant proteins for oral delivery to humans or animals, e.g., for production of a foodstuff having a pharmaceutical quality, e.g., an oral vaccine or for production of a foodstuff having an improved nutritional quality.

Accumulation of proteins in the seed of a plant is also particularly useful as the harvesting of seed is already a major feature of crop based agriculture and is relatively easy to implement using existing techniques. The selective expression of proteins in endosperm, as opposed to constitutive expression throughout the plant, has a reduced risk of interfering with vegetative plant growth. Moreover, such limited expression limits contact with non-target organisms, such as microbes in the biosphere and leaf-eating herbivores (Stoger et al., *Current Opinion in Biotechnology*, 16: 167-173, 2005). There is an ongoing need for regulatory sequences that are capable of conferring expression selectively or specifically in the endosperm e.g., because the majority of sequences isolated to date are leaky or non-selective in so far as they confer expression more generally in vegetative or floral tissues or reproductive organs, mature seeds or embryonic tissues, and/or because they are not operable in different species or confer different patterns of expression across species.

Only a few endosperm promoters are known in the art, and these are mostly derived from a few abundantly-expressed storage protein genes. Moreover, the majority of isolated promoters known in the art confer crown cell expression as opposed to basal endosperm transfer cell expression, and there are few examples of promoters conferring a basal endosperm transfer cell-specific expression pattern. Because of the difficulty in expressing multiple genes in plants from the same promoter, the small number of available promoters makes it difficult to modify or improve plant seeds yield or other seed qualities by gene stacking i.e., the expression of multiple transgenes. For example, competition between cis-acting elements for regulatory DNA binding proteins can reduce promoter efficiency such that expression of multiple transgenes under the control of the same promoter in the same cell may be reduced compared to when different promoters are employed.

It will be apparent to the skilled artisan from the foregoing that the genetic manipulation of seed yield and/or seed quality is beneficial to agriculture and achievable e.g., by expressing genes in the endosperm including crown cells and/or BETL cells. The improved plant seeds provide flow-on benefits, permitting the production of pharmaceuticals for human or veterinary use and/or for improving or altering the nutritional quality of a foodstuff produced from a plant. Accordingly, promoters that confer expression in developing endosperm including crown cells and/or BETL cells are clearly desirable to provide these benefits.

Conventional techniques of molecular biology, recombinant DNA technology are described, for example, in the following texts:

1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Perbal, B., A Practical Guide to Molecular Cloning (1984);

SUMMARY OF INVENTION

In work leading up to the present invention, the present inventors sought to provide such an isolated promoter operable in one or more tissues of the seed endosperm, by employing microarray technology, and subsequently isolating promoter sequences conferring expression in developing endosperm cells. As exemplified herein, the inventors identified a wheat transcript that is expressed in developing endosperm including the basal endosperm transfer layer (BETL) in a development-selective manner, and isolated the wheat promoter that regulates the expression of this transcript in its native context during seed development.

The inventors have also demonstrated that the exemplary wheat promoter of the present invention confers selective expression on a reporter gene to which it is operably connected in the developing endosperm of transgenic wheat and maize e.g., in the period from about 5-10 days after pollination (DAP) to about least about 25 DAP. In both wheat and maize, the promoter of the present invention confers expression in the BETL cells of transgenic plants. In maize plants, the promoter confers high-level expression in BETL cells, suggesting e.g., that expression of a reporter gene to which the promoter of the invention is operably connected is selective to the basal endosperm e.g., selective to BETL cells.

As exemplified herein, a variant of the wheat promoter was identified in the genome of maize. To identify this maize promoter, the inventors identified genes in rice, barley and maize having more than 85% sequence identity to the wheat transcript they had identified by microarray technology, and then conducted chromosome walking to elucidate the related maize promoter sequence. The maize promoter is isolated by amplifying nucleic acid upstream of the coding region in maize genomic DNA, using PCR primers based on the identified promoter sequence.

The exemplified maize and wheat promoters and methods for their isolation as described herein are thus representative of a class of promoters that in their native context confer selective/specific endosperm expression on genes to which they are operably connected e.g., in developing endosperm of cereals such as wheat, maize, rice, barley and sorghum, including the BETL cells.

Accordingly, one example of the present invention provides an isolated promoter or an active fragment or derivative thereof capable of conferring selective expression on a gene to which it is operably connected in the endosperm of a developing plant seed, wherein said promoter in its native context confers endosperm-selective expression or preferential endosperm expression on a genomic gene comprising a sequence selected from the group consisting of:

(i) a sequence set forth in SEQ ID NO: 1;
(ii) a sequence encoding a polypeptide having at least about 50% identity to a polypeptide encoded by SEQ ID NO: 1 wherein said polypeptide is expressed selectively in endosperm of developing seed;
(iii) a sequence that hybridizes under at least moderate stringency conditions to a sequence at (i) or (ii) or a complementary sequence thereto wherein said hybridising sequence is expressed selectively in endosperm of developing seed; and
(iv) a sequence having homology to a sequence at (i) or (ii) as determined by homology searching using the BLASTN algorithm e.g., with a nucleotide mismatch penalty (−q) of at least −1 wherein said homologous sequence is expressed selectively in endosperm of developing seed.

In another example, the isolated promoter, active fragment or derivative is at least capable of conferring endosperm-selective expression or preferential endosperm expression on a gene to which it is operably connected in developing seed. In another example, the isolated promoter, active fragment or derivative confers expression in the basal endosperm e.g., in the basal endosperm transfer layer (BETL) cells. In another example, the isolated promoter, active fragment or derivative confers expression in the basal endosperm such as in BETL cells, and in other endosperm cells e.g., crown cells, e.g., in maize and/or wheat. In another example, the isolated promoter, active fragment or derivative confers expression at a significantly higher level in the basal endosperm such as in BETL cells compared to other endosperm cells e.g., in maize and/or wheat. In another example, the isolated promoter, active fragment or derivative confers preferential expression in the basal endosperm such as in BETL cells e.g., in maize and/or wheat. In another example, the isolated promoter, active fragment or derivative confers selective expression in the basal endosperm such as in BETL cells e.g., in maize.

In another example, the isolated promoter, active fragment or derivative is at least capable of conferring endosperm-selective expression or preferential endosperm expression on a gene to which it is operably connected in the endosperm of a monocotyledonous plant e.g., wheat, maize, rice, barley, sorghum, sugar cane, coix, miscanthus, switch grass or Brachypodium. Other species-range(s) for the promoter, active fragment or derivative of the invention than those specifically recited herein are not to be excluded.

In another example, the promoter, active fragment or derivative is isolated from a monocotyledonous plant e.g., wheat, maize, rice, barley, sorghum, sugar cane, coix, miscanthus, switch grass or Brachypodium. Other sources of the promoter of the invention than those specifically recited herein are not to be excluded.

In another example. the isolated promoter, active fragment or derivative is capable of conferring endosperm-selective expression or preferential endosperm expression on a gene to which it is operably connected during the period of from about 5 days after pollination (DAP) to at least about 25 DAP.

It is to be understood that a preferential expression conferred by the promoter of the invention means that the gene to which the promoter, fragment or derivative is operably connected is expressed at a significantly higher level in endosperm e.g., including basal endosperm and/or is expressed at a significantly higher level in basal endosperm e.g., including BETL cells and/or is expressed at a significantly higher level in BETL cells than in other plant parts, organs, tissues or cells, as determined by detectable level of transcript and/or protein measured by conventional methods of transcript profiling or Northern hybridisation or RT-PCR or by immunological methods such as ELISA or by determining enzyme activity. For example, a preferential expression in endosperm and/or basal endosperm and/or BETL cells includes a significantly higher expression in such organs and/or tissues and/or cells than in one or more vegetative tissues or organs and/or one or more reproductive tissues or organs and/or one or more floral tissues or organs e.g., leaf and/or root and/or node and/or stem internode and/or glume and/or anther and/or ovary and/or pollen and/or husk and/or silk and/or embryo and/or mature seed endosperm.

It is also to be understood that selective expression conferred by the promoter of the invention means that the gene to which the promoter, fragment or derivative is connected is not expressed at a detectable level of transcript and/or protein e.g., as determined by conventional methods of transcript profiling or Northern hybridisation or RT-PCR or by immunological methods such as ELISA or by determining enzyme activity, in one or more vegetative tissues or organs and/or one or more reproductive tissues or organs and/or one or more floral tissues or organs. For example, the promoter of the present invention does not confer detectable expression as determined by such methods in leaf and/or root and/or node and/or stem internode and/or glume and/or anther and/or ovary and/or pollen and/or husk and/or embryo and/or mature seed endosperm.

In another example, the isolated promoter, active fragment or derivative of the present invention confers, induces or activates endosperm-specific or basal endosperm-specific or BETL-specific expression on a gene to which it is operably connected i.e., expression is strictly localized to the endosperm or basal endosperm or BETL cells of a developing seed.

Sequence analysis indicates that, notwithstanding the generally low sequence identity between different promoters, the isolated promoters, active fragments and derivatives thereof provided in accordance with the present invention possess structurally-conserved features which may permit their characterization and identification as a genus or sub-genus of endosperm-selective or endosperm-specific regulatory sequences. In one example, a promoter of the present invention or an active fragment or derivative thereof comprises one or more nucleotide sequences set forth in Table 3 and/or Table 4 e.g., as determined by PLACE analysis of the regulatory sequences to identify cis-acting elements therein. In another example, an isolated promoter of the present invention comprises one or more nucleotide sequences as set forth in Table 1 i.e., corresponding to cis-acting elements conserved between the exemplified wheat and maize endosperm regulatory sequences. In yet another example, an isolated promoter of the present invention or an active fragment or derivative thereof comprises a plurality of each element in the group consisting of an ARR1AT element, a BIHD1OS element, a BOXIINTPATPB element, a CAATBOX1 element, a CACFTPPCA1 element, a DOFCOREZM element, a DPBF-COREDCDC3 element, an EBOXBNNAPA element, a GATABOX element, a GTICONSENSUS element, a GTGANTG10 element, a GTIGMSCAM4 element, an IBOXCORE element, an INRNTPSADB element, a MYB- CORE element, MYBPLANT element, a MYBPZM element, a MYBST1 element, a MYCATERD1 element, a MYCCONSENSUSAT element, a NODCON1GM element, a OSE1ROOTNODULE element, a POLASIG1 element, a POLASIG3 element, a POLLEN1LELAT52 element, a RAV1AAT element, a ROOTMOTIFTAPDX1 element, a SEBFCONSSTPR10A element, a SEF4MOTIFGM7S element, a SORLIP1AT element, a TAAAGSTKST1 element, a TATABOX4 element, a WBOXATNPR1 element, a WBOX-NTERF3 element and WRKY71OS element. Alternatively, or in addition, an isolated promoter of the present invention or an active fragment or derivative comprises more than two copies of an element selected from the group consisting of an ARR1AT element, a BIHD1OS element, a BOXIINTPATPB element, a CAATBOX1 element, a CACFTPPCA1 element, a DOFCOREZM element, a DPBFCOREDCDC3 element, an EBOXBNNAPA element, a GATABOX element, a GT1CONSENSUS element, a GTGANTG10 element, a GT1GMSCAM4 element, an IBOXCORE element, a MYBCORE element, a MYBPZM element, a MYBST1 element, a MYCCONSENSUSAT element, a POLASIG1 element, a POLLEN1LELAT52 element, a RAV1AAT element, a ROOTMOTIFTAPDX1 element, a TATABOX4 element, and a WRKY71OS element. Alternatively, or in addition, an isolated promoter of the present invention or an active fragment or derivative comprises more than three copies of an element selected from the group consisting of an ARR1AT element, a CAATBOX1 element, a CACFTPPCA1 element, a DOFCOREZM element, an EBOXBNNAPA element, a GATABOX element, a GT1CONSENSUS element, a GTGANTG10 element, a GT1GMSCAM4 element, an IBOXCORE element, a MYBCORE element, a MYCCONSENSUSAT element, a POLLEN1LELAT52 element, a RAVIAAT element, a ROOTMOTIFTAPDX1 element, and a WRKY71OS element. Alternatively, or in addition, an isolated promoter of the present invention or an active fragment or derivative comprises more than four copies of an element selected from the group consisting of an ARR1AT element, a CAATBOX1 element, a CACFTPPCA1 element, a DOFCOREZM element, an EBOXBNNAPA element, a GATABOX element, a GT1CONSENSUS element, a GTGANTG10 element, a MYCCONSENSUSAT element, a POLLEN element, a RAV1AAT element, a ROOTMOTIFTAPDX1 element, and a WRKY71OS element. Alternatively, or in addition, an isolated promoter of the present invention or an active fragment or derivative comprises more than five copies of an element selected from the group consisting of an ARR1AT element, a CAATBOX1 element, a CACFTPPCA1 element, a DOFCOREZM element, an EBOXBNNAPA element, a GATABOX element, a GT1CONSENSUS element, a GTGANTG10 element, a MYCCONSENSUSAT element, a ROOTMOTIFTAPDX1 element, and a WRKY71OS element. In accordance with each of the foregoing examples, it is preferred for conserved structural motifs to be present within the proximal 2.5 kb of the promoter relative to the translation start site of the corresponding transcript i.e., a putative or predicted or actual translation start site of the corresponding transcript to which it is operably connected in its native environment. This includes promoters, active fragments and derivatives that comprise the conserved structural motifs within about the proximal 2.0 kb of the promoter relative to the translation start site of the corresponding transcript or within about the proximal 1.5 kb of the promoter relative to the translation start site of the corresponding transcript or within about the proximal 1.2 kb of the promoter relative to the translation start site of the corresponding transcript or within about the proximal 1.0 kb of the promoter relative to the translation start site of the corresponding transcript.

A promoter of the present invention can thus comprise one or multiple copies of a sequence set forth in Table 1 or Table 3 or Table 4 e.g., repeated in the promoter sequence with or without intervening sequences such as tandem repeat sequences, and/or in the opposing orientation e.g., in different species or alleles. A promoter of the present invention may also include reverse complement sequences of any sequence set forth in Table 1 or Table 3 or Table 4 infra. e.g., in different species or alleles.

The sequences presented in Table 1 that are conserved across species, or between different homeologues or alleles within a species, can individually or collectively contribute to the expression of pattern of expression conferred by the promoter of the present invention, thereby explaining one or more conserved patterns of expression observed for the transcript operably connected to the promoter in different or the same species. Accordingly, representative examples of the promoter of the present invention, other than those examples arising by gene duplication, have low sequence identity overall notwithstanding conserved ability to confer expression in a particular temporal or spatial pattern and/or in response to one or more signals, e.g., environment, hormone, etc.

Those skilled in the art will also be aware that such short sequences are useful for conferring expression or a pattern of expression on a heterologous nucleic acid to which it is operably connected e.g., to activate, silence, enhance, repress or otherwise modulate expression and/or cell-type-specificity and/or developmental specificity of a nucleic acid to which it is operably connected.

In yet a further example, the isolated promoter, active fragment or derivative comprises a nucleotide sequence selected from the group consisting of:
(i) a sequence selected from SEQ ID NO: 2 and SEQ ID NOs: 8-10;
(ii) a sequence complementary to a sequence at (i);
(iii) a sequence having at least about 70% sequence identity to a sequence of (i) or (ii); and
(iv) a sequence amplifiable from genomic DNA using one or more amplification primers wherein each of said primers comprises a sequence of at least about 12 contiguous nucleotides in length derived from SEQ ID NO: 2 or 8 or a complementary sequence thereto.

Preferred variants of a promoter exemplified herein lacks translation start codons and/or includes a plurality of translation stop codons th thereby prevent spurious translational initiation from within the promoter e.g., SEQ ID NO: 9 or 10.

For the purposes of nomenclature, the sequence set forth in SEQ ID NO: 2 comprises the promoter designated "WP04" from wheat that confers expression of a gene to which it is operably connected e.g., in its native context or in situ in endosperm cells, including basal endosperm expression e.g., in BETL cells, and/or confers expression of a gene to which it is operably connected e.g., in its native context or in situ in basal endosperm cells, including BETL cells, and/or confers expression of a gene to which it is operably connected e.g., in its native context or in situ in BETL cells. The sequence set forth in SEQ ID NO: 8 comprises a maize variant of the promoter designated "WP04" from wheat, wherein the maize variant confers expression of a gene to which it is operably connected e.g., in its native context or in situ in endosperm cells, including basal endosperm expression e.g., in BETL cells, and/or confers expression of a gene to which it is operably connected e.g., in its native context or in situ in basal endosperm cells, including BETL cells, and/or confers expression of a gene to which it is operably connected e.g., in its native context or in situ in BETL cells. The sequence set forth in SEQ ID NO: 8 comprises a 5'-upstream regulatory sequence of the maize gene locus designated "ZmGSStuc11-12-04.13411.1" in its native context, wherein said maize gene is expressed in developing seed and identified by homology searching as described in the examples hereof. The sequence set forth in SEQ ID NO: 9 relates to variants of the maize 5'-upstream regulatory sequence of SEQ ID NO: 8 wherein a plurality of ATG sequences have been mutated to a sequence other than ATG e.g., the sequence BVH. The sequence set forth in SEQ ID NO: 10 relates to a variant of the maize 5'-upstream regulatory sequence of SEQ ID NO: 8 wherein a plurality of ATG sequences have been mutated to a sequence other than ATG e.g., the sequence BVH, and wherein a plurality of translation stop codons, e.g., TRR, have been introduced.

It is to be understood that the present invention clearly encompasses an isolated promoter, active fragment or derivative comprising a nucleotide sequence selected individually or collectively from the group consisting of:
(i) a sequence selected from the group consisting of SEQ ID NO: 2 and SEQ ID NOs: 8-10; and
(ii) a sequence complementary to any one or more of the sequences at (i).

It is also to be understood that the present invention extends mutatis mutandis to an isolated promoter or an active fragment or derivative thereof comprising a sequence of nucleotides that in its native context confers endosperm expression on nucleic acid defined by SEQ ID NO: 1 or LOC_Os03g025350 or ZmGSStuc11-12-04.13411.1 referred to in the examples hereof, and to any homolog of any one or more of said nucleic acids.

Alternatively, or in addition, the promoter of the present invention will comprise a sequence that in its native context confers endosperm-selective or endosperm-specific expression on nucleic acid that hybridizes under at least moderate stringency conditions, and preferably high stringency conditions, to nucleic acid encoding a polypeptide encoded by SEQ ID NO: 1 or LOC_Os03g025350 or ZmGSStuc11-12-04.13411.1 referred to in the examples hereof Alternatively, or in addition, the promoter of the present invention will comprise a sequence that in its native context confers endosperm-selective or endosperm-specific expression on nucleic acid that hybridizes under at least moderate stringency conditions, and preferably high stringency conditions, to a complement of nucleic acid encoding a polypeptide encoded by SEQ ID NO: 1 or ZmGSStuc11-12-04.13411.1 referred to in the examples hereof Hybridization conditions will be known to the skilled artisan or are described herein. Due to the recognized low overall sequence identity between functionally-related promoters, low stringency hybridization conditions are preferred, however moderate or high stringency may be employed.

More preferably, a promoter of the present invention or an active fragment or derivative thereof comprises a nucleotide sequence that is amplifiable from genomic DNA using one or more amplification primers wherein each of said primers comprises a sequence of at least about 12 contiguous nucleotides in length derived from a sequence set forth in SEQ ID NO: 1 or LOC_Os03g025350 or ZmGSStuc11-12-04.13411.1 referred to in the examples hereof, or a complementary sequence thereto.

In a particularly preferred example, a promoter of the present invention comprises a sequence selected from the group consisting of SEQ ID NO: 2 and SEQ ID NOS: 8-10, or a complementary sequence thereto or an active fragment or derivative of said sequence or complementary sequence.

In an even more particularly preferred example, a promoter of the present invention comprises a sequence set forth in SEQ ID NO: 2 or a complementary sequence thereto or an active fragment or derivative of said sequence or complementary sequence. Alternatively, a promoter of the present invention comprises a sequence set forth in SEQ ID NO: 8 or a complementary sequence thereto or an active fragment or derivative of said sequence or complementary sequence. Alternatively, a promoter of the present invention comprises a sequence set forth in SEQ ID NO: 9 or a complementary sequence thereto or an active fragment or derivative of said sequence or complementary sequence. Alternatively, a promoter of the present invention comprises a sequence set forth in SEQ ID NO: 10 or a complementary sequence thereto or an active fragment or derivative of said sequence or complementary sequence.

The present invention also provides the use of a promoter as described according to any example hereof or an active fragment or derivative thereof in the production of an expression construct.

For example, a promoter of the present invention is particularly useful for the production of an expression construct for expressing nucleic acid to which it is operably connected in cells of developing endosperm e.g., in basal endosperm cells such as in BETL cells, and preferably being preferentially or selectively expressed in such endosperm cells.

The term "expression construct" is to be taken in its broadest context and includes an isolated promoter or active fragment or derivative placed in operable connection with a transgene.

As used herein, the term "transgene" shall be taken to mean nucleic acid other than that upon which the promoter of the invention confers expression or a pattern of expression in its native context i.e., "heterologous nucleic acid". The general applicability of the present invention is not to be limited by the nature of the transgene. Suitable transgenes will be apparent to the skilled artisan based on the description herein, and include a nucleic acid encoding a polypeptide to be expressed in a developing endosperm or cell or tissue thereof e.g., basal endosperm or BETL cells or a nucleic acid capable of reducing expression of a nucleic acid in a developing endosperm or cell or tissue thereof e.g., basal endosperm or BETL cells, e.g., a short interfering RNA (siRNA) or RNAi or antisense RNA or micro RNA (miRNA). Preferably, the nucleic acid is capable of modulating expression of a polypeptide involved in endosperm development, starch or storage protein accumulation or biosynthesis or in conferring disease resistance or nutritional value on the seed. It will be understood from the foregoing that it is preferred for such expression to be modulated by virtue of the promoter conferring expression in the context of one or more factors required for expression, repression, inhibition or reduction to occur. Preferably, expression is modulated preferentially or selectively under these conditions. Additional suitable transgenes will be apparent to the skilled artisan based on the description herein, and clearly include transgenes encoding a polypeptide that confers a nutritional or pharmaceutical quality on a developing endosperm or encoding a polypeptide for production of a useful downstream product or bi-product e.g., starch, brewed or fermented beverages or foods, flour, flour-containing products such as bread, biscuits, pasta or noodles, starches, fatty acids, edible oils, paper, textiles, ethanol, polymers or other industrial application(s). Transgenes that a transporters for one or more sugars, amino acids or other solutes e.g., folate, phosphate, iron, etc., are also preferred.

The present invention also provides a method for producing an expression construct, said method comprising linking a promoter of the present invention or active fragment or derivative as described according to any example hereof to a transgene such that the promoter is capable of conferring expression or a pattern of expression on said transgene in developing endosperm or a cell or tissue thereof e.g., basal endosperm such as BETL cells.

Preferred cells tissues or organs for performing this example are plant cells, tissues or organs, e.g., monocotyledonous plant cells, tissue or organs, such as from wheat, barley, maize, rice, sorghum, rye, millet (e.g. pearl millet or proso millet), buckwheat (e.g., of the family Polygonaceae), oat (e.g., *Avena sativa*) or a cell, tissue or organs from any other plant from the family Graminaceae, Gramineae or Poaceae. This includes any plant cell, tissue or organ having the ability to confer expression on the nucleic acid to which the promoter is operably-connected in its native context as herein before defined.

Preferred linkages between the promoter, active fragment or derivative and the transgene are covalent linkages. It is to be understood that, because the promoter, active fragment or derivative may confer expression at some distance from a transgene to which it is operably connected, the transgene need not be juxtaposed to the promoter, active fragment or derivative, i.e., there may be intervening sequence of up to about 2 kb in length, preferably up to about 1 kb in length, more commonly about 200-500 bp in length. Shorter intervening sequences such as the sequence of an intron of up to about 100 or 200 bp in length may also be employed.

Suitable methods for linking nucleic acids will be apparent to the skilled artisan and/or described herein and include enzymatic ligation, e.g., T4 DNA ligase, topoisomerase-mediated ligation e.g., using Vaccinia DNA topoisomerase I, recombination in cis or trans, e.g., using a recombinase or by random integration, amplification from one or more primer sequences including primer extension means, amplification from a vector, or chemical ligation, e.g., cyanogen bromide-mediated condensation of nucleic acids.

In a further example the present invention also provides an expression construct comprising a promoter of the present invention as described according to any example hereof operably connected to a transgene.

The present invention also provides the use of a promoter as described according to any example hereof or an active fragment or derivative thereof in the production of an expression vector. Preferably, the promoter is used operably linked to a transgene. The skilled artisan will be aware that an expression vector comprises sufficient genetic information to permit expression to be initiated from a promoter or active fragment or derivative e.g., by virtue of the presence of the promoter, active fragment or derivative and one or more transcription termination sequences and/or enhancer element sequences and/or intron sequences and/or intron splice junction sequences in operable connection therewith. An expression vector will generally also include one or more sequences to permit it to be maintained in a cell e.g., one or more selectable marker genes e.g., to confer antibiotic or herbicide resistance on cells comprising the expression construct, and one or more origins of replication e.g., for replication in bacterial cells or yeasts. An expression vector may also include one or more recombinase site sequences to permit excision of a portion of its DNA in a cell and/or to facilitate integration into host cell DNA.

The present invention also provides a method for producing an expression vector, said method comprising linking a promoter of the present invention or active fragment or derivative as described according to any example hereof to an empty vector to thereby produce an expression vector. As used herein, the term "empty vector" shall be taken to mean a vector without a promoter of the present invention or an active fragment or derivative thereof. The skilled artisan will be aware that exemplary vectors include plasmids, phagemids, cosmids, viral genome or subgenomic fragment, phage artificial chromosomes e.g., P1 artificial chromosomes, bacterial artificial chromosomes, yeast artificial chromosomes, or other nucleic acid capable of being maintained chromosomally or extra-chromosomally and/or replicating in a cell.

In one example, the process additionally comprises linking a transgene to the expression vector such that the promoter, active fragment or derivative and the transgene are in operable connection.

In a further alternative, the present invention provides a process for producing an expression vector, said method comprising linking an expression construct as described according to any example hereof to an empty vector to thereby produce an expression vector.

In the present context, the linkages between the various components of the expression vector and the means for achieving such linkage will be understood to be the same as for producing an expression construct of the present invention.

In one example, the method additionally comprises producing or obtaining an expression construct of the present invention.

In another example, the method comprises obtaining a promoter, active fragment or derivative of the invention and/or a transgene and/or an empty vector for use in producing an expression vector of the invention.

In a further example, the present invention also provides an expression vector comprising a promoter of the present invention or active fragment or derivative thereof.

Preferred expression vectors will comprise an expression construct of the present invention i.e., including a promoter of the present invention operably connected to a transgene. For example, the inventors have produced vectors for biolistic or *Agrobacterium*-mediated transformation of wheat, e.g., comprising a sequence set forth in SEQ ID NO: 3 or 4 or 5 or 6 or for *Agrobacterium*-mediated transformation of maize, e.g., comprising a sequence set forth in SEQ ID NO: 7.

A promoter as described according to any example hereof or an active fragment or derivative thereof is also useful for the production of a transgenic plant or plant part, e.g., comprising a promoter, active fragment or derivative of the invention in operable connection with a transgene or in operable connection with an endogenous nucleic acid. By "endogenous nucleic acid" is meant nucleic acid of nuclear or organellar origin in a plant, plant cell or plant part that is made transgenic by virtue of the introduction of the promoter, active fragment or derivative. For example, such "endogenous nucleic acid" occurs naturally in the plant or plant part that is made transgenic by virtue of the introduction of a promoter, active fragment or derivative of the invention.

Accordingly, the present invention provides for use of a promoter, active fragment or derivative of the present invention in the production of a plant cell, plant tissue, plant organ or whole plant, e.g., for modulating endosperm expression of a transgene e.g., including in the basal endosperm such as in BETL cells. For example, the promoter, active fragment or derivative confers expression on an endogenous or heterologous transgene preferentially or selectively in developing endosperm e.g., including in the basal endosperm such as in BETL cells and/or for represses or reduces expression of an endogenous transgene in developing endosperm e.g., including in the basal endosperm such as in BETL cells.

The term "plant part" is to be understood to mean a cell, tissue or organ of a plant, or plurality of cells, tissues or organs of a plant, including any reproductive material e.g., seed, developing endosperm, e.g., including in the basal endosperm such as in BETL cells. Preferred plant parts of the present invention comprise a promoter of the invention or active fragment or derivative thereof.

Alternatively, the present invention provides for use of a promoter, active fragment or derivative of the present invention in the preparation of an expression vector or expression construct for producing a plant cell, tissue or organ or whole plant, e.g., for conferring expression preferentially or selectively in developing endosperm, e.g., including in the basal endosperm such as in BETL cells, and/or for repressing or reducing expression in developing endosperm, e.g., including in the basal endosperm such as in BETL cells.

In one example, a promoter, active fragment or derivative of the present invention is used to produce a plant or plant part in which the expression of an endogenous nucleic acid is altered, i.e., the promoter, active fragment or derivative is operably connected to an endogenous nucleic acid. For example, production of such a plant part or plant permits the expression of an endogenous nucleic acid to be enhanced or reduced. Such modulated expression is useful for, for example, inducible production of an expression product of interest, e.g., a protein of interest or for controlling the timing and/or location of expression of an expression product of interest, or for reducing levels of undesirable expression products or delaying their expression.

Alternatively, a promoter, active fragment or derivative is used to identify and/or isolate a nucleic acid that induces a phenotype of interest. For example, the promoter, active fragment or derivative is introduced into the genome of a plant or plant part such that it is operably connected to genomic nucleic acid to thereby produce a phenotype in said plant or plant part different to the phenotype of otherwise isogenic or near isogenic material lacking said promoter, active fragment or derivative at that genomic location. The nucleic acid operably linked to the promoter, active fragment or derivative in the genome of the plant is optionally identified and/or isolated using standard techniques, e.g., 5' rapid amplification of cDNA ends (RACE) or 3' RACE.

In another example, a promoter, active fragment or derivative of the present invention is used to confer expression as hereinbefore defined on a transgene in a plant part. It is to be understood that an expression construct or expression vector of the present invention is also used to produce a plant cell, plant part or whole plant for the purpose of conferring expression as hereinbefore defined on a plant part. In the case of a transgenic plant or a transgenic plant cell or a transgenic plant part comprising an expression construct, the expression construct can be integrated into the genome of the plant, plant cell or plant part or can be in an episome or is extra-chromosomal.

Preferably, a promoter, active fragment, derivative, expression construct or expression vector of the present invention is used to produce a plant or plant part having an altered phenotype compared to an otherwise isogenic plant part or plant not having the promoter, active fragment, derivative expression vector or expression construct. For example, a transgenic plant or plant part comprises an expression construct or expression vector of the present invention comprising a transgene or structural gene placed operably under control of a promoter of the present invention.

In one example, the open reading frame of a structural gene to be expressed under control of a promoter of the present invention confers or enhances disease or pest tolerance on a plant (e.g., an open reading frame from an insect resistance gene, a bacterial disease resistance gene, a fungal disease resistance gene, a viral disease resistance gene, a nematode disease resistance gene). In another example, the open reading frame of a structural gene to be expressed under control of a promoter of the present invention confers or enhances herbicide tolerance on a plant (e.g., a glyphosate resistance gene or phosphinothricin resistance gene). In another example, the open reading frame of a structural gene to be expressed under control of a promoter of the present invention modifies grain composition or quality, such as endosperm size, endosperm cell number, seed size, or other yield characteristic). In yet further examples, the open reading frame of a structural gene to be expressed under control of a promoter of the present invention modifies nutrient utilization, improves tolerance to a mycotoxin, improves or enhances environmental or other stress tolerance resistance (e.g., a drought tolerance gene, heat tolerance gene, cold tolerance gene, frost tolerance gene, flooding tolerance gene, salt tolerance gene, or oxidative stress tolerance gene), oil quantity and/or quality, amino acid or protein composition, and genes for expression of exogenous products such as enzymes, cofactors, and hormones from plants, other eukaryotes or prokaryotic organisms. Commercial traits in plants are also created through the modified expression of genes that alter starch or protein for the production of paper, textiles, ethanol, polymers or other materials with industrial uses.

In another example, a promoter of the present invention or an active fragment or derivative thereof confers expression on a transgene encoding a phytohormone transporter e.g., a Pin gene that encodes an auxin transport protein. Alternatively, or in addition, a transgene encoding a gibberilinic acid transport protein may be employed.

In another example, a promoter of the present invention or an active fragment or derivative thereof confers expression on a transgene encoding a cell cycle protein e.g., to thereby increase cell number.

In another example, a promoter of the present invention or an active fragment or derivative thereof confers expression on a transgene for delaying of cell death to thereby prolong transport through BETL cells.

In another example, a promoter of the present invention or an active fragment or derivative thereof confers expression on a transgene comprising a solute transport protein e.g., to enhance transport of an amino acid, a sugar (a saccharide or disaccharide), phosphate, sugar phosphate, nucleotide, nucleotidyl-sugar phosphate, iron, folate, etc., and optionally to enhance or confer resistance against disease e.g., resistance to a fungal pathogen. Without being bound by any theory or mode of action, the enhanced expression of a transporter protein in the basal endosperm leads to enhanced transport of one or more metabolites that are otherwise limiting to growth of the endosperm and/or embryo during seed development e.g., in the grain filling period, thereby enhancing size of the endosperm and/or embryo, or alternatively enhancing the ratio of endosperm dry weight to embryo dry weight, or otherwise enhancing seed yield as determined by seed dry weight. Transgenes suitable for such applications include one or more of the following exemplary transgenes: an amino acid selective channel protein (e.g., Pohlmeyer et al., *Proc Natl Acad Sci USA*. 94 (1997), 9504-9509), an ABC-type transporter (ATPase component, EC 3.6.3; Krattinger et al., *Science* 323 (2009), 1360-1363), a phosphate translocator (e.g., Knappe et al. *Plant Physiol*. 131 (2003), 1178-1190), a glucose 6-phosphate/phosphate translocator (e.g., Kammerer et al., *The Plant Cell* 10 (1998), 105-117), a plastidial nucleotide transporter (e.g., Neuhaus et al., *The Plant Journal* 11 (1997), 73-82), an ADP-glucose transporter e.g., a BT1 protein such as ZmBT1 (e.g., Cao et al., *Physiologia Plantarum* 95 (1995), 176-186; Sullivan et al., *Planta* 196 (1995), 477-484; Cao et al., *Physiologia Plantarum* 100 (1997), 400-406) or other transporter of the mitochondrial carrier family (MCF) of transporters (e.g., Sullivan et al., *The Plant Cell* 3 (1991), 1337-1348; Picault et al., *Trends in Plant Sci.* 9 (2004), 138-146).

In another example, the expression of an endogenous endosperm gene is reduced using a promoter of the present invention e.g., by means of expressing one or more transgenes comprising one or more antisense molecules, ribozymes (Haseloff et al. *Nature* 334, 585-591, 1988; Steinecke et al. *EMBO J.* 11, 1525 (1992); Perriman et al., *Antisense Res. Dev.* 3, 253 (1993)), co-suppression molecules, RNAi molecules (Napoli et al. *Plant Cell* 2, 279-289, 1990; U.S. Pat. No. 5,034,323; Sharp et al., *Genes Dev.* 13, 139-141, 1999; Zamore et al., *Cell* 101, 25-33, 2000; and Montgomery et al., *PNAS USA* 95, 15502-15507, 1998), hairpin structures (Smith et al. *Nature* 407, 319-320, 2000; WO 99/53050; and WO 98/53083), microRNAs (Aukerman et al., *Plant Cell* 15, 2730-2741, 2003), transcription factor-targeted genes (e.g., WO 01/52620; WO 03/048345; and WO 00/42219), repressor-encoding genes, transposons, or dominant-negative mutants in the endosperm under operable control of the promoter of the invention. The present invention clearly encompasses the use of other methods or combinations of any two or more of the above procedures known to those of skill in the art.

A promoter of the present invention or active fragment or derivative thereof has particular utility for modifying one or more grain traits by expressing a structural gene e.g., an open reading frame, or molecule to effect reduced transcription of an endogenous endosperm gene to which it is operably connected. Preferred grain traits include e.g., solute transport and/or fatty acid content and/or composition, amino acid content and/or composition including the content of lysine-containing or sulfur-containing proteins and the content and/or composition of seed storage proteins, starch content and/or composition, growth regulatory proteins including cell cycle regulatory proteins, apoptosis or kernel abortion, ratio of endosperm-to-embryo, and environmental stress. In another example, the transgene encodes a siRNA or antisense RNA or RNAi or miRNA that inhibits expression of a polypeptide in developing endosperm. Alternatively, the nucleic acid encodes an antibody fragment capable of binding to and inhibiting activity of a polypeptide in developing endosperm, e.g., including in the basal endosperm such as in BETL cells.

In a further example, a promoter, active fragment or derivative or expression construct or expression vector of the present invention is used to confer resistance to a disease or pest on a plant part or a whole plant. For example, an expression construct or expression vector comprises a transgene confers resistance to a plant disease or a plant pest when expressed such as a chitinase or a thaumatin-like protein, e.g., from wheat, or a coat protein from a pest (e.g., a barley yellow mosaic virus coat protein).

In a still further example, a transgene confers a pharmaceutical quality on a plant or plant part in which it is expressed. For example, the transgene encodes an immunogenic protein, such as, for example, a hepatitis B surface antigen.

The present also encompasses a use of a promoter, active fragment, derivative, expression construct or expression vector of the present invention to confer a nutritional quality on a plant or plant part. For example, an expression construct or expression vector comprises a transgene encoding a seed storage protein, a fatty acid pathway enzyme, a tocopherol biosynthetic enzyme, an amino acid biosynthetic enzyme or a starch branching enzymes. In one example, the transgene encodes a Brazil nut protein, a calcium-binding protein or an iron-binding protein.

The present also encompasses a use of a promoter, active fragment, derivative, expression construct or expression vector of the present invention to modify morphology of a plant or plant part. For example, an expression construct or expression vector comprises a transgene encoding a polypeptide involved in auxin synthesis or metabolism or cytokinin synthesis or metabolism (e.g., cytokinin oxidase). By altering the level of auxin and/or cytokinin in a plant or plant part, the morphology of the plant or plant part is modified.

It is to be understood that the promoter of the present invention has particular utility for the purposes of gene stacking, such as when used with a different promoter to express a plurality of structural genes or transgenes in the endosperm of a plant. In a further example, the promoter of the present invention is used in conjunction with one or more other promoters to express a plurality of structural genes or transgenes in the same or a different cell of the plant e.g., wherein such expression is simultaneous, contemporaneous or synchronous. For example, the promoter of the present invention or an active fragment or derivative thereof is utilized to express different structural genes or transgenes that, when expressed, modify the same biochemical pathway in the plant seed. Alternatively, the promoter of the present invention or an active fragment or derivative thereof is utilized to express functionally distinct or unrelated structural gene or transgene to a structural gene or transgene expressed under control of the other promoter in the plant seed. As will be known to the skilled artisan, gene stacking may be performed by simultaneous or sequential transformation processes involving the introduction of gene constructs to be expressed.

In one example of gene stacking, a construct comprising the promoter of the present invention or an active fragment or derivative thereof operably linked to a transgene or structural gene is introduced to plant endosperm that already expresses a transgene or structural gene under control of another promoter that confers or regulates expression in a number of different plant organs, tissues or cells, e.g., including the endosperm. In another example, a two component system is employed wherein two parent lines are produced each of which expresses a desired transgene under the control of a promoter such that one plant line comprises a promoter, active fragment or derivative thereof in accordance with the present invention and the other plant line comprises the other promoter and wherein the two transgenic plant lines are crossed to produce a progeny plant expressing both transgenes. In another example, a first construct comprising the promoter of the present invention or an active fragment or derivative thereof operably linked to a transgene or structural gene is introduced to plant endosperm alongside a second construct comprising a transgene or structural gene operably linked to a different promoter that confers or regulates expression in a number of different plant organs, tissues or cells, e.g., including the endosperm. Exemplary promoters that confer or regulate expression in a number of different plant organs, tissues or cells, e.g., including the endosperm are known in the art e.g., the p326 promoter, YP0144 promoter, YP0190 promoter, p13879 promoter, YP0050 promoter, p32449 promoter, 21876 promoter, YP0158 promoter, YP0214 promoter, YP0380 promoter, PT0848 promoter, PT0633 promoter, CaMV 35S promoter, mannopine synthase (MAS) promoter, the 1' or 2' promoters derived from T-DNA of *Agrobacterium tumefaciens*, figwort mosaic virus 34S promoter, actin promoters such as from rice, and ubiquitin promoter such as from maize (Ubi-1).

In another example of gene stacking, a construct comprising the promoter of the present invention or an active fragment or derivative thereof operably linked to a transgene or structural gene is introduced to plant endosperm that already expresses a transgene or structural gene under control of a mature endosperm promoter that confers or regulates expression in maturing endosperm albeit not necessarily exclusively or predominantly in the maturing endosperm. In another example, a two component system is employed wherein two parent lines are produced each of which expresses a desired transgene under the control of a promoter such that one plant line comprises a promoter, active fragment or derivative thereof in accordance with the present invention and the other plant line comprises the other promoter active in maturing endosperm and wherein the two transgenic plant lines are crossed to produce a progeny plant expressing both transgenes in the endosperm. In yet another example, a first construct comprising the promoter of the present invention or an active fragment or derivative thereof operably linked to a transgene or structural gene is introduced to plant endosperm alongside a second construct comprising a transgene or structural gene operably linked to a different promoter that confers or regulates expression in maturing endosperm albeit not necessarily exclusively or predominantly in the maturing endosperm.

In another example of gene stacking, a construct comprising the promoter of the present invention or an active fragment or derivative thereof operably linked to a transgene or structural gene is introduced to plant endosperm that already expresses a transgene or structural gene under control of a mature endosperm promoter that confers or regulates expression in the embryo sac or early endosperm albeit not necessarily exclusively or predominantly in the embryo sac/early endosperm. In yet another example, a first construct comprising the promoter of the present invention or an active fragment or derivative thereof operably linked to a transgene or structural gene is introduced to plant endosperm alongside a second construct comprising a transgene or structural gene operably linked to a different promoter that confers or regulates expression in embryo sac or early endosperm albeit not necessarily exclusively or predominantly in the embryo sac/early endosperm. By "embryo sac" or "early endosperm" is meant the polar nuclei and/or the central cell, or in precursors to polar nuclei and preceding cellularization. Exemplary promoters that are active in embryo sac or early endosperm include e.g., the *Arabidopsis* viviparous-1 gene promoter (see, GenBank No. U93215); the *Arabidopsis* Atmyc1 gene promoter (Urao et al., Plant Mol. Biol., 32: 571-57, 1996; Conceicao Plant, 5, 493-505, 1994); the *Arabidopsis* FIE gene promoter (see GenBank No. AF129516); the *Arabidopsis* MEA gene promoter; the *Arabidopsis* FIS2 gene promoter (see GenBank No. AF096096); the *Arabidopsis* FIE 1.1 gene promoter (U.S. Pat. No. 6,906,244), the maize MAC1 gene promoter (Sheridan et al., Genetics, 142, 1009-1020, 1996); and the maize Cat3 gene promoter (see GenBank No. L05934; Abler et al., Plant Mol. Biol., 22, 10131-1038), 1993.

The present invention also provides a method for producing a transgenic plant cell, said method comprising introducing a promoter, active fragment or derivative of the present invention or an expression construct or expression vector of the present invention into the plant cell. Suitable methods for introducing a nucleic acid into a plant cell will be apparent to the skilled artisan, e.g., transformation using $CaCl_2$ and variations thereof, PEG-mediated uptake to protoplasts, microparticle bombardment, electroporation, microinjection, vacuum-infiltration of tissue or *Agrobacterium*-mediated transformation. For example, a transgenic plant cell is produced by performing a method of *Agrobacterium*-mediated transformation as described in International Patent Application No. PCT/AU2007/000021.

Preferably, the method additionally comprises producing, providing or obtaining the promoter, active fragment, derivative, expression construct or expression vector.

In one example, a method for producing a transgenic plant cell of the present invention additionally comprises contacting the produced transgenic plant cell with a compound that induces callus formation and/or induces dedifferentiation of the transgenic cell (or a cell derived therefrom) and/or induces the production of an undifferentiated cell from said transgenic cell for a time and under conditions sufficient to produce a callus and/or dedifferentiated cell and/or undifferentiated cell. A suitable compound will be apparent to the skilled artisan e.g., a synthetic or natural auxin such as, for example, a compound selected from the group consisting of 2,4-dichlorophenoxyacetic acid, 3,6-dichloro-o-anisic acid, 4-amino-3,5,6-trichloropicolinic acid and mixtures thereof. By "callus" is meant a cluster or group of undifferentiated cells resulting from cell division in the absence of regeneration.

Those skilled in the art are aware that a transgenic plant cell can be used without undue experiment to produce a transgenic plant, e.g., by regeneration. By "regeneration" is meant a process by which a plant or plant part, especially a plantlet, is produced from a transgenic plant cell e.g., by a process of organogenesis or embryogenesis.

As used herein, the term "organogenesis" shall be taken to mean a process by which shoots and roots are developed sequentially from meristem centres.

As used herein, the term "embryogenesis" shall be taken to mean a process by which shoots and roots develop together in a concerted fashion (not sequentially), whether from somatic cells or gametes.

As used herein, the term "plantlet" shall be taken to mean a shoot or root that has developed from a plant cell, e.g., using in vitro techniques. For example, a plantlet is a shoot or root that has been induced to grow from a callus using a compound, such as, for example, indole-3-acetic acid, benzyladenine, indole-butyric acid, zeatin, α-naphthaleneacetic acid, 6-benzyl aminopurine, thidiazuron or kinetin, 21P.

Based on the foregoing description, it will be apparent to the skilled artisan that the present invention provides for use of a transgenic plant cell comprising a promoter, active fragment, derivative, expression construct or expression vector of the present invention for the production of a transgenic plant or plantlet.

The present invention also provides a method for producing a transgenic plant or plantlet, said process comprising:
(i) providing, producing or obtaining a transgenic plant cell or callus comprising a promoter, active fragment, derivative, expression construct or expression vector of the present invention; and
(ii) regenerating a transgenic plant or plantlet from the transgenic plant cell or callus at (i), thereby producing a transgenic plant or plantlet.

In one example, the method is for producing a transgenic plant or plantlet in which a promoter, active fragment or derivative of the present invention confers expression as hereinbefore defined on a nucleic acid, e.g., a transgene, preferentially or selectively in developing endosperm, e.g., including in the basal endosperm such as in BETL cells and/or for repressing or reducing expression of a nucleic acid preferentially or selectively in a developing endosperm e.g., including basal endosperm and/or BETL cells.

Methods for regenerating a plant or plantlet from a plant cell or callus will be apparent to the skilled artisan and/or described herein. For example, a transgenic plant cell is contacted with a compound that induces callus formation and/or induces dedifferentiation of the transgenic cell (or a cell derived therefrom) and/or induces the production of an undifferentiated cell from said transgenic cell for a time and under conditions sufficient to produce a callus and/or dedifferentiated cell and/or undifferentiated cell, e.g., a compound described supra. Callus is generally contacted with a compound that induces shoot and/or root formation, e.g., a compound described supra for the production of a plantlet for a time and under conditions for a plantlet to form. To produce a whole plant a plantlet is grown for a time and under conditions for it to develop into a whole plant (e.g., grow to maturity).

In one example, the method for producing a transgenic plant or plantlet as described according to any example hereof additionally comprises providing or obtaining from the transgenic plant or plantlet, an offspring plant and/or seed and/or propagating material and/or reproductive material and/or germplasm, wherein said offspring plant, seed, propagating material or reproductive material comprises a promoter, active fragment, derivative, expression construct or expression vector of the present invention.

The present invention additionally provides a method for producing a transgenic seed from a plant, said method comprising providing, producing or obtaining a transgenic plant or plantlet as described according to any example hereof and growing or maintaining the transgenic plant or plantlet for a time and under conditions sufficient for seed to be produced. Optionally, the method additionally comprises obtaining seed comprising the introduced promoter, active fragment or derivative of the invention or expression construct or expression vector of the invention.

The present invention also provides a transgenic plant or plantlet or plant part or offspring plant or seed or propagating material or reproductive material or germplasm comprising a promoter, active fragment, derivative, expression construct or expression vector of the present invention. In one example, the plant or plantlet or plant part or offspring plant or seed or propagating material or reproductive material or germplasm comprises a promoter, active fragment or derivative operably connected to an endogenous nucleic acid of said plant or plantlet or plant part or offspring plant or seed or propagating material or reproductive material or germplasm.

In a preferred example, the present invention provides a transgenic plant or plantlet or plant part or offspring plant or seed or propagating material or reproductive material or germplasm comprising a nucleic acid in operable connection with a promoter, active fragment or derivative of the present invention, e.g., comprising an expression construct or expression vector of the present invention. Preferably, the promoter, active fragment or derivative confers expression on the nucleic acid preferentially or selectively in developing endosperm e.g., including basal endosperm and/or BETL cells and/or represses or reduces expression of the nucleic acid preferentially or selectively in developing endosperm e.g., including basal endosperm and/or BETL cells.

The present invention additionally provides for use of a transgenic plant, plantlet or plant part for the production of a zygote and/or an offspring plantlet and/or an offspring plant.

Additionally, the present invention provides a method for breeding a transgenic plant. The term "breeding" is to be taken in its broadest context to mean any process by which a zygote and/or an offspring plantlet or plant is produced from or using a parent plant a part thereof or a cell thereof. For example, the term "breeding" encompasses sexual reproduction such as, cross-breeding or cross-pollination, whereby reproductive material, e.g., pollen from one plant is used to fertilize reproductive material, e.g., an egg cell within an ovule from another plant. The term "breeding" also encompasses sexual reproduction such as selfing or self-fertilization, whereby reproductive material from a plant, e.g., pollen is used to fertilize reproductive material, e.g., an egg cell within an ovule, from the same plant. The term "breeding" also encompasses vegetative forms of reproduction, such as the production of a plant from a stolon or a rhizome or a bulb or a tuber or a corm or a cutting or a graft or a bud. The term "breeding" also encompasses in vitro methods, e.g., in vitro fertilization and zygote culture.

In the case of sexual reproduction, the present invention provides a method for breeding a transgenic plant, said method comprising:
(i) providing, producing or obtaining a transgenic plant comprising a promoter, active fragment, derivative, expression construct or expression vector of the present invention; and
(ii) breeding the transgenic plant produced at (i) to thereby produce a zygote comprising a promoter, active fragment, derivative, expression construct or expression vector of the present invention.

Alternatively, the method comprises:
(i) providing, producing or obtaining plant reproductive material comprising a promoter, active fragment, derivative, expression construct or expression vector of the present invention; and
(ii) combining reproductive material of a plant with the reproductive material at (i) such that a zygote comprising a promoter, active fragment, derivative, expression construct or expression vector of the present invention is produced.

Preferably, the method additionally comprises growing the zygote to form a transgenic developing endosperm e.g., including basal endosperm and/or BETL cells and/or a transgenic plantlet and/or a transgenic plant and/or a transgenic plant part, e.g., developing endosperm e.g., including basal endosperm and/or BETL cells.

In one example, the step of obtaining a transgenic plant supra, comprises obtaining a seed or a plantlet or a pant part comprising a promoter, active fragment, derivative, expression construct or expression vector of the present invention, and growing said seed plantlet or plant or plant part to thereby obtain the transgenic plant.

In the case of cross-breeding, the transgenic plant is bred with or transgenic reproductive material is combined with a transgenic plant or transgenic reproductive material to produce a zygote, plant, plantlet or plant part homozygous or heterozygous for a promoter, active fragment, derivative, expression construct or expression vector of the present invention. Alternatively, the transgenic plant is bred with or transgenic reproductive material is combined with a wild-type plant or wild-type reproductive material to produce a zygote, plant, plantlet or plant part heterozygous for a promoter, active fragment, derivative, expression construct or expression vector of the present invention.

Preferably, a method of breeding of the present invention additionally comprises selecting or identifying a zygote, plantlet, plant part or whole plant comprising a promoter, active fragment, derivative, expression construct or expression vector of the present invention.

In one example, a method of breeding of the present invention additionally comprises detecting expression or a pattern of expression of a nucleic acid operably connected to a promoter, active fragment or derivative of the present invention in a plantlet, plant part or whole plant.

In the case of vegetative reproduction, the present invention provides a method comprising:

(i) providing, producing or obtaining a transgenic plant, plantlet or plant part comprising a promoter, active fragment, derivative, expression construct or expression vector of the present invention; and (ii) maintaining the transgenic plant for a time and under conditions sufficient for the plant to reproduce vegetatively.

Suitable conditions will depend on the form of vegetative reproduction and will be apparent to the skilled artisan. For example, a lateral shoot from a plant is induced to form adventitious roots by burying the shoot and, following adventitious root formation, the shoot is separated from the parent plant and a new plant grown. Alternatively, or in addition, a plant or plantlet or plant part is induced to form a callus, e.g., by cutting a part of the plant, plant part or plantlet or using a process described supra, and the callus maintained under conditions sufficient to a plantlet or plant to grow.

As exemplified herein, a promoter as described according to any example hereof is useful for expressing a nucleic acid in a plant or a plant cell or a plant part, e.g., in developing endosperm or a cell or tissue thereof such as basal endosperm and/or BETL cells. Accordingly, the present invention provides for use of a promoter, active fragment, derivative, expression construct or expression vector of the present invention for conferring expression on a nucleic acid, e.g., a transgene in a plant cell or plant part, e.g., for conferring expression on a nucleic acid preferentially or selectively in developing endosperm e.g., including basal endosperm and/or BETL cells and/or for repressing or reducing expression of a nucleic acid preferentially or selectively in developing endosperm e.g., including basal endosperm and/or BETL cells.

The present invention also provides a method for expressing a nucleic acid in a plant or a plant cell or a plant part, said method comprising:

(i) providing, obtaining or producing a transgenic plant, transgenic plant cell or transgenic plant part comprising a promoter, active fragment, or derivative as described according to any example hereof operably connected to a nucleic acid; and (ii) maintaining said transgenic plant or progeny for a time and under conditions sufficient for said nucleic acid to be expressed.

In one example, the promoter, active fragment or derivative is operably connected to a nucleic acid that is endogenous to the plant cell, plant part or plant. Alternatively, the promoter, active fragment or derivative is operably linked to a transgene, e.g., the transgenic plant, transgenic plant cell or transgenic plant part comprises an expression vector or expression construct of the present invention. Suitable transgenes are described herein and are to be taken to apply mutatis mutandis to the present example of the invention.

In one example, a method for expressing a nucleic acid of the present invention is for conferring expression on the nucleic acid preferentially or selectively in developing endosperm e.g., including basal endosperm and/or BETL cells and/or for repressing or reducing expression of the nucleic acid preferentially or selectively in developing endosperm e.g., including basal endosperm and/or BETL cells.

Preferably, the method further comprises determining expression or a pattern of expression of the nucleic acid in a plant, plant cell or plant part.

As will be apparent to the skilled artisan based on the foregoing description, by modulating expression of a nucleic acid in a plant cell or plant part a phenotype or trait of a plant cell, plant part, plantlet or whole plant can also be modulated or a phenotype or trait can be conferred on a plant cell, plant part, plantlet or whole plant. Accordingly, the present invention provides for use of a promoter, active fragment, derivative, expression construct or expression vector for modifying a phenotype or trait in a plant cell, plant part, plantlet or whole plant or for conferring a phenotype or trait on a plant cell, plant part, plantlet or whole plant. For example, the plant cell, plant part, plantlet or whole plant has an improved nutritional quality or has a pharmaceutical quality. Alternatively, or in addition the plant part, plantlet or whole plant has modified morphology. Suitable nucleic acids, e.g., transgenes for modulating or conferring one or more traits described herein above are described herein and are to be taken to apply mutatis mutandis to the present example embodiment of the invention.

The present invention also provides a method for modulating a phenotype or trait in a plant cell, plant part, plantlet or plant or for conferring a phenotype or trait on a plant cell, plant part, plantlet or plant, said method comprising:

(i) providing, producing or obtaining a plant cell, plant part, plantlet or plant comprising a promoter, active fragment or derivative of the present invention in operable connection with a nucleic acid that when expressed modulates a phenotype or trait in a plant cell, plant part, plantlet or plant or that when expressed confers a phenotype or trait on a plant cell, plant part, plantlet or whole plant; and (ii) maintaining the plant cell, plant part, plantlet or plant at (i) for a time and under conditions sufficient for the nucleic acid to be expressed and the phenotype or trait to be modified or conferred.

Exemplary traits, phenotypes and nucleic acids are described herein above and are to be taken to apply mutatis mutandis to the present example of the invention.

The present invention also provides a plant cell, plant part, plantlet or plant having a modified phenotype or trait or a new phenotype or trait, said plant cell, plant part, plantlet or plant comprising a promoter, active fragment or derivative of the present invention in operable connection with a nucleic acid that when expressed modulates a phenotype or trait in a plant cell, plant part, plantlet or plant or that when expressed confers a phenotype or trait on a plant cell, plant part, plantlet or whole plant.

Exemplary traits, phenotypes and nucleic acids are described herein above and are to be taken to apply mutatis mutandis to the present example of the invention.

The present inventors have also provided a method for isolating new promoters, e.g., a promoter capable of conferring expression on a nucleic acid in developing endosperm or a cell or tissue thereof e.g., basal endosperm and/or BETL cells. For example, the inventors have provided a method for isolating an endosperm-selective promoter, said method comprising:

(i) identifying an expression product of a gene that is expressed at an increased level in a immature embryo compared to the level that the expression product is expressed in an imbibed seed or imbibed embryo; and (ii) isolating a promoter operably connected to said gene wherein said promoter confers expression selectively in developing endosperm e.g., including basal endosperm and/or BETL cells.

Preferably, the method for isolating a promoter as described according to any example hereof comprises:

(i) determining the level of expression of a plurality of expression products in a developing endosperm e.g., during grain filling or storage protein deposition such as at about 10-14 DAP;
(ii) determining the level of expression of a plurality of expression products in immature embryo e.g., from seed during grain filling or storage protein deposition such as at about 10-14 DAP;
(iii) identifying one or more expression products expressed at an increased level at (i) compared to (ii); and
(iv) isolating a promoter that confers expression on one or more expression products at (iii).

Preferably, the expression products detected are transcripts or mRNA encoded by a gene. For example, the transcripts or mRNA are detected using a microarray.

This specification contains nucleotide and amino acid sequence information prepared using PatentIn Version 3.5 presented herein after the claims. Each nucleotide sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence are indicated by information provided in the numeric indicator fields <211>, <212> and <213>, respectively. Nucleotide sequences referred to in the specification are defined by the term "SEQ ID NO:", followed by the sequence identifier (e.g. SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and/or all combinations or any two or more of said steps or features.

The present invention is not to be limited in scope by the specific examples described herein, which are intended for the purpose of exemplification only. Functionally-equivalent products, compositions and methods are clearly within the scope of the invention, as described herein.

As used herein the term "derived from" shall be taken to indicate that a specified integer may be obtained from a particular source albeit not necessarily directly from that source.

BRIEF DESCRIPTION OF THE DRAWINGS

FIG. 17 shows a sequence alignment between LOC_Os03g25350.1 (SEQ ID NO: 20) and ZmGSStuc11-12-04.13411.1 (SEQ ID NO: 28) obtained from a BLASTN Search of Maize Genomic Assemblies using LOC_Os03g25350.1 as a query sequence with a nucleotide mismatch penalty of −1.

FIG. 18 provides a schematic representation of a multiple sequence alignment between the following sequences:
(i) Genome Walker primer sequences used to identify the WP04 promoter;
(ii) the terminal 76 nucleotides of WP04 (SEQ ID NO: 2);
(iii) the PUT-153a-*Triticum_aestivum*-74777 sequence;
(iv) the Affymetrix consensus wheat sequence Ta.10064.1.S1_at;
(v) the wheat sequence assigned Accession No. AJ890018.1;
(vi) the maize genome sequence for Accession No. ZmGSStuc11-12-04.13411.1;
(vii) the maize transcript assembly identified using ZmGSStuc11-12-04.13411.1,
(viii) the rice cDNA for LOC_Os03g25350;
(ix) the rice genomic sequence (indica cultivar) for LOC_Os03g25350, and
(x) the rice genomic sequence (japonica cultivar) for LOC_Os03g25350, rc_GW-WP04.r1: SEQ ID NO: 18; WP04: SEQ ID NO: 29; PUT-153a-*Triticum*_ae: SEQ ID NO: 21; affy_g-b_BQ805508.1: SEQ ID NO: 22; ZmGSStuc11-12-04.134: SEQ ID NO: a PUT-157a-*Zea_mays*-01: SEQ ID NO: 24; LOC_Os03g25350.1_345: SEQ ID NO: 25; gi|57015217|gb|CM000: SEQ ID NO: 26; and LOC_Os03g25350.11120: SEQ ID NO: 27.

DETAILED DESCRIPTION OF THE PREFERRED EXAMPLES

Figure 1A:
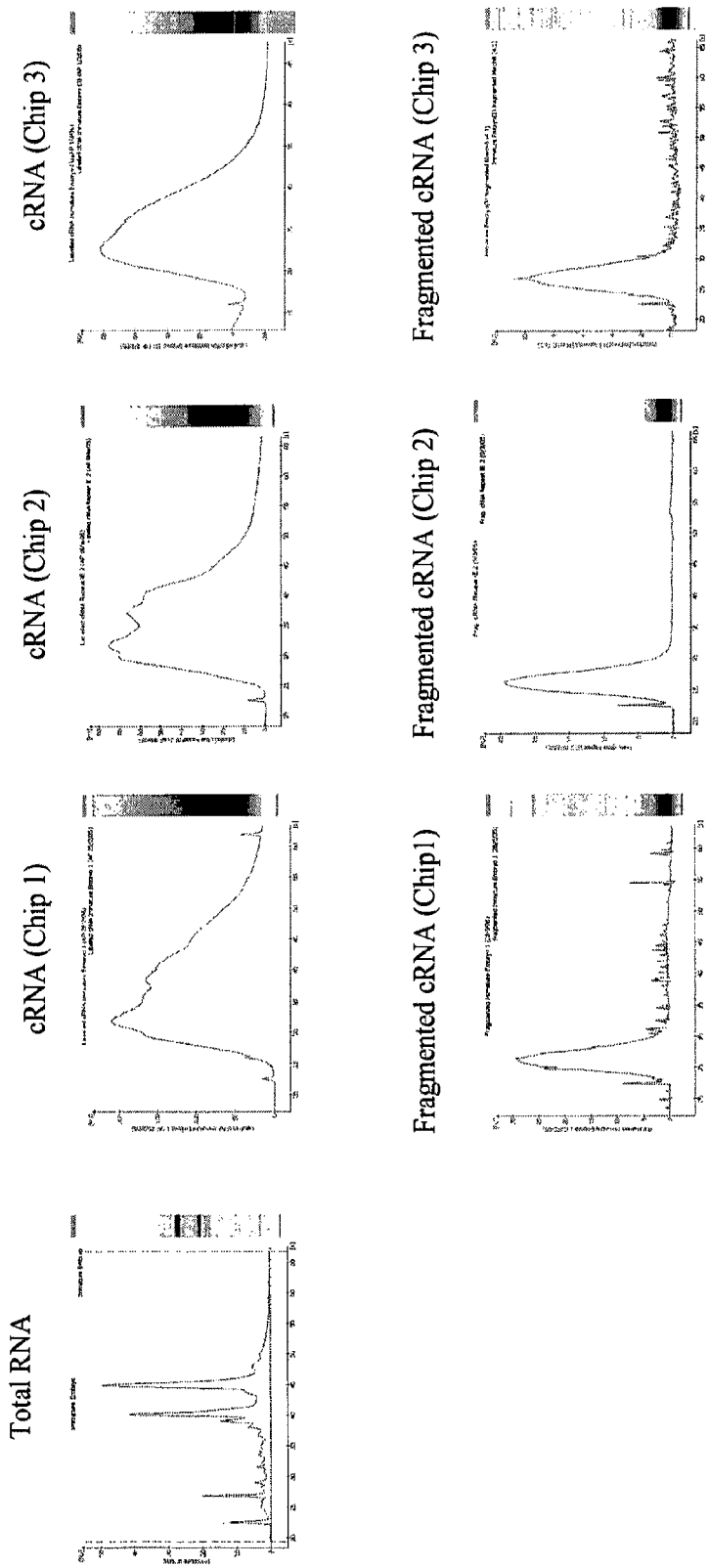
FIG. 1a provides graphical representations showing quality of immature embryo total RNA, labelled cRNA and fragmented cRNA samples used for Affymetrix GeneChip® Wheat Genome Arrays.

Sequence Analysis Parameters for Determining a Promoter of the Invention
a) Sequence Identity Limitations In determining whether or not two amino acid sequences fall within the defined percentage identity limits herein, those skilled in the art will be aware that it is possible to conduct a side-by-side comparison of the amino acid sequences. In such comparisons or alignments, differences will arise in the positioning of non-identical residues depending upon the algorithm used to perform the alignment. In the present context, references to percentage identities and similarities between two or more amino acid sequences shall be taken to refer to the number of identical and similar residues respectively, between said sequences as determined using any standard algorithm known to those skilled in the art. In particular, amino acid identities and similarities are calculated using software of the Computer Genetics Group, Inc., University Research Park, Maddison, Wis., United States of America, e.g., using the GAP program of Devereaux et al., Nucl. Acids Res. 12, 387-395, 1984, which utilizes the algorithm of Needleman and Wunsch, J. Mol. Biol. 48, 443-453, 1970. Alternatively, the CLUSTAL W algorithm of Thompson et al., Nucl. Acids Res. 22, 4673-4680, 1994, is used to obtain an alignment of multiple sequences, wherein it is necessary or desirable to maximize the number of identical/similar residues and to minimize the number and/or length of sequence gaps in the alignment.

Alternatively, a suite of commonly used and freely available sequence comparison algorithms is provided by the National Center for Biotechnology Information (NCBI) Basic Local Alignment Search Tool (BLAST) (Altschul et al. J. Mol. Biol. 215: 403-410, 1990), which is available from several sources, including the NCBI, Bethesda, Md. The BLAST software suite includes various sequence analysis programs including "blastn," that is used to align a known nucleotide sequence with other polynucleotide sequences from a variety of databases and "blastp" used to align a known amino acid sequence with one or more sequences from one or more databases. Also available is a tool called "BLAST 2 Sequences" that is used for direct pairwise comparison of two nucleotide sequences.

In determining whether or not two nucleotide sequences fall within a particular percentage identity limitation recited herein, those skilled in the art will be aware that it is necessary to conduct a side-by-side comparison or multiple alignment of sequences. In such comparisons or alignments, differences may arise in the positioning of non-identical residues, depending upon the algorithm used to perform the alignment. In the present context, reference to a percentage identity between two or more nucleotide sequences shall be taken to refer to the number of identical residues between said sequences as determined using any standard algorithm known to those skilled in the art. For example, nucleotide sequences may be aligned and their identity calculated using the BEST-FIT program or other appropriate program of the Computer Genetics Group, Inc., University Research Park, Madison, Wis., United States of America (Devereaux et al, Nucl. Acids Res. 12, 387-395, 1984). As discussed supra BLAST is also useful for aligning nucleotide sequences and determining percentage identity.

Reference herein to a particular level of sequence identity using the term "at least" or "at least about" shall be taken to encompass any level of sequence identity greater than the recited level. Accordingly, the present invention encompasses a nucleotide sequence or an amino acid sequence at least about 80% identical to a recited sequence, or at least about 85% identical to a recited sequence, or at least about 90% identical to a recited sequence, or at least about 95% identical to a recited sequence, or at least about 98% or 99% identical to a recited sequence.

b) Analysis of Cis-Acting Elements

Methods for determining whether or not a promoter comprises a cis-acting element will be apparent to the skilled artisan. For example, a promoter is isolated using a method known in the art and/or described herein and the sequence of a promoter is determined using a method known in the art and/or described, for example in Ausubel et al (In: Current Protocols in Molecular Biology. Wiley Interscience, ISBN 047 150338, 1987) and Sambrook et al (In: Molecular Cloning: Molecular Cloning: A Laboratory Manual, Cold Spring Harbor Laboratories, New York, Third Edition 2001). For example, a promoter or a fragment thereof of a nucleic acid comprising a sequence encoding a polypeptide comprising at least one minimum GILT domain is isolated using, for example, PCR-based genome walking, or by screening a library of nucleic acids, e.g., as described herein, and the sequence of the promoter determined using, for example, dideoxynucleotide-based sequencing. The sequence is then analysed to determine whether or not it comprises one or more of the cis-acting elements described herein-above.

The sequence of a promoter region may be analysed using suitable software to determine the cis-acting elements contained within that sequence. Suitable software includes:

(i) PLACE (Plant cis-acting DNA elements) as described in Higo et al., *Nucl. Acids Res.* 27: 297-300, 1999, and available from National Institute of Agrobiological Sciences, Ibaraki, Japan;

(ii) Plant CARE (cis-acting regulatory elements) Motif Sampler as described in Thijs et al., *J Comput Biol.* 9: 447-464, 2002 and available from Flanders Interuniversity Institute for Biotechnology (VIB), Zwijnaarde, Belgium; and (iii) PlantProm database as described in Shahmuradov et al., *Nucleic Acids Res.* 31:114-7, 2003.

As discussed herein above, the present inventors have identified a plurality of promoters, and by analyzing the sequences of these promoters have identified conserved cis-acting elements, e.g., conserved cis-acting elements from a promoter capable of conferring expression or a pattern of expression on a nucleic acid in a developing endosperm or a cell or tissue thereof e.g., including basal endosperm and/or BETL cells. Exemplary cis-acting elements contained in the exemplified promoter sequences are set forth in Tables 3 and 4 hereof. Exemplary cis-acting elements that are conserved between the five exemplified are set forth in Table 1. Accordingly, it is preferable that a promoter as described according to any example hereof comprises one or more of the cis-acting elements set forth in Table 1.

It is to be understood that the precise number of any specific cis-acting element in a promoter of the present invention may vary according to length and additional elements to those specifically indicated in Table 1 are permissible. A skilled artisan can readily ascertain any number of variations to the elements presented in Table 1 from the data provided herein e.g., in Tables 3 and 4.

TABLE 1

Conserved structural sequence elements in wheat and maize promoters

| SITE_NAME | CONSENSUS |
| --- | --- |
| 2SSEEDPROTBANAPA | CAAACAC |
| ARFAT | TGTCTC |
| ARR1AT | NGATT |
| BIHD1OS | TGTCA |
| BOXIINTPATPB | ATAGAA |
| CAATBOX1 | CAAT |
| CACTFTPPCA1 | YACT |
| CANBNNAPA | CNAACAC |
| CBFHV | RYCGAC |
| CCAATBOX1 | CCAAT |
| DOFCOREZM | AAAG |
| DPBFCOREDCDC3 | ACACNNG |
| DRE2COREZMRAB17 | ACCGAC |
| DRECRTCOREAT | RCCGAC |
| EBOXBNNAPA | CANNTG |
| ELRECOREPCRP1 | TTGACC |
| GATABOX | GATA |
| GT1CONSENSUS | GRWAAW |
| GT1GMSCAM4 | GAAAAA |
| GTGANTG10 | GTGA |
| IBOXCORE | GATAA |
| INRNTPSADB | YTCANTYY |
| MYB1AT | WAACCA |
| MYB26PS | GTTAGGTT |
| MYB2CONSENSUSAT | YAACKG |
| MYBCORE | CNGTTR |
| MYBCOREATCYCB1 | AACGG |
| MYBPLANT | MACCWAMC |
| MYBPZM | CCWACC |
| MYBST1 | GGATA |
| MYCATERD1 | CATGTG |
| MYCCONSENSUSAT | CANNTG |
| NODCON1GM | AAAGAT |
| NTBBF1ARROLB | ACTTTA |
| OSE1ROOTNODULE | AAAGAT |
| POLASIG1 | AATAAA |
| POLASIG3 | AATAAT |
| POLLEN1LELAT52 | AGAAA |

TABLE 1-continued

Conserved structural sequence elements
in wheat and maize promoters

| SITE_NAME | CONSENSUS |
|---|---|
| PRECONSCRHSP70A | SCGAYNRNNNNNNNNNNNNNNNHD (SEQ ID NO: 11) |
| PYRIMIDINEBOXOSRAMY1A | CCTTTT |
| RAV1AAT | CAACA |
| REALPHALGLHCB21 | AACCAA |
| ROOTMOTIFTAPOX1 | ATATT |
| RYREPEATBNNAPA | CATGCA |
| RYREPEATGMGY2 | CATGCAT |
| RYREPEATLEGUMINBOX | CATGCAY |
| S1FBOXSORPS1L21 | ATGGTA |
| SEBFCONSSTPR10A | YTGTCWC |
| SEF4MOTIFGM7S | RTTTTTR |
| SITEIIATCYTC | TGGGCY |
| SORLIP1AT | GCCAC |
| SORLIP2AT | GGGCC |
| SREATMSD | TTATCC |
| SURECOREATSULTR11 | GAGAC |
| SV40COREENHAN | GTGGWWHG |
| TAAAGSTKST1 | TAAAG |
| TATABOX3 | TATTAAT |
| TATABOX4 | TATATAA |
| TATABOX5 | TTATTT |
| TATCCAOSAMY | TATCCA |
| TATCCAYMOTIFOSRAMY3D | TATCCAY |
| TGTCACACMCUCUMISIN | TGTCACA |
| WBOXATNPR1 | TTGAC |
| WBOXHVISO1 | TGACT |
| WBOXNTERF3 | TGACY |
| WRKY71OS | TGAC |
| XYLAT | ACAAAGAA |

Plant Source of a Promoter of the Invention

In one example, a promoter as described according to any example hereof is from wheat e.g., SEQ ID No: 2 hereof or comprising the repertoire of cis-acting elements presented in Table 3 or a repertoire of cis-acting elements conserved between those presented in Table 1 and Table 5 without necessary regard to their precise orientation and/or positioning in each individual sequence.

The term "wheat" is to be taken in its broadest context to mean an annual or biennial grass capable of producing erect flower spikes and light brown grains and belonging to the Aegilops-Triticum group including Triticum sp. and Aegilops sp. The term "wheat" thus extends to any of various annual cereal grasses of the genus Triticum such as those that are generally cultivated in temperate regions for their edible grain used to produce flour e.g., for use in breadstuffs and/or biscuits and/or noodles and/or pasta. Suitable species and/or cultivars will be apparent to the skilled artisan based on the description herein.

The term "wheat" also includes any tetraploid, hexaploid and allopolyploid (e.g., allotetraploid and allohexaploid) Aegilops sp. or Triticum sp. which carries the A genome and/or the B genome and/or D genome of the allohexaploid Triticum aestivum or a variant thereof. This includes A genome diploids (e.g., T. monococcum and T. urartu), B genome diploids (e.g., Aegilops speltoides and T. searsii) and closely-related S genome diploids (e.g., Aegilops sharonensis), D genome diploids (e.g., T. tauschii and Aegilops squarrosa), tetraploids (e.g., T. turgidum and T. dicoccum (AABB), Aegilops tauschii (AADD)), and hexaploids (e.g., T. aestivum and T. compactum). The term "wheat" may encompass varieties, cultivars and lines of Aegilops sp. or Triticum sp. but is not to be limited to any specific variety, cultivar or line thereof unless specifically stated otherwise.

Preferably, the wheat is T. aestivum or T. turgidum (formerly known as T. durum) or a variety, cultivar or line thereof, optionally selected for a seed quality trait e.g., yield, bread-making quality, biscuit-making quality, or noodle/pasta-making quality.

As will be apparent to the skilled artisan from the foregoing, many varieties of wheat are polyploid. Accordingly, any single wheat genome may comprise a plurality of promoters as defined herein to be part of the invention. The present invention clearly contemplates any and/or all of those promoters.

In another example of the invention, a promoter as described according to any example hereof is from maize e.g., SEQ ID NOs: 8-10 hereof, or comprising the repertoire of cis-acting elements presented in Table 4 or a repertoire of cis-acting elements conserved between those presented in Table 1 and Table 5 without necessary regard to their precise orientation and/or positioning in each individual sequence.

The term "maize" shall be taken to mean grass of the genus Zea. Preferably, the term maize encompasses any plant of the species Zea mays. The term maize includes such species as, for example, Z. mays indurata, Z. mays indenta, Z. mays everta, Z. mays saccharata, Z. mays amylacea, Z. mays tunicata and/or Z. mays Ceratina Kulesh.

In another example of the invention, a promoter as described according to any example hereof is from rice e.g., comprising the repertoire of cis-acting elements presented in Table 1 without necessary regard to their precise orientation and/or positioning in each individual sequence.

The term "rice" shall be taken to mean grass of the genus Oryza, including indica and japonica rice species and varieties. Preferably, the term rice encompasses any plant of the species Oryza sativa.

In further examples, a promoter as described according to any example hereof is from barley or sorghum or rye or millet (e.g. pearl millet or proso millet) or buckwheat (e.g., of the family Polygonaceae) or oat (e.g., Avena sativa) or a cell, tissue or organs from any other plant from the family Gramineaceae, Gramineae or Poaceae.

Isolation of Promoters

A promoter as described according to any example hereof is isolated using any of a variety of molecular biology techniques. For example, a promoter is isolated using polymerase chain reaction using primers based on the sequence of a promoter described herein, e.g., in SEQ ID NO: 2 and/or 8. For example, a pair of primers comprising at least about 20 to about 30 nucleotides that is capable of hybridizing to a nucleic acid comprising a sequence set forth in any one or more of SEQ ID NO: 2 and/or 8 is produced. Preferably, one or both of the primers is capable of hybridizing to a plurality of sequences set forth in SEQ ID NO: 2 and/or 8, i.e., the primers hybridize to a conserved region and/or are degenerate. Suitable methods for designing and producing primers for PCR are known in the art and/or described in Dieffenbach (ed) and Dveksler (ed) (In: PCR Primer: A Laboratory Manual, Cold Spring Harbour Laboratories, NY, 1995). These primers are then hybridized to different strands of a nucleic acid template, e.g., genomic DNA from a plant, and specific nucleic acid copies of the template are amplified enzymatically. Following amplification, the amplified nucleic acid is isolated using a method known in the art and, preferably cloned into a suitable vector. Such a method is useful for isolating a promoter from nucleic acid, preferably genomic DNA, of any plant.

Exemplary hybridization conditions for isolating a promoter according to the present invention comprise e.g., conditions equivalent to hybridization in 7% sodium dodecyl sulfate (SDS), 0.5M NaPO$_4$, 1 mM EDTA at 50° C., followed by washing to remove non-specifically-hybrizing probe in conditions such as in 2×SSC, 0.1% SDS at 50° C. In another example, hybridization conditions equivalent to hybridization in 7% sodium dodecyl sulfate (SDS), 0.5M NaPO$_4$, 1 mM EDTA at 50° C. followed by washing to remove non-specifically-hybrizing probe in conditions such as in 1×SSC, 0.1% SDS at 50° C. In another example, hybridization conditions equivalent to hybridization in 7% sodium dodecyl sulfate (SDS), 0.5M NaPO$_4$, 1 mM EDTA at 50° C. followed by washing to remove non-specifically-hybrizing probe in conditions such as in 0.5×SSC, 0.1% SDS at 50° C. In another example, hybridization conditions equivalent to hybridization in 7% sodium dodecyl sulfate (SDS), 0.5M NaPO$_4$, 1 mM EDTA at 50° C. followed by washing to remove non-specifically-hybrizing probe in conditions such as in 0.1× SSC, 0.1% SDS at 50° C. In another example, hybridization conditions equivalent to hybridization in 7% sodium dodecyl sulfate (SDS), 0.5M NaPO$_4$, 1 mM EDTA at 50° C. followed by washing to remove non-specifically-hybrizing probe in conditions such as in 1×SSC, 0.1% SDS at 65° C.

The hybridization conditions supra are also employed to identify or isolate nucleic acid comprising a coding sequence linked to a variant of a promoter or other transcription regulating nucleotide sequence of the present invention as described according to any example hereof, or a complementary sequence thereto, wherein said coding sequence or complementary sequence thereto hybridizes via a coding sequence or complementary sequence thereto that is linked to a promoter or other transcription regulating nucleotide sequence of the present invention as described according to any example hereof. Thus, the variant promoter or other transcription regulating nucleotide sequence may be isolated by virtue of hybridization between linked coding regions that are at least about 50% or 60% or 70% or 80% or 90% or 95% or more identical at the nucleotide sequence level, and then isolating the linked variant promoter or other transcription regulating nucleotide sequence.

Alternatively, or in addition, an oligonucleotide is produced that is capable of hybridizing to a promoter described according to any example hereof. Preferably, the oligonucleotide is capable of hybridizing to a region of a promoter as described according to any example hereof that is conserved in a plurality of promoters. Alternatively, or in addition, the oligonucleotide is capable of hybridizing to a plurality of promoters as described according to any example hereof under low or moderate stringency conditions. Such an oligonucleotide is then used to screen a nucleic acid library, e.g., a library comprising fragments of genomic DNA from a plant using a method known in the art and described, for example, in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001). A suitable fragment is then isolated and, if necessary, the promoter isolated from the fragment.

A suitable promoter may also be isolated based on its ability to confer expression in developing endosperm e.g., in basal endosperm such as in BETL cells. For example, using one or more oligonucleotide primers that hybridize to a promoter of the invention RT-PCR is performed using mRNA from a developing endosperm or basal endosperm or BETL cells, to amplify a fragment of a cDNA comprising such a nucleic acid. This fragment is then used to isolate a promoter that confers expression or a pattern of expression on said mRNA. For example, as described herein, genome-walking is used to isolate a promoter. In such a method, genomic DNA from a plant is cleaved, e.g., using a restriction endonuclease and subsequently ligated to an adaptor having a known sequence. PCR is then performed using a primer capable of annealing to the adaptor and a primer capable of annealing to the fragment of cDNA. In this manner, sequence upstream or 5' to the sequence linked to the promoter in its native context is isolated, including the promoter sequence.

Alternatively, an oligonucleotide is used to screen a genomic DNA library from a plant to isolate a fragment of genomic DNA comprising a gene or fragment thereof comprising the promoter. Sequence from the isolated genomic DNA fragment may then be used to isolate additional genomic DNA fragments. By analyzing the nucleotide sequence of the genomic DNA, e.g., using a method described herein, the sequence of a promoter is determined.

In-silico screening is also useful for identifying a suitable promoter. For example, the inventors have identified a number of conserved regions of a gene to which a promoter as described according to any example hereof is operably connected in nature. Based on one or more of these sequences, a database of sequences from a plant, e.g., a database comprising genomic DNA sequences is searched, and sequences homologous to the conserved region(s) identified. Sequence upstream of the identified region is then analysed to identify the sequence of a promoter operably connected thereto. In silico methods of promoter prediction are known in the art and described, for example, in Shahmuradov et al., *Nucleic Acids Research* 33:1069-1076, 2005, or using plant promoter prediction software available from the School of Biological Sciences, Royal Holloway University of London.

A promoter identified using any of the methods described supra should be tested empirically to determine its ability to confer expression on a nucleic acid, e.g., in a developing endosperm or a cell or tissue thereof e.g., in basal endosperm such as in BETL cells. Suitable methods for testing a promoter will be apparent to the skilled artisan based on the description herein.

Ability of a Promoter, Active Fragment or Derivative to Confer Endosperm Expression Methods for determining the ability of a promoter or a fragment thereof or a derivative thereof to confer expression on nucleic acid include, for example, determining the ability of the promoter, fragment, derivative to induce expression of a reporter gene in a cell, tissue or organ of a plant.

For example, a promoter or a fragment or a derivative as described according to any example hereof is placed in operable connection with a reporter gene, e.g., a reporter gene that produces a detectable signal or a reporter gene that permits selection of a cell expressing the gene.

Reporter genes will be apparent to the skilled artisan and include, for example, a bar gene (bialaphos resistance gene), a bacterial neomycin phosphotransferase II (nptII) gene, a hygromycin phosphotransferase gene, an aacC3 gene, an aacC4 gene, a chloramphenicol acetyl transferase gene, a gene encoding 5-enolpyruvyl-shikimate-3-phosphate synthase or a gene encoding phosphinothricin synthase. Each of these genes confers resistance to a herbicide or an antibiotic. Alternatively, the reporter gene confers the ability to survive and/or grow in the presence of a compound in which an untransformed plant cell cannot grow and/or survive, e.g., a mana gene (Hansen and Wright, *Trends in Plant Sciences*, 4: 226-231, 1999), a cyanamide hydratase (Cah) gene as described in U.S. Ser. No. 09/518,988, or a D-amino oxidase, (DAAO) gene (Erikson et al., *Nature Biotechnology*, 22: 455-458, 2004).

Reporter genes that produce a detectable expression product when expressed include, for example, a β-glucuronidase gene (GUS; the expression of which is detected by the metabolism of 5-bromo-4-chloro-3-indolyl-1-glucuronide to produce a blue precipitate), a bacterial luciferase gene, a firefly luciferase gene (detectable following contacting a plant cell with luciferin), or a fluorescent reporter gene, e.g., monomeric discosoma red fluorescent protein (Campbell et al., *Proc Natl Acad Sci USA*. 99:7877-7882, 1992) or a monomeric GFP from *Aequorea coerulescens* (Gurskaya et al., *Biochem J*. 373:403-408, 2003).

Following linkage of a promoter or fragment, or derivative as described according to any example hereof to a suitable reporter gene, the resulting expression construct is transformed into a plant cell or plant part or plant, e.g., using a method as described herein. Expression of the reporter gene is then detected. For example, in the case of a selectable reporter gene, transformed plant cell, parts or plants are grown in the presence of a suitable herbicide or antibiotic, and only those embryos or cells expressing the reporter gene are capable of growing. In the case of a detectable reporter gene, a plant cell, plant part or whole plant is analysed to detect expression of the detectable reporter gene expression product, e.g., fluorescence or metabolism of a substrate to produce a detectable metabolite.

Alternatively, a plant cell or tissue is transformed using a method known in the art and/or described herein. The transformed cell or tissue is then used to regenerate a plant. Alternatively, the plant is bred, and offspring of the plant grown. This process provides an additional advantage in so far as it permits the level of expression of a reporter gene to be detected in a variety of tissues and at various developmental stages. In the case of identifying a promoter that confers expression of a nucleic acid in a developing endosperm, e.g., in basal endosperm such as in BETL cells, plants are grown until they produce seeds. Endosperm from the developing seeds is then analysed to detect expression of a reporter gene e.g., in basal endosperm such as in BETL cells. Such a method permits the identification of promoters that preferentially or selectively express a reporter gene in a developing endosperm or a cell or tissue thereof e.g., in basal endosperm such as in BETL cells.

The ability of a promoter to confer expression or a pattern of expression on a nucleic acid, e.g., in a developing endosperm or a cell or tissue thereof, e.g., in basal endosperm such as in BETL cells, may also be determined by determining the expression pattern of an expression product of a nucleic acid linked to the promoter in nature, for example, using Northern blotting, quantitative PCR, microarray analysis or an immunoassay. Suitable methods will be apparent to the skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

For example, as exemplified herein the present inventors have performed microarray analysis to detect the level of expression of a nucleic acid linked to a promoter as described according to any example hereof in various tissues. This process involves isolating mRNA from a variety of tissues from a plant, producing copy RNA (cRNA) and labelling the cRNA, e.g., using a fluorescent label such as Cy5. Copy RNA from a control tissue is also labelled with a different label to that used to label the test cRNA, e.g., Cy5, and the two samples mixed. The labelled cRNA is then contacted with a solid substrate having immobilized thereon an oligonucleotide capable of specifically hybridizing to a nucleic acid linked to the promoter of interest. Following a sufficient time for the labelled mRNA to hybridize to the oligonucleotide, the solid substrate is washed and the level of fluorescence of each label detected. In this manner the level of expression of the nucleic acid of interest in a test sample is determined relative to the level in a control sample. Using such a method, the present inventors showed that a transcript encoded by a gene operably connected to a promoter as described according to any example hereof is expressed at an increased level in a developing endosperm (test sample) relative to a mature seed, vegetative tissue or reproductive tissue in which an exemplified promoter of the invention does not confer significant expression (control sample).

The present inventors have also used quantitative RT-PCR to determine the level of expression of a nucleic acid linked to a promoter as described according to any example hereof. Suitable methods for performing such quantitative RT-PCR will be apparent to the skilled artisan and/or described for example, U.S. Pat. No. 6,174,670.

Active Promoter Fragments

The present invention also encompasses a fragment of a promoter described according to any example hereof. In one example, such an active fragment retains the ability of the promoter to confer expression or a pattern of expression on a nucleic acid in a developing endosperm or a cell or tissue thereof e.g., in basal endosperm such as in BETL cells. In this respect, the fragment need not confer the same level of expression or pattern of expression as a promoter from which it is derived. For example, the fragment induces expression of a nucleic acid to which it is operably connected to a lesser degree than a promoter from which it is derived, e.g., because it lacks a binding site for a transcription factor. Alternatively, a fragment may induce expression of a nucleic acid to which it is operably connected to a greater degree than a promoter from which it is derived, e.g., because it lacks a binding site for a protein that suppresses transcription.

In one example, the present invention provides an active fragment of a promoter as described according to any example hereof, said active fragment comprising at least about 200 base pairs (bp) or at least about 500 bp or at least about 700 bp or at least about 900 bp or at least about 1000 bp e.g., derived from an exemplified promoter set forth in the Sequence Listing.

In another example, an active promoter fragment of the present invention at least comprises a basal promoter regulatory region from a full-length promoter, such as a minimal sequence necessary and/or sufficient for transcription initiation in seed endosperm. A basal promoter regulatory region comprises a functional TATA box element e.g., positioned between about 15 and about 50 nucleotides upstream from the site of transcription initiation, and preferably between about 15 and about 40 nucleotides upstream from the site of transcription initiation, and more preferably between about 15 and about 30 or 35 nucleotides upstream from the site of transcription initiation. For the purposes of nomenclature, a basal promoter regulatory region in this context comprises the terminal 100 or 90 or 80 or 70 or 60 or 50 or 40 nucleotides of SEQ ID No: 2 or 8 or a sequence complementary thereto.

Preferred basal promoter regulatory regions also comprise a CCAAT box element (e.g., the sequence CCAAT or GGGCG) positioned between about 40 and about 200 nucleotides or between about 50 and about 150 nucleotides or between about 60 and about 120 nucleotides upstream from the transcription start site. For the purposes of nomenclature, a basal promoter regulatory region in this context comprises the terminal 200 or 190 or 180 or 170 or 160 or 150 or 140 or 130 or 120 or 110 or 100 or 90 or 80 or 70 or 60 or 50 nucleotides of SEQ ID No: 2 or 8 or a sequence complementary thereto.

Active fragments that comprise a basal promoter regulatory region and one or more upstream elements of the native promoter are also provided by the present invention. For example, active fragments may comprise the terminal 500 nucleotides, or the terminal 400 nucleotides or the terminal 300 nucleotides or the terminal 200 nucleotides of SEQ ID No: 2 or 8 or a sequence complementary thereto. Alternatively, such active fragments may be truncated at their 3'-ends compared to the promoter sequences set forth in SEQ ID No: 2 or 8, e.g., by deletion of sequences downstream of the transcriptional start site. For example, active fragments may comprise a sequence from about 500 nucleotides to about 40 nucleotides upstream of the 3'-end of SEQ ID No: 2 or 8 or complementary thereto, or from about 400 nucleotides to about 40 nucleotides upstream of the 3'-end of SEQ ID No: 2 or 8 or complementary thereto, or from about 300 nucleotides to about 40 nucleotides upstream of the 3'-end of SEQ ID No: 2 or 8 or complementary thereto, or from about 200 nucleotides to about 40 nucleotides upstream of the 3'-end of SEQ ID No: 2 or 8 or complementary thereto, or from about 400 nucleotides to about 50 nucleotides upstream of the 3'-end of SEQ ID No: 2 or 8 or complementary thereto, or from about 500 nucleotides to about 60 nucleotides upstream of the 3'-end of SEQ ID No: 2 or 8 or complementary thereto, or from about 300 nucleotides to about 70 nucleotides upstream of the 3'-end of SEQ ID No: 2 or 8 or complementary thereto, or from about 200 nucleotides to about 80 nucleotides upstream of the 3'-end of SEQ ID No: 2 or 8 or complementary thereto. Other fragments are not to be excluded. Such active fragments preferably comprise one or more conserved sequence motifs as disclosed herein.

Suitable methods for producing a fragment of a promoter as described according to any example hereof will be apparent to the skilled artisan and/or described for example in Ausubel et al (In: Current Protocols in Molecular Biology. Wiley Interscience, ISBN 047 150338, 1987) and Sambrook et al (In: Molecular Cloning: Molecular Cloning: A Laboratory Manual, Cold Spring Harbor Laboratories, New York, Third Edition 2001). For example, a previously isolated promoter is cleaved using any known method, e.g., using one or more restriction endonucleases and the resulting fragment(s) are then assayed to determine their ability to confer expression or a pattern of expression on a nucleic acid in developing endosperm or cell or tissue thereof e.g., basal endosperm or BETL cells. Alternatively, a fragment of a promoter as described according to any example hereof is amplified using a nucleic acid amplification reaction, e.g., PCR. The resulting fragment is then assayed to determine whether or not it is capable of conferring expression or a pattern of expression on a nucleic acid, e.g., in developing endosperm e.g., including basal endosperm or BETL cells.

Suitable methods for determining the ability of a fragment to confer expression or a pattern of expression on a nucleic acid are described herein.

Promoter Derivatives

Promoter derivatives encompassed by the present invention include a promoter derived from a promoter as described according to any example hereof, however comprising one or more additional regulatory elements, derived from either an exemplified promoter or a heterologous promoter. For example, such an additional regulatory element further enhances expression of a nucleic acid to which it is operably connected and/or alters the timing of expression of a sequence to which it is operably connected. For example, such a chimeric promoter that comprise the nucleotide sequence set forth in SEQ ID NO: 2 or 8 may be modified by the inclusion of nucleic acid from a different endosperm-operable promoter to further enhance expression of a nucleic acid to which the promoter is operably connected in developing endosperm or a cell or tissue thereof. The performance of such examples is readily achievable by those skilled in the art.

Those skilled in the art will be aware that it is also possible to modify the level of structural gene expression and/or the timing of structural gene expression and/or the location of structural gene expression in a plant or plant part by mutation of a regulatory genetic sequence (e.g., cis-acting element or 5'-non-coding region, etc) within the promoter sequence to which a nucleic acid is operably connected. For example, to achieve such an objective, the promoter sequence of the present invention is subjected to mutagenesis to produce single or multiple nucleotide substitutions, deletions and/or additions.

Alternatively, or in addition, the arrangement of specific regulatory sequences within the promoter may be altered, including the deletion therefrom of certain regulatory sequences and/or the addition thereto of regulatory sequences derived from the same or a different promoter sequence.

Preferred derivatives of a promoter as described according to any example hereof comprise one or more functional cis-acting elements present in a promoter as described according to any example hereof, for example, a cis-acting element required for or associated with conferring expression or a pattern of expression.

Derivatives of the promoter can be produced by synthetic means or alternatively, derived from naturally-occurring sources.

For example, the promoter sequence may be derivatized without complete loss of function such that it at least comprises one or more of the following sequences:
(i) a 5'-non-coding region; and/or
(ii) one or more cis-regulatory regions, such as one or more functional binding sites for a transcriptional regulatory proteins or translational regulatory proteins, one or more upstream activator sequences, enhancer elements or silencer elements; and/or
(iii) a TATA box motif; and/or
(iv) a CCAAT box motif; and/or
(v) an upstream open reading frame (uORF); and/or
(vi) a transcriptional start site; and/or
(vii) a translational start site; and/or
(viii) a nucleotide sequence which encodes a leader sequence.

As used herein, the term "5'-non-coding region" shall be taken in its broadest context to include all nucleotide sequences which are derived from the upstream region of a gene, e.g., a gene expressed in developing endosperm, other than those sequences which encode amino acid residues comprising the polypeptide product of said gene. Such regions include an intron, e.g., an intron derived from a ubiquitin gene.

As used herein, the term "uORF" refers to a nucleotide sequence localised upstream of a functional translation start site in a gene and generally within the 5'-transcribed region (i.e. leader sequence), which encodes an amino acid sequence. Whilst not being bound by any theory or mode of action, a uORF functions to prevent over-expression of a structural gene sequence to which it is operably connected or alternatively, to reduce or prevent such expression.

Other derivative promoters contemplated by the present invention include, for example, a bi-directional promoter comprising a promoter as described according to any example hereof. Such a bi-directional promoter comprises, for example, (i) a promoter as described according to any example hereof and positioned to confer expression or a pattern of expression on a nucleic acid linked to, e.g., the 3' end thereof; and (ii) a second promoter linked to the 5' end of the promoter at (i) and positioned to confer expression or a pattern of expression on a nucleic acid linked to the 5' end of the second promoter. Clearly, the second promoter may also be a promoter as described according to any example hereof.

Expression Constructs and Expression Vectors

Following isolation of a promoter as described according to any example hereof, an expression construct may be produced. Such an expression construct comprises a promoter, active fragment or derivative as described according to any example hereof operably connected to a nucleic acid to be expressed, i.e., a transgene, e.g., a nucleic acid encoding a polypeptide of interest, or a nucleic acid that is transcribed to encode, e.g., a siRNA, ribozyme, microRNA or RNAi.

The present invention contemplates linking a promoter, active fragment or derivative as described according to any example hereof to any transgene. Suitable examples of transgenes will be apparent to the skilled artisan and/or described herein.

Methods for linking a promoter, active fragment or derivative as described according to any example hereof and a transgene will be apparent to the skilled artisan and include, for example, ligating the promoter, active fragment or derivative to the transgene, e.g., using T4 DNA ligase. Alternatively, or in addition a fusion of the promoter, active fragment or derivative and transgene is produced using recombinant means, e.g., splice-overlap extension. Suitable methods for linking two or more nucleic acids are also described in, for example, Ausubel et al (In: Current Protocols in Molecular Biology. Wiley Interscience, ISBN 047 150338, 1987) and Sambrook et al (In: Molecular Cloning: Molecular Cloning: A Laboratory Manual, Cold Spring Harbor Laboratories, New York, Third Edition 2001).

Such an expression construct may comprise additional components, such as, for example, a sequence encoding a targeting sequence or a detectable label. Such an additional component may be located between the promoter and the transgene, e.g., such that it is expressed as a 5' fusion with the polypeptide encoded by the transgene. Alternatively, the additional component may be located 3' to the transgene.

A targeting sequence is a sequence of amino acids within a polypeptide that directs the polypeptide to a particular subcellular location. Targeting sequences useful for the performance of the invention are known in the art and described in, for example, Johnson et al., *The Plant Cell* 2:525-532, 1990; Mueckler et al. *Science* 229:941-945, 1985; Iturriaga et al. *The Plant Cell* 1:381-390, 1989; McKnight et al., *Nucl. Acid Res.* 18:4939-4943, 1990; Matsuoka and Nakamura, *Proc. Natl. Acad. Sci. USA* 88:834-838, 1991. Furthermore, the book entitled "Recombinant proteins from plants", Eds. C. Cunningham and A. J. R. Porter, 1998 Humana Press Totowa, N.J. describe various suitable methods for the production of recombinant proteins in plants and methods for targeting the proteins to different compartments in the plant cell.

Suitable detectable markers include, for example, an epitope, e.g., influenza virus hemagglutinin (HA), Simian Virus 5 (V5), polyhistidine, c-myc, FLAG.

Alternatively, or in addition, a promoter, active fragment or derivative as described according to any example hereof is included in an expression vector. In this respect, such an expression vector may comprise a transgene operably connected to a promoter, active fragment or derivative as described according to any example hereof. Alternatively, or in addition, an expression vector may comprise a means for inserting a transgene such that it is in operable connection with the promoter, fragment or derivative. Such means include, for example, a multiple cloning site comprising one or more restriction endonuclease cleavage site(s). Additional means include one or more recombination site(s).

Additional components of an expression vector will be apparent to the skilled artisan and include, for example, an origin of replication, e.g., to permit replication of the vector in a bacterial cell, e.g., a ColE1 origin of replication.

An expression vector may also comprise a selectable marker gene operably connected to a promoter. Exemplary selectable marker genes comprise one or more of: a sequence encoding a phosphinothricin acetyltransferase (PAT); a sequence encoding a modified 5-enolpyruvylshikimate-3-phosphate synthase (EPSPS) optionally linked to a sequence encoding a chloroplast transit peptide; a sequence encoding a glyphosate degrading enzyme such as glyphosate oxidoreductase (gox); a sequence encoding a dalapon inactivating dehalogenase (deh); a sequence encoding a sulfonylurea-inactivating acetolactate synthase or an imidazolinone-inactivating acetolactate synthase (e.g., ahas, ALS, a mutated ahas variant or a mutated ALS variant with e.g., the S4, XI12, XA17, and/or Hra mutation as described in EP154204); a sequence encoding a bromoxynil-degrading nitrilase (bxn); a sequence encoding a kanamycin-resistance gene (e.g., NPTII; NPT or neo); a sequence encoding a geneticin-resistance gene (e.g., G418 resistance gene); a sequence encoding a 2-Desoxyglucose-6-phosphate phosphatase (e.g., the DOGR1-gene product; WO 98/45456; EP 0 807 836); a sequence encoding a hygromycin phosphotransferase (e.g., HPT); a sequence encoding a modified dihydrofolate reductase that confers resistance against methotrexate; a sequence encoding a modified or mutant anthranilate synthase that confers resistance to 5-methyl tryptophan. Additional negative selectable marker genes of bacterial origin that confer resistance to antibiotics may also be employed e.g., the aadA gene conferring resistance to the antibiotic spectinomycin, a sequence encoding a gentamycin acetyl transferase or streptomycin phosphotransferase (SPT) or aminoglycoside-3-adenyl transferase, or capable of conferring resistance against bleomycin. Especially preferred negative selectable marker genes confer resistance against the toxic effects imposed by D-amino acids e.g., D-alanine and/or D-serine as described in WO 03/060133. For example, the daol gene (E.C.1.4.3.3; GenBank Accession No. U60066) of *Rhodotorula gracilis* (*Rhodosporidium toruloides*) and/or the *E. coli* dsdA gene encoding D-serine dehydratase (D-serine deaminase) [E.C.4.3.1.18; GenBank Accession No. J01603) may be employed to confer resistance against the toxic effects imposed by D-amino acids. As will be known in the art, combinations of the foregoing selectable markers genes may be employed in a genetic construct.

One or more selectable marker may be operably connected to a ubiquitous promoter, such as a promoter from ubiquitin (ubi) or from the cauliflower mosaic virus, e.g., CaMV 35S. Suitable promoters and selectable markers will be apparent to the skilled artisan.

In the case of an expression vector to be delivered into a plant using *Agrobacterium*-based transformation, the vector preferably comprises a left-border (LB) sequence and a right-border (RB) sequence that flank the transgene to be delivered into the plant cell, i.e., the transfer DNA. Such a vector may also comprise a suitable selectable marker for selection of bacteria comprising the vector, e.g., conferring resistance to ampicillin.

Preferably, the vector is a binary Ti plasmid or Ri plasmid. Binary Ti plasmids or Ri plasmids are produced based on the observation that the T-DNA (nucleic acid transferred to a plant cell) and the vir genes required for transferring the T-DNA may reside on separate plasmids (Hoekema et al., *Nature,* 303: 179-180, 1983). In this respect, the vir function is generally provided by a disarmed Ti plasmid resident in or endogenous to the *Agrobacterium* strain used to transform a plant cell.

Accordingly, a binary Ti plasmid or Ri plasmid comprises a transgene located within transfer-nucleic acid (e.g., T-DNA). Such transfer-nucleic acid comprising the transgene is generally flanked by or delineated by a LB and a RB.

Suitable binary plasmids are known in the art and/or commercially available. For example, a selection of binary Ti vectors includes pBIN19 (Bevan et al., *Nucleic Acids Res.,* 12: 8711-8721, 1984); pC22 (Simoens et al., *Nucleic Acids Res.* 14: 8073-8090, 1986); pGA482 (An et al., *EMBO J.* 4: 277-284, 1985); pPCV001 (Koncz and Schell *Mol. Gen. Genet.* 204: 383-396, 1986); pCGN1547 (McBride and Summerfelt 14: 269-276, 1990); pJJ1881 (Jones et al., *Transgenic Res.* 1: 285-297, 1992); pPZP111 (Hajukiewicz et al., *Plant Mol. Biol.,* 25: 989-994, 1994); and pGreen0029 (Hellens et al., *Plant Mol. Biol.,* 42: 819-832, 2000).

Additional binary vectors are described in, for example, Hellens and Mullineaux *Trends in Plant Science* 5: 446-451, 2000. Variants of these plasmids e.g., as described herein or known in the art may also be employed.

Suitable Ri plasmids are also known in the art and include, for example, pRiA4b (Juouanin *Plasmid,* 12: 91-102, 1984), pRi1724 (Moriguchi et al., *J. Mol. Biol.* 307:771-784, 2001), pRi2659 (Weller et al., *Plant Pathol.* 49:43-50, 2000) or pRi1855 (O'Connell et al., *Plasmid* 18:156-163, 1987).

Transgenes

As discussed supra, the present invention encompasses an expression construct or expression vector comprising a promoter, active fragment or derivative as described according to any example hereof linked to any transgene.

In one example, a transgene encodes a polypeptide that is to be expressed in developing endosperm or cell or tissue thereof e.g., basal endosperm or BETL cells of a plant. For example, the transgene encodes a polypeptide that is involved in biosynthesis of starch or storage protein or transport of one or more solutes required for endosperm development and/or grain filling and/or storage protein deposition e.g., a sugar, sugar phosphate, nucleotidyl sugar phosphate, amino acid, folate, phosphate, iron etc. Expression of such transgenes is useful for prolonging grain filling or enhancing yield characteristics, or to enhance a nutritional quality of seed. Such an expression construct is also useful for, for example, improving end-product traits, and includes, without limitation, those encoding transporter proteins, seed storage proteins, fatty acid pathway enzymes, tocopherol biosynthetic enzymes, amino acid biosynthetic enzymes, and starch branching enzymes.

Exemplary transporter proteins include e.g., an amino acid selective channel protein (e.g., Pohlmeyer et al., *Proc Natl Acad Sci USA.* 94 (1997), 9504-9509), an ABC-type transporter (ATPase component, EC 3.6.3; Krattinger et al., *Science* 323 (2009), 1360-1363), a phosphate translocator (e.g., Knappe et al. *Plant Physiol.* 131 (2003), 1178-1190), a glucose 6-phosphate/phosphate translocator (e.g., Kammerer et al., *The Plant Cell* 10 (1998), 105-117), a plastidial nucleotide transporter (e.g., Neuhaus et al., The *Plant Journal* 11 (1997), 73-82), an ADP-glucose transporter e.g., a BT1 protein such as ZmBT1 (e.g., Cao et al., *Physiologia Plantarum* 95 (1995), 176-186; Sullivan et al., *Planta* 196 (1995), 477-484; Cao et al., *Physiologia Plantarum* 100 (1997), 400-406) or other transporter of the mitochondrial carrier family (MCF) of transporters (e.g., Sullivan et al., *The Plant Cell* 3 (1991), 1337-1348; Picault et al., *Trends in Plant Sci.* 9 (2004), 138-146).

Exemplary seed storage protein includes a zein (e.g., as described in U.S. Pat. Nos. 4,886,878, 4,885,357 and 5,215, 912), 7S proteins (e.g., as described in U.S. Pat. Nos. 5,003, 045, and 5,576,203), a brazil nut protein (e.g., as described in U.S. Pat. No. 5,850,024), a phenylalanine free protein (e.g., as described in PCT Publication WO 96/17064), albumin (e.g., as described in PCT Publication WO 97/35023).

Examples of fatty acid pathway enzymes include, for example, a thioesterase (e.g., as described in U.S. Pat. Nos. 5,512,482, 5,530,186 and 5,945,585), and a desaturase (e.g., as described in U.S. Pat. Nos. 5,689,050, 5,663,068 and 5,614,393). In one example, expression of a stearoyl-ACP desaturase-encoding gene is down-regulated to thereby increase stearic acid content of the seed e.g., Knultzon, et al., Proc. Natl. Acad. Sci. USA 89, 2624 (1992) and WO99/64579. In another example, oleic acid content is elevated or enhanced via FAD-2 gene modification and/or by decreasing linolenic acid content via FAD-3 gene modification e.g., U.S. Pat. Nos. 6,063,947; 6,323,392; and 6,372,965; and WO 93/11245. In another example, the content of conjugated linolenic or linoleic acid content is modified e.g., WO 01/12800. In another example, the expression of one or more genes selected from LEC1, AGP, Dek1, Superal1, mi1ps and 1pa genes (e.g., 1pa1, 1pa3, hpt or hggt) is modified e.g., WO 02/42424, WO 98/22604, WO 03/011015, U.S. Pat. No. 6,423,886, U.S. Pat. No. 6,197,561, U.S. Pat. No. 6,825,397, US Patent Publication Nos. 20030079247, 20030204870, and WO 02/057439 and WO 03/011015, and Rivera-Madrid, et. al., Proc. Natl. Acad. Sci. 92, 5620-5624, 1995.

In another example to achieve a particularly high content of polyunsaturated fatty acid (PUFA; e.g., $C_{18}$-, $C_{20}$- or $C_{22}$- fatty acids having at least two or three or four or five or six double bonds) in transgenic plants, one or more PUFA biosynthesis genes is expressed under control of a promoter, active fragment or derivative of the present invention. Optionally, a plurality of such genes is expressed separately under the control of a plurality of promoters, active fragments or derivatives thereof, wherein at least one promoter, active fragment or derivative is a promoter, active fragment or derivative of the present invention, and one or more other promoters active in embryo and/or endosperm e.g., basal endosperm and/or BETL cells, is employed in a gene stacking approach. For example, PUFA content is enhanced by altering expression of a polypeptide having acyl-CoA:lysophospholipid acyltransferase activity, e.g., wherein the acyl-CoA:lysophospholipid acyltransferases encoded by the nucleic acid sequence specifically convert $C_{16}$-, $C_{18}$-, $C_{20}$- or $C_{22}$-fatty acids, and optionally altering expression of one or more acyl-CoA dehydrogenase(s) and/or one or more acyl-ACP [=acyl carrier protein] desaturase(s) and/or one or more acyl-ACP thioesterase(s) and/or one or more fatty acid acyl transferase(s) and/or one or more fatty acid synthase(s) and/or one or more fatty acid hydroxylase(s) and/or one or more acetylcoenzyme A carboxylase(s) and/or one or more acyl-coenzyme A oxidase(s) and/or one or more fatty acid desaturase(s) and/or one or more fatty acid acetylenases and/or one or more lipoxygenases and/or one or more triacylglycerol lipases and/or one or more allenoxide synthases and/or one or more hydroperoxide lyases and/or one or more fatty acid elongase(s). Particularly preferred transgenes to be expressed under control of a promoter of the present invention or an active fragment or derivative thereof include, for example, one or more Δ4-desaturases and/or one or more Δ5-desaturases and/or one or more Δ6-desaturases and/or one or more Δ8-desaturases and/or one or more Δ9-desaturases and/or one or more Δ12-desaturases and/or one or more Δ5-elongases and/or one or more Δ6-elongases and/or one or more Δ9-elongases (US Pat. Pub. No. 20090094707). In such examples involving gene stacking, only one of the introduced transgenes e.g., a Δ4-desaturase or Δ5-desaturases or Δ6-desaturase or Δ8-desaturase or Δ9-desaturase or Δ12-desaturase or Δ5-elongase or Δ6-elongase or Δ9-elongase, need be placed operably under control of a promoter of the present invention in the sense or antisense orientation. Transgenic plants which contain the polyunsaturated fatty acids synthesized in the process according to the invention are marketed directly without there being any need for the oils, lipids or fatty acids synthesized to be isolated. Harvested material, plant tissue, reproductive tissue and cell cultures which are derived from the transgenic plant may also be used. Products of the transgenic plants according to the invention can also be isolated in the form of oils, fats, lipids and/or free fatty acids. Polyunsaturated fatty acids produced by this process can be obtained by harvesting the organisms, either from the crop in which they grow, or from the field e.g., by pressing or other extraction process such as cold-beating or cold-pressing or pretreating seeds by comminution, steam or roasting and solvent-based extraction e.g., using warm hexane. Thereafter, the resulting products are processed further, i.e. refined to remove plant mucilage and suspended matter, desliming, and base extraction of fatty acids e.g., using sodium hydroxide, drying, bleaching, and deodorizing.

In another example, phosphorus content of the endosperm is modified by expressing a phytase-encoding gene under the control of a promoter, active fragment or derivative thereof in the endosperm e.g., basal endosperm and/or BETL cells to thereby enhance breakdown of phytate and increase the availability of free phosphate to the transformed plant. An *Aspergillus niger* phytase gene is disclosed e.g., by Van Hartingsveldt et al., Gene 127:87 (1993).

In another example, a gene that reduces phytate content is expressed operably under the control of a promoter or active fragment or derivative thereof according to the present invention. In maize, this is accomplished by expressing an LPA allele (e.g., Raboy et al., (1990) *Maydica* 35:383) and/or by altering inositol kinase activity (e.g., WO 02/059324, US Patent Publication No. 20030009011, WO 03/027243, US Pat. Publication No. 20030079247, WO 99/05298, U.S. Pat. No. 6,197,561, U.S. Pat. No. 6,291,224, U.S. Pat. No. 6,391, 348, WO2002/059324, US Patent Publication No. 2003/ 0079247, WO 98/45448, WO 99/55882, WO 01/04147).

In yet another example, a promoter of the present invention or an active fragment or derivative thereof is employed to express a nutritional protein such as a phytase. Grain from graminaceous plants is also widely used as an animal feed for non-ruminant animals and phytase of *Aspergillus niger* is used as a supplement in animal feeds to improve the digestibility and also improve the bioavailability of phosphate and minerals. In one example, a promoter, active fragment or derivative as described according to any example hereof is used to express the phyA gene from *A. niger* in the developing endosperm e.g., basal endosperm and/or BETL cells.

In another example, the promoter, active fragment or derivative of the present invention is utilized to modify tocotrienol and/or tocopherol content. Tocotrienols are vitamin E-related compounds whose occurrence in plants is limited primarily to the seeds of monocots e.g., palm, wheat, rice and barley. Tocotrienols are structurally similar to tocopherols, including alpha-tocopherol which is a form of vitamin E. Tocopherols and tocotrienols are potent lipid-soluble antioxidants having considerable nutritive value in human and animal diets e.g., Packer et al. J. Nutr. 131:369 S-373S (2001), and as cholesterol lowering compounds e.g., Theriault et al. Clin. Biochem. 32, 309-319, 1999; Qureshii et al. J. Biol. Chem. 261, 10544-10550, 1986. By expressing 2-methyl-6-phytylbenzoquinol methyltransferase (VTE3) and/or tocopherol cyclase (VTE1) and/or gamma-tocopherol methyltransferase (VTE4) operably under control of a promoter of the present invention, the levels of one or more tocopherols in the seed endosperm is modified. Preferably, a gene encoding an enzyme selected from VTE1, VTE3 and VTE4 is expressed operably under control of the promoter, active fragment or derivative, and a different gene of the tocopherol biosynthetic pathway is expressed operably under the control of another promoter in the endosperm e.g., by gene stacking. In another example, a gene encoding a homogentisate geranylgeranyl transferase (HGGT) enzyme is expressed operably under control of the promoter, active fragment or derivative of the present invention to modulate the level of a tocotrienol in the endosperm. In another example, the expression of transgenes encoding HGGT and VTE3 and VTE4 polypeptides is regulated in the endosperm e.g., basal endosperm and/or BETL cells, wherein at least one of said transgenes is operably under control of a promoter, active fragment or derivative of the present invention. Further examples of tocopherol biosynthetic enzymes, the expression of which is modulated using a promoter of the present invention, include, for example, tyrA, slr1736, ATPT2, dxs, dxr, GGPPS, HPPD, GMT, MT1, tMT2, AANT1, slr 1737 (Kridl et al., *Seed Sci. Res.* 1:209:219 (1991); *Keegstra, Cell* 56(2): 247-53 (1989); Nawrath et al., *Proc. Natl. Acad. Sci. U.S.A.* 91:12760-12764 (1994); Xia et al., *J. Gen. Microbiol.* 138: 1309-1316 (1992); Lois et al., *Proc. Natl. Acad. Sci. U.S.A.* 95 (5):2105-2110 (1998); Takahashi et al. *Proc. Natl. Acad. Sci. U.S.A.* 95 (17), 9879-9884 (1998); Norris et al., *Plant Physiol.* 117:1317-1323 (1998); Bartley and Scolnik, Plant Physiol. 104:1469-1470 (1994); Smith et al., *Plant J.* 11: 83-92 (1997); WO 00/32757; WO 00/10380; Saint Guily et al., *Plant Physiol.*, 100(2):1069-1071 (1992); Sato et al., *J. DNA Res.* 7 (1):31-63 (2000)).

In yet another example, the level of plant proteins, particularly modified proteins that improve the nutrient value of the plant, is increased by expressing one or more proteins having enhanced nutritional value or content of specific amino acids in the endosperm e.g., basal endosperm and/or BETL cells, operably under control of a promoter of the present invention or an active fragment or derivative thereof. For example, hordothionin protein modifications are described in WO 94/16078; WO 96/38562; WO 96/38563 and U.S. Pat. No. 5,703,409. U.S. Pat. No. 6,127,600 and U.S. Pat. No. 6,080, 913 also describe transgenes for increasing accumulation of essential amino acids in seeds. Lysine-enriched and/or sulfur-enriched albumins are also described in WO 97/35023 and U.S. Pat. No. 5,990,389 and U.S. Pat. No. 5,885,802 (high methionine) and U.S. Pat. No. 5,939,599 (high sulfur) and U.S. Pat. No. 5,912,414 (increased methionine). U.S. Pat. No. 6,459,019 describes transgenes for increasing lysine and threonine content, and WO96/01905 describes transgenes for increasing threonine content. Examples of amino acid biosynthetic enzymes include anthranilate synthase (e.g., as described in U.S. Pat. No. 5,965,727, PCT Publications WO 97/26366, WO 99/11800, and WO 99/49058), tryptophan decarboxylase (e.g., as described in PCT Publication WO 99/06581), threonine decarboxylase (e.g., as described in U.S. Pat. Nos. 5,534,421, and 5,942,660; PCT Publication WO 95/19442), threonine deaminase (PCT Publications WO 99/02656 and WO 98/55601), dihydrodipicolinic acid synthase (e.g., as described in U.S. Pat. No. 5,258,300), diacylglycerol acyltransferase (e.g., as described in U.S. Patent Publications 20030115632A1 and 20030028923A1), and aspartate kinase (e.g., as described in U.S. Pat. Nos. 5,367, 110, 5,858,749, and 6,040,160).

In yet another example, altered carbohydrate metabolism is effected, for example, by altering expression of a gene for an enzyme that affects the branching pattern of starch or a gene altering thioredoxin such as NTR and/or TRX (e.g., U.S. Pat. No. 6,531,648) and/or *Bacillus subtilis* levansucrase gene (e.g., Steinmetz, et al., (1985) *Mol. Gen. Genet.* 200:220) and/or an alpha-amylase gene (e.g., Pen, et al., (1992) *Bio/Technology* 10:292; Sogaard, et al., (1993) *J. Biol. Chem.* 268:22480) and/or a tomato invertase gene (Elliot, et al., (1993) *Plant Mol. Biol.* 21:515) and/or starch branching enzymes (e.g., U.S. Pat. Nos. 6,232,122 and 6,147,279 and PCT Publication WO 97/22703) including a maize endosperm starch branching enzyme II (Fisher, et al., (1993) *Plant Physiol.* 102:1045 and/or UDP-D-xylose 4-epimerase or Fragile-1 or Fragile-2 or Ref1 or HCHL or C4H gene (e.g., WO 99/10498) and/or an ADP-glucose pyrophosphorylase (AGP; e.g., U.S. Pat. No. 6,232,529. It is also within the scope of the invention to achieve indirect modification of fatty acid levels or composition by directly modifying starch or other carbohydrate content in view of the interrelationship of the starch and oil pathways, and vice versa.

In yet another example, the promoter of the present invention or an active fragment or derivative thereof is employed to modulate ethylene production and/or perception and/or endosperm apoptosis associated with ethylene production and/or perception. For example, by down-regulating ethylene production and/or reception, apoptosis of cereal endosperm is delayed or repressed e.g., Campbell and Drew, Planta 157: 350-357 (1983); Drew et al, Planta 147:83-88 (1979); He et al., Plant Physiol. 112:1679-1685 (1996); Young et al., Plant Physiol. 119:737-751 (1997); Young and Gallie, Plant Mol. Biol. 39:915-926 (1999); Young and Gallie, Plant Mol. Biol. 42:397-414 (2000)). Ethylene perception in cereals most likely involves homologs of the *Arabidopsis* membrane-localized receptors ETR1, ERS1, ETR2, ERS2 and E1N4 (Chang et al., Science 262:539-544 (1993); Hua et al., Science 269:1712-1714 (1995), Hua et al., Plant Cell 10:1321-1332 (1998), Sakai et al., Proc. Natl. Acad. Sci. USA 95:5812-5817 (1998)), or products of the maize ethylene receptor genes ZmETR2 and ZmERS1, ZmETR9 and ZmETR40. The endosperm of cereals serves as the major storage organ for grain but undergoes cell death during mid to late seed development, regulated by ethylene. By down-regulating expression of an ethylene receptor gene in the endosperm e.g., basal endosperm and/or BETL cells, apoptosis of the organ is delayed or reduced or suppressed, thereby extending the period of grain filling and storage protein deposition.

In another example, a promoter, active fragment or derivative as described according to any example hereof is used to express a therapeutic protein, such as, for example, a vaccine or an antibody fragment. Improved 'plantibody' vectors (e.g., as described in Hendy et al. J. Immunol. Methods 231:137-146, 1999) and purification strategies render such a method a practical and efficient means of producing recombinant immunoglobulins, not only for human and animal therapy, but for industrial applications as well (e.g., catalytic antibodies). Moreover, plant produced antibodies have been shown to be safe and effective and avoid the use of animal-derived materials and therefore the risk of contamination with a transmissible spongiform encephalopathy (TSE) agent. Furthermore, the differences in glycosylation patterns of plant and mammalian cell-produced antibodies have little or no effect on antigen binding or specificity. In addition, no evidence of toxicity or human anti-mouse antibody (HAMA) has been observed in patients receiving topical oral application of a plant-derived secretory dimeric IgA antibody (see Larrick et al. *Res. Immunol.* 149:603-608, 1998).

For example, a promoter of the present invention or an active fragment or derivative thereof is employed to express a recombinant antibody in the endosperm e.g., basal endosperm and/or BETL cells, such as an anti-CD4 antibody capable of inhibiting HIV-1 virus-to-cell or infected cell-to-uninfected cell transmission or for suppressing or reducing an inflammatory response or for treatment of CD-4 autoimmune disorders such as rheumatoid arthritis or psoriasis.

Various methods may be used to express recombinant antibodies in transgenic plants. For example, antibody heavy and light chains can be independently cloned into a nucleic acid construct, followed by the transformation of plant cells in vitro using the method of the invention. Subsequently, whole plants expressing individual chains are regenerated followed by their sexual cross, ultimately resulting in the production of a fully assembled and functional antibody (see, for example, Hiatt et al. Nature 342:76-87, 1989). In various examples, signal sequences may be utilized to promote the expression, binding and folding of unassembled antibody chains by directing the chains to the appropriate plant environment.

In another example, a transgene encoding a peptide or polypeptide capable of eliciting an immune response in a host is linked to a promoter, active fragment or derivative as described according to any example hereof. For example, a transgene encoding Hepatitis B surface antigen is inserted into a nucleic acid construct described herein and used to produce a transgenic plant using a method described according to any example hereof. In accordance with this example, a food product produced using the plant or a part thereof is then administered to humans (e.g., fed to a human) as a medicinal foodstuff or oral vaccine.

Without detracting from the general applicability of the promoter, active fragment or derivative of the invention, the present invention also encompasses linking said promoter, active fragment or derivative to a nucleic acid that encodes a protein that confers or enhances protection against a plant pathogen, such as, for example, a seed-borne fungus, seed-borne virus, seed-borne bacterium, or insect that feeds on the seed. Such proteins are known to those skilled in the art and include, for example, a range of structurally and functionally diverse plant defense proteins or pathogenesis-related proteins (e.g., chitinase, in particular acid chitinase or endochitinase; beta-glucanase in particular beta-1,3-glucanase; ribosome-inactivating protein (RIP); a-kafirin polypeptide e.g., α-kafirin, β-kafirin, β-kafirin; *Hevea brasiliensis* hevein; potato win1 or wing proteins, or related protein from wheat such as, for example, wheatwin or WPR4 or, related protein from barley such as, for example, barwin); thionin, in particular K-thionin; thaumatin or thaumatin-like protein such as zeamatin; a proteinase inhibitor such as, for example, trypsin or chymotrypsin; or sormatin), virus coat proteins, and proteins that convert one or more pathogen toxins to non-toxic products. Nucleic acid encoding such proteins are publicly available and/or described in the scientific literature. The structures of such genes and their encoded proteins are fully described in the database of the National Center for Biotechnology Information of the US National Library of Medicine, 8600 Rockville Pike, Bethesda, Md. 20894, USA.

A promoter or active fragment or derivative as described according to any example hereof may also be placed in operable connection with a nucleic acid encoding a polypeptide for recombinant production of that polypeptide. As discussed supra, tissues of plant seeds, e.g., developing endosperm, are useful for the production of recombinant polypeptides. Accordingly, the present invention provides a method for producing a recombinant polypeptide, e.g., for commercial purposes.

It is to be understood that the present invention also extends to the production of transgenic plants that express transgenes that do not encode a protein. For example, the transgene encodes an interfering RNA, an antisense RNA, a ribozyme, an abzyme, co-suppression molecule, gene-silencing molecule or gene-targeting molecule, which prevents or reduces the expression of a nucleic acid of interest.

Suitable methods for producing interfering RNA or a ribozyme, or an abzyme are known in the art.

For example, a number of classes of ribozymes have been identified. One class of ribozymes is derived from a number of small circular RNAs that are capable of self-cleavage and replication in plants. Examples include RNAs from avocado sunblotch viroid and the satellite RNAs from tobacco ringspot virus, lucerne transient streak virus, velvet tobacco mottle virus, *solanum* nodiflorum mottle virus and subterranean clover mottle virus. The design and use of transgenes encoding a ribozyme capable of selectively cleaving a target RNA is described, for example, in Haseloff et al. *Nature*, 334:585-591 (1988).

Alternatively, a transgene expresses a nucleic acid capable of inducing sense suppression of a target nucleic acid. For example, a transgene is produced comprising nucleic acid configured in the sense orientation as a promoter of a target nucleic acid. Such a method is described, for example, in Napoli et al., *The Plant Cell* 2:279-289 1990; or U.S. Pat. No. 5,034,323.

To reduce or prevent expression of a nucleic acid by sense suppression, the transgene need not be absolutely identical to the nucleic acid. Furthermore, the transgene need not comprise the complete sequence of the nucleic acid to reduce or prevent expression of said nucleic acid by sense-suppression.

RNA interference is also useful for reducing or preventing expression of a nucleic acid. Suitable methods of RNAi are described in Marx, *Science*, 288:1370-1372, 2000. Exemplary methods for reducing or preventing expression of a nucleic acid are described in WO 99/49029, WO 99/53050 and WO0/75164. Briefly a transgene is produced that expresses a nucleic acid that is complementary to a sequence of nucleotides in the target nucleic acid. The transgene additionally expresses nucleic acid substantially identical to said sequence of nucleotides in the target nucleic acid. The two nucleic acids expressed by the transgene are capable of hybridizing and reducing or preventing expression of the target nucleic acid, presumably at the post-transcriptional level.

MicroRNA or miRNA is a small double stranded RNA that regulates or modulates the expression of target messenger RNAs either by mRNA cleavage, translational repression/inhibition or heterochromatic silencing (see for example Ambros, 2004, Nature, 431, 350-355; Bartel, 2004, *Cell*, 116, 281-297; Cullen, 2004, *Virus Research.*, 102, 3-9; He et al., 2004, Nat. Rev. Genet., 5, 522-531; and Ying et al., 2004, Gene, 342, 25-28). Such microRNA can be expressed using a promoter, active fragment or derivative as described according to any example hereof. Alternatively, a nucleic acid is capable of conferring expression or a pattern of expression on a miRNA using a promoter, active fragment or derivative as described according to any example hereof.

Plant Transformation or Transfection

Following production of a suitable expression construct or expression vector the construct or vector is introduced into a plant cell or tissue. Means for introducing recombinant DNA into plant tissue or cells include, but are not limited to, transformation using $CaCl_2$ and variations thereof, e.g., as described by Hanahan (1983), direct DNA uptake into protoplasts (Krens et al, Nature 296, 72-74, 1982; Paszkowski et al., *EMBO J.* 3, 2717-2722, 1984), PEG-mediated uptake to protoplasts (Armstrong et al., *Plant Cell Rep.* 9, 335-339, 1990) microparticle bombardment, electroporation (Fromm et al., *Proc. Natl. Acad. Sci. (USA)*, 82, 5824-5828, 1985), microinjection of DNA (Crossway et al., *Mol. Gen. Genet.* 202, 179-185, 1986), microparticle bombardment of tissue explants or cells (Christou et al, *Plant Physiol.* 87, 671-674, 1988; Sanford, *Part. Sci. Technol.* 5, 27-37, 1988), vacuum-infiltration of tissue with nucleic acid, or in the case of plants, T-DNA-mediated transfer from *Agrobacterium* to the plant tissue as described essentially by An et al., *EMBO J.* 4, 277-284, 1985; Herrera-Estrella et al., Herrera-Estrella et al., *Nature* 303, 209-213, 1983; Herrera-Estella et al., *EMBO J.* 2, 987-995, 1983; or Herrera-Estella et al., *In*: Plant Genetic Engineering, Cambridge University Press, N.Y., pp 63-93, 1985.

Particle bombardment-mediated transformation also delivers naked nucleic acid into plant cells (Sanford et al., *J. Part. Sci. Technol.* 5: 27, 37, 1987). This technique involves the acceleration of dense nucleic acid-coated microparticles, e.g., gold or tungsten particles, to a sufficient velocity to penetrate the plant cell wall and nucleus. The introduced nucleic acid is then incorporated into the plant genome, thereby producing a transgenic plant cell. This cell is then used to regenerate a transgenic plant. Exemplary apparatus and procedures are disclosed by Stomp et al. (U.S. Pat. No. 5,122,466) and Sanford and Wolf (U.S. Pat. No. 4,945,050). Suitable methods are also exemplified herein. Examples of microparticles suitable for use in such systems include 1 to 5 micron gold spheres. The DNA construct may be deposited on the microparticle by any suitable technique, such as by precipitation.

Alternatively, an expression construct or expression vector is introduced into a plant protoplast. To produce a protoplast, it is necessary to remove the cell wall from a plant cell. Methods for producing protoplasts are known in the art and described, for example, by Potrykus and Shillito, *Methods in Enzymology* 118, 449-578, 1986. Naked nucleic acid (i.e., nucleic acid that is not contained within a carrier, vector, cell, bacteriophage or virus) is introduced into a plant protoplast by physical or chemical permeabilization of the plasma membrane of the protoplast (Lörz et al., *Mol. Gen. Genet.* 199: 178-182, 1985 and Fromm et al., *Nature*, 319: 791-793, 1986).

The preferred physical means for introducing nucleic acid into protoplasts is electroporation, which comprises the application of brief, high-voltage electric pulses to the protoplast, thereby forming nanometer-sized pores in the plasma membrane. Nucleic acid is taken up through these pores and into the cytoplasm. Alternatively, the nucleic acid may be taken up through the plasma membrane as a consequence of the redistribution of membrane components that accompanies closure of the pores. From the cytoplasm, the nucleic acid is transported to the nucleus where it is incorporated into the genome.

The preferred chemical means for introducing nucleic acid into protoplasts utilizes polyethylene glycol (PEG). PEG-mediated transformation generally comprises treating a protoplast with nucleic acid of interest in the presence of a PEG solution for a time and under conditions sufficient to permeabilize the plasma membranes of the protoplast. The nucleic acid is then taken up through pores produced in the plasma membrane and either maintained as an episomal plasmid or incorporated into the genome of the protoplast.

In another example of this invention, the expression vector or construct is introduced into a plant cell by electroporation (Fromm et al., *Proc. Natl. Acad. Sci. USA* 82:5824, 1985). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) is also useful as a vector for introducing an expression vector or construct into plant cells (Hohn et al., (1982) "Molecular Biology of Plant Tumors," Academic Press, New York, pp. 549-560; Howell, U.S. Pat. No. 4,407,956). CaMV viral DNA genome is inserted into a parent bacterial plasmid creating a recombinant DNA molecule that can be propagated in bacteria. After cloning, the recombinant plasmid is again cloned and further modified by introduction of the desired nucleic acid. The modified viral portion of the recombinant plasmid is then excised from the parent bacterial plasmid, and used to inoculate the plant cells or plants.

A further method for introducing an expression construct into plant cells is to infect a plant cell, an explant, a meristem or a seed with *Agrobacterium tumefaciens* transformed with the expression construct. Under appropriate conditions known in the art, the transformed plant cells are grown to form shoots, roots, and develop further into plants. The expression construct is introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., *Proc. Natl. Acad. Sci. USA* 80:4803, 1984).

There are presently at least three different ways to transform plant cells with *Agrobacterium*: (1) co-cultivation of *Agrobacterium* with cultured isolated protoplasts; (2) transformation of cells or tissues with *Agrobacterium*, or (3) transformation of seeds, apices or meristems with *Agrobacterium*.

Method (1) uses an established culture system that allows culturing protoplasts and plant regeneration from cultured protoplasts.

Method (2) implies (a) that the plant cells or tissues can be transformed by *Agrobacterium* and (b) that the transformed cells or tissues can be induced to regenerate into whole plants.

Method (3) uses micropropagation. In the binary system, to have infection, two plasmids are needed: a T-DNA containing plasmid and a vir plasmid. Any one of a number of T-DNA containing plasmids can be used, the main issue being that one be able to select independently for each of the two plasmids.

After transformation of the plant cell or plant, those plant cells or plants transformed by the Ti plasmid so that the desired DNA segment is integrated can be selected by an appropriate phenotypic marker expressed by the transformation vector. These phenotypic markers include, but are not limited to, antibiotic resistance, herbicide resistance or a trait detectable by visual observation. Other phenotypic markers are known in the art and may be used in this invention.

Alternatively, the transformed plants are produced by an in planta transformation method using *Agrobacterium tumefaciens*, such as, for example, the method described by Bechtold et al., *CR Acad. Sci. (Paris, Sciences de la vie/Life Sciences)* 316, 1194-1199, 1993 or Clough et al., *Plant J* 16: 735-74, 1998, wherein *A. tumefaciens* is applied to the outside of the developing flower bud and the binary vector DNA is then introduced to the developing microspore and/or macrospore and/or the developing seed, so as to produce a transformed seed. Those skilled in the art will be aware that the selection of tissue for use in such a procedure may vary, however it is preferable generally to use plant material at the zygote formation stage for in planta transformation procedures.

In a further example, a graminaceous plant is transformed using a method comprising contacting a mature embryo, e.g., a wheat embryo from a seed that has completed grain filling, with an *Agrobacterium* comprising an expression vector for a time and under conditions sufficient for the expression vector to be delivered to one or more cells of the mature embryo. Such transformation may additionally comprise removing the seed coat and or performing the transformation in the presence of Soytone™, both of which improve transformation efficiency. The transformed cells may be used to regenerate a plant or plant part.

The present invention also encompasses products of repeated cycles of transformation employing transformed plant cells or plant parts comprising a promoter, active fragment or derivative of the present invention or a transgene placed operably under the control of said promoter, active fragment or derivative or a gene construct comprising said transgene operably under the control of said promoter, active fragment or derivative.

In one example, gene stacking is performed. Gene stacking may be performed sequentially or simultaneously. In one example of simultaneous gene stacking, a plant cell, plant tissue, plant organ or whole plant is transformed with two gene constructs wherein at least one of said gene constructs comprises a promoter, active fragment or derivative or transgene or gene construct of the present invention. In an example of sequential gene stacking, a transformed first plant cell comprising a first promoter, active fragment or derivative or transgene or gene construct is transformed with a second gene construct different to that used to produce the first plant cell, tissue, organ or whole plant e.g., wherein the second gene construct comprises a second transgene placed operably under the control of a second promoter that is different to the first promoter of the first plant cell, tissue, organ or whole plant. For example, the second gene construct or second transgene may comprise a second promoter, active fragment or derivative of the present invention different to a first promoter, active fragment or derivative of the invention present in the first plant cell, tissue, organ or plant. In another example, the second promoter is operable in the seed, preferably in the endosperm of a plant e.g., a promoter that confers or regulates expression in a number of different plant organs, tissues or cells, e.g., including the endosperm, or regulates such expression predominantly or exclusively in the endosperm, including early endosperm and/or maturing endosperm and/or basal endosperm and/or BETL cells. In another example, the second promoter is operable in the embryo of plant seed. In another example, the second gene construct may further comprise a second transgene different to the first transgene i.e., wherein the promoters regulating each transgene are different. For example, the first and second transgenes are utilized to express functionally distinct or structurally distinct or unrelated first and second structural genes or transgenes. Such different transgenes may catalyse or regulate different steps in the same biochemical pathway, or entirely different biochemical pathways, and/or they may act in concert i.e., cooperatively to produce one or more desired traits. Preferably, different selectable markers are used to monitor the first and second and subsequent transformations.

Specific examples of first and second transgenes for such gene stacking approaches will be apparent from the disclosure herein of exemplary promoters that may be used in combination with a promoter, active fragment or derivative of the present invention, and the disclosure herein of exemplary transgenes that may be expressed in plants e.g., operably under the control of a promoter, active fragment or derivative of the present invention. It is to be understood that, in gene stacking approaches, the description of transgenes that may be expressed in plants e.g., operably under the control of a promoter, active fragment or derivative of the present invention apply mutatis mutandis to second gene constructs and second transgenes of this example.

Regeneration and Propagation of a Plant from a Transformed Cell/Plastid

A whole plant may be regenerated from the transformed or transfected cell, in accordance with procedures known in the art. Plant tissue capable of subsequent clonally propagation, whether by organogenesis or embryogenesis, may be transformed with a vector or construct as described according to any example hereof.

The term "organogenesis", as used herein, means a process by which shoots and roots are developed sequentially from meristematic centres.

The term "embryogenesis", as used herein, means a process by which shoots and roots develop together in a concerted fashion (not sequentially), whether from somatic cells or gametes.

Plant regeneration from cultural protoplasts is described, for example, in Evans et al., "Protoplast Isolation and Culture—Handbook of Plant Cell Cultures 1" (MacMillan Publishing Co., 1983) and Binding "Regeneration of Plants"—Plant Protoplasts, pp 21-73 (CRC Press, Boca Raton, 1985). Regeneration varies from species to species. Generally, a suspension of transformed protoplasts is produced (e.g., using a method described herein). In some species the transformed protoplast is then induced to form an embryo and then to the stage of ripening and germination. Such induction involves, for example, the addition of compounds to the culture media of the protoplast, for example, glutamic acid and/or proline in the case of corn or alfalfa.

In an example, a plant or a plant part or a plantlet is regenerated using a transformed graminaceous plant cell produced using a method described herein. Preferably, a transformed cell is contacted with a compound that induces callus formation for a time and under conditions sufficient for callus formation. Alternatively, or in addition, a transgenic plant cell is contacted with a compound that induces cell de-differentiation for a time and under conditions sufficient for a cell to de-differentiate. Alternatively, or in addition, a transgenic plant cell is contacted with a compound that induces growth of an undifferentiated cell for a time and under conditions sufficient for an undifferentiated cell to grow. Compounds that induce callus formation and/or induce production of undifferentiated and/or de-differentiated cells will be apparent to the skilled artisan and include, for example, an auxin, e.g., 2,4-D, 3,6-dichloro-o-anisic acid (dicambia), 4-amino-3,5,6-thrichloropicolinic acid (picloram) or thidiazuron (TDZ).

Such a medium may additionally comprise one or more compounds that facilitate callus formation/de-differentiation or growth of undifferentiated cells. For example, Mendoza and Kaeppler (*In vitro Cell Dev. Biol.*, 38: 39-45, 2002) found that media comprising maltose rather than sucrose enhanced the formation of calli in the presence of 2,4-D.

Alternatively, or in addition, the embryonic cell is additionally contacted with myo-inositol. Studies have indicated that myo-inositol is useful for maintaining cell division in a callus (Biffen and Hanke, *Biochem. J.* 265: 809-814, 1990).

Similarly, casein hydrolysate appears to induce cell division in a callus and maintain callus morphogenetic responses. Accordingly, in another example, the embryonic graminaceous plant cell is additionally contacted with casein hydrolysate.

Suitable culture medium and methods for inducing callus formation and/or cell de-differentiation and/or the growth of undifferentiated cells from mature embryonic graminaceous plant cells are known in the art and/or described in Mendoza and Kaeppler, *In vitro Cell Dev. Biol.*, 38: 39-45, 2002, Özgen et al., *Plant Cell Reports*, 18: 331-335, 1998, Patnaik and Khurana *BMC Plant Biology*, 3: 1-11, Zale et al., *Plant Cell, Tissue and Organ Culture*, 76: 277-281, 2004 and Delporte et al., *Plant Cell, Tissue and Organ Culture*, 80: 139-149, 2005.

Following callus induction, cell de-differentiation and/or growth of undifferentiated cells, the plant cells and/or a cell derived therefrom (e.g., a callus derived therefrom or a de-differentiated or undifferentiated cell thereof) is contacted with a compound that induces shoot formation for a time and under conditions sufficient for a shoot to develop. Suitable compounds and methods for inducing shoot formation are known in the art and/or described, for example, in Mendoza and Kaeppler, *In vitro Cell Dev. Biol.*, 38: 39-45, 2002, Özgen et al., *Plant Cell Reports*, 18: 331-335, 1998, Patnaik and Khurana *BMC Plant Biology*, 3: 1-11, Zale et al., *Plant Cell, Tissue and Organ Culture*, 76: 277-281, 2004, Murashige and Skoog, *Plant Physiol.*, 15: 473-479, 1962 or Kasha et al., (In: Gene manipulation in plant improvement II, Gustafson ed., Plenum Press, 1990). For example, a callus or an undifferentiated or de-differentiated cell is contacted with one or more plant growth regulator(s) that induces shoot formation. Examples of suitable compounds (i.e., plant growth regulators) include indole-3-acetic acid (IAA), benzyladenine (BA), indole-butyric acid (IBA), zeatin, a-naphthaleneacetic acid (NAA), 6-benzyl aminopurine (BAP), thidiazuron, kinetin, 21P or combinations thereof.

Suitable sources of media comprising compounds for inducing shoot formation are known in the art and include, for example, Sigma-Aldrich Pty Ltd (Sydney, Australia).

Alternatively, or in addition, the callus or an undifferentiated or de-differentiated cell is maintained in or on a medium that does not comprise a plant growth modulator for a time and under conditions sufficient to induce shoot formation and produce a plantlet.

At the time of shoot formation or following shoot formation the callus or an undifferentiated or de-differentiated cell is preferably contacted with a compound that induces root formation for a time and under conditions sufficient to initiate root growth and produce a plantlet.

Suitable compounds that induce root formation are known to the skilled artisan and include a plant growth regulator, e.g., as described supra.

Suitable methods for inducing root induction are known in the art and/or described in Mendoza and Kaeppler, *In vitro Cell Dev. Biol.*, 38: 39-45, 2002, Özgen et al., *Plant Cell Reports*, 18: 331-335, 1998, Patnaik and Khurana *BMC Plant Biology*, 3: 1-11, Zale et al., *Plant Cell, Tissue and Organ Culture*, 76: 277-281, 2004, Murashige and Skoog, *Plant Physiol.*, 15: 473-479, 1962 or Kasha et al., (In: Gene manipulation in plant improvement II, Gustafson ed., Plenum Press, 1990).

In an example of the invention, a callus and/or de-differentiated cell and/or undifferentiated cell is contacted with media comprising zeatin for a time and under conditions sufficient to induce shoot formation and contacted with medium comprising NAA for a time and under conditions sufficient to induce root formation.

Plantlets are then grown for a period of time sufficient for root growth before being potted (e.g., in potting mix and/or sand) and being grown.

The generated transformed plants may be propagated by a variety of means, such as by clonal propagation or classical breeding techniques. For example, a first generation (or T1) transformed plant may be selfed to give homozygous second generation (or T2) transformant, and the T2 plants further propagated through classical breeding techniques. In this respect, the skilled artisan will be aware that the term "selfed" refers to the process of selfing, which is discussed supra.

The present invention also encompasses products of repeated cycles of transformation employing plant material transformed with a promoter, active fragment or derivative of the present invention or a transgene placed operably under the control of said promoter, active fragment or derivative or a gene construct comprising said transgene operably under the control of said promoter, active fragment or derivative.

In one example, gene stacking is performed. In one example of gene stacking, a first plant cell, first plant tissue or first plant organ or first whole plant comprising a first promoter, active fragment or derivative or transgene or gene construct is transformed with a second gene construct different to that used to produce the first plant cell, tissue, organ or whole plant e.g., wherein the second gene construct comprises a second transgene placed operably under the control of a second promoter that is different to the first promoter of the first plant cell, tissue, organ or whole plant. For example, the second gene construct or second transgene may comprise a second promoter, active fragment or derivative of the present invention different to a first promoter, active fragment or derivative of the invention present in the first plant cell, tissue, organ or plant. In another example, the second promoter is operable in the seed, preferably in the endosperm of a plant e.g., a promoter that confers or regulates expression in a number of different plant organs, tissues or cells, e.g., including the endosperm, or regulates such expression predominantly or exclusively in the endosperm, including early endosperm and/or maturing endosperm and/or basal endosperm and/or BETL cells. In another example, the second promoter is operable in the embryo of plant seed. In another example, the second gene construct may further comprise a second transgene different to the first transgene i.e., wherein the promoters regulating each transgene are different. For example, the first and second transgenes are utilized to express functionally distinct or structurally distinct or unrelated first and second structural genes or transgenes. Such different transgenes may catalyse or regulate different steps in the same biochemical pathway, or entirely different biochemical pathways, and/or they may act in concert i.e., cooperatively to produce one or more desired traits.

Specific examples of first and second transgenes for such gene stacking approaches will be apparent from the disclosure herein of exemplary promoters that may be used in combination with a promoter, active fragment or derivative of the present invention, and the disclosure herein of exemplary transgenes that may be expressed in plants e.g., operably under the control of a promoter, active fragment or derivative of the present invention. It is to be understood that, in gene stacking approaches, the description of transgenes that may be expressed in plants e.g., operably under the control of a promoter, active fragment or derivative of the present invention apply mutatis mutandis to second gene constructs and second transgenes of this example.

The present invention also encompasses products of traditional breeding or asexual or clonal propagation employing plant material transformed with a promoter, active fragment or derivative of the present invention or a transgene placed operably under the control of said promoter, active fragment or derivative or a gene construct comprising said transgene operably under the control of said promoter, active fragment or derivative.

In one example, gene stacking is performed. In one example of gene stacking, a first plant comprising a first promoter, active fragment or derivative or transgene or gene construct is cross sexually with a second plant expressing one or more desired traits or having a desired genetic background, and progeny carrying the first promoter, active fragment or derivative or transgene or gene construct and expressing the desired trait(s) are identified and optionally, isolated. As will be known to those skilled in the art, if the parents of such a cross do not each contribute the same genetic material to their progeny, then such progeny plants are heterozygous for the parentally-derived first promoter, active fragment or derivative or transgene or gene construct and the desired trait(s). In another example, the heterozygous progeny are then selfed and the homozygous progeny identified and optionally, isolated. Where such crosses are intended to introgress a promoter; active fragment or derivative or transgene or gene construct of the invention into a desired genetic background, repeated backcrossing is performed between the progeny of each cross and a plant comprising the desired genetic background. Generally, sufficient backcrosses are performed to ensure that the introduced promoter, active fragment or derivative or transgene or gene construct of the primary transformant is present in a genetic background that is substantially or significantly the same as the desired genetic background.

In another example, the one or more desired traits present in a parent of such a breeding or crossing program is/are conferred by a second gene construct different to the first gene construct of the other parent or is conferred by a second transgene placed operably under the control of a second promoter that is different to the first promoter of the other parent. For example, the second gene construct or second transgene may comprise a second promoter, active fragment or derivative of the present invention different to the first promoter, active fragment or derivative. In another example, the second promoter is operable in the seed, preferably in the endosperm of a plant e.g., a promoter that confers or regulates expression in a number of different plant organs, tissues or cells, e.g., including the endosperm, or regulates such expression predominantly or exclusively in the endosperm, including early endosperm and/or maturing endosperm and/or basal endosperm and/or BETL cells. In another example, the second promoter is operable in the embryo of plant seed. In another example, the second gene construct may further comprise a second transgene different to the first transgene i.e., wherein the promoters regulating each transgene are different. For example, the first and second transgenes are utilized to express functionally distinct or structurally distinct or unrelated first and second structural genes or transgenes. Such different transgenes may catalyse or regulate different steps in the same biochemical pathway, or entirely different biochemical pathways, and/or they may act in concert i.e., cooperatively to produce one or more desired traits.

Specific examples of first and second transgenes for such gene stacking approaches will be apparent from the disclosure herein of exemplary promoters that may be used in combination with a promoter, active fragment or derivative of the present invention, and the disclosure herein of exemplary transgenes that may be expressed in plants e.g., operably under the control of a promoter, active fragment or derivative of the present invention. It is to be understood that, in gene stacking approaches, the description of transgenes that may be expressed in plants e.g., operably under the control of a promoter, active fragment or derivative of the present invention apply mutatis mutandis to second transgenes of this example.

As will be apparent from the foregoing, the present invention additionally provides progeny or reproductive tissue of a genetically modified cell or organism of the invention, subject to the proviso that the progeny or reproductive tissue comprises nucleic acid encoding the fusion protein of the invention.

The generated transformed organisms contemplated herein may take a variety of forms. For example, they may be chimeras of transformed cells and non-transformed cells; clonal transformants (e.g., all cells transformed to contain the expression construct or vector); grafts of transformed and untransformed tissues (e.g., in plants, a transformed root stock grafted to an untransformed scion).

Identification of Additional Promoters

As discussed herein-above, the inventors have also provided a method for identifying or isolating a promoter capable of conferring expression or a pattern of expression on a nucleic acid, e.g., in developing endosperm of a plant or a cell or tissue thereof such as basal endosperm or more particularly in BETL cells. In a preferred example, the method comprises:
(i) determining the level of expression of a plurality of expression products in a developing endosperm;
(ii) determining the level of expression of a plurality of expression products in control tissue or cell or plant part;
(iii) identifying one or more expression products expressed at an increased level at (i) compared to (ii); and
(iv) isolating a promoter that confers expression on the one or more expression products at (iii) in developing endosperm.

A suitable control plant part, tissue or cell will be apparent to the skilled artisan and include any plant part, tissue or cell that is not from endosperm. Preferably, the control plant part, tissue or cell is from a non-dormant seed or embryo, e.g., from an imbibed embryo or seed or from a germinating embryo or seed.

Preferably, the expression products detected are transcripts or mRNA encoded by a gene. For example, the transcripts or mRNA are detected using a microarray.

In one example, the level of expression in a developing endosperm is compared to the level of expression in a plurality of control tissues, cells or plant parts. For example, the plurality of control tissues, cells or plant parts includes a plant part, tissue or cell is from a non-dormant seed or embryo and a non-embryonic plant part, non-embryonic tissue or non-embryonic cell. In this manner, a promoter that confers expression on a nucleic acid preferentially or selectively in developing endosperm or a cell or tissue thereof is identified.

In one example, the method as described according to any example hereof additionally comprises:
(v) optionally, determining the structure of the promoter, e.g., the sequence of the promoter;
(vi) optionally, providing the structure of the promoter; and
(vii) providing the promoter.

In one example, the promoter is provided in an expression vector. The present invention clearly extends to the direct product of any method of identification or isolation of a promoter described herein.

The present invention is further described with reference to the following non-limiting examples.

EXAMPLE 1

Identification of Wheat Genes Expressed Selectively in Developing Wheat Seeds

This example provides support for the seed-selective expression of a wheat gene which is regulated in its native context by the wheat promoter of the present invention designated WP04.

Affymetrix GeneChip® Wheat Genome Arrays were interrogated with probes derived from different RNA samples (immature embryo and developing endosperm) and candidate genes with an endosperm-preferred expression profile were identified.

Figure 1B:
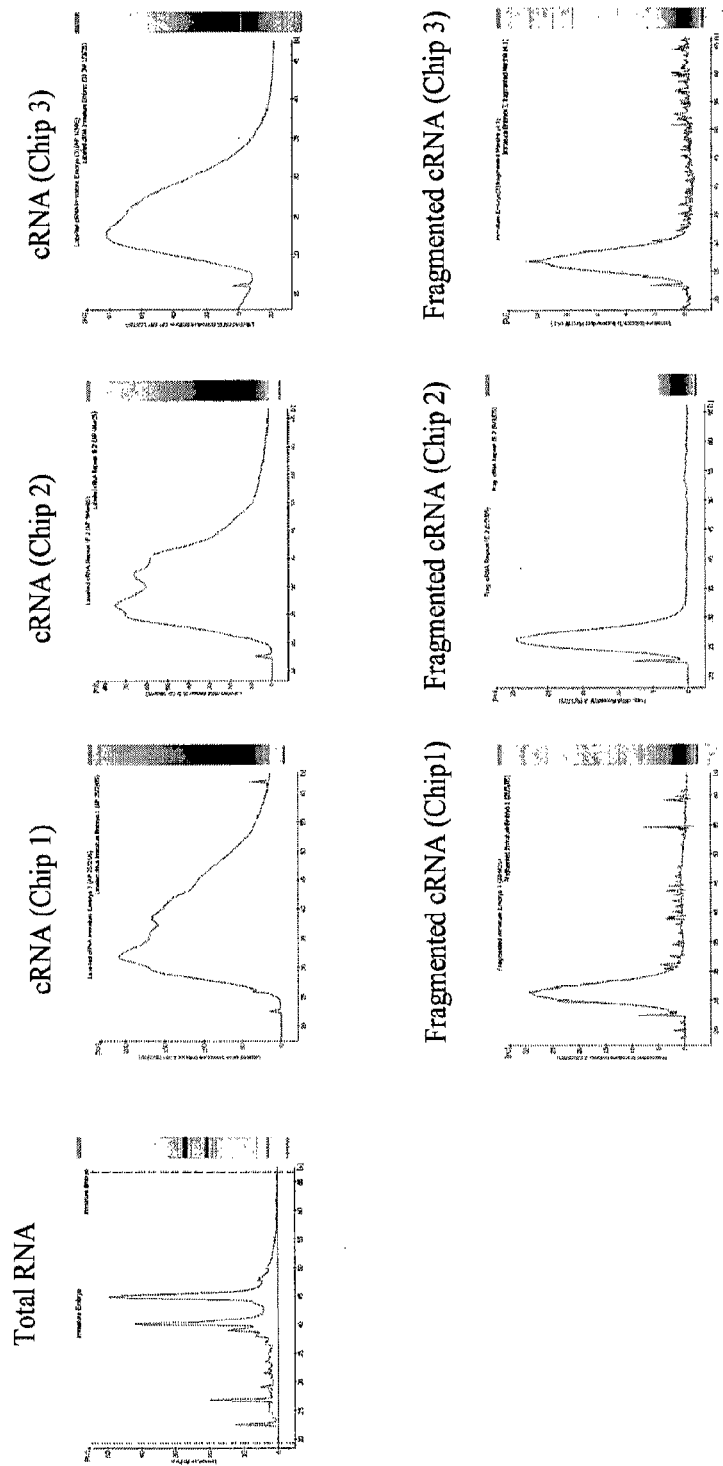
FIG. 1b provides graphical representations showing quality of developing endosperm total RNA, labelled cRNA and fragmented cRNA samples used for Affymetrix GeneChip® Wheat Genome Arrays.

Immature wheat embryos (from seed 10-14 d post anthesis) and endosperm (from seed 10-14 d post anthesis) material were harvested, RNA extracted and further purified, and the quality and yield of RNA confirmed (FIGS. 1a and 1b). The RNA was labelled and hybridised to GeneChip® Wheat Genome Arrays and the data analysed to derive lists of genes in rank order.

Microarray expression was analysed using AVADIS™ software (Strand Genomics Pvt. Ltd. Bangalore). The .CEL files for all chips were imported into AVADIS and the RMA algorithm (Irazarry et al., *Biostatistics* 4 (2003), 249-264) were applied for background correction, normalisation and probe aggregation. Absolute calls and p-values were generated for each gene and all probesets that were Absent (absolute call) across all arrays were removed from the analysis.

For determination of transcripts preferentially or selectively expressed in seeds, two differential expression analyses were conducted using either endosperm or immature embryo as the reference tissue for comparison. For the endosperm analysis, for each comparison pair, only genes Present (absolute call) in all endosperm arrays and Absent (absolute call) in the comparison tissue were retained and the lists filtered to retain only genes appearing in ALL comparison pairs. For the immature embryo analysis, for each comparison pair, only genes Present (absolute call) in all immature embryo arrays and Absent (absolute call) in the comparison tissue were retained and the lists filtered to retain only genes appearing in ALL comparison pairs. The endosperm and immature embryo lists were combined to make a list of genes express in either endosperm OR immature embryo, but not in any other tissue.

The mean, standard deviation and % CV of the fold change values were calculated. The gene list was ranked on the p-value of differential expression levels and filtered to retain only those genes expressed differentially by greater than 10-fold and more than 6000 the mean signal for expression in the reference tissue.

Based on these criteria a list of candidate genes was prepared whose function was unknown, and for which no corresponding upstream genomic sequence was available in public domain databases.

Sequences for the candidate genes present on the Affymetrix GeneChip® Wheat Genome Arrays were obtained through the NetAffx web portal (affymetrix.com/analysis/netaffx/index.affx).

The Affymetrix sequences and the corresponding public sequences from GenBank were downloaded and aligned using Sequencher™ software. In obvious cases, e.g. long stretches of poly-T at the start of the sequence, sequences were reverse-complemented to yield "sense" orientation, exported from Sequencher™ and consequently used for the primer design. In all other, non-obvious cases it was assumed that the sequences were in the "sense" orientation. The GenBank sequences were used as input files for primer design.

Primers for RT-QPCR validation were designed using the "TaqMan MGB probe and primer design" module of Primer-Express™ version 1.5 used with the default settings. Two primer pairs were identified for each target candidate gene and internal standard.

RT-QPCR was performed using SYBR® Green fluorescence to detect amplification of candidate gene sequences from the cDNA samples used for the microarray experiments. A standard real-time PCR mixture for each candidate gene contained 1×SYBR® Green master mix, 200-300 nM of each primer, 2 µl of cDNA (about 20 ng) and water to a final volume of 25 µl. The thermo-cycling conditions for the PCR were: 1 cycle of 95° C. for 10 minutes followed by 40 cycles of 95° C. for 30 seconds, 60° C. for 1 minute. Real-time PCRs and data analysis was performed on a Stratagene MX3000p Real Time PCR machine. The dissociation protocol was used to demonstrate single amplicons with the correct Tm.

The sequence of one seed specific candidate gene validated to be seed specific by RT-QPCR is presented as SEQ ID NO: 1. The sequence of SEQ ID NO: 1 corresponds to an mRNA sequence from *Triticum aestivum* (gb:BQ805508/DB_XREF=gi:22029717/DB XREF=WHE3567_G07_M13ZS/CLONE=WHE3567_G07_M13/TID=Ta10064.1/CNT=22/FEA=EST/TIER-ConsEnd/STK=0/UG=Ta.10064).

EXAMPLE 2

Isolation of Endosperm-Selective Promoter from Wheat Genes Expressed Selectively in Developing Wheat Seeds This example provides support for the isolation of the wheat-derived promoter of the present invention designated WP04.

For the purposes of nomenclature, the promoter designated herein as "WP04" is operably linked in its native context to the Affymetrix clone Ta.10064.1.S1.

To clone the promoter regions of the Affymetrix clone Ta.10064.1.S1, genome walking was performed using the Genome Walker™ kit available from Clontech Laboratories, Inc, (Mountain View, Calif., USA). Briefly, Genomic DNA was extracted from *Triticum aestivum* cultivar Bobwhite 26 and digested with the blunt end restriction enzymes SspI, ScaI, EcoRV, StuI, DraI. The resulting fragments were then used to create several Genome Walker™ libraries comprising wheat genomic DNA. Digested DNA was then purified with phenol chloroform and redissolved in TE buffer (10 mM Tris HCl, 0.1 mM EDTA, pH 7.5) and ligated to adaptors from the Genome Walker™ kit.

Figure 2:
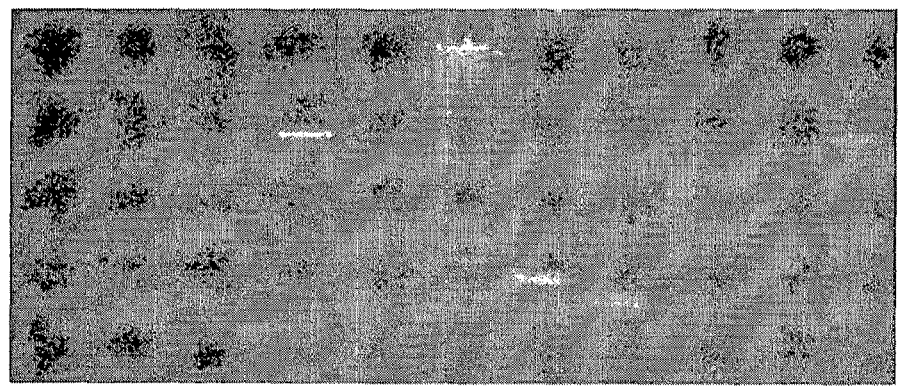
FIG. 2 is a copy of a photographic representation showing an agarose gel within which nucleic acid fragments from wheat amplified in a GenomeWalker™ assay have been resolved for the isolated of the WP04 promoter sequence. Molecular weight standard has been resolved in lane 6.

The resulting libraries were designated:
1. DL 1—SspI
2. DL 2—DraI
3. DL 3—ScaI
4. DL 4—EcoRV
5. DL 5—StuI Nested PCR was performed on the wheat DNA library templates with adapter and sequence-specific primers. PCR products were resolved using electrophoresis using 0.7% (w/v) agarose gels (FIGS. 2a, 2b). Fragments with sizes around or greater than 1.0 kb in length were excised from the gels, purified and ligated into the vector pGEM-T Easy essentially according to manufacturer's instructions (Promega Corporation, Madison, Wis., USA). Fragments were sequenced and aligned with sequence data from Affymetrix and GenBank for each target candidate gene. The promoter sequence designated WP04 was identified from alignments as those regions upstream of predicted open reading frames.

A total of 13 separate PCR amplification products were isolated for the Affymetrix clone Ta.10064.1.S1_at (Table 2), and the WP04 promoter fragment was determined to be localized in a 2.5 kb fragment (fragment WPR04.3.1).

The sequence of a 2126 bp fragment comprising the functional WP04 promoter is set forth in SEQ ID NO: 2.

TABLE 2

| Affymetrix Code | No Genome Walker Bands | Fragment Codes | Fragment Size (kb) | Contig result |
|---|---|---|---|---|
| Ta.10064.1.S1._at | 13 | WP04.1.1 | 2.00 | |
| | | WP04.3.1 | 0.30 | |
| | | WP04.4.1 | 1.00 | |
| | | WP04.5.1 | 2.00 | |
| | | WP04.5.2 | 0.65 | |
| | | WP04.2.1 | 1.70 | |
| | | WP04.3.1 | 2.50 | WP04 promoter |
| | | WP04.3.2 | 1.10 | |
| | | WP04.4.2 | 3.00 | |
| | | WP04.1.2 | 0.50 | |
| | | WP04.3.2 | 1.40 | |
| | | WP04.4.2 | 0.50 | |
| | | WP04.5.2 | 2.50 | |

EXAMPLE 3

Validation of Functionality of Endosperm-Selective Promoter WP04

Figure 3:
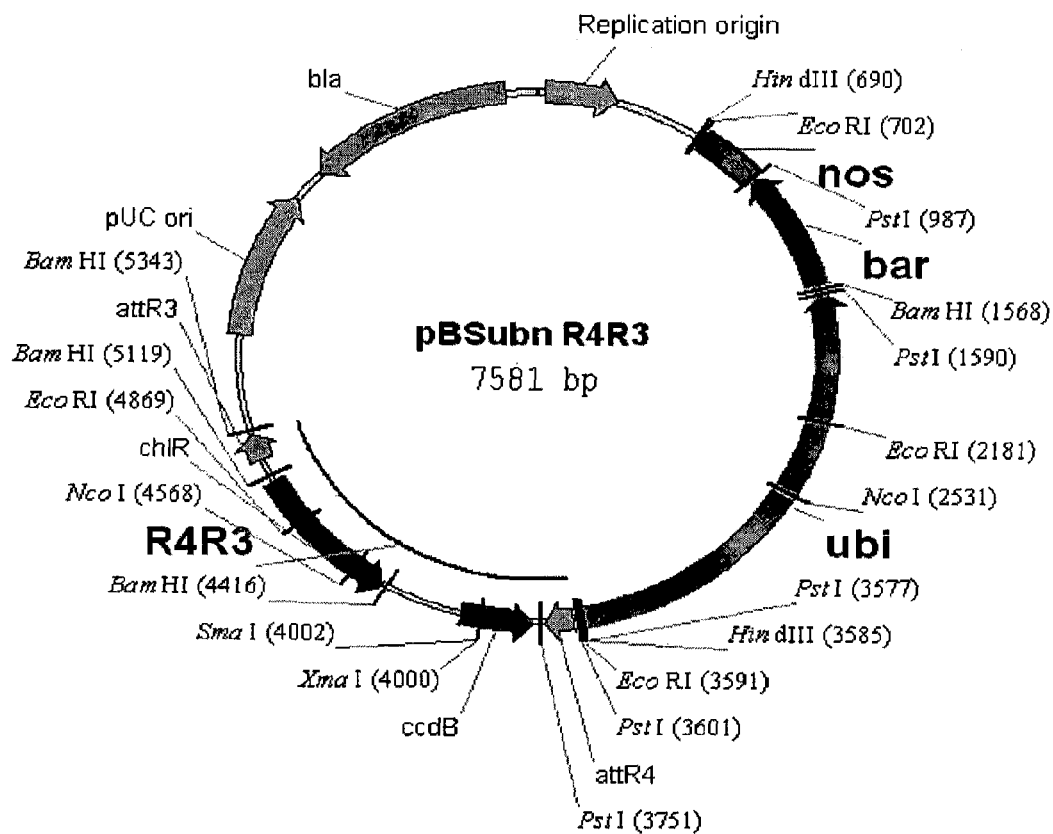
FIG. 3 is a representation of the vector designated pBSubi::bar-nos_R4R3 (SEQ ID NO: 3) which is a base vector for cloning a promoter and/or reporter gene. The vector comprises an Ubi::bar-nos selection cassette and the R4R3 multi-site Gateway™ entry point for promoter, reporter gene and termination sequence Entry Clones. This base vector was used to generate biolistic transformation vectors for each promoter.
Figure 4:
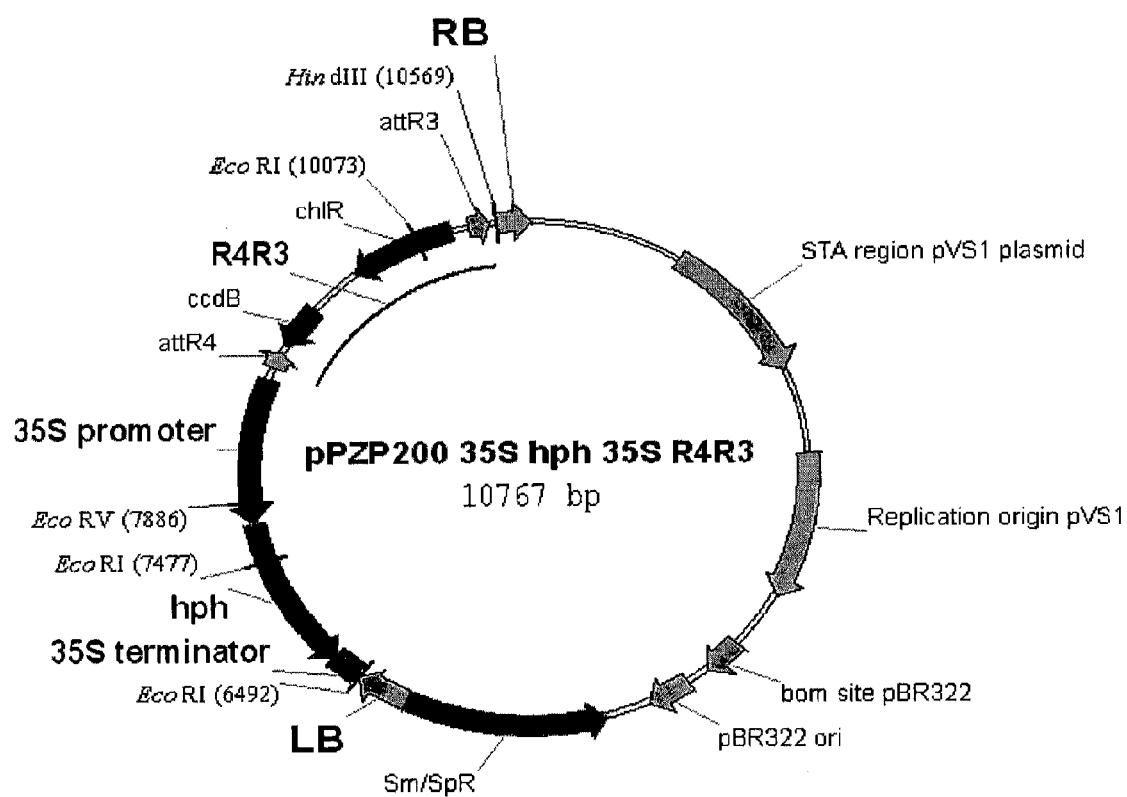
FIG. 4 is a representation of the vector pPZP200 35S hph 35S R4R3 (SEQ ID NO: 4) containing the 35S::hph-35St selection cassette and the R4R3 multi-site Gateway™ entry point for promoter, reporter gene and termination sequence Entry Clones. This base vector was used to generate binary transformation vectors for each promoter.

This example provides support for the functionality of the isolated wheat-derived promoter of the present invention designated WP04 in conferring expression selectively or specifically in endosperm of developing seeds including the basal endosperm transfer layer (BETL) cells, by virtue of the promoter regulating expression of a reporter gene selectively or specifically in developing endosperm of wheat including the BETL cells, and predominantly in BETL cells of transformed maize seeds.
1. Plant Transformation Methods
a) Wheat Transformation Vectors A base vector pBSubn R4R3 (FIG. 3; SEQ ID NO: 3) was used as a source of a selectable marker cassette wherein a ubiquitin promoter regulates expression of the bar selectable marker gene operably linked to the nopaline synthase (NOS) gene terminator i.e., Ubi::bar-nos. A base vector pPZP200 35D hph 35S R4R3 (FIG. 4; SEQ ID NO: 4) was used as a source of a selectable marker cassette wherein a CaMV 35S promoter regulates expression of the hygromycin phosphotransferase (hph) selectable marker gene operably linked to the CaMV 35S gene terminator i.e., 35S::hph-35S. Binary vectors were generated from the base vectors, for use in the transformation of plants. Briefly, reporter gene cassettes comprising the 2126 bp WP04 wheat promoter (SEQ ID NO: 2) operably linked to the green fluorescent protein gene (gfp) and either CaMV 35S or NOS terminator were produced, amplified by PCR using Gateway™ (Invitrogen) adapted primers, and cloned into entry vectors. These were subsequently cloned using recombination into destination vectors containing the conventionally cloned selectable marker cassettes. All vectors were fully sequenced following strict quality assurance protocols.

Figure 5:
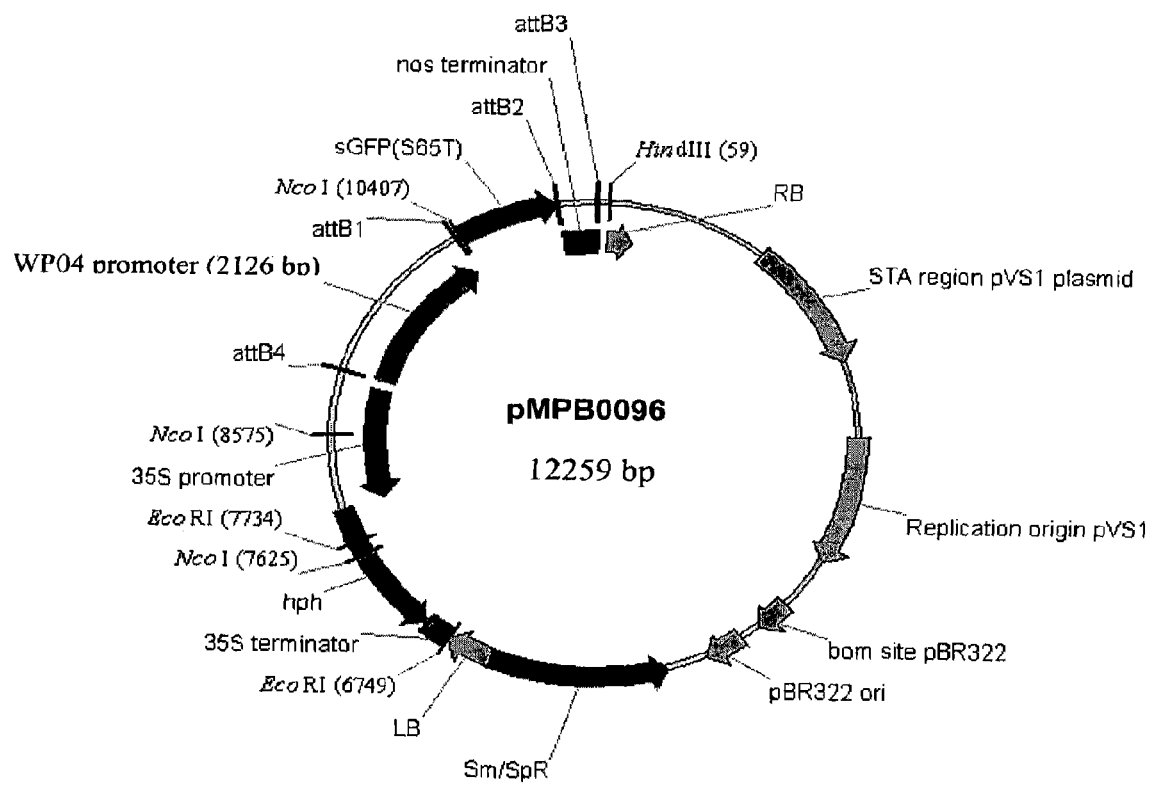
FIG. 5 is a representation of the vector pMPB0096 (SEQ ID NO: 5) which is a binary vector for introducing the 2126 bp WP04 wheat promoter (SEQ ID NO: 2) into cells using *Agrobacterium*. This vector is derived from pPZP200 35S hph 35S R4R3 into which the wheat promoter, synthetic green fluorescent protein (sGFP) and NOS terminator has been inserted into the R4R3 multi-site Gateway™ entry point.
Figure 6:
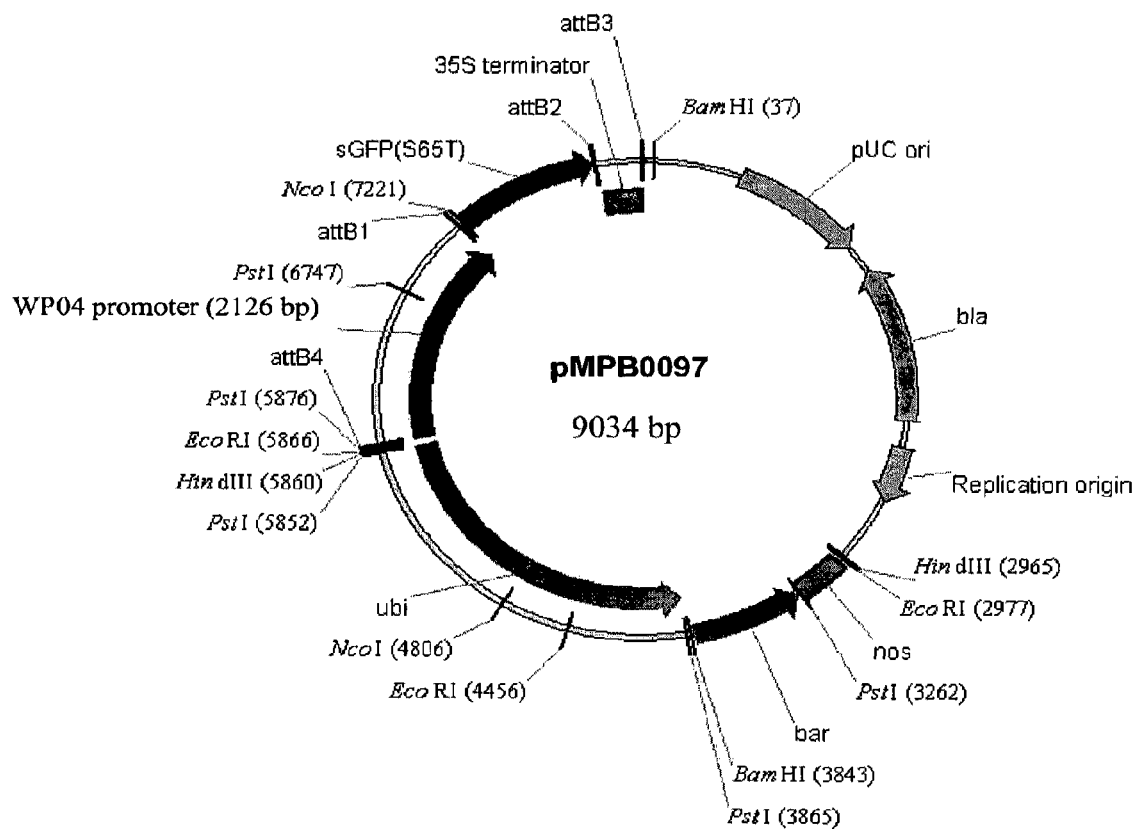
FIG. 6 is a representation showing the vector pMPB0097 (SEQ ID NO: 6) which is a vector for introduction of the 2126 bp WP04 wheat promoter (SEQ ID NO: 2) into cells using particle bombardment. This vector is derived from pBSubi::bar-nos_R4R3 into which the wheat promoter, synthetic green fluorescent protein (sGFP) and NOS terminator has been inserted into the R4R3 multi-site Gateway™ entry point.

Each binary vector produced has the pPZP200 vector backbone (Hajdukiewicz et al., *Plant Mol. Biol.* 25:989-94, 1994) and contains a chimeric reporter gene cassette and selectable marker cassette as follows:

(i) WP04::sgfp-nos reporter gene cassette and 35S::hph-35S selectable marker cassette (pMPB0096; FIG. 5; SEQ ID NO: 5); and (ii) WP04::sgfp-nos reporter gene cassette and Ubi::bar-nos selectable marker cassette (pMPB0097; FIG. 6; SEQ ID NO: 6).

b) Maize Transformation Vectors

To generate an expression vector to validate functionality of the WP04 promoter in maize, the promoter (SEQ ID No: 2) was amplified and cloned into pENTR™ 5'-TOPO TA Cloning vector (Invitrogen, Carlsbad, Calif., USA). The resulting vector was used as Gateway entry vector to generate the binary vector RHF113qcz (FIG. 7; SEQ ID NO: 7) comprising the WP04 promoter regulating expression of the beta-glucuronidase (GUS) gene operably linked to a NOS gene terminator.

c) Biolistic Transformation of Wheat (*Triticum aestivum* L.)

Figure 8:
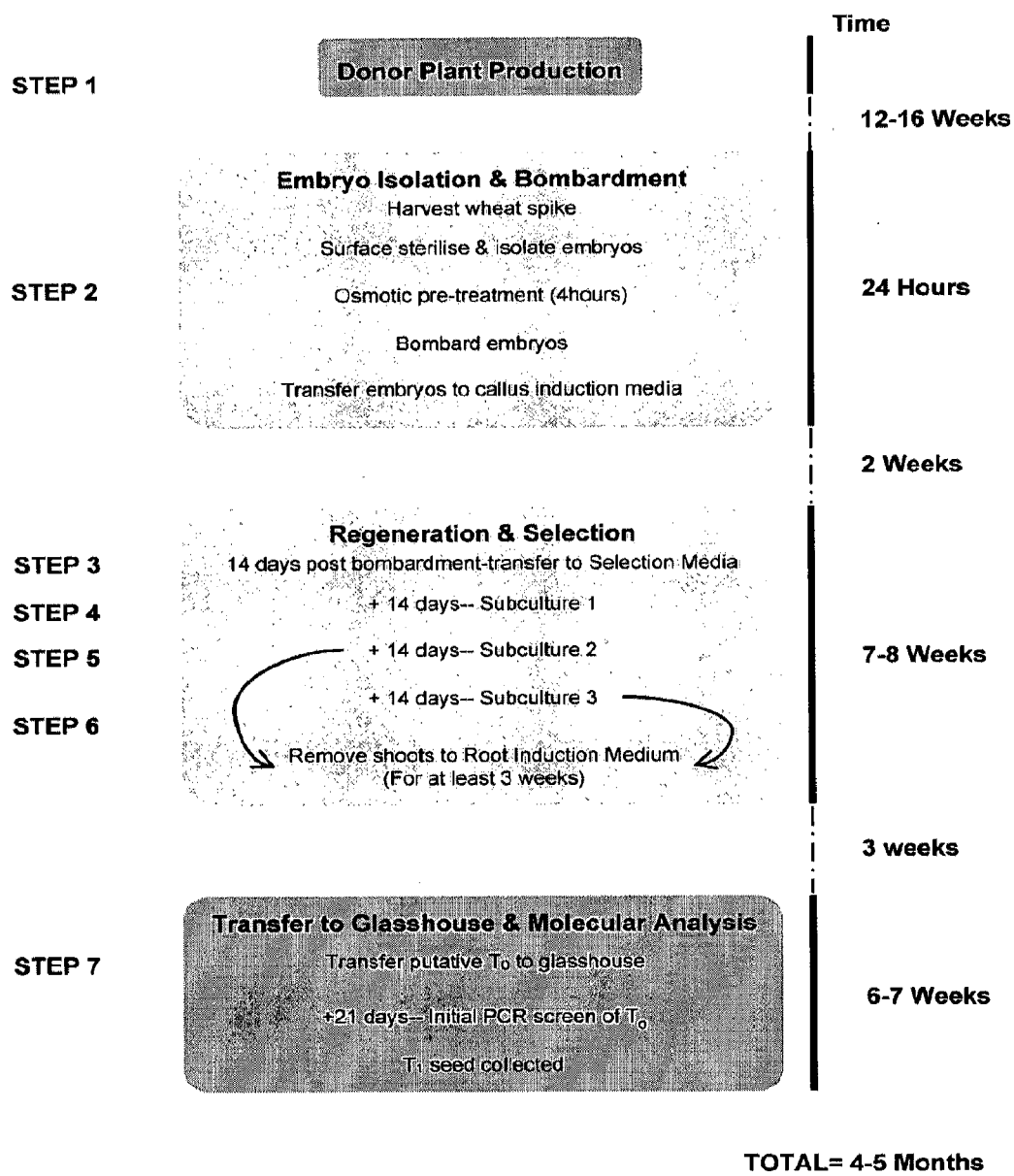
FIG. 8 is a schematic representation showing the process for used to transform wheat using biolistic transformation.
Figure 9:
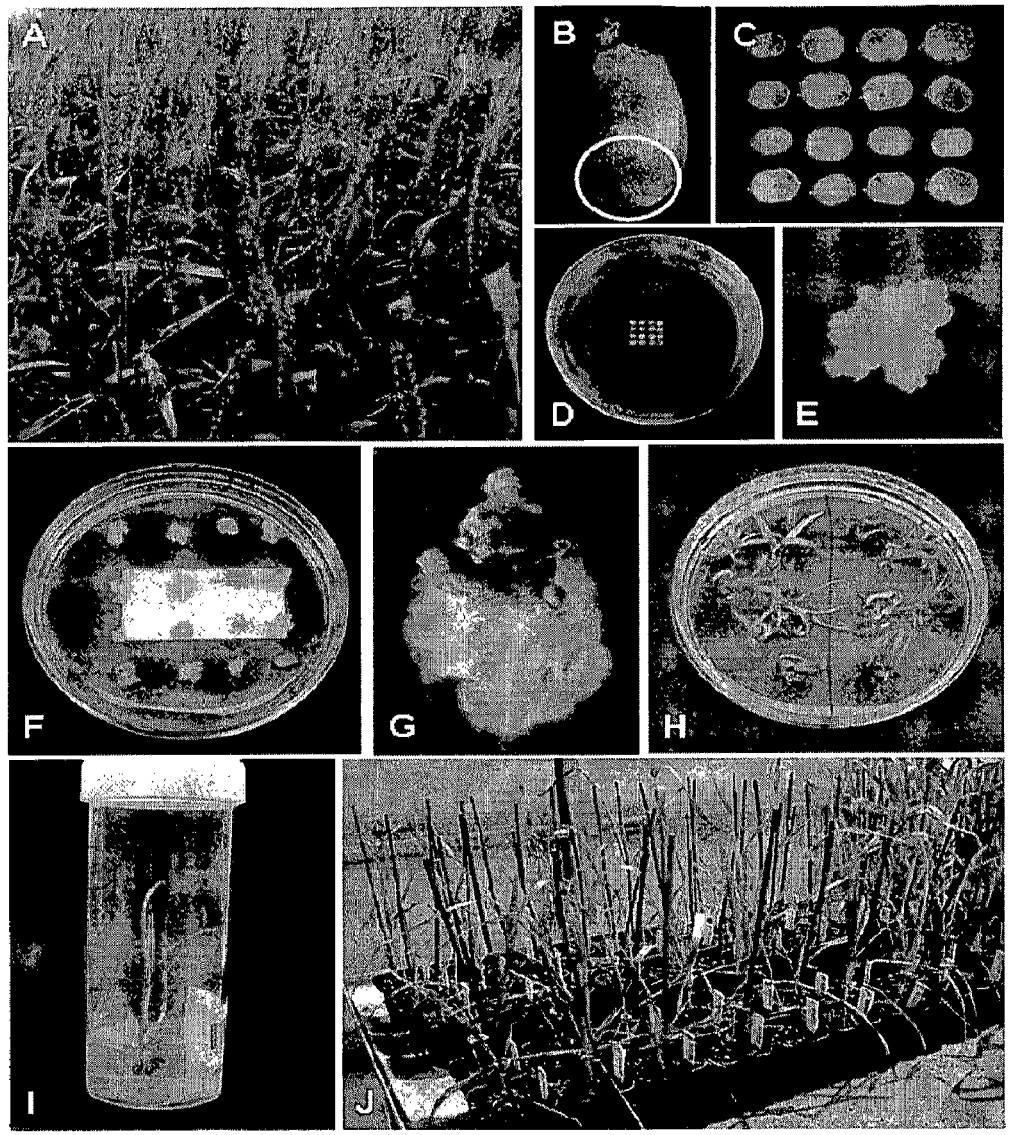
FIG. 9 provides photographic representations showing the various stages of biolistic transformation of wheat (MPB Bobwhite 26). Panel A shows donor plant production; panels B-D show zygotic embryo isolation and bombardment; panels E-H show callus induction and regeneration under glufosinate selection; panel I shows root formation under selection; panel J shows T0 plants growing under containment glasshouse conditions for recovery of transgenic offspring.

The wheat transformation vectors described herein above were used for biolistic transformation of wheat (*Triticum aestivum* L. MPB Bobwhite 26). A schematic of the transformation procedure is depicted in FIG. 8. The transformation procedure includes the following steps:

Step 1 (Donor Plant Production):

*Triticum aestivum* (Bobwhite 26) seed was used for the production of donor plant material. Wheat plants were grown in a nursery mix consisting of composted pine bark, perlite and vermiculite, with five plants per pot to a maximum pot size of 20 cm. Plants were kept under glasshouse conditions at approximately 22-24° C. for 12-16 weeks (FIG. 9a). Once the first spike emerged from the flag leaf, plants were tagged and embryos collected from the tallest heads 12-15 days post anthesis.

Step 2 (Day 1)

Spikes at the desired stage of development were harvested. Caryopses were removed from the spikes and surface sterilised for 20 minutes in a 0.8% (v/v) NaOCl solution and rinsed at least four times in sterile distilled water. Embryos up to 10 mm in length were aseptically excised from each caryopsis (removing the axis) using a dissecting microscope and cultured axial side down on an osmotic medium (E3maltose) consisting of 2× Murashige and Skoog (1962) macronutrients, 1× micronutrients and organic vitamins, 40 mg/L thiamine, 150 mg/L L-asparagine, supplemented with 15% (w/v) maltose, 0.8% (w/v) Sigma-agar and 2.5 mg/L 2,4-D.

Embryos were cultured on 60 mm×15 mm clear polypropylene Petri dishes with 15 mL of media. Culture plates were incubated at 24° C. in the dark for 4 hours prior to bombardment. Embryos were bombarded using a BioRad PDS1000 gene gun at 900 psi and at 6 cm with 1 μg of vector plasmid DNA precipitated onto 0.6 μm gold particles. Following bombardment, embryos were incubated overnight in the dark on the osmotic media. This step is shown in FIGS. 9b, 9c and 9d.

Step 3 (Day 2):

Embryos were transferred to a callus induction medium (E3calli) consisting of 2× Murashige and Skoog (1962) macronutrients and 1× micronutrients and organic vitamins, 40 mg/L thiamine, 150 mg/L L-asparagine, supplemented with 6% (w/v) sucrose, 0.8% (w/v) Sigma-agar and 2.5 mg/L 2,4-D. Embryos were cultured for two weeks at 24° C. in the dark.

Step 4 (Day16):

After 2 weeks of culture on E3 calli, embryos producing embryogenic callus were subcultured onto a selection medium (E3Select) consisting of 2× Murashige and Skoog (1962) macronutrients and 1× micronutrients and organic vitamins, 40 mg/L thiamine, 150 mg/L L-asparagine, supplemented with 2% (w/v) sucrose, 0.8% (w/v) Sigma-agar, 5 mg/L of D,L phosphinothricin (PPT) and no plant growth regulators. Cultures were incubated for further 14 days on E3Select at 24° C. in the light and a 12-hour photoperiod. This step is shown in FIGS. 9e, 9f.

Step 5 (Day 30):

After 14 days culture on E3Select, embryogenic calli were sub-cultured onto fresh E3Select for a further 14 days.

Step 6 (Day 44):

After about 4 weeks on E3Select, developing plantlets (FIGS. 9g, 9h) were excised from the embryonic callus mass and grown for a further three weeks in 65 mm×80 mm or 65 mm×150 mm polycarbonate tissue culture vessels containing root induction medium (RM) as shown in FIG. 9i. Root induction medium consists of 1× Murashige and Skoog (1962) macronutrients, micronutrients and organic vitamins, 40 mg/L thiamine, 150 mg/L L-asparagine, supplemented with 2% (w/v) sucrose, 0.8% (w/v) Sigma-agar, and 5 mg/L of PPT. Remaining embryogenic callus is sub-cultured onto E3Select for another 14 days.

Step 7 (Day 65+):

Regenerated plantlets surviving greater than 3 weeks on root induction medium with healthy root formation were potted into a nursery mix consisting of peat and sand (1:1) and kept at 22-24° C. with elevated humidity under a nursery humidity chamber system (FIG. 9h). After two weeks, plants were removed from the humidity chamber and hand watered and liquid fed Aquasol™ weekly until maturity. The $T_0$ plants were sampled for genomic DNA and molecular analysis. T1 seeds are collected and planted for high-throughput Q-PCR analysis.

c) *Agrobacterium*-Mediated Transformation of *Arabidopsis thaliana*

Figure 10:
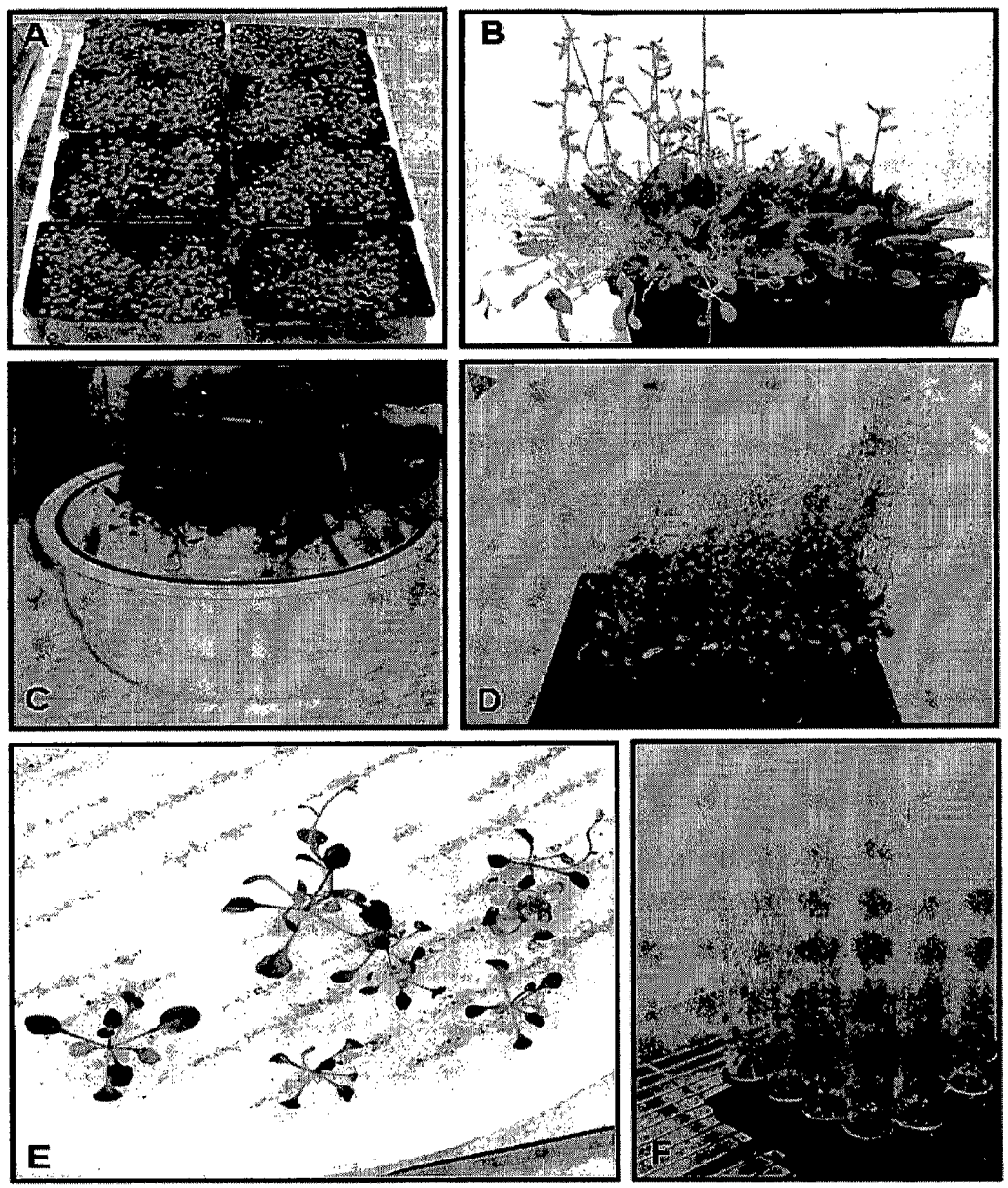
FIG. 10 provides photographic representations showing the various stages of *Agrobacterium*-mediated transformation of *Arabidopsis thaliana* using vacuum infiltration. Panel A shows wheat (MPB Bobwhite 26). Panel A shows *Arabidopsis thaliana* Columbia seeds germinated in small punnets; Panels B and C show approximately 4-week old seedlings used for floral dipping in *Agrobacterium* suspension under vacuum; Panel D shows *Arabidopsis* plants isolated and grown to maturity; Panels E and F show seeds surface sterilised and plated on selection media with putative transgenic plants being transferred to soil with an ARACON™ base and tube for T2 seed collection.

Binary vectors described herein above are transformed into the *Agrobacterium tumefaciens* strain AGL1 and in planta transformation of *Arabidopsis thaliana* is performed via vacuum infiltration of floral tissues. Briefly, a container (500 or 1,000 mL capacity) is placed inside a vacuum dessicator and filled with bacterial suspension. A punnet containing approximately 4-week-old *Arabidopsis* plants is inverted and immersed in the bacterial suspension, including rosette leaves. The lid of the dessicator was attached and vacuum applied until the gauge read approximately 250 mm (10 inches) Hg. Plants are left under vacuum for two minutes. Plants are then removed and excess bacterial suspension is allowed to drain from the plants. The plants are returned to the growth room, covered with a dome or plastic wrap and kept away from direct light overnight. The following day plants are returned to direct light and the dome or plastic wrap is removed. Plants are allowed to grow until the siliques are fully developed and dry seed is harvested. *Arabidopsis* seed is surface-sterilised and plated on selective media and putative transgenic *Arabidopsis* plants transferred to soil for the recovery of $T_2$ transgenic seed. These steps are shown in FIG. 10.

d) *Agrobacterium*-Mediated Transformation of Maize

The transformation of maize is performed using, for example, a technique described in International Patent Publication No. WO 2006/136596 A2 and/or WO 2007/014744 A2.

Step 1: Preparation of *Agrobacterium*

Briefly, inoculums of *Agrobacterium* were streaked from glycerol stocks onto YP agar medium containing appropriate antibiotics (e.g. 50 mg/L spectinomycin and/or 10 mg/L tetracycline). The bacterial cultures are incubated in the dark at 28° C. for 1 to 3 days, or until single colonies are visible. The obtained plate is stored at 4° C. for 1 month and used as a master plate to streak out fresh cells. Fresh cells are streaked onto YP agar with the appropriate antibiotic from a single colony on the master plate, at least 2 days in advance of transformation. These bacterial cultures are incubated in the dark at 28° C. for 1 to 3 days.

Alternatively a frozen *Agrobacterium* stock is prepared by streaking *Agrobacterium* cells from a frozen stock onto a plate B-YP-002 (YP+50 mg/L spectinomycin+10 mg/L tetracycline), and grown at 28° C. for 2 to 3 days. A master plate is produced and stored at 4° C. for up to a month. From the master plate, cells are picked and added to a flask containing 25 ml liquid B-YP-000 medium supplemented with 50 mg/L Spectinomycin+10 mg/L tetracycline. The flask is incubated at 28° C. on a shaker set at 300 rpm for 2 to 3 days. A frozen *Agrobacterium* stock is prepared by mixing 1 part of the resulting culture with 1 part of sterile 30% glycerol. The mixture is then vortexed to mix well and 10 μl of the *Agrobacterium*/glycerol mixture dispensed to an Eppendorf tube. This stock is stored at −80° C.

To prepare cells for infection, cells from the bacterial culture described in the previous paragraphs are suspended in 1.0 to 1.8 mL LS-inf medium supplemented with 100 μM acetosyringone. This yields a bacterial suspension with approximate optical density (OD600) between 0.5 and 2.0. The mixture is vortexed for 0.5 to 3 hours. Approximately 100 μL of the *Agrobacterium* cell suspension is mixed with 900 μL of LS-inf solution in a cuvette, and the optical density (OD600) is measured. The optical density ($OD_{600}$) of the *Agrobacterium* solution is adjusted to between about 0.6 and about 2.0 with LS-Inf (with 100 μM acetosyringone) solution. This *Agrobacterium* suspension is vortexed in the LS-inf+acetosyringone media for at least 0.5 to 3 hours prior to infection.

Alternatively, *Agrobacterium* suspensions for maize transformation are prepared as follows, two days before transformation, *Agrobacteria* solution from a frozen stock is streaked onto a plate containing B-YP-002 (solidified YP+50 mg/L spectinomycin+10 mg/L tetracycline) and grown at 28° C. in the dark for two days. About 1 to 4 hrs before transformation, a sample of bacterial cells is added to 1.5 ml M-LS-002 medium (LSinf+200 μM acetosyringone) in a 2 ml Eppendorf tube and the sample vortexed at about 1000 rpm for 1 to 4 hrs. The OD600 of the resulting solution should be in the range of about 0.6 to about 1.0 or about 108 cfu/mL.

For the purpose of the following example maize are transformed with *Agrobacterium tumefaciens* strain LBA4404 or disarmed *Agrobacterium* strain K599 (NCPPB 2659) transformed with a binary vector containing an acetohydroxyacid synthase (ahas gene) (as a selectable marker) and a GUS reporter gene.

Step 2: Surface Sterilization of Maize Ear and Isolation of Immature Embryos

Maize ears are harvested from one or more plants in a greenhouse 8 to 12 days after pollination. All husk and silks are removed and ears are transported into a tissue culture laboratory. A large pair of forceps is inserted into the basal end of the ear and the forceps are used as a handle for handling the cob.

Optionally, when insects/fungus are present on the ear, the ear is sterilized with 20% commercial bleach for 10 min (alternatively 30% Clorox solution for 15 min), and then rinsed with sterilized water three times. While holding the cob by the forceps, the ear is completely sprayed with 70% ethanol and then rinsed with sterile ddH$_2$O.

Step 3: Inoculation

Method 1: The Modified "Tube" Method

The cob with the forceps handle is placed in a large Petri plate. The top portion (approximately two thirds) of each kernel is removed, e.g., with a scalpel. The immature embryos are then excised from the kernels on the cob, e.g., with a scalpel. In this respect, the scalpel blade is inserted on an angle into one end of a kernel, and the endosperm is lifted upwards away from the embryo which is positioned under the endosperm. Excised embryos are collected in a microfuge tube (or a small Petri plate) containing roughly 1.5 to 1.8 mL of *Agrobacterium* suspension in LS-inf liquid medium containing acetosyringone. The tube containing embryos is hand-mixed several times, and the incubated at room temperature (20 to 25° C.) for 30 min. Excess bacterial suspension is removed from the tube/plate with a pipette. Immature embryos and bacteria are transferred in the residue LS-inf medium to a Petri plate containing co-cultivation agar medium. The immature embryos are placed on the co-cultivation medium with the flat side down (scutellum upward). The majority of the excess bacterial suspension is removed with a pipette. A small amount of liquid is left on the plate to avoid drying of the embryos while plating.

The plate cover is left open in a sterile hood for about 15 min to evaporate excess moisture covering immature embryos. Petri dishes are sealed and incubated in the dark at 22° C. for 2 to 3 days. A selection of immature embryos (e.g., three to five embryos) is removed for GUS staining if a GUS construct is used to assess transient GUS expression.

Method 2: The "Prop" Method

Excised immature embryos are directly placed onto co-cultivation medium with the flat side down (scutellum upward). Five microliters of diluted *Agrobacterium* cell suspension is added each immature embryo. Excess moisture covering immature embryos is evaporated by leaving the plate cover open in the hood for about 15 min. The plate is then sealed and incubated in the dark at 22° C. for 2 to 3 days. A selection of immature embryos (e.g., three to five embryos) is then analysed for GUS staining if a GUS construct is used to assess transient GUS expression.

Step 4: Recovery

After co-cultivation, the embryos are transferred to recovery media and incubated in the dark at 27° C. for about 5 to 10 days, with the scutellum side up.

Step 5: Selection

Immature embryos are transferred to first selection media. Petri plates are sealed and incubated in the dark at 27° C. for 10 to 14 days (First selection). All immature embryos that produce variable calli are subcultured into second selection media. At this stage, any shoots that have formed are removed. Plates are then sealed and incubated in the dark at 27° C. for about 2 weeks under the same conditions for the first selection. Regenerable calli are then excised from the scutellum under a stereoscopic microscope. Calli are transferred to fresh the 2nd selection media, sealed and incubated in the dark at 27° C. for 2 weeks.

Step 6: Regeneration and Transplanting of Transformed Plants

Proliferating calli are excised in the same manner as for second selection and transferred to regeneration media in 25×100 mm plates. Plates are sealed and placed under light (ca. 2,000 lux; 14/10 hr light/dark) at 25° C. or 27° C. for two to three weeks, or until shoot-like structures are visible.

Calli sections with regenerated shoots or shoot-like structures are transferred to a Phytatray or Magenta box containing rooting medium and incubated for 2 weeks under the same conditions discussed in the previous paragraph, or until rooted plantlets have developed. After 2 to 4 weeks on rooting media, calli that still have green regions are transferred to fresh rooting Phytatrays. Seedling samples are taken for Taq-Man analysis to determine the number of transfer DNA (T-DNA) insertions.

Rooted seedlings are then transferred to Metromix soil in greenhouse and covered with a plastic dome until seedlings have established, which is generally about one week. Plants are maintained with daily watering, and liquid fertilizer twice a week. When plants reach the 3 to 4-leaf stage, they are fertilized with Osmocote™. If needed, putative transgenic plants are sprayed with 70 to 100 g/ha Pursuit™, and grown in the greenhouse for another two weeks. Non-transgenic plants generally develop herbicidal symptoms or die within this time. Surviving plants are transplanted into 10 inch pots with Metromix and 1 teaspoon Osmocote™.

At the flowering stage, tassels of transgenic plants are bagged with brown paper bags to prevent pollen escape. Pollination is performed on the transgenic plants. If silking and anthesis are not synchronized, a wild-type pollen donor or recipient plant with same genetic background as the transgenic $T_0$ plant is used for cross-pollination. $T_1$ seeds are harvested, dried and stored properly with adequate label on the seed bag. After harvesting the transgenic $T_1$ seeds, $T_0$ plants including the soil and pot may be sterilized by heat-treatment in an autoclave.

Using such a procedure, the binary vectors pRHF112 and pRHF121 were used to produce transformed maize.

Figure 11:
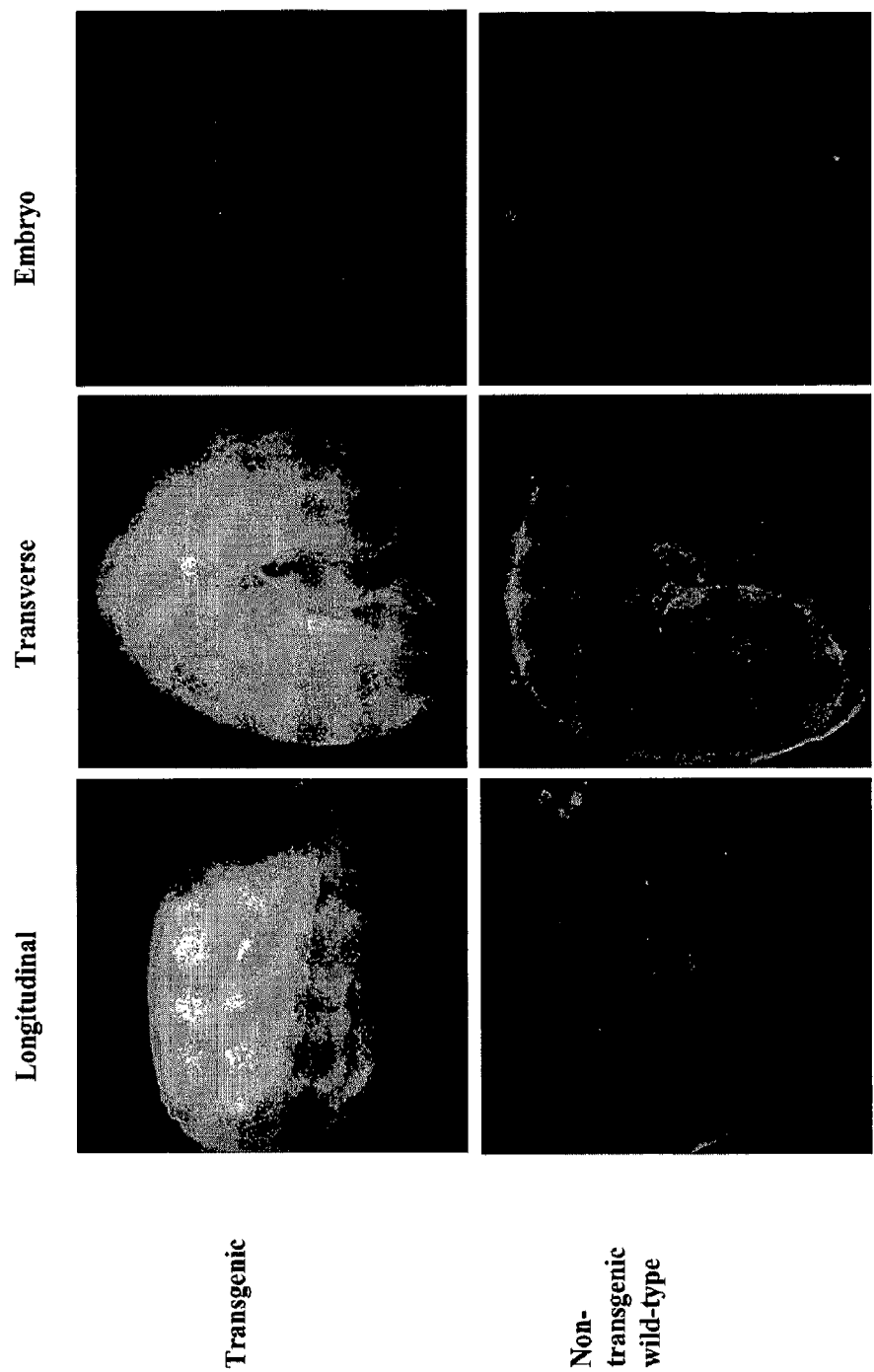
FIG. 11 provides photographic representations showing GFP expression driven by the wheat WP04 promoter at 10-14 DAP localized to the endosperm of transgenic seeds including the basal endosperm transfer layer (BETL) cells, but not in embryo or non-transgenic seed.
Figure 12:
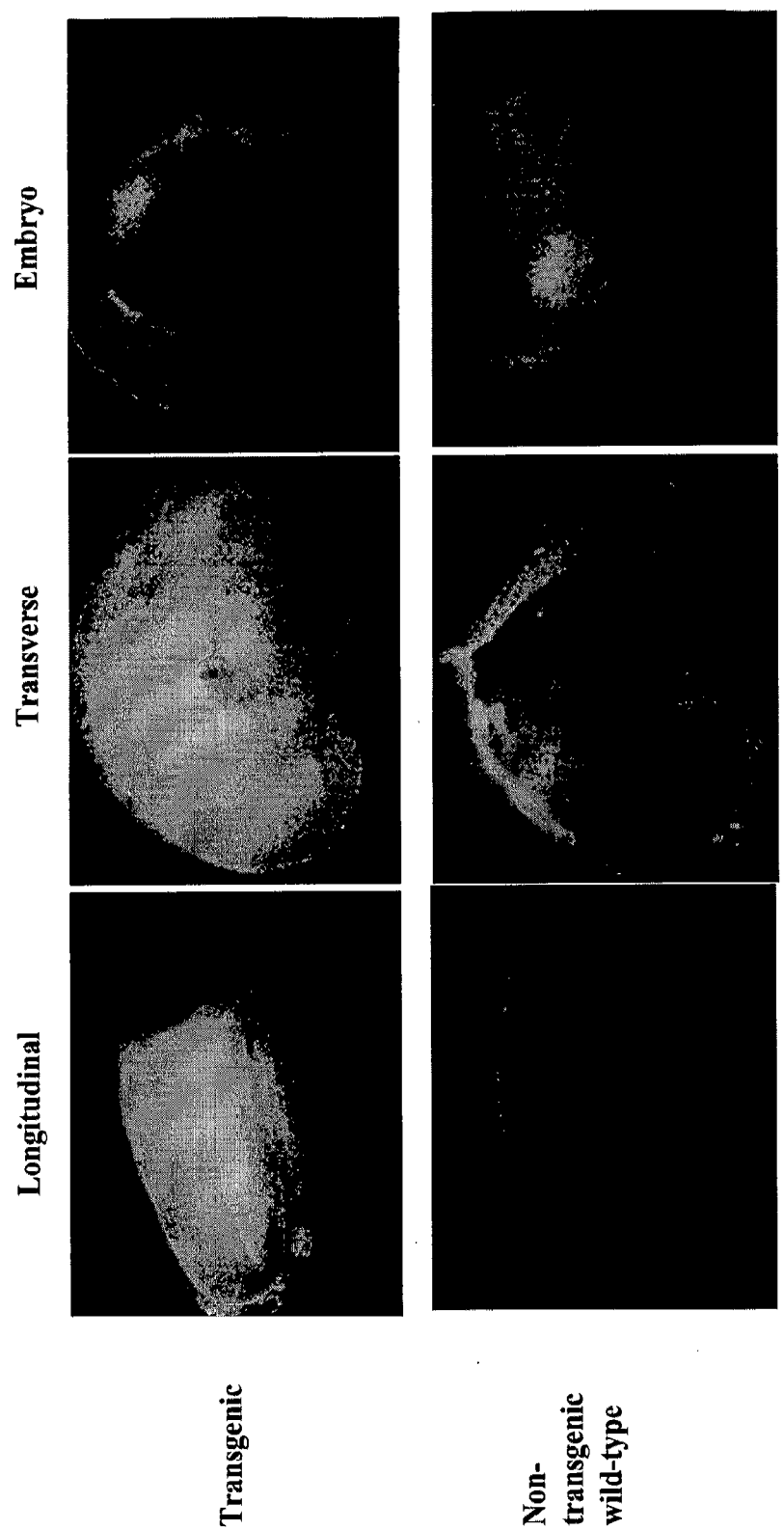
FIG. 12 provides photographic representations showing GFP expression driven by the wheat WP04 promoter at 25-30 DAP localized to the endosperm of transgenic seeds including the basal endosperm transfer layer (BETL) cells, but not in embryo or non-transgenic seed.

2. Plant Transformation Results
a) Expression of Reporter Gene in Wheat Under Control of WP04 Promoter The WP04::sgfp-nos transformation vector was used for biolistic transformation of wheat (*Triticum aestivum* L. MPB Bobwhite 26) and the resulting transgenics were sectioned and analysed for presence of GFP to demonstrate the spatial expression of the wheat promoters (FIGS. 11 and 12). Expression of GFP under control of the WP04 promoter was detected predominantly in the endosperm including the basal endosperm of the developing seed about ten days after pollination (DAP) and continues throughout grain development e.g., to about 30 DAP. This corresponds to the period of grain filling. No expression was evident in vegetative organs e.g., leaves, root, stem node, stem internode or glumes, or in the reproductive tissues e.g., anthers, ovaries or pollen, or in mature seed (data not shown). These data indicate that the WP04 promoter both confers endosperm-selective expression including basal endosperm expression, and even more likely strictly endosperm-specific expression, on a gene to which the promoter is operably connected in developing seeds of wheat.

b) Expression of Reporter Gene in Maize Under Control of WP04 Promoter

Figure 7:
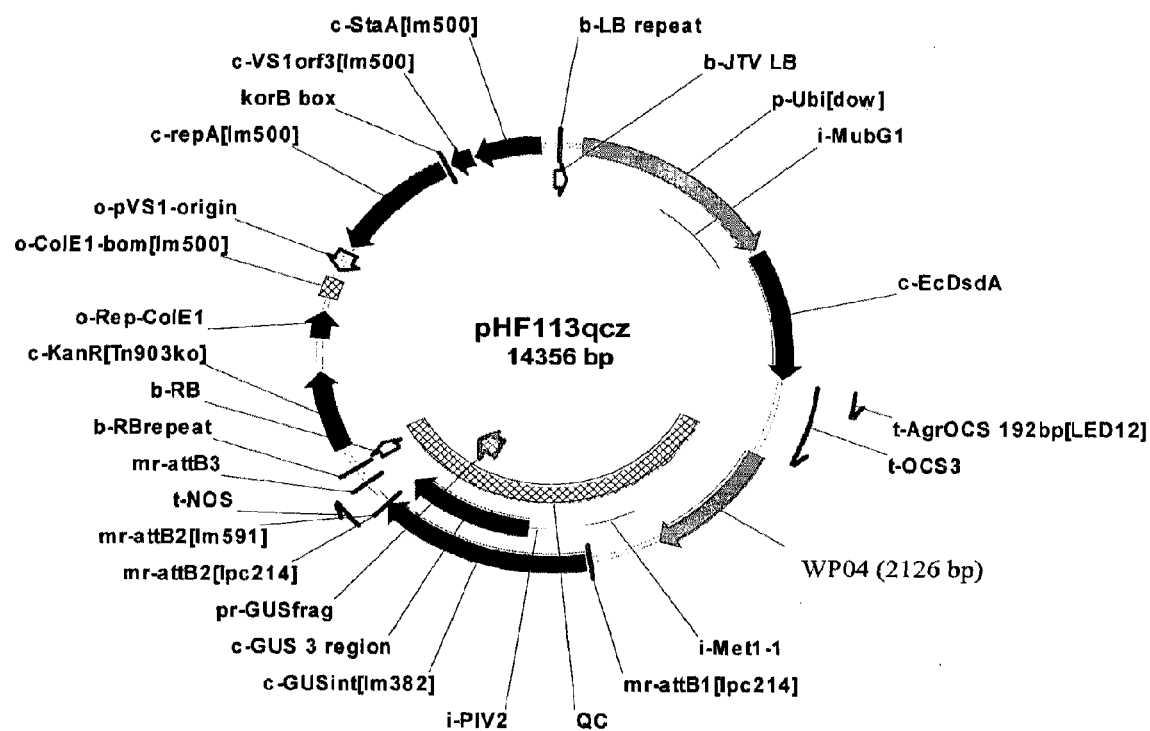
FIG. 7 is a representation showing the vector RHF113qc (SEQ ID NO: 7) for expression of the WP04::GUS-nos expression cassette in transgenic maize.

The binary vector RHF11qcz (FIG. 7; SEQ ID NO: 7), comprising a GUS expression cassette driven by the wheat WP04 promoter was used to transform maize plants. The resulting transgenics were sectioned and analyzed for GUS expression. Kernals at 15 DAP were embedded in wax, sectioned, and stained for GUS expression and observed by light microscopy to identify cell-type specific expression.

Figure 13:
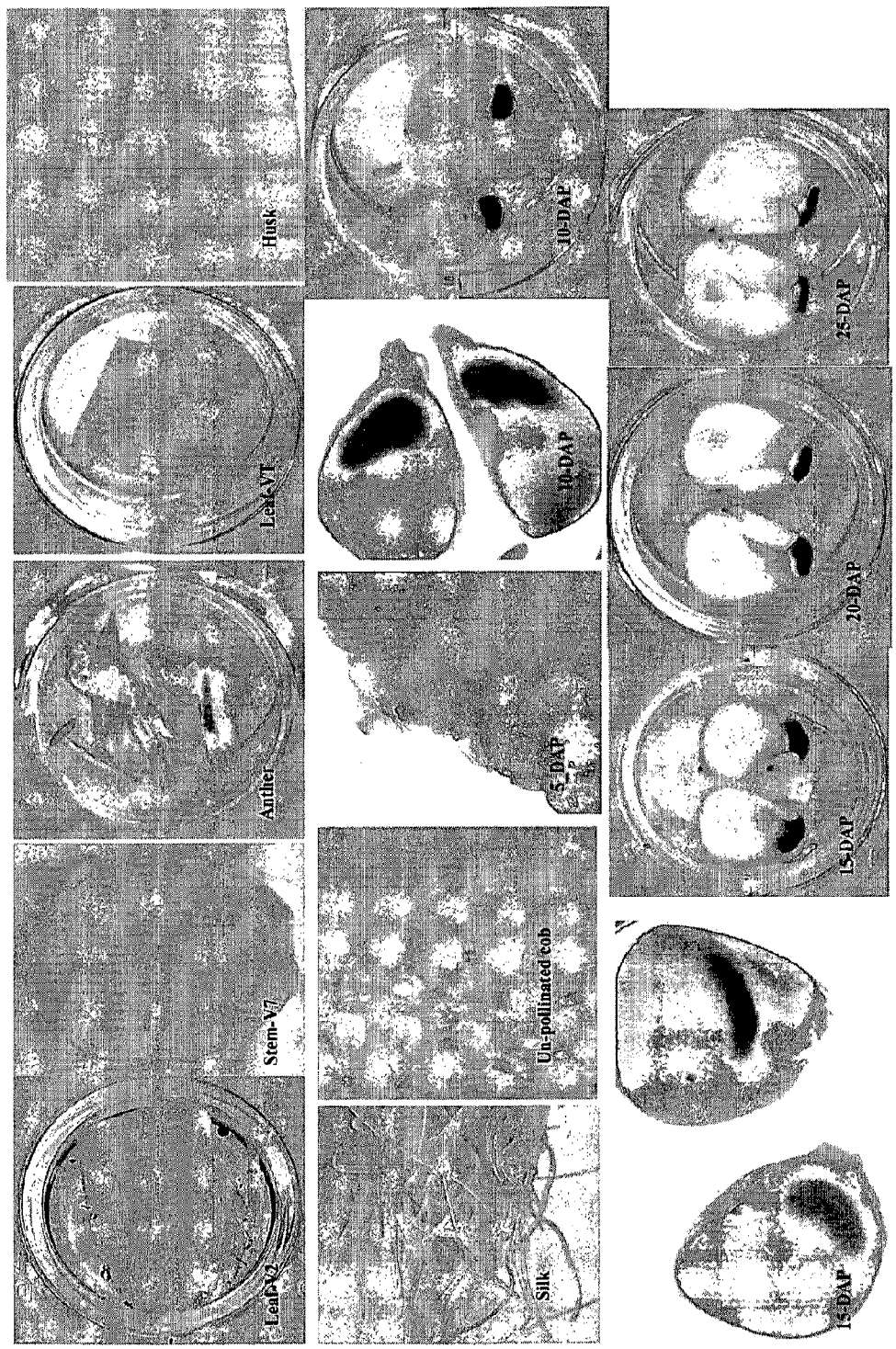
FIG. 13 provides photographic representations showing strong spatial expression of GUS reporter gene driven by the wheat WP04 promoter in the endosperm of transgenic maize seeds, predominantly in the basal endosperm transfer layer (BETL) cells. Expression is visible at 5 DAP in basal endosperm of transgenic seed and continues at least until 25 DAP.
Figure 14:
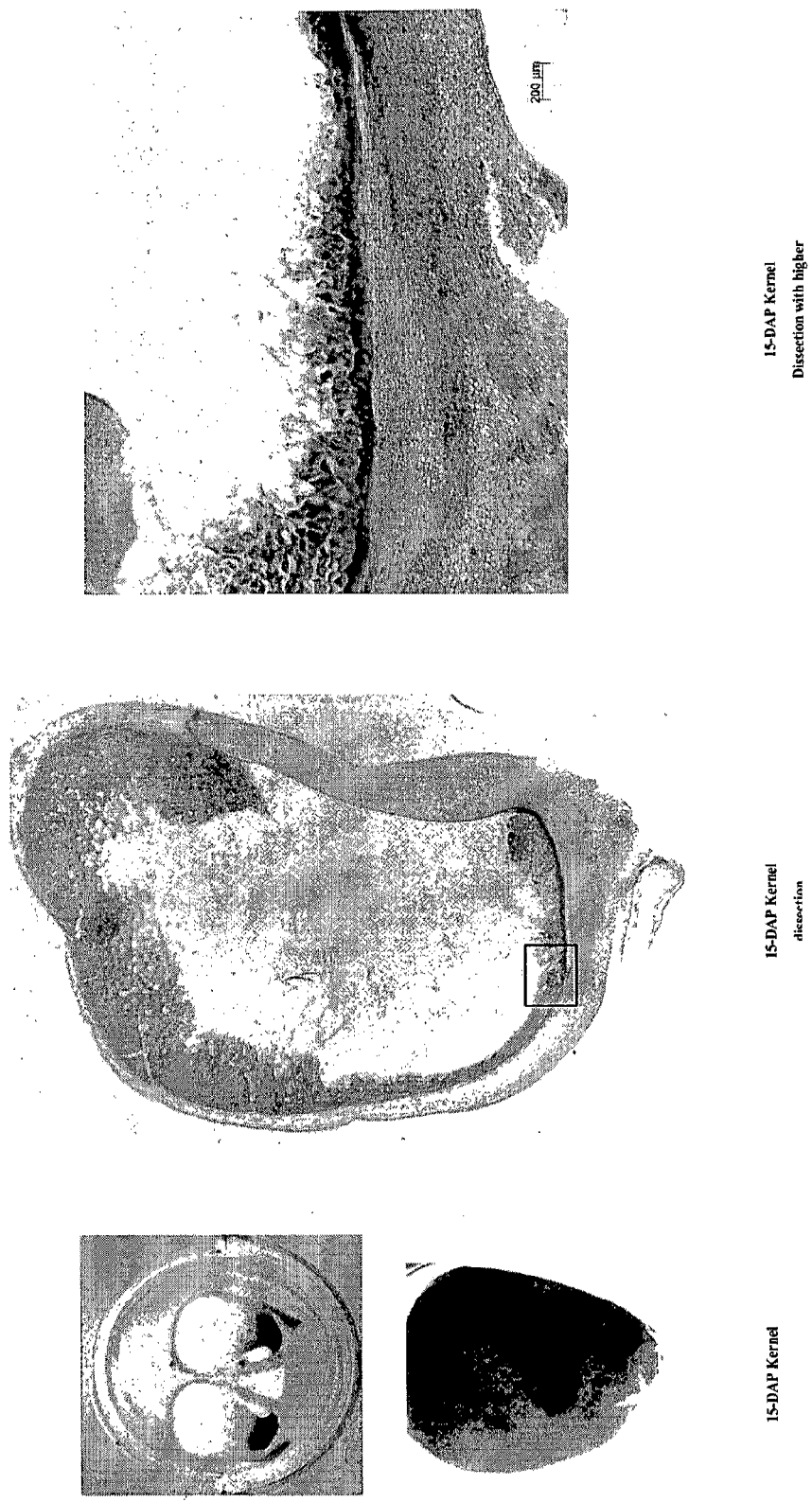
FIG. 14 provides photographic representations of longitudinal sections (middle and right panels) of developing seed at 15 DAP (left panels) showing localization of expression of GUS reporter gene driven by the wheat WP04 promoter to the basal endosperm, especially BETL cells, of transgenic maize seeds. The boxed region in the middle panel corresponds to the right panel at lower magnification than shown for the right panel. The scale for the right panel is shown in the lower right corner thereof.
Figure 15:
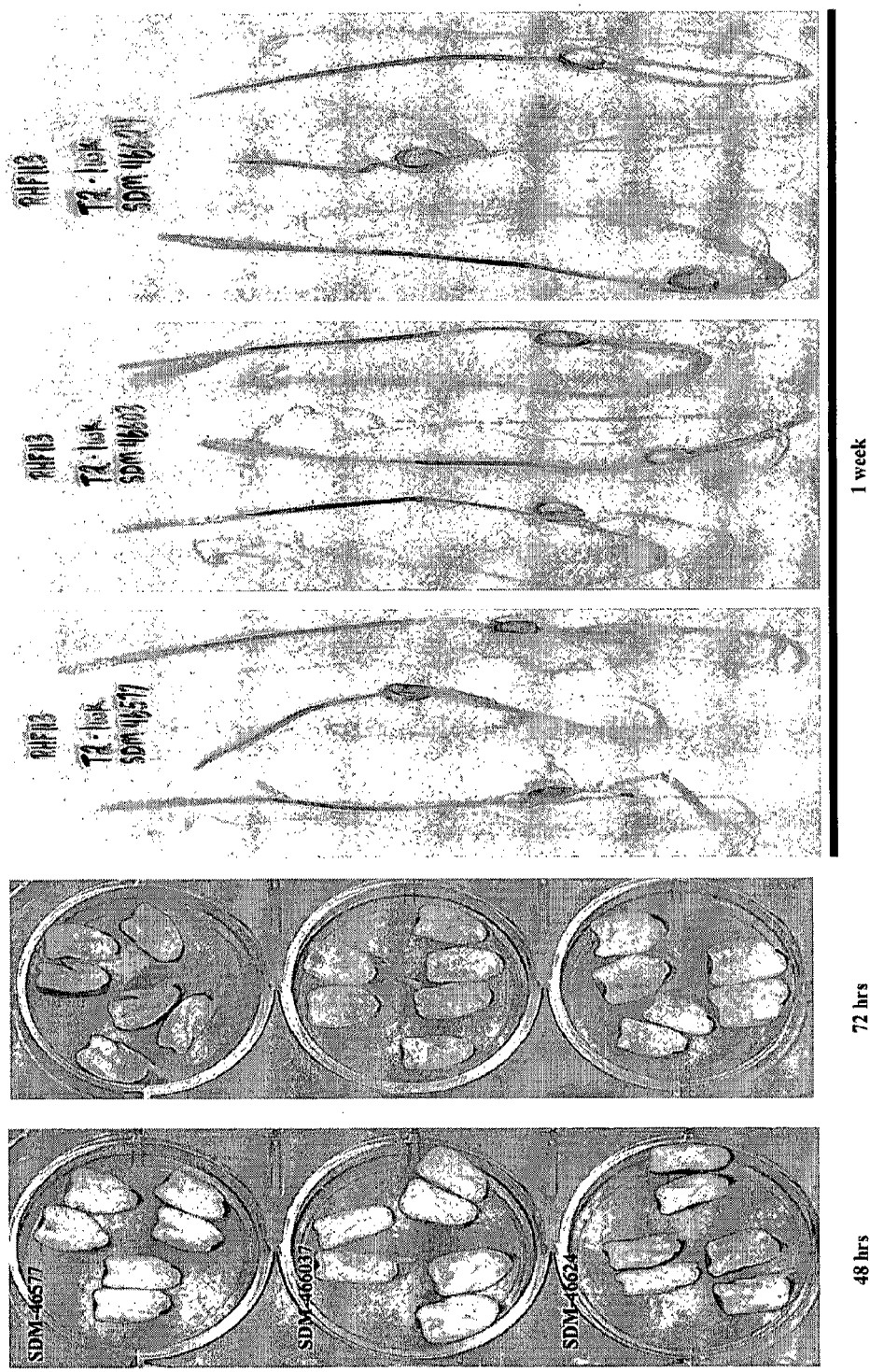
FIG. 15 provides photographic representations showing low expression of GUS reporter gene driven by the wheat WP04 promoter in the basal endosperm of germinating maize seeds following 48 hours imbibation (left row), 72 hours imbibation (second row), and in germinated seedlings (last 3 rows).

Data presented in FIGS. 13 through 15 demonstrate that expression of the GUS reporter gene under control of the WP04 promoter is predominantly localized to the basal endosperm, especially the basal endosperm transfer layer cells (FIG. 14), five DAP and throughout grain development e.g., at least until 25 DAP.

As with expression in wheat, no reporter expression was apparent in vegetative organs e.g., leaves, root or stem, or in husks. However, expression was also evident in the silks of maize (data not shown).

These data indicate that the WP04 promoter confers endosperm-selective expression, especially in BETL cells, on a gene to which the promoter is operably connected in developing seeds of maize.

EXAMPLE 4

Characterization of WP04 Equivalents from Monocots

This example provides support for a sub-genus of endosperm-selective promoters in monocotyledonous plants that are equivalents to the isolated wheat-derived promoter WP04 e.g., by virtue of regulating genes that are structurally related to the genes that the WP04 promoter controls in its native context.

1. Equivalents of WP04 in Maize, Barley and Rice

To identify equivalent promoters to WP04, the wheat Affymetrix Consensus Ta.10064.1.S1_at sequence was used as a BLASTN query against the NCBI non-redundant nucleotide database and a database of wheat assembled ESTs downloaded from the Plant Genome Database (plantgdb.org/). This approach identified two wheat-derived sequences in the GenBank non-redundant database, the closest match being assigned Accession No. AJ890018.1 with 93% maximum identity to WP04. A barley clone assigned Accession No. Z69631.1 with 85% maximum identity was also identified.

A search of the wheat assembled ESTs also identified a sequence with 98% maximum identity assigned Accession No. PUT-153a-*Triticum_aestivum*-74777. An alignment of Accession Nos. AJ890018.1 and PUT-153a-*Triticum_aestivum*-74777 between the terminal 76 nucleotides of SEQ ID NO: 2 and the Genome Walker primer sequences used to identify the WP04 promoter confirmed the relatedness of Accession Nos. AJ890018.1 and PUT-153a-*Triticum_aestivum*-74777 to the structural gene regulated by the WP04 promoter in its native context (not shown). The sequences of the Genome Walker primer sequences used to identify the WP04 promoter were:

(i) CCATAGTCATGGCAAAACTCATGTGCA (SEQ ID NO: 18); and (ii) CTCACTATTGGGGTAGCCATGTCGGCT (SEQ ID NO: 19).

A second clone assigned Accession No. PUT-153a-*Triticum_aestivum*-25138 having 94% maximum identity was also identified by this approach.

Figure 16:
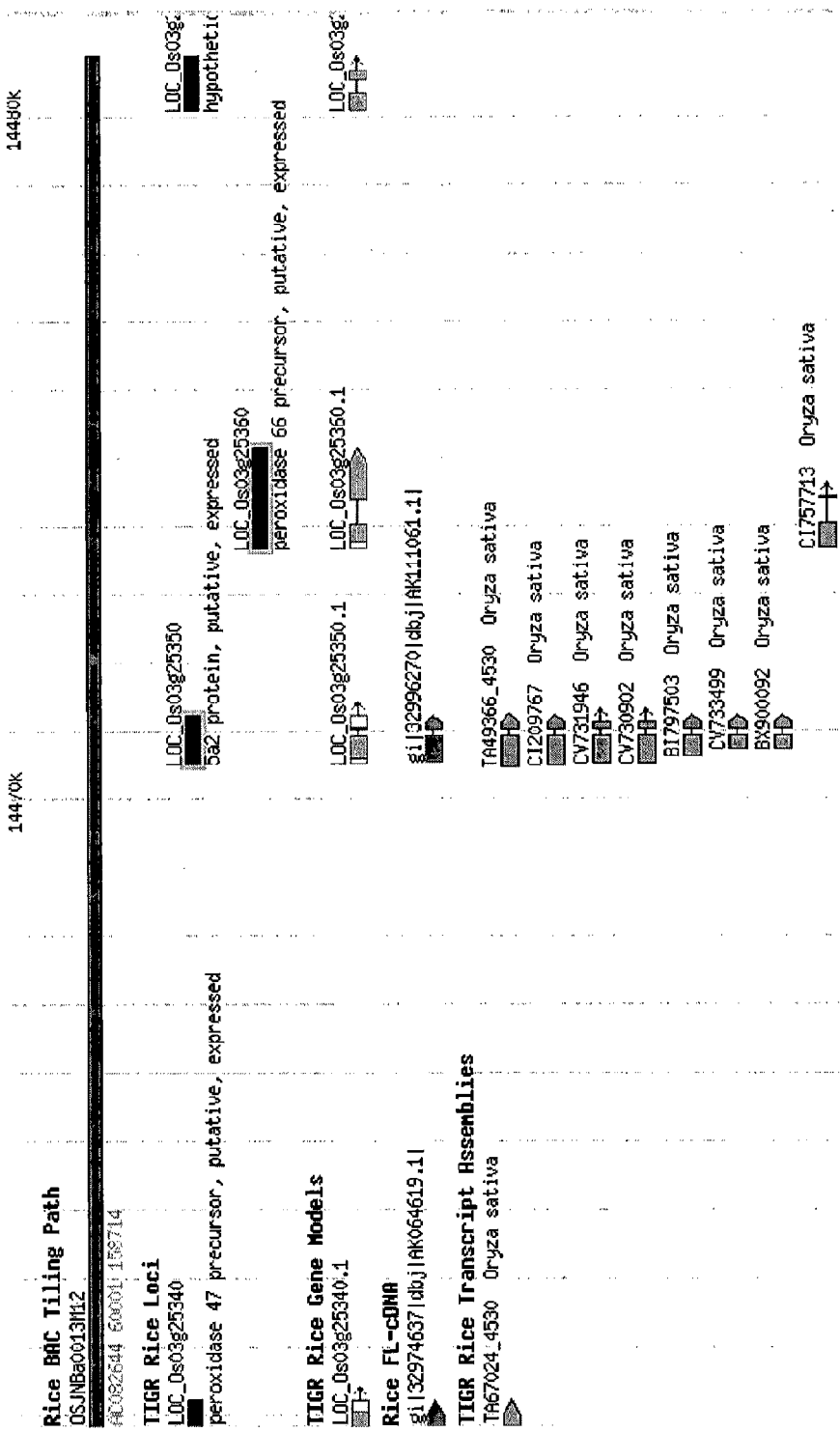
FIG. 16 provides a schematic representation of the rice locus designated LOC_Os03g25350 and 20 kb flanking sequence as shown in the TIGR genome browser.

The PUT-153a-*Triticum_aestivum*-74777 sequence was used to search cDNA sequences extracted from the database of rice pseudomolecules produced by the TIGR Rice Genome Annotation Project (blast.jcvi.org/euk-blast/index.cgi) using the BLASTN algorithm with a nucleotide mismatch penalty (−q) of −1. A related sequence was identified, assigned Accession No. LOC_Os03g25350 encoding a putative peroxidase protein designated 5a2 (FIG. 16). MPSS expression profiling indicates that LOC_Os03g25350 is expressed in 6 day old developing rice seed e.g., consistent with the expression pattern for SEQ ID NO: 1 which is regulated in its native context by the WP04 promoter. The positioning of LOC_Os03g25350 as determined using the TIGR genome browser shows that the next upstream structural gene is located approximately 10 kb from LOC_Os03g25350.

Contig assemblies of the maize genome assembled by the Plant Genome Database (plantgdb.org/) were downloaded and searched using the complete genomic sequence of LOC_Os03g25350 with a nucleotide mismatch penalty (−q) of −1. One maize genomic DNA assembly, assigned Accession No. ZmGSStuc11-12-04.13411.1 was identified having close sequence identity to residues 232 to 311 of LOC_Os03g25350 (FIG. 17). Multiple Alignments as shown in FIG. 18 were performed for the following sequences:

(i) Genome Walker primer sequences used to identify the WP04 promoter;
(ii) the terminal 76 nucleotides of WP04 (SEQ ID NO: 2);
(iii) the PUT-153a-*Triticum_aestivum*-74777 sequence;
(iv) the Affymetrix consensus wheat sequence Ta.10064.1.S1_at;
(v) the wheat sequence assigned Accession No. AJ890018.1;
(vi) the maize genome sequence for Accession No. ZmGSStuc11-12-04.13411.1;
(vii) the maize transcript assembly identified using ZmGSStuc11-12-04.13411.1,
(viii) the rice cDNA for LOC_Os03g25350;
(ix) the rice genomic sequence (indica cultivar) for LOC_Os03g25350, and
(x) the rice genomic sequence (japonica cultivar) for LOC_Os03g25350.

This alignment permitted identification of a putative translation start codon (not shown). The 3'-end of the WP04 promoter sequence (SEQ ID NO: 2) aligned to these sequences upstream of this putative translation start codon.

These data suggest that Accession No. LOC_Os03g25350, Accession No. ZmGSStuc11-12-04.13411.1, and Accession No. PUT-153 a-*Triticum_aestivum*-74777 comprise equivalents, e.g., functional and/or structural equivalents, to the WP04 promoter exemplified herein.

The sequence of the 5'-upstream region of ZmGSStuc11-12-04. 13411.1 is presented in SEQ ID NO: 8. The full-length promoter sequence (SEQ ID NO: 8) is de-limited at the 3'-end by alignment with the maize consensus transcript PUT-157a-*Zea mays*-015099. The ATG at the end of the promoter is the predicted ATG from the TIGR maize gene index sequence PUT-157a-*Zea mays*-015099 when the maize sequences are aligned with the rice and wheat sequences (data not shown). The 5'-end of the promoter is defined by the end of the ZmGSStuc11-12-04.13411.1 consensus sequence as no ESTs match this end of the sequence.

EXAMPLE 5

Structural Analysis of Promoters

This example provides support for structural conservation between the functional endosperm promoters WP04 (SEQ ID NO: 2) and the 5'-upstream sequence of Accession No. ZmGSStuc11-12-04.3411.1 (SEQ ID NO: 8). This analysis is readily applied to any variant of the exemplified promoters, including SEQ ID NO: 9 and/or 10.

Briefly, the nucleotide sequences of the wheat and maize promoters set forth in SEQ ID NOs: 2 and 8 were analyzed to determine cis-acting elements in the promoters, using PLACE (Plant cis-acting DNA elements) as described in Higo et al., *Nucl. Acids Res.* 27: 297-300, 1999, and available from National Institute of Agrobiological Sciences, Ibaraki, Japan. The results of this analysis are set forth in Tables 3 and 4.

TABLE 3

PLACE analysis results of the WP04 (2126 bp) promoter

| SITE_NAME | POSITION | STRAND | CONSENSUS |
|---|---|---|---|
| 2SSEEDPROTBANAPA | 1289 | (+) | CAAACAC |
| AACACOREOSGLUB1 | 523 | (+) | AACAAAC |
| AACACOREOSGLUB1 | 750 | (+) | AACAAAC |
| ABRELATERD1 | 274 | (−) | ACGTG |
| ABRELATERD1 | 1616 | (−) | ACGTG |
| ABRERATCAL | 1615 | (−) | MACGYGB |
| ACGTATERD1 | 275 | (+) | ACGT |
| ACGTATERD1 | 1617 | (+) | ACGT |
| ACGTATERD1 | 275 | (−) | ACGT |
| ACGTATERD1 | 1617 | (−) | ACGT |
| AGMOTIFNTMYB2 | 1409 | (+) | AGATCCAA |
| AMMORESIIUDCRNIA1 | 997 | (−) | GGWAGGGT |
| AMYBOX1 | 148 | (+) | TAACARA |

TABLE 3-continued

PLACE analysis results of the WP04 (2126 bp) promoter

| SITE_NAME | POSITION | STRAND | CONSENSUS |
|---|---|---|---|
| AMYBOX1 | 749 | (+) | TAACARA |
| AMYBOX2 | 955 | (−) | TATCCAT |
| AMYBOX2 | 1705 | (−) | TATCCAT |
| ANAERO1CONSENSUS | 546 | (+) | AAACAAA |
| ANAERO1CONSENSUS | 1051 | (+) | AAACAAA |
| ANAERO1CONSENSUS | 1107 | (+) | AAACAAA |
| ANAERO1CONSENSUS | 596 | (−) | AAACAAA |
| ARFAT | 1256 | (−) | TGTCTC |
| ARR1AT | 1035 | (+) | NGATT |
| ARR1AT | 1016 | (+) | NGATT |
| ARR1AT | 515 | (+) | NGATT |
| ARR1AT | 129 | (+) | NGATT |
| ARR1AT | 216 | (+) | NGATT |
| ARR1AT | 574 | (+) | NGATT |
| ARR1AT | 658 | (+) | NGATT |
| ARR1AT | 1483 | (+) | NGATT |
| ARR1AT | 83 | (−) | NGATT |
| ARR1AT | 103 | (−) | NGATT |
| ARR1AT | 279 | (−) | NGATT |
| ARR1AT | 372 | (−) | NGATT |
| ARR1AT | 396 | (−) | NGATT |
| ARR1AT | 419 | (−) | NGATT |
| ARR1AT | 428 | (−) | NGATT |
| ARR1AT | 474 | (−) | NGATT |
| ARR1AT | 489 | (−) | NGATT |
| ARR1AT | 701 | (−) | NGATT |
| ARR1AT | 801 | (−) | NGATT |
| ARR1AT | 808 | (−) | NGATT |
| ARR1AT | 825 | (−) | NGATT |
| ARR1AT | 857 | (−) | NGATT |
| ARR1AT | 887 | (−) | NGATT |
| ARR1AT | 943 | (−) | NGATT |
| ARR1AT | 985 | (−) | NGATT |
| ARR1AT | 1076 | (−) | NGATT |
| ARR1AT | 1392 | (−) | NGATT |
| BIHD1OS | 162 | (−) | TGTCA |
| BIHD1OS | 178 | (−) | TGTCA |
| BIHD1OS | 817 | (−) | TGTCA |

TABLE 3-continued

PLACE analysis results of the WP04 (2126 bp) promoter

| SITE_NAME | POSITION | STRAND | CONSENSUS |
|---|---|---|---|
| BIHD1OS | 1286 | (−) | TGTCA |
| BIHD1OS | 1963 | (−) | TGTCA |
| BOXIINTPATPB | 10 | (+) | ATAGAA |
| BOXIINTPATPB | 1988 | (+) | ATAGAA |
| BOXIINTPATPB | 1647 | (−) | ATAGAA |
| BOXLCOREDCPAL | 315 | (+) | ACCWWCC |
| BOXLCOREDCPAL | 358 | (+) | ACCWWCC |
| BOXLCOREDCPAL | 1065 | (−) | ACCWWCC |
| BS1EGCCR | 880 | (−) | AGCGGG |
| BS1EGCCR | 1302 | (−) | AGCGGG |
| CAATBOX1 | 86 | (+) | CAAT |
| CAATBOX1 | 115 | (+) | CAAT |
| CAATBOX1 | 1075 | (+) | CAAT |
| CAATBOX1 | 1093 | (+) | CAAT |
| CAATBOX1 | 1153 | (+) | CAAT |
| CAATBOX1 | 1523 | (+) | CAAT |
| CAATBOX1 | 1886 | (+) | CAAT |
| CAATBOX1 | 1939 | (+) | CAAT |
| CAATBOX1 | 2096 | (+) | CAAT |
| CAATBOX1 | 218 | (−) | CAAT |
| CAATBOX1 | 228 | (−) | CAAT |
| CAATBOX1 | 470 | (−) | CAAT |
| CAATBOX1 | 517 | (−) | CAAT |
| CAATBOX1 | 932 | (−) | CAAT |
| CAATBOX1 | 1018 | (−) | CAAT |
| CAATBOX1 | 1037 | (−) | CAAT |
| CAATBOX1 | 1485 | (−) | CAAT |
| CAATBOX1 | 1672 | (−) | CAAT |
| CAATBOX1 | 1810 | (−) | CAAT |
| CAATBOX1 | 1957 | (−) | CAAT |
| CACTFTPPCA1 | 367 | (+) | YACT |
| CACTFTPPCA1 | 385 | (+) | YACT |
| CACTFTPPCA1 | 432 | (+) | YACT |
| CACTFTPPCA1 | 691 | (+) | YACT |
| CACTFTPPCA1 | 820 | (+) | YACT |
| CACTFTPPCA1 | 867 | (+) | YACT |
| CACTFTPPCA1 | 134 | (+) | YACT |
| CACTFTPPCA1 | 159 | (+) | YACT |

TABLE 3-continued

PLACE analysis results of the WP04 (2126 bp) promoter

| SITE_NAME | POSITION | STRAND | CONSENSUS |
|---|---|---|---|
| CACTFTPPCA1 | 254 | (+) | YACT |
| CACTFTPPCA1 | 400 | (+) | YACT |
| CACTFTPPCA1 | 483 | (+) | YACT |
| CACTFTPPCA1 | 735 | (+) | YACT |
| CACTFTPPCA1 | 761 | (+) | YACT |
| CACTFTPPCA1 | 981 | (+) | YACT |
| CACTFTPPCA1 | 1148 | (+) | YACT |
| CACTFTPPCA1 | 1246 | (+) | YACT |
| CACTFTPPCA1 | 1307 | (+) | YACT |
| CACTFTPPCA1 | 512 | (−) | YACT |
| CACTFTPPCA1 | 1438 | (−) | YACT |
| CACTFTPPCA1 | 1549 | (−) | YACT |
| CACTFTPPCA1 | 1635 | (−) | YACT |
| CACTFTPPCA1 | 1677 | (−) | YACT |
| CACTFTPPCA1 | 1728 | (−) | YACT |
| CACTFTPPCA1 | 1758 | (−) | YACT |
| CACTFTPPCA1 | 1935 | (−) | YACT |
| CACTFTPPCA1 | 2129 | (−) | YACT |
| CANBNNAPA | 1289 | (+) | CNAACAC |
| CARGCW8GAT | 347 | (+) | CWWWWWWWG (SEQ ID NO: 12) |
| CARGCW8GAT | 836 | (+) | CWWWWWWWG (SEQ ID NO: 12) |
| CARGCW8GAT | 347 | (−) | CWWWWWWWG (SEQ ID NO: 12) |
| CARGCW8GAT | 836 | (−) | CWWWWWWWG (SEQ ID NO: 12) |
| CBFHV | 894 | (+) | RYCGAC |
| CBFHV | 1014 | (−) | RYCGAC |
| CBFHV | 1783 | (−) | RYCGAC |
| CCAATBOX1 | 1152 | (+) | CCAAT |
| CCAATBOX1 | 517 | (−) | CCAAT |
| CGCGBOXAT | 1332 | (+) | VCGCGB |
| CGCGBOXAT | 1332 | (−) | VCGCGB |
| CIACADIANLELHC | 97 | (+) | CAANNNNATC (SEQ ID NO: 13) |
| CIACADIANLELHC | 575 | (−) | CAANNNNATC (SEQ ID NO: 13) |
| CURECORECR | 535 | (+) | GTAC |
| CURECORECR | 980 | (+) | GTAC |
| CURECORECR | 1550 | (+) | GTAC |
| CURECORECR | 1636 | (+) | GTAC |
| CURECORECR | 1729 | (+) | GTAC |
| CURECORECR | 1759 | (+) | GTAC |

TABLE 3-continued

PLACE analysis results of the WP04 (2126 bp) promoter

| SITE_NAME | POSITION | STRAND | CONSENSUS |
|---|---|---|---|
| CURECORECR | 1947 | (+) | GTAC |
| CURECORECR | 2164 | (+) | GTAC |
| CURECORECR | 535 | (−) | GTAC |
| CURECORECR | 980 | (−) | GTAC |
| CURECORECR | 1550 | (−) | GTAC |
| CURECORECR | 1636 | (−) | GTAC |
| CURECORECR | 1729 | (−) | GTAC |
| CURECORECR | 1759 | (−) | GTAC |
| CURECORECR | 1947 | (−) | GTAC |
| CURECORECR | 2164 | (−) | GTAC |
| DOFCOREZM | 15 | (+) | AAAG |
| DOFCOREZM | 626 | (+) | AAAG |
| DOFCOREZM | 631 | (+) | AAAG |
| DOFCOREZM | 653 | (+) | AAAG |
| DOFCOREZM | 710 | (+) | AAAG |
| DOFCOREZM | 725 | (+) | AAAG |
| DOFCOREZM | 842 | (+) | AAAG |
| DOFCOREZM | 1055 | (+) | AAAG |
| DOFCOREZM | 1111 | (+) | AAAG |
| DOFCOREZM | 1470 | (+) | AAAG |
| DOFCOREZM | 1908 | (+) | AAAG |
| DOFCOREZM | 2109 | (+) | AAAG |
| DOFCOREZM | 2144 | (+) | AAAG |
| DOFCOREZM | 2171 | (+) | AAAG |
| DOFCOREZM | 4 | (−) | AAAG |
| DOFCOREZM | 595 | (−) | AAAG |
| DOFCOREZM | 618 | (−) | AAAG |
| DOFCOREZM | 1645 | (−) | AAAG |
| DPBFCOREDCDC3 | 449 | (+) | ACACNNG |
| DPBFCOREDCDC3 | 671 | (+) | ACACNNG |
| DPBFCOREDCDC3 | 715 | (+) | ACACNNG |
| DPBFCOREDCDC3 | 2127 | (−) | ACACNNG |
| DRE2COREZMRAB17 | 894 | (+) | ACCGAC |
| DRECRTCOREAT | 894 | (+) | RCCGAC |
| E2FCONSENSUS | 1387 | (−) | WTTSSCSS |
| EBOXBNNAPA | 66 | (+) | CANNTG |
| EBOXBNNAPA | 579 | (+) | CANNTG |
| EBOXBNNAPA | 672 | (+) | CANNTG |

TABLE 3-continued

PLACE analysis results of the WP04 (2126 bp) promoter

| SITE_NAME | POSITION | STRAND | CONSENSUS |
|---|---|---|---|
| EBOXBNNAPA | 674 | (+) | CANNTG |
| EBOXBNNAPA | 716 | (+) | CANNTG |
| EBOXBNNAPA | 828 | (+) | CANNTG |
| EBOXBNNAPA | 921 | (+) | CANNTG |
| EBOXBNNAPA | 1007 | (+) | CANNTG |
| EBOXBNNAPA | 2000 | (+) | CANNTG |
| EBOXBNNAPA | 66 | (−) | CANNTG |
| EBOXBNNAPA | 579 | (−) | CANNTG |
| EBOXBNNAPA | 672 | (−) | CANNTG |
| EBOXBNNAPA | 674 | (−) | CANNTG |
| EBOXBNNAPA | 716 | (−) | CANNTG |
| EBOXBNNAPA | 828 | (−) | CANNTG |
| EBOXBNNAPA | 921 | (−) | CANNTG |
| EBOXBNNAPA | 1007 | (−) | CANNTG |
| EBOXBNNAPA | 2000 | (−) | CANNTG |
| EECCRCAH1 | 130 | (+) | GANTTNC |
| EECCRCAH1 | 436 | (+) | GANTTNC |
| EECCRCAH1 | 393 | (−) | GANTTNC |
| EECCRCAH1 | 698 | (−) | GANTTNC |
| ELRECOREPCRP1 | 891 | (+) | TTGACC |
| GARE1OSREP1 | 148 | (+) | TAACAGA |
| GAREAT | 749 | (+) | TAACAAR |
| GATABOX | 155 | (+) | GATA |
| GATABOX | 221 | (+) | GATA |
| GATABOX | 243 | (+) | GATA |
| GATABOX | 733 | (+) | GATA |
| GATABOX | 927 | (+) | GATA |
| GATABOX | 950 | (+) | GATA |
| GATABOX | 958 | (+) | GATA |
| GATABOX | 1401 | (+) | GATA |
| GATABOX | 1476 | (+) | GATA |
| GATABOX | 1565 | (+) | GATA |
| GATABOX | 1659 | (+) | GATA |
| GATABOX | 1708 | (+) | GATA |
| GATABOX | 1744 | (+) | GATA |
| GATABOX | 1851 | (+) | GATA |
| GATABOX | 1882 | (+) | GATA |
| GATABOX | 1903 | (+) | GATA |

TABLE 3-continued

PLACE analysis results of the WP04 (2126 bp) promoter

| SITE_NAME | POSITION | STRAND | CONSENSUS |
|---|---|---|---|
| GATABOX | 1985 | (+) | GATA |
| GATABOX | 2114 | (+) | GATA |
| GATABOX | 2138 | (+) | GATA |
| GATABOX | 61 | (−) | GATA |
| GATABOX | 258 | (−) | GATA |
| GATABOX | 262 | (−) | GATA |
| GATABOX | 457 | (−) | GATA |
| GATABOX | 615 | (−) | GATA |
| GATABOX | 664 | (−) | GATA |
| GATABOX | 1281 | (−) | GATA |
| GATABOX | 1642 | (−) | GATA |
| GATABOX | 1650 | (−) | GATA |
| GATABOX | 1735 | (−) | GATA |
| GATABOX | 1748 | (−) | GATA |
| GATABOX | 1829 | (−) | GATA |
| GATABOX | 1889 | (−) | GATA |
| GATABOX | 1894 | (−) | GATA |
| GATABOX | 2010 | (−) | GATA |
| GATABOX | 2064 | (−) | GATA |
| GT1CONSENSUS | 168 | (+) | GRWAAW |
| GT1CONSENSUS | 243 | (+) | GRWAAW |
| GT1CONSENSUS | 341 | (+) | GRWAAW |
| GT1CONSENSUS | 393 | (+) | GRWAAW |
| GT1CONSENSUS | 410 | (+) | GRWAAW |
| GT1CONSENSUS | 541 | (+) | GRWAAW |
| GT1CONSENSUS | 706 | (+) | GRWAAW |
| GT1CONSENSUS | 770 | (+) | GRWAAW |
| GT1CONSENSUS | 1120 | (+) | GRWAAW |
| GT1CONSENSUS | 1213 | (+) | GRWAAW |
| GT1CONSENSUS | 1240 | (+) | GRWAAW |
| GT1CONSENSUS | 308 | (−) | GRWAAW |
| GT1CONSENSUS | 662 | (−) | GRWAAW |
| GT1CONSENSUS | 1624 | (−) | GRWAAW |
| GT1CORE | 297 | (+) | GGTTAA |
| GT1GMSCAM4 | 168 | (+) | GAAAAA |
| GT1GMSCAM4 | 341 | (+) | GAAAAA |
| GT1GMSCAM4 | 541 | (+) | GAAAAA |
| GT1GMSCAM4 | 706 | (+) | GAAAAA |

TABLE 3-continued

PLACE analysis results of the WP04 (2126 bp) promoter

| SITE_NAME | POSITION | STRAND | CONSENSUS |
|---|---|---|---|
| GT1GMSCAM4 | 770 | (+) | GAAAAA |
| GT1GMSCAM4 | 1120 | (+) | GAAAAA |
| GT1GMSCAM4 | 1624 | (−) | GAAAAA |
| GTGANTG10 | 177 | (+) | GTGA |
| GTGANTG10 | 677 | (+) | GTGA |
| GTGANTG10 | 990 | (+) | GTGA |
| GTGANTG10 | 1285 | (+) | GTGA |
| GTGANTG10 | 1434 | (+) | GTGA |
| GTGANTG10 | 1460 | (+) | GTGA |
| GTGANTG10 | 1865 | (+) | GTGA |
| GTGANTG10 | 44 | (−) | GTGA |
| GTGANTG10 | 690 | (−) | GTGA |
| GTGANTG10 | 827 | (−) | GTGA |
| GTGANTG10 | 1448 | (−) | GTGA |
| GTGANTG10 | 2076 | (−) | GTGA |
| HBOXCONSENSUSPVCHS | 1267 | (+) | CCTACCNNNNNNNCT (SEQ ID NO: 14) |
| IBOX | 256 | (−) | GATAAG |
| IBOX | 613 | (−) | GATAAG |
| IBOXCORE | 243 | (+) | GATAA |
| IBOXCORE | 257 | (−) | GATAA |
| IBOXCORE | 614 | (−) | GATAA |
| IBOXCORE | 663 | (−) | GATAA |
| IBOXCORENT | 612 | (−) | GATAAGR |
| INRNTPSADB | 305 | (+) | YTCANTYY |
| INRNTPSADB | 1073 | (+) | YTCANTYY |
| INRNTPSADB | 1620 | (+) | YTCANTYY |
| INRNTPSADB | 1714 | (+) | YTCANTYY |
| INRNTPSADB | 205 | (−) | YTCANTYY |
| INRNTPSADB | 226 | (−) | YTCANTYY |
| INRNTPSADB | 351 | (−) | YTCANTYY |
| INRNTPSADB | 851 | (−) | YTCANTYY |
| INRNTPSADB | 1223 | (−) | YTCANTYY |
| LTRE1HVBLT49 | 1626 | (−) | CCGAAA |
| LTRECOREATCOR15 | 668 | (+) | CCGAC |
| LTRECOREATCOR15 | 895 | (+) | CCGAC |
| MARTBOX | 1121 | (−) | TTWTWTTWTT (SEQ ID NO: 15) |
| MYB1AT | 283 | (+) | WAACCA |
| MYB26PS | 52 | (−) | GTTAGGTT |

TABLE 3-continued

PLACE analysis results of the WP04 (2126 bp) promoter

| SITE_NAME | POSITION | STRAND | CONSENSUS |
|---|---|---|---|
| MYB2AT | 1096 | (+) | TAACTG |
| MYB2CONSENSUSAT | 1366 | (+) | YAACKG |
| MYB2CONSENSUSAT | 1414 | (+) | YAACKG |
| MYB2CONSENSUSAT | 1096 | (+) | YAACKG |
| MYBCORE | 645 | (+) | CNGTTR |
| MYBCORE | 1344 | (−) | CNGTTR |
| MYBCORE | 1366 | (−) | CNGTTR |
| MYBCORE | 1414 | (−) | CNGTTR |
| MYBCORE | 148 | (−) | CNGTTR |
| MYBCORE | 1096 | (−) | CNGTTR |
| MYBCOREATCYCB1 | 1262 | (+) | AACGG |
| MYBCOREATCYCB1 | 1326 | (+) | AACGG |
| MYBCOREATCYCB1 | 1367 | (+) | AACGG |
| MYBCOREATCYCB1 | 1415 | (+) | AACGG |
| MYBGAHV | 749 | (+) | TAACAAA |
| MYBPLANT | 52 | (+) | MACCWAMC |
| MYBPLANT | 284 | (+) | MACCWAMC |
| MYBPLANT | 357 | (+) | MACCWAMC |
| MYBPZM | 312 | (+) | CCWACC |
| MYBPZM | 316 | (+) | CCWACC |
| MYBPZM | 359 | (+) | CCWACC |
| MYBPZM | 999 | (+) | CCWACC |
| MYBPZM | 1267 | (+) | CCWACC |
| MYBST1 | 926 | (+) | GGATA |
| MYBST1 | 957 | (+) | GGATA |
| MYBST1 | 1707 | (+) | GGATA |
| MYBST1 | 2113 | (+) | GGATA |
| MYBST1 | 457 | (−) | GGATA |
| MYBST1 | 664 | (−) | GGATA |
| MYBST1 | 2064 | (−) | GGATA |
| MYCATERD1 | 674 | (+) | CATGTG |
| MYCATERD1 | 2000 | (+) | CATGTG |
| MYCATERD1 | 672 | (−) | CATGTG |
| MYCATERD1 | 716 | (−) | CATGTG |
| MYCATRD22 | 672 | (+) | CACATG |
| MYCATRD22 | 716 | (+) | CACATG |
| MYCATRD22 | 674 | (−) | CACATG |
| MYCATRD22 | 2000 | (−) | CACATG |

TABLE 3-continued

PLACE analysis results of the WP04 (2126 bp) promoter

| SITE_NAME | POSITION | STRAND | CONSENSUS |
|---|---|---|---|
| MYCCONSENSUSAT | 66 | (+) | CANNTG |
| MYCCONSENSUSAT | 579 | (+) | CANNTG |
| MYCCONSENSUSAT | 672 | (+) | CANNTG |
| MYCCONSENSUSAT | 674 | (+) | CANNTG |
| MYCCONSENSUSAT | 716 | (+) | CANNTG |
| MYCCONSENSUSAT | 828 | (+) | CANNTG |
| MYCCONSENSUSAT | 921 | (+) | CANNTG |
| MYCCONSENSUSAT | 1007 | (+) | CANNTG |
| MYCCONSENSUSAT | 2000 | (+) | CANNTG |
| MYCCONSENSUSAT | 66 | (−) | CANNTG |
| MYCCONSENSUSAT | 579 | (−) | CANNTG |
| MYCCONSENSUSAT | 672 | (−) | CANNTG |
| MYCCONSENSUSAT | 674 | (−) | CANNTG |
| MYCCONSENSUSAT | 716 | (−) | CANNTG |
| MYCCONSENSUSAT | 828 | (−) | CANNTG |
| MYCCONSENSUSAT | 921 | (−) | CANNTG |
| MYCCONSENSUSAT | 1007 | (−) | CANNTG |
| MYCCONSENSUSAT | 2000 | (−) | CANNTG |
| NAPINMOTIFBN | 1801 | (+) | TACACAT |
| NAPINMOTIFBN | 1507 | (−) | TACACAT |
| NAPINMOTIFBN | 1600 | (−) | TACACAT |
| NODCON1GM | 616 | (−) | AAAGAT |
| NODCON1GM | 1643 | (−) | AAAGAT |
| NODCON2GM | 402 | (+) | CTCTT |
| NODCON2GM | 611 | (+) | CTCTT |
| NODCON2GM | 1059 | (−) | CTCTT |
| NODCON2GM | 1112 | (−) | CTCTT |
| NODCON2GM | 1203 | (−) | CTCTT |
| NTBBF1ARROLB | 724 | (−) | ACTTTA |
| OPAQUE2ZMB32 | 2007 | (−) | GATGAYRTGG (SEQ ID NO: 16) |
| OSE1ROOTNODULE | 616 | (−) | AAAGAT |
| OSE1ROOTNODULE | 1643 | (−) | AAAGAT |
| OSE2ROOTNODULE | 402 | (+) | CTCTT |
| OSE2ROOTNODULE | 611 | (+) | CTCTT |
| OSE2ROOTNODULE | 1059 | (−) | CTCTT |
| OSE2ROOTNODULE | 1112 | (−) | CTCTT |
| OSE2ROOTNODULE | 1203 | (−) | CTCTT |
| PALBOXAPC | 975 | (−) | CCGTCC |

TABLE 3-continued

PLACE analysis results of the WP04 (2126 bp) promoter

| SITE_NAME | POSITION | STRAND | CONSENSUS |
|---|---|---|---|
| PALBOXLPC | 311 | (+) | YCYYACCWACC (SEQ ID NO: 17) |
| PE2FNTRNR1A | 1387 | (-) | ATTCGCGC |
| POLASIG1 | 87 | (+) | AATAAA |
| POLASIG1 | 99 | (+) | AATAAA |
| POLASIG1 | 202 | (+) | AATAAA |
| POLASIG1 | 413 | (+) | AATAAA |
| POLASIG1 | 551 | (+) | AATAAA |
| POLASIG3 | 1669 | (-) | AATAAT |
| POLASIG3 | 1875 | (-) | AATAAT |
| POLLEN1LELAT52 | 12 | (+) | AGAAA |
| POLLEN1LELAT52 | 340 | (+) | AGAAA |
| POLLEN1LELAT52 | 705 | (+) | AGAAA |
| POLLEN1LELAT52 | 1088 | (+) | AGAAA |
| POLLEN1LELAT52 | 1119 | (+) | AGAAA |
| POLLEN1LELAT52 | 1239 | (+) | AGAAA |
| POLLEN1LELAT52 | 1646 | (-) | AGAAA |
| PRECONSCRHSP70A | 2134 | (-) | SCGAYNRNNNNNNNNNNNNNNNNHD (SEQ ID NO: 11) |
| PROXBBNNAPA | 1289 | (+) | CAAACACC |
| PYRIMIDINEBOXOSRAMY1A | 625 | (-) | CCTTTT |
| PYRIMIDINEBOXOSRAMY1A | 841 | (-) | CCTTTT |
| QARBNEXTA | 1615 | (-) | AACGTGT |
| RAV1AAT | 782 | (+) | CAACA |
| RAV1AAT | 918 | (+) | CAACA |
| RAV1AAT | 964 | (+) | CAACA |
| RAV1AAT | 1337 | (+) | CAACA |
| RAV1AAT | 1344 | (+) | CAACA |
| RAV1AAT | 636 | (-) | CAACA |
| RAV1AAT | 1585 | (-) | CAACA |
| RAV1BAT | 828 | (+) | CACCTG |
| REALPHALGLHCB21 | 284 | (+) | AACCAA |
| REALPHALGLHCB21 | 357 | (+) | AACCAA |
| REBETALGLHCB21 | 457 | (-) | CGGATA |
| RHERPATEXPA7 | 1283 | (-) | KCACGW |
| ROOTMOTIFTAPOX1 | 930 | (+) | ATATT |
| ROOTMOTIFTAPOX1 | 1477 | (+) | ATATT |
| ROOTMOTIFTAPOX1 | 1711 | (+) | ATATT |
| ROOTMOTIFTAPOX1 | 1951 | (+) | ATATT |
| ROOTMOTIFTAPOX1 | 91 | (-) | ATATT |

TABLE 3-continued

PLACE analysis results of the WP04 (2126 bp) promoter

| SITE_NAME | POSITION | STRAND | CONSENSUS |
|---|---|---|---|
| ROOTMOTIFTAPOX1 | 1517 | (−) | ATATT |
| ROOTMOTIFTAPOX1 | 1797 | (−) | ATATT |
| ROOTMOTIFTAPOX1 | 1887 | (−) | ATATT |
| RYREPEATBNNAPA | 1998 | (−) | CATGCA |
| RYREPEATGMGY2 | 1997 | (−) | CATGCAT |
| RYREPEATLEGUMINBOX | 1997 | (−) | CATGCAY |
| S1FBOXSORPS1L21 | 1551 | (−) | ATGGTA |
| S1FBOXSORPS1L21 | 1637 | (−) | ATGGTA |
| S1FBOXSORPS1L21 | 1730 | (−) | ATGGTA |
| SEBFCONSSTPR10A | 177 | (−) | YTGTCWC |
| SEBFCONSSTPR10A | 1256 | (−) | YTGTCWC |
| SEBFCONSSTPR10A | 1285 | (−) | YTGTCWC |
| SEF1MOTIF | 87 | (−) | ATATTTAWW |
| SEF4MOTIFGM7S | 379 | (−) | RTTTTTR |
| SEF4MOTIFGM7S | 1104 | (−) | RTTTTTR |
| SEF4MOTIFGM7S | 1374 | (−) | RTTTTTR |
| SEF4MOTIFGM7S | 415 | (−) | RTTTTTR |
| SITEIIATCYTC | 1273 | (−) | TGGGCY |
| SORLIP1AT | 463 | (+) | GCCAC |
| SORLIP1AT | 2086 | (+) | GCCAC |
| SORLIP2AT | 1329 | (+) | GGGCC |
| SREATMSD | 663 | (+) | TTATCC |
| SURECOREATSULTR11 | 1256 | (+) | GAGAC |
| SURECOREATSULTR11 | 1160 | (−) | GAGAC |
| SV40COREENHAN | 513 | (+) | GTGGWWHG |
| T/GBOXATPIN2 | 1616 | (−) | AACGTG |
| TAAAGSTKST1 | 724 | (+) | TAAAG |
| TAAAGSTKST1 | 1907 | (+) | TAAAG |
| TATABOX3 | 1952 | (+) | TATTAAT |
| TATABOX3 | 1514 | (−) | TATTAAT |
| TATABOX4 | 1569 | (+) | TATATAA |
| TATABOX4 | 1663 | (+) | TATATAA |
| TATABOX4 | 2031 | (+) | TATATAA |
| TATABOX5 | 1443 | (+) | TTATTT |
| TATABOX5 | 1876 | (+) | TTATTT |
| TATABOX5 | 98 | (−) | TTATTT |
| TATABOX5 | 412 | (−) | TTATTT |
| TATABOX5 | 550 | (−) | TTATTT |

TABLE 3-continued

PLACE analysis results of the WP04 (2126 bp) promoter

| SITE_NAME | POSITION | STRAND | CONSENSUS |
|---|---|---|---|
| TATABOX5 | 1125 | (−) | TTATTT |
| TATAPVTRNALEU | 2031 | (−) | TTTATATA |
| TATCCAOSAMY | 925 | (−) | TATCCA |
| TATCCAOSAMY | 956 | (−) | TATCCA |
| TATCCAOSAMY | 1706 | (−) | TATCCA |
| TATCCAYMOTIFOSRAMY3D | 955 | (−) | TATCCAY |
| TATCCAYMOTIFOSRAMY3D | 1705 | (−) | TATCCAY |
| TBOXATGAPB | 3 | (+) | ACTTTG |
| TBOXATGAPB | 652 | (−) | ACTTTG |
| TGTCACACMCUCUMISIN | 176 | (−) | TGTCACA |
| TRANSINITDICOTS | 2147 | (−) | AMNAUGGC |
| TRANSINITMONOCOTS | 2043 | (−) | RMNAUGGC |
| TRANSINITMONOCOTS | 2147 | (−) | RMNAUGGC |
| UP2ATMSD | 266 | (+) | AAACCCTA |
| UP2ATMSD | 526 | (+) | AAACCCTA |
| UP2ATMSD | 1028 | (+) | AAACCCTA |
| WBOXATNPR1 | 478 | (+) | TTGAC |
| WBOXATNPR1 | 816 | (+) | TTGAC |
| WBOXATNPR1 | 891 | (+) | TTGAC |
| WBOXATNPR1 | 1962 | (+) | TTGAC |
| WBOXHVISO1 | 479 | (+) | TGACT |
| WBOXHVISO1 | 2057 | (−) | TGACT |
| WBOXNTERF3 | 479 | (+) | TGACY |
| WBOXNTERF3 | 892 | (+) | TGACY |
| WBOXNTERF3 | 2057 | (−) | TGACY |
| WRKY71OS | 162 | (+) | TGAC |
| WRKY71OS | 178 | (+) | TGAC |
| WRKY71OS | 479 | (+) | TGAC |
| WRKY71OS | 817 | (+) | TGAC |
| WRKY71OS | 892 | (+) | TGAC |
| WRKY71OS | 1286 | (+) | TGAC |
| WRKY71OS | 1963 | (+) | TGAC |
| WRKY71OS | 2058 | (−) | TGAC |
| XYLAT | 1053 | (+) | ACAAAGAA |
| XYLAT | 593 | (−) | ACAAAGAA |

TABLE 4

PLACE analysis results of the maize equivalent (1164 bp) to the wheat WP04 promoter

| SITE_NAME | POSITION (STRAND) CONSENSUS |
|---|---|
| -10PEHVPSBD | 890 (-)TATTCT |
| -10PEHVPSBD | 971 (-)TATTCT |
| -300ELEMENT | 201 (+)TGHAAARK |
| -300ELEMENT | 604 (-)TGHAAARK |
| 2SSEEDPROTBANAPA | 222 (+)CAAACAC |
| ACGTABOX | 1044 (+)TACGTA |
| ACGTABOX | 1044 (-)TACGTA |
| ACGTATERD1 | 1045 (+)ACGT |
| ACGTATERD1 | 1045 (-)ACGT |
| ACIIIPVPAL2 | 117 (+)GTTAGGTTC |
| ANAERO2CONSENSUS | 649 (+)AGCAGC |
| ARFAT | 713 (+)TGTCTC |
| ARR1AT | 197 (+)NGATT |
| ARR1AT | 138 (+)NGATT |
| ARR1AT | 318 (+)NGATT |
| ARR1AT | 671 (+)NGATT |
| ARR1AT | 18 (-)NGATT |
| ARR1AT | 150 (-)NGATT |
| ARR1AT | 429 (-)NGATT |
| ARR1AT | 616 (-)NGATT |
| ASF1MOTIFCAMV | 1139 (-)TGACG |
| BIHD1OS | 1097 (+)TGTCA |
| BIHD1OS | 252 (-)TGTCA |
| BIHD1OS | 368 (-)TGTCA |
| BOXIINTPATPB | 770 (+)ATAGAA |
| BOXIINTPATPB | 816 (+)ATAGAA |
| BOXIINTPATPB | 888 (+)ATAGAA |
| BOXLCOREDCPAL | 528 (+)ACCWWCC |
| CAATBOX1 | 17 (+)CAAT |
| CAATBOX1 | 170 (+)CAAT |
| CAATBOX1 | 428 (+)CAAT |
| CAATBOX1 | 595 (+)CAAT |
| CAATBOX1 | 666 (+)CAAT |
| CAATBOX1 | 695 (+)CAAT |
| CAATBOX1 | 824 (+)CAAT |
| CAATBOX1 | 995 (+)CAAT |
| CAATBOX1 | 7 (-)CAAT |
| CAATBOX1 | 199 (-)CAAT |
| CAATBOX1 | 502 (-)CAAT |
| CAATBOX1 | 552 (-)CAAT |
| CAATBOX1 | 673 (-)CAAT |
| CACTFTPPCA1 | 11 (+)YACT |
| CACTFTPPCA1 | 218 (+)YACT |
| CACTFTPPCA1 | 268 (+)YACT |
| CACTFTPPCA1 | 432 (+)YACT |
| CACTFTPPCA1 | 542 (+)YACT |
| CACTFTPPCA1 | 1081 (+)YACT |
| CACTFTPPCA1 | 1120 (+)YACT |
| CACTFTPPCA1 | 44 (+)YACT |
| CACTFTPPCA1 | 479 (+)YACT |
| CACTFTPPCA1 | 571 (+)YACT |
| CACTFTPPCA1 | 638 (+)YACT |
| CACTFTPPCA1 | 757 (+)YACT |
| CACTFTPPCA1 | 795 (+)YACT |
| CACTFTPPCA1 | 856 (+)YACT |
| CACTFTPPCA1 | 929 (+)YACT |
| CACTFTPPCA1 | 96 (-)YACT |
| CACTFTPPCA1 | 471 (-)YACT |
| CACTFTPPCA1 | 801 (-)YACT |
| CACTFTPPCA1 | 804 (-)YACT |
| CACTFTPPCA1 | 811 (-)YACT |
| CACTFTPPCA1 | 847 (-)YACT |
| CACTFTPPCA1 | 1095 (-)YACT |
| CANBNNAPA | 222 (+)CNAACAC |
| CBFHV | 440 (-)RYCGAC |
| CCAATBOX1 | 694 (+)CCAAT |
| CEREGLUBOX3PSLEGA | 603 (-)TGTAAAAGT |
| CPBCSPOR | 767 (-)TATTAG |
| CPBCSPOR | 885 (-)TATTAG |
| DOFCOREZM | 185 (+)AAAG |
| DOFCOREZM | 205 (+)AAAG |
| DOFCOREZM | 342 (+)AAAG |
| DOFCOREZM | 348 (+)AAAG |

TABLE 4-continued

PLACE analysis results of the maize equivalent (1164 bp) to the wheat WP04 promoter

| NAME | POSITION (STRAND) | CONSENSUS |
|---|---|---|
| DOFCOREZM | 904 (+) | AAAG |
| DOFCOREZM | 1086 (+) | AAAG |
| DOFCOREZM | 72 (−) | AAAG |
| DOFCOREZM | 397 (−) | AAAG |
| DOFCOREZM | 604 (−) | AAAG |
| DOFCOREZM | 640 (−) | AAAG |
| DOFCOREZM | 949 (−) | AAAG |
| DPBFCOREDCDC3 | 267 (+) | ACACNNG |
| DPBFCOREDCDC3 | 370 (+) | ACACNNG |
| DPBFCOREDCDC3 | 988 (+) | ACACNNG |
| DRE2COREZMRAB17 | 440 (−) | ACCGAC |
| DRECRTCOREAT | 440 (−) | RCCGAC |
| EBOXBNNAPA | 371 (+) | CANNTG |
| EBOXBNNAPA | 411 (+) | CANNTG |
| EBOXBNNAPA | 989 (+) | CANNTG |
| EBOXBNNAPA | 1145 (+) | CANNTG |
| EBOXBNNAPA | 371 (−) | CANNTG |
| EBOXBNNAPA | 411 (−) | CANNTG |
| EBOXBNNAPA | 989 (−) | CANNTG |
| EBOXBNNAPA | 1145 (−) | CANNTG |
| ELRECOREPCRP1 | 422 (−) | TTGACC |
| GATABOX | 42 (+) | GATA |
| GATABOX | 497 (+) | GATA |
| GATABOX | 815 (+) | GATA |
| GATABOX | 944 (+) | GATA |
| GATABOX | 305 (−) | GATA |
| GATABOX | 744 (−) | GATA |
| GATABOX | 760 (−) | GATA |
| GATABOX | 764 (−) | GATA |
| GATABOX | 806 (−) | GATA |
| GATABOX | 827 (−) | GATA |
| GATABOX | 852 (−) | GATA |
| GATABOX | 878 (−) | GATA |
| GATABOX | 882 (−) | GATA |
| GATABOX | 946 (−) | GATA |
| GATABOX | 978 (−) | GATA |
| GATABOX | 1003 (−) | GATA |
| GATABOX | 1007 (−) | GATA |
| GT1CONSENSUS | 202 (+) | GRWAAW |
| GT1CONSENSUS | 335 (+) | GRWAAW |
| GT1CONSENSUS | 345 (+) | GRWAAW |
| GT1CONSENSUS | 352 (+) | GRWAAW |
| GT1CONSENSUS | 497 (+) | GRWAAW |
| GT1CONSENSUS | 773 (+) | GRWAAW |
| GT1CONSENSUS | 159 (−) | GRWAAW |
| GT1CONSENSUS | 303 (−) | GRWAAW |
| GT1CONSENSUS | 1001 (−) | GRWAAW |
| GT1CONSENSUS | 399 (−) | GRWAAW |
| GT1CONSENSUS | 876 (−) | GRWAAW |
| GT1GMSCAM4 | 202 (+) | GAAAAA |
| GT1GMSCAM4 | 335 (+) | GAAAAA |
| GT1GMSCAM4 | 345 (+) | GAAAAA |
| GT1GMSCAM4 | 773 (+) | GAAAAA |
| GTGANTG10 | 251 (+) | GTGA |
| GTGANTG10 | 367 (+) | GTGA |
| GTGANTG10 | 217 (−) | GTGA |
| GTGANTG10 | 431 (−) | GTGA |
| GTGANTG10 | 643 (−) | GTGA |
| GTGANTG10 | 924 (−) | GTGA |
| GTGANTG10 | 1099 (−) | GTGA |
| GTGANTG10 | 1119 (−) | GTGA |
| IBOXCORE | 497 (+) | GATAA |
| IBOXCORE | 304 (−) | GATAA |
| IBOXCORE | 877 (−) | GATAA |
| IBOXCORE | 1002 (−) | GATAA |
| INRNTPSADB | 1118 (+) | YTCANTYY |
| INRNTPSADB | 197 (−) | YTCANTYY |
| LTRECOREATCOR15 | 440 (−) | CCGAC |
| MYB1AT | 230 (+) | WAACCA |
| MYB26PS | 117 (+) | GTTAGGTT |
| MYB2CONSENSUSAT | 115 (−) | YAACKG |
| MYB2CONSENSUSAT | 1145 (−) | YAACKG |
| MYBCORE | 115 (+) | CNGTTR |

TABLE 4-continued

PLACE analysis results of the maize equivalent (1164 bp) to the wheat WP04 promoter

| NAME | POSITION (STRAND) | CONSENSUS |
|---|---|---|
| MYBCORE | 434 (+) | CNGTTR |
| MYBCORE | 1145 (+) | CNGTTR |
| MYBCORE | 1142 (-) | CNGTTR |
| MYBCOREATCYCB1 | 115 (-) | AACGG |
| MYBPLANT | 527 (+) | MACCWAMC |
| MYBPLANT | 117 (-) | MACCWAMC |
| MYBPZM | 529 (+) | CCWACC |
| MYBPZM | 1069 (+) | CCWACC |
| MYBPZM | 52 (-) | CCWACC |
| MYBST1 | 41 (+) | GGATA |
| MYBST1 | 496 (+) | GGATA |
| MYBST1 | 814 (+) | GGATA |
| MYCATERD1 | 371 (-) | CATGTG |
| MYCATERD1 | 989 (-) | CATGTG |
| MYCATRD22 | 371 (+) | CACATG |
| MYCATRD22 | 989 (+) | CACATG |
| MYCCONSENSUSAT | 371 (+) | CANNTG |
| MYCCONSENSUSAT | 411 (+) | CANNTG |
| MYCCONSENSUSAT | 989 (+) | CANNTG |
| MYCCONSENSUSAT | 1145 (+) | CANNTG |
| MYCCONSENSUSAT | 371 (-) | CANNTG |
| MYCCONSENSUSAT | 411 (-) | CANNTG |
| MYCCONSENSUSAT | 989 (-) | CANNTG |
| MYCCONSENSUSAT | 1145 (-) | CANNTG |
| NODCON1GM | 1086 (+) | AAAGAT |
| NODCON1GM | 947 (-) | AAAGAT |
| NRRBNEXTA | 810 (+) | TAGTGGAT |
| NTBBF1ARROLB | 903 (-) | ACTTTA |
| OSE1ROOTNODULE | 1086 (+) | AAAGAT |
| OSE1ROOTNODULE | 947 (-) | AAAGAT |
| POLASIG1 | 901 (+) | AATAAA |
| POLASIG1 | 300 (-) | AATAAA |
| POLASIG3 | 596 (+) | AATAAT |
| POLASIG3 | 973 (+) | AATAAT |
| POLASIG3 | 325 (-) | AATAAT |
| POLLEN1LELAT52 | 344 (+) | AGAAA |
| POLLEN1LELAT52 | 512 (+) | AGAAA |
| POLLEN1LELAT52 | 655 (+) | AGAAA |
| POLLEN1LELAT52 | 772 (+) | AGAAA |
| POLLEN1LELAT52 | 173 (-) | AGAAA |
| PRECONSCRHSP70A | 421 (-) | SCGAYNRNNNNNNNNNNNNNNHD (SEQ ID NO: 11) |
| PYRIMIDINEBOXOSRAMY1A | 347 (-) | CCTTTT |
| RAV1AAT | 425 (+) | CAACA |
| RAV1AAT | 736 (+) | CAACA |
| RAV1AAT | 867 (+) | CAACA |
| RAV1AAT | 1142 (+) | CAACA |
| RAV1AAT | 435 (-) | CAACA |
| RAV1BAT | 411 (-) | CACCTG |
| REALPHALGLHCB21 | 189 (+) | AACCAA |
| ROOTMOTIFTAPOX1 | 259 (+) | ATATT |
| ROOTMOTIFTAPOX1 | 278 (+) | ATATT |
| ROOTMOTIFTAPOX1 | 871 (+) | ATATT |
| ROOTMOTIFTAPOX1 | 912 (+) | ATATT |
| ROOTMOTIFTAPOX1 | 1016 (+) | ATATT |
| ROOTMOTIFTAPOX1 | 1034 (+) | ATATT |
| ROOTMOTIFTAPOX1 | 1 (-) | ATATT |
| ROOTMOTIFTAPOX1 | 258 (-) | ATATT |
| ROOTMOTIFTAPOX1 | 667 (-) | ATATT |
| ROOTMOTIFTAPOX1 | 742 (-) | ATATT |
| ROOTMOTIFTAPOX1 | 783 (-) | ATATT |
| ROOTMOTIFTAPOX1 | 825 (-) | ATATT |
| ROOTMOTIFTAPOX1 | 850 (-) | ATATT |
| ROOTMOTIFTAPOX1 | 892 (-) | ATATT |
| ROOTMOTIFTAPOX1 | 911 (-) | ATATT |
| ROOTMOTIFTAPOX1 | 976 (-) | ATATT |
| ROOTMOTIFTAPOX1 | 1013 (-) | ATATT |
| ROOTMOTIFTAPOX1 | 1033 (-) | ATATT |
| RYREPEATBNNAPA | 836 (+) | CATGCA |
| RYREPEATBNNAPA | 863 (+) | CATGCA |
| RYREPEATBNNAPA | 991 (+) | CATGCA |
| RYREPEATBNNAPA | 838 (-) | CATGCA |
| RYREPEATGMGY2 | 836 (+) | CATGCAT |
| RYREPEATGMGY2 | 837 (-) | CATGCAT |

TABLE 4-continued

PLACE analysis results of the maize equivalent (1164 bp) to the wheat WP04 promoter

| | POSITION (STRAND) | CONSENSUS |
|---|---|---|
| RYREPEATLEGUMINBOX | 836 (+) | CATGCAY |
| RYREPEATLEGUMINBOX | 837 (−) | CATGCAY |
| RYREPEATVFLEB4 | 836 (+) | CATGCATG |
| RYREPEATVFLEB4 | 836 (−) | CATGCATG |
| S1FBOXSORPS1L21 | 401 (−) | ATGGTA |
| SEBFCONSSTPR10A | 712 (+) | YTGTCWC |
| SEBFCONSSTPR10A | 251 (−) | YTGTCWC |
| SEF3MOTIFGM | 482 (−) | AACCCA |
| SEF4MOTIFGM7S | 873 (+) | RTTTTTR |
| SEF4MOTIFGM7S | 583 (+) | RTTTTTR |
| IIATCYTC | 83 (−) | TGGGCY |
| SORLIP1AT | 65 (−) | GCCAC |
| SORLIP1AT | 505 (−) | GCCAC |
| SORLIP2AT | 83 (−) | GGGCC |
| SP8BFIBSP8BIB | 571 (+) | TACTATT |
| SREATMSD | 496 (−) | TTATCC |
| SURE1STPAT21 | 769 (+) | AATAGAAAA |
| SURECOREATSULTR11 | 714 (−) | GAGAC |
| SV40COREENHAN | 812 (+) | GTGGWWHG |
| TAAAGSTKST1 | 903 (+) | TAAAG |
| TAAAGSTKST1 | 1085 (+) | TAAAG |
| TATABOX2 | 659 (−) | TATAAAT |
| TATABOX3 | 1035 (+) | TATTAAT |
| TATABOX4 | 896 (+) | TATATAA |
| TATABOX4 | 934 (+) | TATATAA |
| TATABOX4 | 1020 (+) | TATATAA |
| TATABOX4 | 1019 (−) | TATATAA |
| TATABOX5 | 326 (+) | TTATTT |
| TATABOXOSPAL | 790 (−) | TATTTAA |
| TATABOXOSPAL | 908 (−) | TATTTAA |
| TATABOXOSPAL | 1030 (−) | TATTTAA |
| TATCCACHVAL21 | 812 (−) | TATCCAC |
| TATCCAOSAMY | 813 (−) | TATCCA |
| TATCCAYMOTIFOSRAMY3D | 812 (−) | TATCCAY |
| TGTCACACMCUCUMISIN | 1097 (+) | TGTCACA |
| TGTCACACMCUCUMISIN | 250 (−) | TGTCACA |
| WBOXATNPR1 | 423 (−) | TTGAC |

TABLE 4-continued

PLACE analysis results of the maize equivalent (1164 bp) to the wheat WP04 promoter

| | POSITION (STRAND) | CONSENSUS |
|---|---|---|
| WBOXATNPR1 | 1140 (−) | TTGAC |
| WBOXHVISO1 | 389 (+) | TGACT |
| WBOXNTERF3 | 389 (+) | TGACY |
| WBOXNTERF3 | 422 (−) | TGACY |
| WRKY71OS | 252 (+) | TGAC |
| WRKY71OS | 368 (+) | TGAC |
| WRKY71OS | 389 (+) | TGAC |
| WRKY71OS | 423 (−) | TGAC |
| WRKY71OS | 1098 (−) | TGAC |
| WRKY71OS | 1140 (−) | TGAC |
| XYLAT | 183 (+) | ACAAGAA |

Notwithstanding the variations in lengths of the promoters and 5' upstream regulatory sequences analysed, the data presented in Table 3 and Table 4 indicate the presence of several conserved structural features in the isolated wheat and maize promoters, including e.g., at least one element selected from the group set forth in Table 5.

TABLE 5

Conserved structural sequence elements in wheat and maize promoters

| SITE_NAME | CONSENSUS |
|---|---|
| 2SSEEDPROTBANAPA | CAAACAC |
| ARFAT | TGTCTC |
| ARR1AT | NGATT |
| BIHD1OS | TGTCA |
| BOXIINTPATPB | ATAGAA |
| CAATBOX1 | CAAT |
| CACTFTPPCA1 | YACT |
| CANBNNAPA | CNAACAC |
| CBFHV | RYCGAC |
| CCAATBOX1 | CCAAT |
| DOFCOREZM | AAAG |
| DPBFCOREDCDC3 | ACACNNG |
| DRE2COREZMRAB17 | ACCGAC |
| DRECRTCOREAT | RCCGAC |
| EBOXBNNAPA | CANNTG |
| ELRECOREPCRP1 | TTGACC |
| GATABOX | GATA |
| GT1CONSENSUS | GRWAAW |

TABLE 5-continued

Conserved structural sequence elements in wheat and maize promoters

| SITE_NAME | CONSENSUS |
|---|---|
| GT1GMSCAM4 | GAAAAA |
| GTGANTG10 | GTGA |
| IBOXCORE | GATAA |
| INRNTPSADB | YTCANTYY |
| MYB1AT | WAACCA |
| MYB26PS | GTTAGGTT |
| MYB2CONSENSUSAT | YAACKG |
| MYBCORE | CNGTTR |
| MYBCOREATCYCB1 | AACGG |
| MYBPLANT | MACCWAMC |
| MYBPZM | CCWACC |
| MYBST1 | GGATA |
| MYCATERD1 | CATGTG |
| MYCCONSENSUSAT | CANNTG |
| NODCON1GM | AAAGAT |
| NTBBF1ARROLB | ACTTTA |
| OSE1ROOTNODULE | AAAGAT |
| POLASIG1 | AATAAA |
| POLASIG3 | AATAAT |
| POLLEN1LELAT52 | AGAAA |
| PRECONSCRHSP70A | SCGAYNRNNNNNNNNNNNNNNNHD (SEQ ID NO: 11) |
| PYRIMIDINEBOXOSRAMY1A | CCTTTT |
| RAV1AAT | CAACA |
| REALPHALGLHCB21 | AACCAA |
| ROOTMOTIFTAPOX1 | ATATT |
| RYREPEATBNNAPA | CATGCA |
| RYREPEATGMGY2 | CATGCAT |
| RYREPEATLEGUMINBOX | CATGCAY |
| S1FBOXSORPS1L21 | ATGGTA |
| SEBFCONSSTPR10A | YTGTCWC |
| SEF4MOTIFGM7S | RTTTTTR |
| SITEIIATCYTC | TGGGCY |
| SORLIP1AT | GCCAC |
| SORLIP2AT | GGGCC |
| SREATMSD | TTATCC |
| SURECOREATSULTR11 | GAGAC |
| SV40COREENHAN | GTGGWWHG |
| TAAAGSTKST1 | TAAAG |
| TATABOX3 | TATTAAT |
| TATABOX4 | TATATAA |
| TATABOX5 | TTATTT |
| TATCCAOSAMY | TATCCA |
| TATCCAYMOTIFOSRAMY3D | TATCCAY |
| TGTCACACMCUCUMISIN | TGTCACA |
| WBOXATNPR1 | TTGAC |
| WBOXHVISO1 | TGACT |
| WBOXNTERF3 | TGACY |
| WRKY71OS | TGAC |
| XYLAT | ACAAAGAA |

The wheat and maize promoter sequences are also characterized by a plurality of each element in the group consisting of an ARR1AT element, a BIHD1OS element, a BOXIINTPATPB element, a CAATBOX1 element, a CACFTPPCA1 element, a DOFCOREZM element, a DPBFCOREDCDC3 element, an EBOXBNNAPA element, a GATABOX element, a GT1CONSENSUS element, a GTGANTG10 element, a GT1GMSCAM4 element, an IBOXCORE element, an INRNTPSADB element, a MYBCORE element, MYBPLANT element, a MYBPZM element, a MYBST1 element, a MYCATERD1 element, a MYCCONSENSUSAT element, a NODCON1GM element, a OSE1ROOTNODULE element, a POLASIG1 element, a POLASIG3 element, a POLLEN1LELAT52 element, a RAV1AAT element, a ROOTMOTIFTAPDX1 element, a SEBFCONSSTPR10A element, a SEF4MOTIFGM7S element, a SORLIP1AT element, a TAAAGSTKST1 element, a TATABOX4 element, a WBOXATNPR1 element, a WBOXNTERF3 element and WRKY71OS element.

Both promoters contain the following elements more than twice: an ARR1AT element, a BIHD1OS element, a BOXIINTPATPB element, a CAATBOX1 element, a CACFTPPCA1 element, a DOFCOREZM element, a DPBFCOREDCDC3 element, an EBOXBNNAPA element, a GATABOX element, a GT1CONSENSUS element, a GTGANTG10 element, a GT1GMSCAM4 element, an IBOXCORE element, a MYBCORE element, a MYBPZM element, a MYBST1 element, a MYCCONSENSUSAT element, a POLASIG1 element, a POLLEN1LELAT52 element, a RAV element, a ROOTMOTIFTAPDX1 element, a TATABOX4 element, and a WRKY71OS element.

Both promoters contain the following elements more than three times: an ARR1AT element, a CAATBOX1 element, a CACFTPPCA1 element, a DOFCOREZM element, an EBOXBNNAPA element, a GATABOX element, a GT1CONSENSUS element, a GTGANTG10 element, a GT1GMSCAM4 element, an IBOXCORE element, a MYBCORE element, a MYCCONSENSUSAT element, a POLLEN1LELAT52 element, a RAV1AAT element, a ROOTMOTIFTAPDX1 element, and a WRKY71OS element.

Both promoters contain the following elements more than four times: an ARR1AT element, a CAATBOX1 element, a CACFTPPCA1 element, a DOFCOREZM element, an EBOXBNNAPA element, a GATABOX element, a GT1CONSENSUS element, a GTGANTG10 element, a MYCCONSENSUSAT element, a POLLEN1LELAT52 element, a RAV1AAT element, a ROOTMOTIFTAPDX1 element, and a WRKY71OS element.

Both promoters contain the following elements more than five times: an ARR1AT element, a CAATBOX1 element, a CACFTPPCA1 element, a DOFCOREZM element, an EBOXBNNAPA element, a GATABOX element, a GT1CONSENSUS element, a GTGANTG10 element, a MYCCONSENSUSAT element, a ROOTMOTIFTAPDX1 element, and a WRKY71OS element.

We claim:

1. An expression construct comprising a promoter operably connected to a heterologous transgene, wherein said promoter confers expression of said transgene in the basal endosperm transfer layer (BETL) of an endosperm and comprises a nucleotide sequence selected from the group consisting of:
   (i) the nucleotide sequence of SEQ ID NO: 2; and
   (ii) a nucleotide sequence having at least 95% sequence identity to the nucleotide sequence of (i).

2. The expression construct of claim 1, wherein said promoter is obtained from a monocotyledonous plant.

3. The expression construct of claim 1, wherein said promoter confers expression of the transgene during the period of from 5 days after pollination (DAP) to at least 25 DAP.

4. An expression vector comprising the expression construct of claim 1.

5. A transgenic plant cell comprising:
   (i) the expression construct of claim 1; or
   (ii) an expression vector comprising the expression construct of (i).

6. The transgenic plant cell of claim 5, wherein the expression construct is integrated into the genome of the plant cell.

7. A plant, plantlet or plant part comprising the transgenic plant cell of claim 5.

8. A method for producing a transgenic plant, transgenic plant part or transgenic plant cell, comprising introducing into a plant, plant part or plant cell:
   (i) the expression construct of claim 1; or
   (ii) an expression vector comprising the expression construct of (i).

9. A method for producing a transgenic plant, transgenic plantlet or transgenic plant part, comprising:
   (i) obtaining a transgenic plant cell produced by the method of claim 8; and
   (ii) regenerating the transgenic plant cell to produce a transgenic plant, transgenic plantlet or transgenic plant part.

10. A method of modulating expression of a transgene in the basal endosperm transfer layer (BETL) of a developing endosperm, comprising transforming a plant with:
   (i) the expression construct of claim 1; or
   (ii) an expression vector comprising the expression construct of (i).

11. A method for expressing a nucleic acid in developing endosperm, basal endosperm, or BETL cells, comprising:
   (i) obtaining a transgenic plant, transgenic plant cell or transgenic plant part comprising an expression construct comprising a promoter operably connected to a nucleic acid; and
   (ii) maintaining said transgenic plant, transgenic plant cell or transgenic plant part for a time and under conditions sufficient for said nucleic acid to be expressed, wherein said promoter comprises a nucleotide sequence selected from the group consisting of:
   (i) the nucleotide sequence of SEQ ID NO: 2; and
   (ii) a nucleotide sequence having at least 95% sequence identity to the nucleotide sequence of (i); and
   wherein said promoter confers expression of said nucleic acid in developing endosperm, basal endosperm, or BETL cells.

12. The method of claim 11, wherein said nucleic acid is endogenous to the transgenic plant, transgenic plant cell or transgenic plant part.

13. The method of claim 11, wherein said nucleic acid is a transgene.

14. The method of claim 11, wherein said promoter is obtained from a monocotyledonous plant.

15. The method of claim 11, wherein said promoter confers expression of the nucleic acid during the period of from 5 days after pollination (DAP) to at least 25 DAP.

\* \* \* \* \*

SEQUENCE LISTING

```
<160> NUMBER OF SEQ ID NOS: 29

<210> SEQ ID NO 1
<211> LENGTH: 583
<212> TYPE: DNA
<213> ORGANISM: Artificial sequence
<220> FEATURE:
<223> OTHER INFORMATION: transcribed sequence in Affymetrix clone
      Ta.10064.1.S1_at
<220> FEATURE:
<221> NAME/KEY: misc_feature
<222> LOCATION: (539)..(539)
<223> OTHER INFORMATION: n is a, c, g, or t

<400> SEQUENCE: 1
ggatagagaa ggctctagtg tagcagatac aaaagccata gtcatggcaa aactcatgtg      60
cttatgtttc atcatcctca ctattggggt agccatgtcg gctgacgaat gcgagggtga     120
ccgacaggca atgatcaagg agtgtgctaa gtatcaacaa tggccagcaa atccgaagct     180
agatccatcg gatgcatgtt gcgccgtgtg gaaaaacgca aacatcccat gcctttgcgc     240
tggtgtcacc aaggagaaag agaagatata ttgtatggag aaggttggct acgttgccaa     300
tttctgcaag aagccgttcc cacatggcta caagtgcgga agttacacat tccctcctct     360
ggcgtagtca ctctagttta gctgtgggag gagaagtgtt ggcttttaca ttccatgtac     420
ctggcctaac aataactttc ctttcagatc tgtaattcgt gaggctgtgc cagaaaactt     480
tatgccaaga actttgtacg agaacgtttg tgaaactaat aaagccttct cctcaaaana     540
aaaaaaaaaa aaaaaaaaaa aaaaaaaaaa aaaaaaaaaa aaa                       583

<210> SEQ ID NO 2
<211> LENGTH: 2126
<212> TYPE: DNA
<213> ORGANISM: Artificial sequence
<220> FEATURE:
<223> OTHER INFORMATION: WP04 promoter

<400> SEQUENCE: 2
aaaacatcgc acggcattag tcctcaccca taacctaaca tatctcatct gaatggtcgt      60
taaatcaata aatatacaaa taaatcaaga agcacaatgc ataagctatg atttactagg     120
caaacattaa cagagatata ctgacatgaa aaaaatgtga caaacatag atctagaatg      180 gaataaaatg aaccttgatt gatacaaatt gaaactagcc ctgataaaaa aattacttat     240
ctatcaaacc ctacacgtaa tcaaaccaaa ctcgagggtt aaacctcatt tcctacctac     300
cagacaaaaa acatgaacta gaaaaactaa aaaatgaacc aaccccccact gaatctagca   360 aaaacactaa atgaaaatct actcttgctg aaaataaaaa tcctatgaat ccactgaatt     420
ccctacacac acaagctatc cggccaccca ttgaatcttg actactaaaa tccccttgct     480
ccctacattc gagtggattg ggaacaaacc ctaggtacat gaaaaaaaca aataaaacga     540
ggtatgtata agttgattca tttgtgcggt gcttctttgt ttatgttcgg ctcttatctt     600
ttaaaaaagg aaagttgttg tagactgtta gcaaagttga ttttatcccg acacatgtga     660
```

| | |
|---|---:|
| tccgaatgtt cactaaggca aatcagaaaa aagaacacat gtataaagtt atgatactgg | 720 |
| acaaacctta acaaacatta tacttacatg aaaaaatgga acaacatgga tctagactaa | 780 |
| aatctaaaat caaccttgac actaaatcac ctgaactaaa aaaagggcat agactgaatc | 840 |
| tctgcgcact acccagcgac ccgcttaatc ttgaccgact ggaacccccc ccctcccaa | 900 |
| catttggata tattgatgaa caaatcctag atagatggat acacaacaaa atagggacgg | 960 |
| tactaatctg tgaggaaccc tacccacatt tgggtcgatt gtgggacaaa ccctagattg | 1020 |
| atgaatgcac aaacaaagaa gaggggatgg tgctcaatct atgagcaaga aacaataact | 1080 |
| ggacaaaaac aaagaggaag aaaaaaataa gaacagggca aaaaacttac tccaatggcg | 1140 |
| tctctctccc ttctcgttct ccagagcccc tggatgaggc cgaagaggaa tgggaaatgg | 1200 |
| gcaaaatgaa tgcgagggag aaaattactc tgagggagac aaacggccta ccagcccaac | 1260 |
| tatcgtgaca aacaccccga cccgctacta gcatcaacct gaaaacgggc cgcgcaacac | 1320 |
| acaacagtcg cgtgcgaatg caccaacggg acaaaaatag gtttgcgcga atcttgaaga | 1380 |
| tagacgagat ccaacggctc tagacttaga tgtgaagtag ttatttcaca tctagatgtg | 1440 |
| aaatagcaaa gctgatatta tgattgtaat gttatagcat gtagatgtgt aattaatata | 1500 |
| caattcattt ttttgatgca gtaccatacc ttcaagatat atataattaa tgtaatgttg | 1560 |
| tagcatgtag atgtgtaatt aatgcacacg ttcattttc ggtgcagtac catatctttc | 1620 |
| tatcttcaag atatatataa ttattgtagt attatagcat gtagatgtgc aactaatgga | 1680 |
| tatattcatt ttttatgcag taccatatct tcaagatata tcatatatag tacaactaat | 1740 |
| gtatgtataa tgtgtcgatg tggagttaat atacacattc attgttcgat gctatttcgt | 1800 |
| atcttcaagg tatagcatgt agatatagag ttaatgtgaa cattcattat ttgatacaat | 1860 |
| atcgtatctt caagatataa agctaatgta tgatgtagcc tctagagtgc aattaatgta | 1920 |
| catattaatt gcttgacatg gtgccataac ttcaagatat agaactgatg catgtgccca | 1980 |
| tatcatcatc tcaaacaagg ctatataaac cgagccatag ctaacgaagt catgtatccc | 2040 |
| acacattcac agagaagcca cacaaacaat tataacatca aagggataga gaaggctcta | 2100 |
| gtgtagcaga tacaaaagcc atagtc | 2126 |

```
<210> SEQ ID NO 3
<211> LENGTH: 7581
<212> TYPE: DNA
<213> ORGANISM: Artificial sequence
<220> FEATURE:
<223> OTHER INFORMATION: Vector pBSubi::bar-nos_R3R4

<400> SEQUENCE: 3
```

| | |
|---|---:|
| cacctgacgc gccctgtagc ggcgcattaa gcgcggcggg tgtggtggtt acgcgcagcg | 60 |
| tgaccgctac acttgccagc gccctagcgc ccgctccttt cgctttcttc ccttcctttc | 120 |
| tcgccacgtt cgccggcttt ccccgtcaag ctctaaatcg ggggctccct ttagggttcc | 180 |
| gatttagtgc tttacggcac ctcgacccca aaaaacttga ttagggtgat ggttcacgta | 240 |
| gtgggccatc gccctgatag acggtttttc gccctttgac gttggagtcc acgttcttta | 300 |
| atagtggact cttgttccaa actggaacaa cactcaaccc tatctcggtc tattcttttg | 360 |
| atttataagg gattttgccg atttcggcct attggttaaa aaatgagctg atttaacaaa | 420 |
| aatttaacgc gaattttaac aaaatattaa cgcttacaat ttccattcgc cattcaggct | 480 |
| gcgcaactgt tgggaagggc gatcggtgcg ggcctcttcg ctattacgcc agctggcgaa | 540 |
| agggggatgt gctgcaaggc gattaagttg ggtaacgcca gggttttccc agtcacgacg | 600 |

```
ttgtaaaacg acggccagtg aattgtaata cgactcacta tagggcgaat tgggtaccgg    660
gccccccctc gaggtcgacg gtatcgataa gcttgatatc gaattctcat gtttgacagc    720
ttatcatcgg atctagtaac atagatgaca ccgcgcgcga taatttatcc tagtttgcgc    780
gctatatttt gttttctatc gcgtattaaa tgtataattg cgggactcta atcataaaaa    840
cccatctcat aaataacgtc atgcattaca tgttaattat tacatgctta acgtaattca    900
acagaaatta tatgataatc atcgcaagac cggcaacagg attcaatctt aagaaacttt    960
attgccaaat gtttgaacga tctgcaggtc gacggatcag atctcggtga cgggcaggac   1020
cggacggggc ggtaccggca ggctgaagtc cagctgccag aaacccacgt catgccagtt   1080
cccgtgcttg aagccggccg cccgcagcat gccgcggggg gcatatccga gcgcctcgtg   1140
catgcgcacg ctcgggtcgt tgggcagccc gatgacagcg accacgctct tgaagccctg   1200
tgcctccagg gacttcagca ggtgggtgta gagcgtggag cccagtcccg tccgctggtg   1260
gcgggggag acgtacacgg tcgactcggc cgtccagtcg taggcgttgc gtgccttcca   1320
ggggcccgcg taggcgatgc cggcgacctc gccgtccacc tcggcgacga gccagggata   1380
gcgctcccgc agacggacga ggtcgtccgt ccactcctgc ggttcctgcg gctcggtacg   1440
gaagttgacc gtgcttgtct cgatgtagtg gttgacgatg gtgcagaccg ccggcatgtc   1500
cgcctcggtg gcacggcgga tgtcggccgg gcgtcgttct gggctcatgg ttacttccta   1560
atcgatggat cctctagagt cgacctgcag aagtaacacc aaacaacagg gtgagcatcg   1620
acaaagaaa cagtaccaag caaataaata gcgtatgaag gcagggctaa aaaaatccac   1680
atatagctgc tgcatatgcc atcatccaag tatatcaaga tcaaaataat tataaaacat   1740
acttgtttat tataatagat aggtactcaa ggttagagca tatgaataga tgctgcatat   1800
gccatcatgt atatgcatca gtaaaaccca catcaacatg tatacctatc ctagatcgat   1860
atttccatcc atcttaaact cgtaactatg aagatgtatg acacacacat acagttccaa   1920
aattaataaa tacaccaggt agtttgaaac agtattctac tccgatctag aacgaatgaa   1980
cgaccgccca accacaccac atcatcacaa ccaagcgaac aaaaagcatc tctgtatatg   2040
catcagtaaa acccgcatca acatgtatac ctatcctaga tcgatatttc catccatcat   2100
tttcaattcg taactatgaa tatgtatggc acacacatac agatccaaaa ttaataaatc   2160
caccaggtag tttgaaacag aattctactc cgatctagaa cgaccgccca accagaccac   2220
atcatcacaa ccaagacaaa aaaagcatg aaaagatgac ccgacaaaca agtgcacggc   2280
atatattgaa ataaaggaaa agggcaaacc aaacccctatg caacgaaaca aaaaaaatca   2340
tgaaatcgat cccgtctgcg gaacggctag agccatccca ggattcccca aagagaaaca   2400
ctggcaagtt agcaatcaga acgtgtctga cgtacaggtc gcatccgtgt acgaacgcta   2460
gcagcacgga tctaacacaa acacggatct aacacaaaca tgaacagaag tagaactacc   2520
gggccctaac catggaccgg aacgccgatc tagagaaggt agagagggg ggggggggag   2580
gacgagcggc gtaccttgaa gcggaggtgc cgacgggtgg atttggggga gatctggttg   2640
tgtgtgtgtg cgctccgaac aacacgaggt tggggaaaga gggtgtggag ggggtgtcta   2700
tttattacgg cgggcgagga agggaaagcg aaggagcggt gggaaaggaa tcccccgtag   2760
ctgccggtgc cgtgagagga ggaggaggcc gcctgccgtg ccggctcacg tctgccgctc   2820
cgccacgcaa tttctggatg ccgacagcgg agcaagtcca acggtggagc ggaactctcg   2880
agaggggtcc agaggcagcg acagagatgc cgtgccgtct gcttcgcttg gcccgacgcg   2940
acgctgctgg ttcgctggtt ggtgtccgtt agactcgtcg acggcgttta acaggctggc   3000
```

```
attatctact cgaaacaaga aaaatgtttc cttagttttt ttaatttctt aaagggtatt    3060
tgtttaattt ttagtcactt tattttattc tattttatat ctaaattatt aaataaaaaa    3120
actaaaatag agttttagtt ttcttaattt agaggctaaa atagaataaa atagatgtac    3180
taaaaaaatt agtctataaa aaccattaac cctaaaccct aaatggatgt actaataaaa    3240
tggatgaagt attatatagg tgaagctatt tgcaaaaaaa aaggagaaca catgcacact    3300
aaaaagataa aactgtagag tcctgttgtc aaaatactca attgtccttt agaccatgtc    3360
taactgttca tttatatgat tctctaaaac actgatatta ttgtagtact atagattata    3420
ttattcgtag agtaaagttt aaatatatgt ataaagatag ataaactgca cttcaaacaa    3480
gtgtgacaaa aaaaatatgt ggtaattttt tataacttag acatgcaatg ctcattatct    3540
ctagagaggg gcacgaccgg gtcacgctgc actgcaggca tgcaagcttg aattcctgca    3600
gccccgccaa gctatcaact ttgtatagaa aagttgaacg agaaacgtaa aatgatataa    3660
atatcaatat attaaattag attttgcata aaaaacagac tacataatac tgtaaaacac    3720
aacatatcca gtcactatgg tcgacctgca gactggctgt gtataaggga gcctgacatt    3780
tatattcccc agaacatcag gttaatggcg ttttgatgt cattttcgcg gtggctgaga     3840
tcagccactt cttccccgat aacggagacc ggcacactgg ccatatcggt ggtcatcatg    3900
cgccagcttt catccccgat atgcaccacc gggtaaagtt cacggggac tttatctgac     3960
agcagacgtg cactggccag ggggatcacc atccgtcgcc cgggcgtgtc aataatatca    4020
ctctgtacat ccacaaacag acgataacgg ctctctcttt tataggtgta aaccttaaac    4080
tgcatttcac cagcccctgt tctcgtcggc aaaagagccg ttcatttcaa taaaccgggc    4140
gacctcagcc atcccttcct gattttccgc tttccagcgt tcggcacgca gacgacgggc    4200
ttcattctgc atggttgtgc ttaccgaacc ggagatattg acatcatata tgccttgagc    4260
aactgatagc tgtcgctgtc aactgtcact gtaatacgct gcttcatagc atacctcttt    4320
ttgacatact tcgggtatac atatcagtat atattcttat accgcaaaaa tcagcgcgca    4380
aatacgcata ctgttatctg gcttttagta agccggatcc tctagattac gccccgccct    4440
gccactcatc gcagtactgt tgtaattcat taagcattct gccgacatgg aagccatcac    4500
aaacggcatg atgaacctga atcgccagcg gcatcagcac cttgtcgcct tgcgtataat    4560
atttgcccat ggtgaaaacg ggggcgaaga agttgtccat attggccacg tttaaatcaa    4620
aactggtgaa actcacccag ggattggctg agacgaaaaa catattctca ataaaccctt    4680
tagggaaata ggccaggttt tcaccgtaac acgccacatc ttgcgaatat atgtgtagaa    4740
actgccggaa atcgtcgtgg tattcactcc agagcgatga aaacgtttca gtttgctcat    4800
ggaaaacggt gtaacaaggg tgaacactat cccatatcac cagctcaccg tctttcattg    4860
ccatacggaa ttccggatga gcattcatca ggcgggcaag aatgtgaata aaggccggat    4920
aaaacttgtg cttatttttc tttacggtct taaaaaggc cgtaatatcc agctgaacgg     4980
tctggttata ggtacattga gcaactgact gaaatgcctc aaaatgttct ttacgatgcc    5040
attgggatat atcaacggtg gtatatccag tgatttttt ctccatttta gcttccttag     5100
ctcctgaaaa tctcgacgga tcctaactca aaatccacac attatacgag ccggaagcat    5160
aaagtgtaaa gcctggggt gcctaatgcg ccgccatag tgactggata tgttgtgttt      5220
tacagtatta tgtagtctgt tttttatgca aaatctaatt taatatattg atatttatat    5280
cattttacgt ttctcgttca actttattat acatagttga taattcactg gccgtcgtgg    5340
gggatccact agttctagag cggccgccac cgcggtggag ctccagcttt tgttcccttt    5400
```

```
agtgagggtt aatttcgagc ttggcgtaat catggtcata gctgtttcct gtgtgaaatt      5460
gttatccgct cacaattcca cacaacatac gagccggaag cataaagtgt aaagcctggg      5520
gtgcctaatg agtgagctaa ctcacattaa ttgcgttgcg ctcactgccc gctttccagt      5580
cgggaaacct gtcgtgccag ctgcattaat gaatcggcca acgcgcgggg agaggcggtt      5640
tgcgtattgg cgctcttccg cttcctcgc tcactgactc gctgcgctcg tcgttcggc        5700 tgcggcgagc ggtatcagct cactcaaagg cggtaatacg gttatccaca gaatcagggg      5760
ataacgcagg aaagaacatg tgagcaaaag gccagcaaaa ggccaggaac cgtaaaaagg      5820
ccgcgttgct ggcgtttttc cataggctcc gcccccctga cgagcatcac aaaaatcgac      5880
gctcaagtca gaggtggcga aacccgacag gactataaag ataccaggcg tttccccctg      5940
gaagctccct cgtgcgctct cctgttccga ccctgccgct taccggatac ctgtccgcct      6000 ttctccttc gggaagcgtg gcgctttctc atagctcacg ctgtaggtat ctcagttcgg       6060
tgtaggtcgt tcgctccaag ctgggctgtg tgcacgaacc ccccgttcag cccgaccgct      6120
gcgccttatc cggtaactat cgtcttgagt ccaacccggt aagacacgac ttatcgccac      6180
tggcagcagc cactggtaac aggattagca gagcgaggta tgtaggcggt gctacagagt      6240
tcttgaagtg gtgcctaac tacggctaca ctagaaggac agtatttggt atctgcgctc       6300
tgctgaagcc agttaccttc ggaaaaagag ttggtagctc ttgatccggc aaacaaacca      6360
ccgctggtag cggtggtttt tttgtttgca agcagcagat tacgcgcaga aaaaaggat       6420 ctcaagaaga tcctttgatc ttttctacgg ggtctgacgc tcagtggaac gaaaactcac      6480
gttaagggat tttggtcatg agattatcaa aaaggatctt cacctagatc cttttaaatt      6540
aaaaatgaag ttttaaatca atctaaagta tatatgagta acttggtct gacagttacc       6600 aatgcttaat cagtgaggca cctatctcag cgatctgtct atttcgttca tccatagttg      6660
cctgactccc cgtcgtgtag ataactacga tacgggaggg cttaccatct ggccccagtg     6720
ctgcaatgat accgcgagac ccacgctcac cggctccaga tttatcagca ataaaccagc      6780
cagccggaag ggccgagcgc agaagtggtc ctgcaacttt atccgcctcc atccagtcta      6840
ttaattgttg ccgggaagct agagtaagta gttcgccagt taatagtttg cgcaacgttg      6900
ttgccattgc tacaggcatc gtggtgtcac gctcgtcgtt tggtatggct tcattcagct      6960
ccggttccca acgatcaagg cgagttacat gatcccccat gttgtgcaaa aaagcggtta     7020
gctccttcgg tcctccgatc gttgtcagaa gtaagttggc cgcagtgtta tcactcatgg      7080
ttatggcagc actgcataat tctcttactg tcatgccatc cgtaagatgc ttttctgtga      7140
ctggtgagta ctcaaccaag tcattctgag aatagtgtat gcggcgaccg agttgctctt      7200
gcccggcgtc aatacgggat aataccgcgc cacatagcag aactttaaaa gtgctcatca     7260
ttggaaaacg ttcttcgggg cgaaaactct caaggatctt accgctgttg agatccagtt      7320
cgatgtaacc cactcgtgca cccaactgat cttcagcatc ttttactttc accagcgttt      7380
ctgggtgagc aaaaacagga aggcaaaatg ccgcaaaaaa gggaataagg gcgacacgga      7440
aatgttgaat actcatactc ttcctttttc aatattattg aagcatttat cagggttatt      7500
gtctcatgag cggatacata tttgaatgta tttagaaaaa taaacaaata ggggttccgc      7560
gcacatttcc ccgaaaagtg c                                                7581

<210> SEQ ID NO 4
<211> LENGTH: 10767
<212> TYPE: DNA
<213> ORGANISM: Artificial sequence
```

<220> FEATURE:
<223> OTHER INFORMATION: Vector pPZP200 35S::hph-35St_R3R4

<400> SEQUENCE: 4

```
agtactttga tccaacccct ccgctgctat agtgcagtcg gcttctgacg ttcagtgcag      60
ccgtcttctg aaaacgacat gtcgcacaag tcctaagtta cgcgacaggc tgccgccctg     120
cccttttcct ggcgttttct tgtcgcgtgt tttagtcgca taaagtagaa tacttgcgac     180
tagaaccgga gacattacgc catgaacaag agcgccgccg ctggcctgct ggcgtatgcc     240
cgcgtcagca ccgacgacca ggacttgacc aaccaacggg ccgaactgca cgcggccggc     300
tgcaccaagc tgtttttccga gaagatcacc ggcaccaggc gcgaccgccc ggagctggcc     360
aggatgcttg accacctacg ccctggcgac gttgtgacag tgaccaggct agaccgcctg     420
gcccgcagca cccgcgacct actggacatt gccgagcgca tccaggaggc cggcgcgggc     480
ctgcgtagcc tggcagagcc gtgggccgac accaccacgc cggccggccg catggtgttg     540
accgtgttcg ccggcattgc cgagttcgag cgttccctaa tcatcgaccg cacccggagc     600
gggcgcgagg ccgccaaggc ccgaggcgtg aagtttggcc ccgccctac cctcacccccg     660
gcacagatcg cgcacgcccg cgagctgatc gaccaggaag gccgcaccgt gaaagaggcg     720
gctgcactgc ttggcgtgca tcgctcgacc ctgtaccgcg cacttgagcg cagcgaggaa     780
gtgacgccca ccgaggccag gcggcgcggt gccttccgtg aggacgcatt gaccgaggcc     840
gacgccctgg cggccgccga gaatgaacgc caagaggaac aagcatgaaa ccgcaccagg     900
acggccagga cgaaccgttt ttcattaccg aagagatcga gcggagatg atcgcggccg     960
ggtacgtgtt cgagccgccc gcgcacgtct caaccgtgcg gctgcatgaa atcctggccg    1020
gtttgtctga tgccaagctg gcggcctggc cggccagctt ggccgctgaa gaaaccgagc    1080
gccgccgtct aaaaaggtga tgtgtatttg agtaaaacag cttgcgtcat gcggtcgctg    1140
cgtatatgat gcgatgagta aataaacaaa tacgcaaggg gaacgcatga aggttatcgc    1200
tgtacttaac cagaaaggcg ggtcaggcaa gacgaccatc gcaacccatc tagcccgcgc    1260
cctgcaactc gccggggccg atgttctgtt agtcgattcc gatccccagg gcagtgcccg    1320
cgattgggcg gccgtgcggg aagatcaacc gctaaccgtt gtcggcatcg accgcccgac    1380
gattgaccgc gacgtgaagg ccatcggccg gcgcgacttc gtagtgatcg acggagcgcc    1440
ccaggcggcg gacttggctg tgtccgcgat caaggcagcc gacttcgtgc tgattccggt    1500
gcagccaagc ccttacgaca tatgggccac cgccgacctg gtggagctgg ttaagcagcg    1560
cattgaggtc acggatggaa ggctacaagc ggcctttgtc gtgtcgcggg cgatcaaagg    1620
cacgcgcatc ggcggtgagg ttgccgaggc gctggccggg tacgagctgc ccattcttga    1680
gtcccgtatc acgcagcgcg tgagctaccc aggcactgcc gccgccggca caaccgttct    1740
tgaatcagaa cccgagggcg acgctgcccg cgaggtccag gcgctggccg ctgaaattaa    1800
atcaaaactc atttgagtta atgaggtaaa gagaaaatga gcaaaagcac aaacacgcta    1860
agtgccggcc gtccgagcgc acgcagcagc aaggctgcaa cgttggccag cctggcagac    1920
acgccagcca tgaagcgggt caactttcag ttgccggcgg aggatcacac caagctgaag    1980
atgtacgcgg tacgccaagg caagaccatt accgagctgc tatctgaata catcgcgcag    2040
ctaccagagt aaatgagcaa atgaataaat gagtagatga attttagcgg ctaaaggagg    2100
cggcatggaa aatcaagaac aaccaggcac cgacgccgtg gaatgcccca tgtgtggagg    2160
aacgggcggt tggccaggcg taagcggctg ggttgtctgc cggccctgca atggcactgg    2220
```

| | |
|---|---|
| aacccccaag cccgaggaat cggcgtgacg gtcgcaaacc atccggcccg gtacaaatcg | 2280 |
| gcgcggcgct gggtgatgac ctggtggaga agttgaaggc cgcgcaggcc gcccagcggc | 2340 |
| aacgcatcga ggcagaagca cgccccggtg aatcgtggca agcggccgct gatcgaatcc | 2400 |
| gcaaagaatc ccggcaaccg ccggcagccg gtgcgccgtc gattaggaag ccgcccaagg | 2460 |
| gcgacgagca accagatttt ttcgttccga tgctctatga cgtgggcacc cgcgatagtc | 2520 |
| gcagcatcat ggacgtggcc gttttccgtc tgtcgaagcg tgaccgacga gctggcgagg | 2580 |
| tgatccgcta cgagcttcca gacgggcacg tagaggtttc cgcagggccg gccggcatgg | 2640 |
| ccagtgtgtg ggattacgac ctggtactga tggcggtttc ccatctaacc gaatccatga | 2700 |
| accgataccg ggaagggaag ggagacaagc ccggccgcgt gttccgtcca cacgttgcgg | 2760 |
| acgtactcaa gttctgccgg cgagccgatg gcggaaagca gaaagacgac ctggtagaaa | 2820 |
| cctgcattcg gttaaacacc acgcacgttg ccatgcagcg tacgaagaag gccaagaacg | 2880 |
| gccgcctggt gacggtatcc gagggtgaag ccttgattag ccgctacaag atcgtaaaga | 2940 |
| gcgaaaccgg gcggccggag tacatcgaga tcgagctagc tgattggatg taccgcgaga | 3000 |
| tcacagaagg caagaacccg gacgtgctga cggttcaccc cgattacttt ttgatcgatc | 3060 |
| ccggcatcgg ccgttttctc taccgcctgg cacgccgcgc cgcaggcaag cagaagcca | 3120 |
| gatggttgtt caagacgatc tacgaacgca gtggcagcgc cggagagttc aagaagttct | 3180 |
| gtttcaccgt gcgcaagctg atcgggtcaa atgacctgcc ggagtacgat ttgaaggagg | 3240 |
| aggcggggca ggctggcccg atcctagtca tgcgctaccg caacctgatc gagggcgaag | 3300 |
| catccgccgg ttcctaatgt acggagcaga tgctagggca aattgcccta gcaggggaaa | 3360 |
| aaggtcgaaa aggtctcttt cctgtggata gcacgtacat tgggaaccca agccgtaca | 3420 |
| ttgggaaccg gaaccgtac attgggaacc caaagccgta cattgggaac cggtcacaca | 3480 |
| tgtaagtgac tgatataaaa gagaaaaaag gcgattttc cgcctaaaac tctttaaaac | 3540 |
| ttattaaaac tcttaaaacc cgcctggcct gtgcataact gtctggccag cgcacagccg | 3600 |
| aagagctgca aaaagcgcct acccttcggt cgctgcgctc cctacgcccc gccgcttcgc | 3660 |
| gtcggcctat cgcggccgct ggccgctcaa aaatggctgg cctacggcca ggcaatctac | 3720 |
| cagggcgcgg acaagccgcg ccgtcgccac tcgaccgccg gcgcccacat caaggcaccc | 3780 |
| tgcctcgcgc gtttcggtga tgacggtgaa aacctctgac acatgcagct cccggagacg | 3840 |
| gtcacagctt gtctgtaagc ggatgccggg agcagacaag cccgtcaggg cgcgtcagcg | 3900 |
| ggtgttggcg ggtgtcgggg cgcagccatg acccagtcac gtagcgatag cggagtgtat | 3960 |
| actggcttaa ctatgcggca tcagagcaga ttgtactgag agtgcaccat atgcggtgtg | 4020 |
| aaataccgca cagatgcgta aggagaaaat accgcatcag cgctcttcc gcttcctcgc | 4080 |
| tcactgactc gctgcgctcg gtcgttcggc tgcggcgagc ggtatcagct cactcaaagg | 4140 |
| cggtaatacg gttatccaca gaatcagggg ataacgcagg aaagaacatg tgagcaaaag | 4200 |
| gccagcaaaa ggccaggaac cgtaaaaagg ccgcgttgct ggcgtttttc cataggctcc | 4260 |
| gcccccctga cgagcatcac aaaaatcgac gctcaagtca gaggtggcga aacccgacag | 4320 |
| gactataaag ataccaggcg tttccccctg gaagctccct cgtgcgctct cctgttccga | 4380 |
| ccctgccgct taccggatac ctgtccgcct ttctcccttc gggaagcgtg cgctttctc | 4440 |
| atagctcacg ctgtaggtat ctcagttcgg tgtaggtcgt tcgctccaag ctgggctgtg | 4500 |
| tgcacgaacc cccgttcag cccgaccgct gcgccttatc cggtaactat cgtcttgagt | 4560 |
| ccaacccggt aagacacgac ttatcgccac tggcagcagc cactggtaac aggattagca | 4620 |

```
gagcgaggta tgtaggcggt gctacagagt tcttgaagtg gtggcctaac tacggctaca    4680
ctagaaggac agtatttggt atctgcgctc tgctgaagcc agttaccttc ggaaaaagag    4740
ttggtagctc ttgatccggc aaacaaacca ccgctggtag cggtggtttt tttgtttgca    4800
agcagcagat tacgcgcaga aaaaaaggat ctcaagaaga tcctttgatc ttttctacgg    4860
ggtctgacgc tcagtggaac gaaaactcac gttaagggat tttggtcatg catgatatat    4920
ctcccaattt gtgtagggct tattatgcac gcttaaaaat aataaaagca gacttgacct    4980
gatagtttgg ctgtgagcaa ttatgtgctt agtgcatcta atcgcttgag ttaacgccgg    5040
cgaagcggcg tcggcttgaa cgaatttcta gctagacatt atttgccgac taccttggtg    5100
atctcgcctt tcacgtagtg acaaattct tccaactgat ctgcgcgcga ggccaagcga    5160
tcttcttctt gtccaagata agcctgtcta gcttcaagta tgacgggctg atactgggcc    5220
ggcaggcgct ccattgccca gtcggcagcg acatccttcg gcgcgatttt gccggttact    5280
gcgctgtacc aaatgcggga caacgtaagc actacatttc gctcatcgcc agcccagtcg    5340
ggcggcgagt tccatagcgt taaggtttca tttagcgcct caaatagatc ctgttcagga    5400
accggatcaa agagttcctc cgccgctgga cctaccaagg caacgctatg ttctcttgct    5460
tttgtcagca agatagccag atcaatgtcg atcgtggctg gctcgaagat acctgcaaga    5520
atgtcattgc gctgccattc tccaaattgc agttcgcgct tagctggata acgcacgga    5580 atgatgtcgt cgtgcacaac aatggtgact tctacagcgc ggagaatctc gctctctcca    5640
ggggaagccg aagtttccaa aaggtcgttg atcaaagctc gccgcgttgt tcatcaagc    5700 cttacggtca ccgtaaccag caaatcaata tcactgtgtg gcttcaggcc gccatccact    5760
gcggagccgt acaaatgtac ggccagcaac gtcggttcga gatggcgctc gatgacgcca    5820
actacctctg atagttgagt cgatacttcg gcgatcaccg cttcccccat gatgtttaac    5880
tttgttttag ggcgactgcc ctgctgcgta acatcgttgc tgctccataa catcaaacat    5940
cgacccacgg cgtaacgcgc ttgctgcttg gatgcccgag gcatagactg tacccccaaaa    6000 aaacatgtca taacaagaag ccatgaaaac cgccactgcg ccgttaccac cgctgcgttc    6060
ggtcaaggtt ctggaccagt tgcgtgacgg cagttacgct acttgcatta cagcttacga    6120
accgaacgag gcttatgtcc actgggttcg tgcccgaatt gatcacaggc agcaacgctc    6180
tgtcatcgtt acaatcaaca tgctaccctc cgcgagatca tccgtgtttc aaacccggca    6240
gcttagttgc cgttcttccg aatagcatcg gtaacatgag caaagtctgc cgccttacaa    6300
cggctctccc gctgacgccg tcccggactg atgggctgcc tgtatcgagt ggtgattttg    6360
tgccgagctg ccggtcgggg agctgttggc tggctggtgg caggatatat tgtggtgtaa    6420
acaaattgac gcttagacaa cttaataaca cattgcggac gttttaatg tactgaatta    6480 acgccgaatt gaattcgagc tcggtacccg gggatctgga ttttagtact ggattttggt    6540
tttaggaatt agaaatttta ttgatagaag tattttacaa atacaaatac atactaaggg    6600
tttcttatat gctcaacaca tgagcgaaac cctataagaa ccctaatttc ccttatcggg    6660
aaactactca cacattagga tcccggtcgg catctactct attcctttgc cctcggacga    6720
gtgctggggc gtcggtttcc actatcgcg agtacttcta cacagccatc ggtccagacg    6780
gccgcgcttc tgcgggcgat ttgtgtacgc ccgacagtcc cggctccgga tcggacgatt    6840
gcgtcgcatc gaccctgcgc ccaagctgca tcatcgaaat tgccgtcaac caagctctga    6900
tagagttggt caagaccaat gcggagcata tacgcccgga gccgcggcga tcctgcaagc    6960
tccggatgcc tccgctcgaa gtagcgcgtc tgctgctcca tacaagccaa ccacggcctc    7020
```

```
cagaagaaga tgttggcgac ctcgtattgg gaatccccga acatcgcctc gctccagtca    7080
atgaccgctg ttatgcggcc attgtccgtc aggacattgt tggagccgaa atccgcgtgc    7140
acgaggtgcc ggacttcggg gcagtcctcg gcccaaagca tcagctcatc gagagcctgc    7200
gcgacggacg cactgacggt gtcgtccatc acagtttgcc agtgatacac atggggatca    7260
gcaatcgcgc atatgaaatc acgccatgta gtgtattgac cgattccttg cggtccgaat    7320
gggccgaacc cgctcgtctg gctaagatcg gccgcagcga tcgcatccat ggcctccgcg    7380
accggctgca gaacagcggg cagttcggtt tcaggcaggt cttgcaacgt gacaccctgt    7440
gcacggcggg agatgcaata ggtcaggctc tcgctgaatt ccccaatgtc aagcacttcc    7500
ggaatcggga gcgcggccga tgcaaagtgc cgataaacat aacgatcttt gtagaaacca    7560
tcggcgcagc tatttacccg caggacatat ccacgccctc ctacatcgaa gctgaaagca    7620
cgagattctt cgccctccga gagctgcatc aggtcggaga cgctgtcgaa cttttcgatc    7680
agaaacttct cgacagacgt cgcggtgagt tcaggctttt tcatatctca ttgccccccg    7740
ggatccttat agagagagat agatttgtag agagagactg gtgatttcag cgtgtcctct    7800
ccaaatgaaa tgaacttcct tatatagagg aagggtcttg cgaaggatag tgggattgtg    7860
cgtcatccct tacgtcagtg gagatatcac atcaatccac ttgctttgaa gacgtggttg    7920
gaacgtcttc ttttccacg atgctcctcg tgggtggggg tccatctttg ggaccactgt    7980
cggcagaggc atcttgaacg atagcctttc ctttatcgca atgatggcat ttgtaggtgc    8040
caccttcctt ttctactgtc ttcatgatga agtgacagat agctgggcaa tggaatccga    8100
ggaggttttcc cgaaattacc ctttgttgga aagtctcaat tgcccctttgg tcttctgaga    8160
ctgtatcctt gatatttttg gagtagacca gagtgtcgtg ctccaccatg ttgacgaaga    8220
ttttcttctt gtcattgagt cgtaagagac tctgtatgaa ctgttcgcca gttttcacgg    8280
cgagttctgt tagatcctcg atttgaatct ttgactccat ggcctttgat tcagtaggaa    8340
ctactttttt agagactcca atctctatta cttgccttgg tttatgaagc aagccttgaa    8400
tcgtccatac tggaatagta cttctgatct tgagaaatat atctttctct gtgttcttga    8460
tgcagttagt cctgaatctt ttgactgcat ctttaacctt cttgggaagg tatttgatct    8520
cctggagatt attactcggg tagatcgtct taatgagacc tgctgcgtag gcctctctaa    8580
ccatctgtgg gttagcgttc tttctgaaat tgaagaggct aatcttctca ttatcagtgg    8640
tgaacatagt atcgtcacct tcaccgtcga actttcttcc tagatcgtag agatagagga    8700
agtcgtccat tgtaatctcc ggggcaaagg agatcctcta gagtcgaggg tacccgggga    8760
tcctctagag tcgagggtac ccggggatcc tctagagtcg aatgattacg ccaagctatc    8820
aactttgtat agaaaagttg aacgagaaac gtaaaatgat ataaatatca atatattaaa    8880
ttagattttg cataaaaaac agactacata atactgtaaa acacaacata tccagtcact    8940
atggtcgacc tgcagactgg ctgtgtataa gggagcctga catttatatt ccccagaaca    9000
tcaggttaat ggcgttttg atgtcatttt cgcggtggct gagatcagcc acttcttccc    9060
cgataacgga gaccggcaca ctggccatat cggtggtcat catgcgccag ctttcatccc    9120
cgatatgcac caccgggtaa agttcacggg ggacttatc tgacagcaga cgtgcactgg    9180
ccaggggggat caccatccgt cgcccgggcg tgtcaataat atcactctgt acatccacaa    9240
acagacgata acggctctct cttttatagg tgtaaacctt aaactgcatt tcaccagccc    9300
ctgttctcgt cggcaaaaga gccgttcatt tcaataaacc gggcgacctc agccatccct    9360
tcctgatttt ccgctttcca gcgttcggca cgcagacgac gggcttcatt ctgcatggtt    9420
```

```
gtgcttaccg aaccggagat attgacatca tatatgcctt gagcaactga tagctgtcgc      9480
tgtcaactgt cactgtaata cgctgcttca tagcatacct ctttttgaca tacttcgggt      9540
atacatatca gtatatattc ttataccgca aaaatcagcg cgcaaatacg catactgtta      9600
tctggctttt agtaagccgg atcctctaga ttacgcccg ccctgccact catcgcagta       9660
ctgttgtaat tcattaagca ttctgccgac atggaagcca tcacaaacgg catgatgaac      9720
ctgaatcgcc agcggcatca gcaccttgtc gccttgcgta taatatttgc ccatggtgaa      9780
aacgggggcg aagaagttgt ccatattggc cacgtttaaa tcaaaactgg tgaaactcac      9840
ccagggattg gctgagacga aaacatatt ctcaataaac cctttaggga aataggccag       9900
gttttcaccg taacacgcca catcttgcga atatatgtgt agaaactgcc ggaaatcgtc      9960
gtggtattca ctccagagcg atgaaaacgt tcagtttgc tcatggaaaa cggtgtaaca       10020
agggtgaaca ctatcccata tcaccagctc accgtctttc attgccatac ggaattccgg      10080
atgagcattc atcaggcggg caagaatgtg aataaaggcc ggataaaact tgtgcttatt      10140
tttctttacg gtctttaaaa aggccgtaat atccagctga acggtctggt tataggtaca      10200
ttgagcaact gactgaaatg cctcaaaatg ttctttacga tgccattggg atatatcaac      10260
ggtggtatat ccagtgattt ttttctccat tttagcttcc ttagctcctg aaaatctcga      10320
cggatcctaa ctcaaaatcc acacattata cgagccggaa gcataaagtg taaagcctgg      10380
gggtgcctaa tgcggccgcc atagtgactg gatatgttgt gttttacagt attatgtagt      10440
ctgtttttta tgcaaaatct aatttaatat attgatattt atatcatttt acgtttctcg      10500
ttcaacttta ttatacatag ttgataattc actggccgtc gttttacaac tcgacctgca      10560
ggcatgcaag cttagcttga gcttggatca gattgtcgtt tcccgccttc agtttaaact      10620
atcagtgttt gacaggatat attggcgggt aaacctaaga gaaagagcg tttattagaa        10680 taacggatat ttaaagggc gtgaaaaggt ttatccgttc gtccatttgt atgtgcatgc        10740
caaccacagg gttcccctcg ggatcaa                                           10767

<210> SEQ ID NO 5
<211> LENGTH: 12259
<212> TYPE: DNA
<213> ORGANISM: Artificial sequence
<220> FEATURE:
<223> OTHER INFORMATION: Vector pMPB0096

<400> SEQUENCE: 5
ttatacatag ttgataattc actggccgtc gttttacaac tcgacctgca ggcatgcaag        60
cttagcttga gcttggatca gattgtcgtt tcccgccttc agtttaaact atcagtgttt        120
gacaggatat attggcgggt aaacctaaga gaaagagcg tttattagaa taacggatat         180 ttaaagggc gtgaaaaggt ttatccgttc gtccatttgt atgtgcatgc caaccacagg         240
gttcccctcg ggatcaaagt actttgatcc aaccccctcc g ctgctatagt gcagtcggct      300
tctgacgttc agtgcagccg tcttctgaaa acgacatgtc gcacaagtcc taagttacgc        360
gacaggctgc cgccctgccc ttttcctggc gttttcttgt cgcgtgtttt agtcgcataa        420
agtagaatac ttgcgactag aaccggagac attacgccat gaacaagagc gccgccgctg        480
gcctgctggg ctatgcccgc gtcagcaccg acgaccagga cttgaccaac caacgggccg        540
aactgcacgc ggccgctgc accaagctgt tttccgagaa gatcaccggc accaggcgcg         600
accgcccgga gctggccagg atgcttgacc acctacgccc tggcgacgtt gtgacagtga       660
ccaggctaga ccgcctggcc cgcagcaccc gcgacctact ggacattgcc gagcgcatcc        720
```

```
aggaggccgg cgcgggcctg cgtagcctgg cagagccgtg ggccgacacc accacgccgg    780
ccggccgcat ggtgttgacc gtgttcgccg gcattgccga gttcgagcgt tccctaatca    840
tcgaccgcac ccggagcggg cgcgaggccg ccaaggcccg aggcgtgaag tttggccccc    900
gccctaccct caccccggca cagatcgcgc acgcccgcga gctgatcgac caggaaggcc    960
gcaccgtgaa agaggcggct gcactgcttg gcgtgcatcg ctcgaccctg taccgcgcac   1020
ttgagcgcag cgaggaagtg acgcccaccg aggccaggcg gcgcggtgcc ttccgtgagg   1080
acgcattgac cgaggccgac gccctggcgg ccgccgagaa tgaacgccaa gaggaacaag   1140
catgaaaccg caccaggacg gccaggacga accgttttc attaccgaag agatcgaggc   1200
ggagatgatc gcggccgggt acgtgttcga gccgcccgcg cacgtctcaa ccgtgcggct   1260
gcatgaaatc ctggccggtt tgtctgatgc caagctggcg gcctggccgg ccagcttggc   1320
cgctgaagaa accgagcgcc gccgtctaaa aaggtgatgt gtatttgagt aaaacagctt   1380
gcgtcatgcg gtcgctgcgt atatgatgcg atgagtaaat aaacaaatac gcaaggggaa   1440
cgcatgaagg ttatcgctgt acttaaccag aaaggcgggt caggcaagac gaccatcgca   1500
acccatctag cccgcgccct gcaactcgcg ggggccgatg ttctgttagt cgattccgat   1560
ccccagggca gtgcccgcga ttgggcggcc gtgcgggaag atcaaccgct aaccgttgtc   1620
ggcatcgacc gcccgacgat tgaccgcgac gtgaaggcca tcggccggcg cgacttcgta   1680
gtgatcgacg gagcgcccca gcggcggac ttggctgtgt ccgcgatcaa ggcagccgac   1740
ttcgtgctga ttccggtgca gccaagccct tacgacatat gggccaccgc cgacctggtg   1800
gagctggtta agcagcgcat tgaggtcacg gatggaaggc tacaagcggc ctttgtcgtg   1860
tcgcgggcga tcaaaggcac gcgcatcggc ggtgaggttg ccgaggcgct ggccgggtac   1920
gagctgccca ttcttgagtc ccgtatcacg cagcgcgtga gctacccagg cactgccgcc   1980
gccggcacaa ccgttcttga atcagaaccc gagggcgacg ctgcccgcga ggtccaggcg   2040
ctggccgctg aaattaaatc aaaactcatt tgagttaatg aggtaaagag aaaatgagca   2100
aaagcacaaa cacgctaagt gccggccgtc cgagcgcacg cagcagcaag gctgcaacgt   2160
tggccagcct ggcagacacg ccagccatga agcgggtcaa ctttcagttg ccggcggagg   2220
atcacaccaa gctgaagatg tacgcggtac gccaaggcaa gaccattacc gagctgctat   2280
ctgaatacat cgcgcagcta ccagagtaaa tgagcaaatg aataaatgag tagatgaatt   2340
ttagcggcta aggaggcgg catggaaaat caagaacaac caggcaccga cgccgtggaa   2400
tgccccatgt gtggaggaac gggcggttgg ccaggcgtaa gcggctgggt tgtctgccgg   2460
ccctgcaatg gcactggaac ccccaagccc gaggaatcgg cgtgacggtc gcaaaccatc   2520
cggcccggta caaatcggcg cggcgctggg tgatgacctg gtggagaagt tgaaggccgc   2580
gcaggccgcc cagcggcaac gcatcgaggc agaagcacgc cccggtgaat cgtggcaagc   2640
ggccgctgat cgaatccgca agaatcccg gcaaccgccg gcagccggtg cgccgtcgat   2700
taggaagccg cccaagggcg acgagcaacc agatttttc gttccgatgc tctatgacgt   2760
gggcacccgc gatagtcgca gcatcatgga cgtggccgtt ttccgtctgt cgaagcgtga   2820
ccgacgagct ggcgaggtga tccgctacga gcttccagac gggcacgtag aggtttccgc   2880
agggccggcc ggcatggcca gtgtgtggga ttacgacctg gtactgatgg cggtttccca   2940
tctaaccgaa tccatgaacc gataccggga agggaaggga acaagcccg gccgcgtgtt   3000 ccgtccacac gttgcggacg tactcaagtt ctgccggcga gccgatggcg gaaagcagaa   3060
agacgacctg gtagaaacct gcattcggtt aaacaccacg cacgttgcca tgcagcgtac   3120
```

```
gaagaaggcc aagaacggcc gcctggtgac ggtatccgag ggtgaagcct tgattagccg    3180
ctacaagatc gtaaagagcg aaaccgggcg gccggagtac atcgagatcg agctagctga    3240
ttggatgtac cgcgagatca cagaaggcaa gaacccggac gtgctgacgg ttcaccccga    3300
ttactttttg atcgatcccg gcatcggccg ttttctctac cgcctggcac gccgcgccgc    3360
aggcaaggca gaagccagat ggttgttcaa gacgatctac gaacgcagtg gcagcgccgg    3420
agagttcaag aagttctgtt tcaccgtgcg caagctgatc gggtcaaatg acctgccgga    3480
gtacgatttg aaggaggagg cggggcaggc tggcccgatc ctagtcatgc gctaccgcaa    3540
cctgatcgag ggcgaagcat ccgccggttc ctaatgtacg gagcagatgc tagggcaaat    3600
tgccctagca ggggaaaaag gtcgaaaagg tctctttcct gtggatagca cgtacattgg    3660
gaacccaaag ccgtacattg ggaaccgaaa cccgtacatt gggaacccaa agccgtacat    3720
tgggaaccgg tcacacatgt aagtgactga tataaaagag aaaaaaggcg attttttccgc    3780
ctaaaactct ttaaaactta ttaaaactct taaaacccgc ctggcctgtg cataactgtc    3840
tggccagcgc acagccgaag agctgcaaaa agcgcctacc cttcggtcgc tgcgctccct    3900
acgccccgcc gcttcgcgtc ggcctatcgc ggccgctggc cgctcaaaaa tggctggcct    3960
acggccaggc aatctaccag ggcgcggaca agccgcgccg tcgccactcg accgccggcg    4020
cccacatcaa ggcaccctgc ctcgcgcgtt tcggtgatga cggtgaaaac ctctgacaca    4080
tgcagctccc ggagacggtc acagcttgtc tgtaagcgga tgccgggagc agacaagccc    4140
gtcagggcgc gtcagcgggt gttggcgggt gtcgggcgc agccatgacc cagtcacgta     4200
gcgatagcgg agtgtatact ggcttaacta tgcggcatca gagcagattg tactgagagt    4260
gcaccatatg cggtgtgaaa taccgcacag atgcgtaagg agaaaatacc gcatcaggcg    4320
ctcttccgct tcctcgctca ctgactcgct gcgctcggtc gttcggctgc ggcgagcggt    4380
atcagctcac tcaaaggcgg taatacggtt atccacagaa tcaggggata acgcaggaaa    4440
gaacatgtga gcaaaaggcc agcaaaaggc caggaaccgt aaaaaggccg cgttgctggc    4500
gttttttccat aggctccgcc cccctgacga gcatcacaaa aatcgacgct caagtcagag    4560
gtggcgaaac ccgacaggac tataaagata ccaggcgttt ccccctggaa gctccctcgt    4620
gcgctctcct gttccgaccc tgccgcttac cggatacctg tccgcctttc tcccttcggg    4680
aagcgtggcg ctttctcata gctcacgctg taggtatctc agttcggtgt aggtcgttcg    4740
ctccaagctg ggctgtgtgc acgaaccccc cgttcagccc gaccgctgcg ccttatccgg    4800
taactatcgt cttgagtcca acccggtaag acacgactta tcgccactgg cagcagccac    4860
tggtaacagg attagcagag cgaggtatgt aggcggtgct acagagttct tgaagtggtg    4920
gcctaactac ggctacacta aggacagt atttggtatc tgcgctctgc tgaagccagt      4980
taccttcgga aaaagagttg gtagctcttg atccggcaaa caaccaccg ctggtagcgg      5040
tggtttttttt gtttgcaagc agcagattac gcgcagaaaa aaggatctc aagaagatcc      5100
tttgatcttt tctacgggt ctgacgctca gtggaacgaa aactcacgtt aagggatttt       5160
ggtcatgcat gatatatctc ccaatttgtg tagggcttat tatgcacgct taaaaataat     5220
aaaagcagac ttgacctgat agtttggctg tgagcaatta tgtgcttagt gcatctaatc    5280
gcttgagtta acgccggcga agcggcgtcg gcttgaacga atttctagct agacattatt    5340
tgccgactac cttggtgatc tcgcctttca cgtagtggac aaattcttcc aactgatctg    5400
cgcgcgaggc caagcgatct tcttcttgtc caagataagc ctgtctagct tcaagtatga    5460
cgggctgata ctgggccggc aggcgctcca ttgcccagtc ggcagcgaca tccttcggcg    5520
```

```
cgattttgcc ggttactgcg ctgtaccaaa tgcgggacaa cgtaagcact acatttcgct      5580
catcgccagc ccagtcgggc ggcgagttcc atagcgttaa ggtttcattt agcgcctcaa      5640
atagatcctg ttcaggaacc ggatcaaaga gttcctccgc cgctggacct accaaggcaa      5700
cgctatgttc tcttgctttt gtcagcaaga tagccagatc aatgtcgatc gtggctggct      5760
cgaagatacc tgcaagaatg tcattgcgct gccattctcc aaattgcagt tcgcgcttag      5820
ctggataacg ccacggaatg atgtcgtcgt gcacaacaat ggtgacttct acagcgcgga      5880
gaatctcgct ctctccaggg gaagccgaag tttccaaaag gtcgttgatc aaagctcgcc      5940
gcgttgtttc atcaagcctt acggtcaccg taaccagcaa atcaatatca ctgtgtggct      6000
tcaggccgcc atccactgcg gagccgtaca aatgtacggc cagcaacgtc ggttcgagat      6060
ggcgctcgat gacgccaact acctctgata gttgagtcga tacttcggcg atcaccgctt      6120
cccccatgat gtttaacttt gttttagggc gactgccctg ctgcgtaaca tcgttgctgc      6180
tccataacat caaacatcga cccacggcgt aacgcgcttg ctgcttggat gcccgaggca      6240
tagactgtac cccaaaaaaa catgtcataa caagaagcca tgaaaaccgc cactgcgccg      6300
ttaccaccgc tgcgttcggt caaggttctg gaccagttgc gtgacggcag ttacgctact      6360
tgcattacag cttacgaacc gaacgaggct tatgtccact gggttcgtgc ccgaattgat      6420
cacaggcagc aacgctctgt catcgttaca atcaacatgc taccctccgc gagatcatcc      6480
gtgtttcaaa cccggcagct tagttgccgt tcttccgaat agcatcggta acatgagcaa      6540
agtctgccgc cttacaacgg ctctcccgct gacgccgtcc cggactgatg gctgcctgt       6600 atcgagtggt gattttgtgc cgagctgccg gtcggggagc tgttggctgg ctggtggcag      6660
gatatattgt ggtgtaaaca aattgacgct tagacaactt aataacacat gcggacgtt       6720 tttaatgtac tgaattaacg ccgaattgaa ttcgagctcg gtacccgggg atctggattt      6780
tagtactgga ttttggtttt aggaattaga aattttattg atagaagtat tttacaaata      6840
caaatacata ctaagggttt cttatatgct caacacatga gcgaaaccct ataagaaccc      6900
taatttccct tatcgggaaa ctactcacac attaggatcc cggtcggcat ctactctatt      6960
cctttgccct cggacgagtg ctggggcgtc ggtttccact atcggcgagt acttctacac      7020
agccatcggt ccagacggcc gcgcttctgc gggcgatttg tgtacgcccg acagtcccgg      7080
ctccggatcg gacgattgcg tcgcatcgac cctgcgccca agctgcatca tcgaaattgc      7140
cgtcaaccaa gctctgatag agttggtcaa gaccaatgcg gagcatatac gcccggagcc      7200
gcggcgatcc tgcaagctcc ggatgcctcc gctcgaagta gcgcgtctgc tgctccatac      7260
aagccaacca cggcctccag aagaagatgt tggcgacctc gtattgggaa tccccgaaca      7320
tcgcctcgct ccagtcaatg accgctgtta tgcggccatt gtccgtcagg acattgttgg      7380
agccgaaatc cgcgtgcacg aggtgccgga cttcggggca gtcctcggcc caaagcatca      7440
gctcatcgag agcctgcgcg acggacgcac tgacggtgtc gtccatcaca gtttgccagt      7500
gatacacatg gggatcagca atcgcgcata tgaaatcacg ccatgtagtg tattgaccga      7560
ttccttgcgg tccgaatggg ccgaacccgc tcgtctggct aagatcggcc gcagcgatcg      7620
catccatggc ctccgcgacc ggctgcagaa cagcgggcag ttcggtttca ggcaggtctt      7680
gcaacgtgac accctgtgca cggcgggaga tgcaataggt caggctctcg ctgaattccc      7740
caatgtcaag cacttccgga atcgggagcg cggccgatgc aaagtgccga taaacataac      7800
gatctttgta gaaaccatcg gcgcagctat ttacccgcag gacatatcca cgccctccta      7860
catcgaagct gaaagcacga gattcttcgc cctccgagag ctgcatcagg tcggagacgc      7920
```

-continued

```
tgtcgaactt ttcgatcaga aacttctcga cagacgtcgc ggtgagttca ggcttttttca    7980
tatctcattg cccccccggga tccttataga gagagataga tttgtagaga gagactggtg    8040
atttcagcgt gtcctctcca aatgaaatga acttccttat atagaggaag ggtcttgcga    8100
aggatagtgg gattgtgcgt catcccttac gtcagtggag atatcacatc aatccacttg    8160
ctttgaagac gtggttggaa cgtcttcttt ttccacgatg ctcctcgtgg gtggggggtcc    8220
atctttggga ccactgtcgg cagaggcatc ttgaacgata gcctttcctt tatcgcaatg    8280
atggcatttg taggtgccac cttccttttc tactgtcttc atgatgaagt gacagatagc    8340
tgggcaatgg aatccgagga ggtttcccga aattacccctt tgttggaaag tctcaattgc    8400
cctttggtct tctgagactg tatccttgat attttttggag tagaccagag tgtcgtgctc    8460
caccatgttg acgaagattt tcttcttgtc attgagtcgt aagagactct gtatgaactg    8520
ttcgccagtt ttcacggcga gttctgttag atcctcgatt tgaatctttg actccatggc    8580
ctttgattca gtaggaacta ctttttttaga gactccaatc tctattactt gccttggttt    8640
atgaagcaag ccttgaatcg tccatactgg aatagtactt ctgatcttga aaatatatc    8700
tttctctgtg ttcttgatgc agttagtcct gaatcttttg actgcatctt taaccttctt    8760
gggaaggtat ttgatctcct ggagattatt actcgggtag atcgtcttaa tgagacctgc    8820
tgcgtaggcc tctctaacca tctgtgggtt agcgttcttt ctgaaattga agaggctaat    8880
cttctcatta tcagtggtga acatagtatc gtcaccttca ccgtcgaact ttcttcctag    8940
atcgtagaga tagaggaagt cgtccattgt aatctccggg gcaaaggaga tcctctagag    9000
tcgagggtac ccgggggatcc tctagagtcg agggtacccg gggatcctct agagtcgaat    9060
gattacgcca agctatcaac tttgtataga aaagttgcta catcgcacgg cattagtcct    9120
cacccataac ctaacatatc tcatctgaat ggtcgttaaa tcaataaata tacaaataaa    9180
tcaagaagca caatgcataa gctatgatttt actaggcaaa cattaacaga gatatactga    9240
catgaaaaaa atgtgacaaa acatagatct agaatggaat aaaatgaacc ttgattgata    9300
caaattgaaa ctagccctga taaaaaaatt acttatctat caaaccctac acgtaatcaa    9360
accaaactcg agggttaaac ctcatttcct acctaccaga caaaaaacat gaactagaaa    9420
aactaaaaaa tgaaccaacc cccactgaat ctagcaaaaa cactaaatga aaatctactc    9480
ttgctgaaaa taaaaatcct atgaatccac tgaattccct acacacacaa gctatccggc    9540
cacccattga atcttgacta ctaaaatccc cttgctccct acattcgagt ggattgggaa    9600
caaaccctag gtacatgaaa aaaacaaata aaacgaggta tgtataagtt gattcatttg    9660
tgcggtgctt cttttgttttat gttcggctct tatcttttaa aaaaggaaag ttgttgtaga    9720
ctgttagcaa agttgatttt atcccgacac atgtgatccg aatgttcact aaggcaaatc    9780
agaaaaaaga acacatgtat aaagttatga tactggacaa accttaacaa acattatact    9840
tacatgaaaa aatggaacaa catggatcta gactaaaatc taaaatcaac cttgacacta    9900
aatcacctga actaaaaaaa gggcatagac tgaatctctg cgcactaccc agcgacccgc    9960
ttaatcttga ccgactggaa ccccccccccc tcccaacatt tggatatatt gatgaacaaa   10020
tcctagatag atggatacac aacaaaatag ggacggtact aatctgtgag gaaccctacc   10080
cacatttggg tcgattgtgg gacaaaccct agattgatga atgcacaaac aaagaagagg   10140
ggatggtgct caatctatga gcaagaaaca ataactggac aaaaacaaag aggaagaaaa   10200
aaataagaac agggcaaaaa acttactcca atggcgtctc tctcccttct cgttctccag   10260
agcccctgga tgaggccgaa gaggaatggg aaatgggcaa aatgaatgcg agggagaaaa   10320
```

-continued

```
ttactctgag ggagacaaac ggcctaccag cccaactatc gtgacaaaca ccccgacccg    10380
ctactagcat caacctgaaa acgggccgcg caacacacaa cagtcgcgtg cgaatgcacc    10440
aacgggacaa aaataggttt gcgcgaatct tgaagataga cgagatccaa cggctctaga    10500
cttagatgtg aagtagttat ttcacatcta gatgtgaaat agcaaagctg atattatgat    10560
tgtaatgtta tagcatgtag atgtgtaatt aatatacaat tcattttttt gatgcagtac    10620
cataccttca agatatatat aattaatgta atgttgtagc atgtagatgt gtaattaatg    10680
cacacgttca tttttcggtg cagtaccata tctttctatc ttcaagatat atataattat    10740
tgtagtatta tagcatgtag atgtgcaact aatggatata ttcattttttt atgcagtacc    10800
atatcttcaa gatatatcat atatagtaca actaatgtat gtataatgtg tcgatgtgga    10860
gttaatatac acattcattg ttcgatgcta tttcgtatct tcaaggtata gcatgtagat    10920
atagagttaa tgtgaacatt cattatttga tacaatatcg tatcttcaag atataaagct    10980
aatgtatgat gtagcctcta gagtgcaatt aatgtacata ttaattgctt gacatggtgc    11040
cataacttca agatatagaa ctgatgcatg tgcccatatc atcatctcaa acaaggctat    11100
ataaaccgag ccatagctaa cgaagtcatg tatcccacac attcacagag aagccacaca    11160
aacaattata acatcaaagg gatagagaag gctctagtgt agcagataca aaagccatag    11220
tcgcaagttt gtacaaaaaa gcaggctttc catggtgagc aagggcgagg agctgttcac    11280
cggggtggtg cccatcctgg tcgagctgga cggcgacgta aacggccaca gttcagcgt    11340
gtccggcgag ggcgagggcg atgccaccta cggcaagctg accctgaagt tcatctgcac    11400
caccggcaag ctgcccgtgc cctggcccac cctcgtgacc accttcacct acggcgtgca    11460
gtgcttcagc cgctaccccg accacatgaa gcagcacgac ttcttcaagt ccgccatgcc    11520
cgaaggctac gtccaggagc gcaccatctt cttcaaggac gacggcaact acaagacccg    11580
cgccgaggtg aagttcgagg gcgacaccct ggtgaaccgc atcgagctga agggcatcga    11640
cttcaaggag gacggcaaca tcctggggca caagctggag tacaactaca acagccacaa    11700
cgtctatatc atggccgaca agcagaagaa cggcatcaag gtgaacttca gatccgcca    11760
caacatcgag gacggcagcg tgcagctcgc cgaccactac cagcagaaca ccctcatcgg    11820
cgacggcccc gtgctgctgc ccgacaacca ctacctgagc acccagtccg ccctgagcaa    11880
agaccccaac gagaagcgcg atcacatggt cctgctggag ttcgtgaccg ccgccgggat    11940
cactcacggc atggacgagc tgtacaagta agatacccag ctttcttgta caaagtggga    12000
tcgttcaaac atttggcaat aaagtttctt aagattgaat cctgttgccg gtcttgcgat    12060
gattatcata aatttctgt tgaattacgt taagcatgta ataattaaca tgtaatgcat    12120
gacgttattt atgagatggg ttttatgat tagagtcccg caattataca tttaatacgc    12180
gatagaaaac aaaatatagc gcgcaaacta ggataaatta tcgcgcgcgg tgtcatctat    12240
gttactagat ccaacttta                                                 12259
```

<210> SEQ ID NO 6
<211> LENGTH: 9034
<212> TYPE: DNA
<213> ORGANISM: Artificial sequence
<220> FEATURE:
<223> OTHER INFORMATION: Vector pMPB0097

<400> SEQUENCE: 6

```
ttatacatag ttgataattc actggccgtc gtgggggatc cactagttct agagcggccg     60
ccaccgcggt ggagctccag cttttgttcc ctttagtgag ggttaatttc gagcttggcg    120
```

```
taatcatggt catagctgtt tcctgtgtga aattgttatc cgctcacaat tccacacaac      180
atacgagccg gaagcataaa gtgtaaagcc tggggtgcct aatgagtgag ctaactcaca      240
ttaattgcgt tgcgctcact gcccgctttc cagtcgggaa acctgtcgtg ccagctgcat      300
taatgaatcg gccaacgcgc ggggagaggc ggtttgcgta ttgggcgctc ttccgcttcc      360
tcgctcactg actcgctgcg ctcggtcgtt cggctgcggc gagcggtatc agctcactca      420
aaggcggtaa tacggttatc cacagaatca ggggataacg caggaaagaa catgtgagca      480
aaaggccagc aaaaggccag gaaccgtaaa aaggccgcgt tgctggcgtt tttccatagg      540
ctccgccccc ctgacgagca tcacaaaaat cgacgctcaa gtcagaggtg gcgaaacccg      600
acaggactat aaagatacca ggcgtttccc cctggaagct ccctcgtgcg ctctcctgtt      660
ccgaccctgc cgcttaccgg atacctgtcc gcctttctcc cttcgggaag cgtggcgctt      720
tctcatagct cacgctgtag gtatctcagt tcggtgtagg tcgttcgctc caagctgggc      780
tgtgtgcacg aaccccccgt tcagcccgac cgctgcgcct tatccggtaa ctatcgtctt      840
gagtccaacc cggtaagaca cgacttatcg ccactggcag cagccactgg taacaggatt      900
agcagagcga ggtatgtagg cggtgctaca gagttcttga agtggtggcc taactacggc      960
tacactagaa ggacagtatt tggtatctgc gctctgctga agccagttac cttcggaaaa      1020
agagttggta gctcttgatc cggcaaacaa accaccgctg gtagcggtgg ttttttgtt       1080 tgcaagcagc agattacgcg cagaaaaaaa ggatctcaag aagatccttt gatcttttct      1140
acggggtctg acgctcagtg gaacgaaaac tcacgttaag ggattttggt catgagatta      1200
tcaaaaagga tcttcaccta gatccttta aattaaaaat gaagttttaa atcaatctaa       1260
agtatatatg agtaaacttg gtctgacagt taccaatgct taatcagtga ggcacctatc      1320
tcagcgatct gtctatttcg ttcatccata gttgcctgac tccccgtcgt gtagataact      1380
acgatacggg agggcttacc atctggcccc agtgctgcaa tgataccgcg agacccacgc      1440
tcaccggctc cagatttatc agcaataaac cagccagccg aaggccgag cgcagaagt       1500 ggtcctgcaa ctttatccgc ctccatccag tctattaatt gttgccggga agctagagta      1560
agtagttcgc cagttaatag tttgcgcaac gttgttgcca ttgctacagg catcgtggtg      1620
tcacgctcgt cgtttggtat ggcttcattc agctccggtt cccaacgatc aaggcgagtt      1680
acatgatccc ccatgttgtg caaaaaagcg gttagctcct tcggtcctcc gatcgttgtc      1740
agaagtaagt tggccgcagt gttatcactc atggttatgg cagcactgca taattctctt      1800
actgtcatgc catccgtaag atgcttttct gtgactggtg agtactcaac caagtcattc      1860
tgagaatagt gtatgcggcg accgagttgc tcttgcccgg cgtcaatacg ggataatacc      1920
gcgccacata gcagaacttt aaaagtgctc atcattggaa aacgttcttc ggggcgaaaa      1980
ctctcaagga tcttaccgct gttgagatcc agttcgatgt aacccactcg tgcacccaac      2040
tgatcttcag catcttttac tttcaccagc gtttctgggt gagcaaaaac aggaaggcaa      2100
aatgccgcaa aaaagggaat aagggcgaca cggaaatgtt gaatactcat actcttcctt      2160
tttcaatatt attgaagcat ttatcagggt tattgtctca tgagcggata catatttgaa      2220
tgtatttaga aaaataaaca aataggggtt ccgcgcacat ttccccgaaa agtgccacct      2280
gacgcgccct gtagcggcgc attaagcgcg gcgggtgtgg tggttacgcg cagcgtgacc      2340
gctacacttg ccagcgccct agcgcccgct cctttcgctt tcttcccttc ctttctcgcc      2400
acgttcgccg gctttccccg tcaagctcta aatcgggggc tccctttagg gttccgattt      2460
agtgctttac ggcacctcga ccccaaaaaa cttgattagg gtgatggttc acgtagtggg      2520
```

```
ccatcgccct gatagacggt ttttcgccct tgacgttgg agtccacgtt ctttaatagt    2580
ggactcttgt tccaaactgg aacaacactc aaccctatct cggtctattc ttttgattta    2640
taagggattt tgccgatttc ggcctattgg ttaaaaaatg agctgattta acaaaaattt    2700
aacgcgaatt ttaacaaaat attaacgctt acaatttcca ttcgccattc aggctgcgca    2760
actgttggga agggcgatcg gtgcgggcct cttcgctatt acgccagctg gcgaaagggg    2820
gatgtgctgc aaggcgatta agttgggtaa cgccagggtt ttcccagtca cgacgttgta    2880
aaacgacggc cagtgaattg taatacgact cactataggg cgaattgggt accgggcccc    2940
ccctcgaggt cgacggtatc gataagcttg atatcgaatt ctcatgtttg acagcttatc    3000
atcggatcta gtaacataga tgacaccgcg cgcgataatt tatcctagtt tgcgcgctat    3060
attttgtttt ctatcgcgta ttaaatgtat aattgcggga ctctaatcat aaaaacccat    3120
ctcataaata acgtcatgca ttacatgtta attattacat gcttaacgta attcaacaga    3180
aattatatga taatcatcgc aagaccggca acaggattca atcttaagaa actttattgc    3240
caaatgtttg aacgatctgc aggtcgacgg atcagatctc ggtgacgggc aggaccggac    3300
ggggcggtac cggcaggctg aagtccagct gccagaaacc cacgtcatgc cagttcccgt    3360
gcttgaagcc ggccgcccgc agcatgccgc gggggggcata tccgagcgcc tcgtgcatgc    3420
gcacgctcgg gtcgttgggc agcccgatga cagcgaccac gctcttgaag ccctgtgcct    3480
ccagggactt cagcaggtgg gtgtagagcg tggagcccag tcccgtccgc tggtggcggg    3540
gggagacgta cacggtcgac tcggccgtcc agtcgtaggc gttgcgtgcc ttccaggggc    3600
ccgcgtaggc gatgccggcg acctcgccgt ccacctcggc gacgagccag ggatagcgct    3660
cccgcagacg gacgaggtcg tccgtccact cctgcggttc ctgcggctcg gtacggaagt    3720
tgaccgtgct tgtctcgatg tagtggttga cgatggtgca gaccgccggc atgtccgcct    3780
cggtggcacg gcggatgtcg gccgggcgtc gttctgggct catggttact tcctaatcga    3840
tggatcctct agagtcgacc tgcagaagta acaccaaaca acaggtgag catcgacaaa    3900
agaaacagta ccaagcaaat aaatagcgta tgaaggcagg gctaaaaaaa tccacatata    3960
gctgctgcat atgccatcat ccaagtatat caagatcaaa ataattataa aacatacttg    4020
tttattataa tagataggta ctcaaggtta gagcatatga atagatgctg catatgccat    4080
catgtatatg catcagtaaa acccacatca acatgtatac ctatcctaga tcgatatttc    4140
catccatctt aaactcgtaa ctatgaagat gtatgacaca cacatacagt tccaaaatta    4200
ataaatacac caggtagttt gaaacagtat tctactccga tctagaacga atgaacgacc    4260
gcccaaccac accacatcat cacaaccaag cgaacaaaaa gcatctctgt atatgcatca    4320
gtaaaacccg catcaacatg tatacctatc ctagatcgat atttccatcc atcattttca    4380
attcgtaact atgaatatgt atggcacaca catacagatc caaaattaat aaatccacca    4440
ggtagtttga acagaattc tactccgatc tagaacgacc gcccaaccag accacatcat    4500
cacaaccaag acaaaaaaaa gcatgaaaag atgacccgac aaacaagtgc acggcatata    4560
ttgaaataaa ggaaagggc aaaccaaacc ctatgcaacg aaacaaaaaa aatcatgaaa    4620
tcgatcccgt ctgcggaacg gctagagcca tcccaggatt ccccaaagag aaacactggc    4680
aagttagcaa tcagaacgtg tctgacgtac aggtcgcatc cgtgtacgaa cgctagcagc    4740
acggatctaa cacaaacacg gatctaacac aaacatgaac agaagtagaa ctaccgggcc    4800
ctaaccatgg accggaacgc cgatctagag aaggtagaga gggggggggg gggaggacga    4860
gcggcgtacc ttgaagcgga ggtgccgacg ggtggatttg ggggagatct ggttgtgtgt    4920
```

```
gtgtgcgctc cgaacaacac gaggttgggg aaagagggtg tggaggggggt gtctatttat    4980
tacggcgggc gaggaaggga aagcgaagga gcggtgggaa aggaatcccc cgtagctgcc    5040
ggtgccgtga gaggaggagg aggccgcctg ccgtgccggc tcacgtctgc cgctccgcca    5100
cgcaatttct ggatgccgac agcggagcaa gtccaacggt ggagcggaac tctcgagagg    5160
ggtccagagg cagcgacaga gatgccgtgc cgtctgcttc gcttggcccg acgcgacgct    5220
gctggttcgc tggttggtgt ccgttagact cgtcgacggc gtttaacagg ctggcattat    5280
ctactcgaaa caagaaaaat gtttccttag ttttttttaat ttcttaaagg gtatttgttt    5340
aattttttagt cactttattt tattctattt tatatctaaa ttattaaata aaaaaactaa    5400
aatagagttt tagttttctt aatttagagg ctaaaataga ataaaataga tgtactaaaa    5460
aaattagtct ataaaaacca ttaaccctaa accctaaatg gatgtactaa taaaatggat    5520
gaagtattat ataggtgaag ctatttgcaa aaaaaaagga gaacacatgc acactaaaaa    5580
gataaaactg tagagtcctg ttgtcaaaat actcaattgt cctttagacc atgtctaact    5640
gttcattat atgattctct aaaacactga tattattgta gtactataga ttatattatt    5700
cgtagagtaa agtttaaata tatgtataaa gatagataaa ctgcacttca aacaagtgtg    5760
acaaaaaaaa tatgtggtaa ttttttataa cttagacatg caatgctcat tatctctaga    5820
gaggggcacg accgggtcac gctgcactgc aggcatgcaa gcttgaattc ctgcagcccc    5880
gccaagctat caactttgta tagaaaagtt gctacatcgc acggcattag tcctcaccca    5940
taacctaaca tatctcatct gaatggtcgt taaatcaata aatatacaaa taaatcaaga    6000
agcacaatgc ataagctatg atttactagg caaacattaa cagagatata ctgacatgaa    6060
aaaaatgtga caaaacatag atctagaatg gaataaaatg aaccttgatt gatacaaatt    6120
gaaactagcc ctgataaaaa aattacttat ctatcaaacc ctacacgtaa tcaaaccaaa    6180
ctcgagggtt aaacctcatt tcctacctac cagacaaaaa acatgaacta gaaaaactaa    6240
aaaatgaacc aaccccccact gaatctagca aaaacactaa atgaaaatct actcttgctg    6300
aaaataaaaa tcctatgaat ccactgaatt ccctacacac acaagctatc cggccaccca    6360
ttgaatcttg actactaaaa tccccttgct ccctacattc gagtggattg ggaacaaacc    6420
ctaggtacat gaaaaaaaca aataaaacga ggtatgtata agttgattca tttgtgcggt    6480
gcttctttgt ttatgttcgg ctcttatctt ttaaaaaagg aaagttgttg tagactgtta    6540
gcaaagttga ttttatcccg acacatgtga tccgaatgtt cactaaggca aatcagaaaa    6600
aagaacacat gtataaagtt atgatactgg acaaaccttta acaaacatta tacttacatg    6660
aaaaaatgga acaacatgga tctagactaa aatctaaaat caaccttgac actaaatcac    6720
ctgaactaaa aaaagggcat agactgaatc tctgcgcact acccagcgac ccgcttaatc    6780
ttgaccgact ggaacccccc ccctcccaa catttggata tattgatgaa caaatcctag    6840
atagatggat acacaacaaa ataggacggg tactaatctg tgaggaaccc tacccacatt    6900
tgggtcgatt gtgggacaaa ccctagattg atgaatgcac aaacaaagaa gaggggatgg    6960
tgctcaatct atgagcaaga aacaataact ggacaaaaac aaagaggaag aaaaaaataa    7020
gaacagggca aaaaacttac tccaatggcg tctctctccc ttctcgttct ccagagcccc    7080
tggatgaggc cgaagaggaa tgggaaatgg gcaaaatgaa tgcgagggag aaaattactc    7140
tgagggagac aaaacggccta ccagcccaac tatcgtgaca acacccccga cccgctacta    7200
gcatcaacct gaaaacgggc cgcgcaacac acaacagtcg cgtgcgaatg caccaacggg    7260
acaaaaatag gtttgcgcga atcttgaaga tagacgagat ccaacggctc tagacttaga    7320
```

| | |
|---|---:|
| tgtgaagtag ttatttcaca tctagatgtg aaatagcaaa gctgatatta tgattgtaat | 7380 |
| gttatagcat gtagatgtgt aattaatata caattcattt ttttgatgca gtaccatacc | 7440 |
| ttcaagatat ataaattaa tgtaatgttg tagcatgtag atgtgtaatt aatgcacacg | 7500 |
| ttcattttc ggtgcagtac catatctttc tatcttcaag atatatataa ttattgtagt | 7560 |
| attatagcat gtagatgtgc aactaatgga tatattcatt ttttatgcag taccatatct | 7620 |
| tcaagatata tcatatatag tacaactaat gtatgtataa tgtgtcgatg tggagttaat | 7680 |
| atacacattc attgttcgat gctatttcgt atcttcaagg tatagcatgt agatatagag | 7740 |
| ttaatgtgaa cattcattat ttgatacaat atcgtatctt caagatataa agctaatgta | 7800 |
| tgatgtagcc tctagagtgc aattaatgta catattaatt gcttgacatg gtgccataac | 7860 |
| ttcaagatat agaactgatg catgtgccca tcatcatc tcaaacaagg ctatataaac | 7920 |
| cgagccatag ctaacgaagt catgtatccc acacattcac agagaagcca cacaaacaat | 7980 |
| tataacatca aagggataga gaaggctcta gtgtagcaga tacaaaagcc atagtcgcaa | 8040 |
| gtttgtacaa aaaagcaggc tttccatggt gagcaagggc gaggagctgt tcaccggggt | 8100 |
| ggtgcccatc ctggtcgagc tggacggcga cgtaaacggc cacaagttca gcgtgtccgg | 8160 |
| cgagggcgag ggcgatgcca cctacggcaa gctgaccctg aagttcatct gcaccaccgg | 8220 |
| caagctgccc gtgccctggc ccaccctcgt gaccaccttc acctacggcg tgcagtgctt | 8280 |
| cagccgctac cccgaccaca tgaagcagca cgacttcttc aagtccgcca tgcccgaagg | 8340 |
| ctacgtccag gagcgcacca tcttcttcaa ggacgacggc aactacaaga cccgcgccga | 8400 |
| ggtgaagttc gagggcgaca ccctggtgaa ccgcatcgag ctgaagggca tcgacttcaa | 8460 |
| ggaggacggc aacatcctgg ggcacaagct ggagtacaac tacaacagcc acaacgtcta | 8520 |
| tatcatggcc gacaagcaga agaacggcat caaggtgaac ttcaagatcc gccacaacat | 8580 |
| cgaggacggc agcgtgcagc tcgccgacca ctaccagcag aacacccctca tcggcgacgg | 8640 |
| ccccgtgctg ctgcccgaca accactacct gagcacccag tccgccctga gcaaagaccc | 8700 |
| caacgagaag cgcgatcaca tggtcctgct ggagttcgtg accgccgccg ggatcactca | 8760 |
| cggcatggac gagctgtaca gtaagatac ccagctttct tgtacaaagt ggagtccgca | 8820 |
| aaaatcacca gtctctctct acaaatctat ctctctctat ttttctccag aataatgtgt | 8880 |
| gagtagttcc cagataaggg aattagggtt cttataggt ttcgctcatg tgttgagcat | 8940 |
| ataagaaacc cttagtatgt atttgtattt gtaaaatact tctatcaata aaatttctaa | 9000 |
| ttcctaaaac caaaatccag tgacctcaac ttta | 9034 |

<210> SEQ ID NO 7
<211> LENGTH: 14355
<212> TYPE: DNA
<213> ORGANISM: Artificial sequence
<220> FEATURE:
<223> OTHER INFORMATION: Vector pRHF113qcz

<400> SEQUENCE: 7

| | |
|---|---:|
| atcagtgatt ttgtgccgag ctgccggtcg gggagctgtt ggctggctgg tggcaggata | 60 |
| tattgtggtg taaacaaatt gacgcttaga caacttaata acacattgcg gacgtcttta | 120 |
| atgtactgaa ttagtactct agtttacagc actcgtctcc gtcttggtag gttctttgag | 180 |
| cttaagaagg ttgacgttgt ggtgataggt ctaaggcgga ggctaggcta gttgatatcg | 240 |
| gtaccaagct tccgcggctg cagtgcagcg tgacccggtc gtgcccctct ctagagataa | 300 |
| tgagcattgc atgtctaagt tataaaaaat taccacatat tttttttgtc acacttgttt | 360 |

```
gaagtgcagt ttatctatct ttatacatat atttaaactt tactctacga ataatataat    420
ctatagtact acaataatat cagtgtttta gagaatcata taaatgaaca gttagacatg    480
gtctaaagga caattgagta ttttgacaac aggactctac agttttatct ttttagtgtg    540
catgtgttct cctttttttt tgcaaatagc ttcacctata taatacttca tccattttat    600
tagtacatcc atttagggtt tagggttaat ggttttttata gactaatttt tttagtacat    660
ctattttatt ctattttagc ctctaaatta agaaaactaa aactctattt tagtttttt    720 atttaatagt ttagatataa aatagaataa aataaagtga ctaaaaatta aacaaatacc    780 cttttaagaaa ttaaaaaaac taaggaaaca tttttcttgt ttcgagtaga taatgccagc    840
ctgttaaacg ccgtcgacga gtctaacgga caccaaccag cgaaccagca gcgtcgcgtc    900
gggccaagcg aagcagacgg cacggcatct ctgtcgctgc ctctggaccc ctctcgagag    960
ttccgctcca ccgttggact tgctccgctg tcggcatcca gaattgcgt ggcggagcgg   1020 cagacgtgag ccggcacggc aggcggcctc ctcctcctct cacggcaccg gcagctacgg   1080
gggattcctt tcccaccgct ccttcgcttt cccttcctcg cccgccgtaa taaatagaca   1140
ccccctccac accctctttc cccaacctcg tgttgttcgg agcgcacaca cacacaacca   1200
gatctccccc aaatccaccc gtcggcacct ccgcttcaag gtacgccgct cgtcctcccc   1260
cccccccccc ctctctacct tctctagatc ggcgttccgg tccatggtta gggcccggta   1320
gttctacttc tgttcatgtt tgtgttagat ccgtgtttgt gttagatccg tgctgctagc   1380
gttcgtacac ggatgcgacc tgtacgtcag acacgttctg attgctaact tgccagtgtt   1440
tctctttggg gaatcctggg atggctctag ccgttccgca gacgggatcg atttcatgat   1500 ttttttgtt tcgttgcata gggtttggtt tgcccttttc ctttatttca atatatgccg   1560
tgcacttgtt tgtcgggtca tcttttcatg ctttttttg tcttggttgt gatgatgtgg   1620
tctggttggg cggtcgttct agatcggagt agaattctgt ttcaaactac ctggtggatt   1680
tattaatttt ggatctgtat gtgtgtgcca tacatattca tagttacgaa ttgaagatga   1740
tggatggaaa tatcgatcta ggataggtat acatgttgat gcgggtttta ctgatgcata   1800
tacagagatg cttttttgttc gcttggttgt gatgatgtgg tgtggttggg cggtcgttca   1860
ttcgttctag atcggagtag aatactgttt caaactacct ggtgtattta ttaattttgg   1920
aactgtatgt gtgtgtcata catcttcata gttacgagtt taagatggat ggaaatatcg   1980
atctaggata ggtatacatg ttgatgtggg ttttactgat gcatatacat gatggcatat   2040
gcagcatcta ttcatatgct ctaaccttga gtacctatct attataataa acaagtatgt   2100
tttataatta tttcgatctt gatatacttg gatgatggca tatgcagcag ctatatgtgg   2160
atttttttag ccctgccttc atacgctatt tatttgcttg gtactgtttc ttttgtcgat   2220
gctcaccctg ttgtttggtg ttacttctgc agggtacgga tcctcatcta agcgcaaaga   2280
gacgtactat ggaaaacgct aaaatgaact cgctcatcgc ccagtatccg ttggtaaagg   2340
atctggttgc tcttaaagaa accacctggt ttaatcctgg cacgacctca ttggctgaag   2400 gtttaccttta tgttggcctg accgaacagg atgttcagga cgcccatgcg cgcttatccc   2460
gttttgcacc ctatctggca aaagcatttc ctgaaactgc tgccactggg gggattattg   2520
aatcagaact ggttgccatt ccagctatgc aaaaacggct ggaaaagaa tatcagcaac   2580 cgatcagcgg gcaactgtta ctgaaaaaag atagccattt gcccatttcc ggctccataa   2640
aagcacgcgc cggatttat gaagtcctgg cacacgcaga aaaactggct ctggaagcgg   2700
ggttgctgac gcttgatgat gactacagca aactgctttc tccggagttt aaacagttct   2760
```

```
ttagccaata cagcattgct gtgggctcaa ccggaaatct ggggttatca atcggcatta    2820
tgagcgcccg cattggcttt aaggtgacag ttcatatgtc tgctgatgcc cgggcatgga    2880
aaaaagcgaa actgcgcagc catggcgtta cggtcgtgga atatgagcaa gattatggtg    2940
ttgccgtcga ggaaggacgt aaagcagcgc agtctgaccc gaactgtttc tttattgatg    3000
acgaaaattc ccgcacgttg ttccttgggt attccgtcgc tggccagcgt cttaaagcgc    3060
aatttgccca gcaaggccgt atcgtcgatg ctgataaccc tctgtttgtc tatctgccgt    3120
gtggtgttgg cggtggtcct ggtggcgtcg cattcgggct taaactggcg tttggcgatc    3180
atgttcactg cttttttgcc gaaccaacgc actccccttg tatgttgtta ggcgtccata    3240
caggattaca cgatcagatt tctgttcagg atattggtat cgacaacctt accgcagcgg    3300
atggccttgc agttggtcgc gcatcaggct ttgtcgggcg ggcaatggag cgtctgctgg    3360
atggcttcta tacccttagc gatcaaacca tgtatgacat gcttggctgg ctggcgcagg    3420
aagaaggtat tcgtcttgaa ccttcggcac tggcgggtat ggccggacct cagcgcgtgt    3480
gtgcatcagt aagttaccaa cagatgcacg gtttcagcgc agaacaactg cgtaatacca    3540
ctcatctggt gtgggcgacg ggaggtggaa tggtgccgga agaagagatg aatcaatatc    3600
tggcaaaagg ccgttaataa cgtttcaacg cagcatggat cgtaccgagc tcaatcgatc    3660
ctgctttaat gagatatgcg agacgcctat gatcgcatga tatttgcttt caattctgtt    3720
gtgcacgttg taaaaaacct gagcatgtgt agctcagatc cttaccgccg gtttcggttc    3780
attctaatga atatatcacc cgttactatc gtatttttat gaataatatt ctccgttcaa    3840
tttactgatt gtaccctact acttatatgt acaatattaa aatgaaaaca atatattgtg    3900
ctgaataggt ttatagcgac atctatgata gagcgccaca ataacaaaca attgcgtttt    3960
attattacaa atccaatttt aaaaaagcg gcagaaccgg tcaaacctaa aagactgatt    4020
acataaatct tattcaaatt tcaaagtgc cccaggggct agtatctacg acacaccgag    4080
cggcgaacta ataacgctca ctgaagggaa ctccggttcc ccgccggcgc gcatgggtga    4140
gattccttga agttgagtat tggccgtccg ctctaccgaa agttacgggc accattcaac    4200
ccggtccagc acgcggccg ggtaaccgac ttgctgcccc gagaattatg cagcattttt    4260
ttggtgtatg tgggccccaa atgaagtgca ggtcaaacct tgacagtgac gacaaatcgt    4320
tgggcgggtc cagggcgaat tttgcgacaa catgtcgagg ctcagcagga tgggcccagg    4380
tacagaattc gcggccgtac aacgcgtacc ggttaattaa gctacatcgc acggcattag    4440
tcctcaccca taacctaaca tatctcatct gaatggtcgt taaatcaata aatatacaaa    4500
taaatcaaga agcacaatgc ataagctatg atttactagg caaacattaa cagagatata    4560 ctgcatgaa aaaatgtga caaaacatag atctagaatg gaataaaatg aaccttgatt    4620
gatacaaatt gaaactagcc ctgataaaaa aattacttat ctatcaaacc ctacacgtaa    4680
tcaaaccaaa ctcgagggtt aaacctcatt tcctacctac cagacaaaaa acatgaacta    4740
gaaaaactaa aaaatgaacc aacccccact gaatctagca aaaacactaa atgaaaatct    4800
actcttgctg aaaataaaaa tcctatgaat ccactgaatt ccctacacac acaagctatc    4860
cggccaccca ttgaatcttg actactaaaa tccccttgct ccctcattc gagtggattg    4920 ggaacaaacc ctaggtacat gaaaaaaaca aataaaacga ggtatgtata agttgattca    4980
tttgtgcggt gcttctttgt ttatgttcgg ctcttatctt ttaaaaaagg aaagttgttg    5040
tagactgtta gcaaagttga ttttatcccg acacatgtga tccgaatgtt cactaaggca    5100
aatcagaaaa aagaacacat gtataaagtt atgatactgg acaaaccttg acaaacatta    5160
```

```
tacttacatg aaaaaatgga acaacatgga tctagactaa atctaaaat caaccttgac     5220 actaaatcac ctgaactaaa aaaagggcat agactgaatc tctgcgcact acccagcgac    5280
ccgcttaatc ttgaccgact ggaaccccc  cccctcccaa catttggata tattgatgaa    5340
caaatcctag atagatggat acacaacaaa ataggggcgg tactaatctg tgaggaaccc    5400
tacccacatt tgggtcgatt gtgggacaaa ccctagattg atgaatgcac aaacaaagaa    5460
gaggggatgg tgctcaatct atgagcaaga acaataact  ggacaaaaac aaagaggaag    5520
aaaaaaataa gaacagggca aaaaacttac tccaatggcg tctctctccc ttctcgttct    5580
ccagagcccc tggatgaggc cgaagaggaa tgggaaatgg gcaaaatgaa tgcgagggag    5640
aaaattactc tgagggagac aaacggccta ccagcccaac tatcgtgaca acaccccga    5700 cccgctacta gcatcaacct gaaacgggc  cgcgcaacac acaacagtcg cgtgcgaatg    5760
caccaacggg acaaaaatag gtttgcgcga atcttgaaga tagacgagat ccaacggctc    5820
tagacttaga tgtgaagtag ttatttcaca tctagatgtg aaatagcaaa gctgatatta    5880
tgattgtaat gttatagcat gtagatgtgt aattaatata caattcattt ttttgatgca    5940
gtaccatacc ttcaagatat atataattaa tgtaatgttg tagcatgtag atgtgtaatt    6000
aatgcacacg ttcatttttc ggtgcagtac catatctttc tatcttcaag atatatataa    6060
ttattgtagt attatagcat gtagatgtgc aactaatgga tatattcatt ttttatgcag    6120
taccatatct tcaagatata tcatatatag tacaactaat gtatgtataa tgtgtcgatg    6180
tggagttaat atacacattc attgttcgat gctatttcgt atcttcaagg tatagcatgt    6240
agatatagag ttaatgtgaa cattcattat ttgatacaat atcgtatctt caagatataa    6300
agctaatgta tgatgtagcc tctagagtgc aattaatgta catattaatt gcttgacatg    6360
gtgccataac ttcaagatat agaactgatg catgtgccca tatcatcatc tcaaacaagg    6420
ctatataaac cgagccatag ctaacgaagt catgtatccc acacattcac agagaagcca    6480
cacaaacaat tataacatca aagggataga gaaggctcta gtgtagcaga tacaaaagcc    6540
atagtcgcgc ggccgcacta agcgctattt aaatgccagc tgtacactag ttatcgtacg    6600
gcctaggcct tcacctgcgg agggtaagat ccgatcacca tcttctgaat ttctgttctt    6660
gatctgtcat gtataataac tgtctagtct tggtgttggt gagatggaaa ttcggtggat    6720
ctcggaaggg atattgttcg tttgctgggg ttttttttgt gtgttgtgat ccgtagagaa    6780
tttgtgttta tccatgttgt tgatcttggt atgtattcat gacatattga catgcatgtg    6840
ttgtatgtgt catatgtgtg cctctccttg ggatttgttt tggataatag aacatgttat    6900
ggactcaata gtctgtgaac aaatctttt  ttagatggtg gccaaatctg atgatgatct    6960
ttcttgagag gaaaagttc  atgatagaaa aatcttttt  gagatggtgg cttaatgtga    7020
tgatgatctt tcttgagagg aaaaaaaga  ttcattatag gagattttga tttagctcct    7080
ttccaccgat attaaatgag gagcatgcat gctgattgct gataaggatc tgatttttt     7140 atcccctctt ctttgaacag acaagaaata ggctctgaat ttctgattga ttatttgtac    7200
atgcagaagg gcgaattcga cctaggccaa gtttgtacaa aaaagcaggc ttgataacca    7260
accatggtcc gtcctgtaga aaccccaacc cgtgaaatca aaaaactcga cggcctgtgg    7320
gcattcagtc tggatcgcga aaactgtgga attgatcagc gttggtggga agcgcgtta    7380 caagaaagcc gggcaattgc tgtgccaggc agttttaacg atcagttcgc cgatgcagat    7440
attcgtaatt atgcgggcaa cgtctggtat cagcgcgaag tctttatacc gaaaggttgg    7500
gcaggccagc gtatcgtgct gcgtttcgat gcggtcactc attacggcaa agtgtgggtc    7560
```

```
aataatcagg aagtgatgga gcatcagggc ggctatacgc catttgaagc cgatgtcacg   7620
ccgtatgtta ttgccgggaa aagtgtacgt aagtttctgc ttctaccttt gatatatata   7680
taataattat cattaattag tagtaatata atatttcaaa tattttttc aaaataaaag    7740 aatgtagtat atagcaattg cttttctgta gtttataagt gtgtatattt taatttataa   7800
cttttctaat atatgaccaa aatttgttga tgtgcaggta tcaccgtttg tgtgaacaac   7860
gaactgaact ggcagactat cccgccggga atggtgatta ccgacgaaaa cggcaagaaa   7920
aagcagtctt acttccatga tttctttaac tatgccggaa tccatcgcag cgtaatgctc   7980
tacaccacgc cgaacacctg ggtggacgat atcaccgtgg tgacgcatgt cgcgcaagac   8040
tgtaaccacg cgtctgttga ctggcaggtg gtggccaatg gtgatgtcag cgttgaactg   8100
cgtgatgcgg atcaacaggt ggttgcaact ggacaaggca ctagcgggac tttgcaagtg   8160
gtgaatccgc acctctggca accgggtgaa ggttatctct atgaactgtg cgtcacagcc   8220
aaaagccaga cagagtgtga tatctacccg cttcgcgtcg gcatccggtc agtggcagtg   8280
aagggcgaac agttcctgat taaccacaaa ccgttctact ttactggctt tggtcgtcat   8340
gaagatgcgg acttgcgtgg caaaggattc gataacgtgc tgatggtgca cgaccacgca   8400
ttaatggact ggattgggc caactcctac cgtacctcgc attaccctta cgctgaagag    8460
atgctcgact gggcagatga acatggcatc gtggtgattg atgaaactgc tgctgtcggc   8520
tttaacctct ctttaggcat tggtttcgaa gcggcaaca agccgaaaga actgtacagc    8580
gaagaggcag tcaacgggga aactcagcaa gcgcacttac aggcgattaa agagctgata   8640
gcgcgtgaca aaaccaccc aagcgtggtg atgtggagta ttgccaacga accggatacc    8700
cgtccgcaag gtgcacggga atatttcgcg ccactggcgg aagcaacgcg taaactcgac   8760
ccgacgcgtc cgatccacctg cgtcaatgta atgttctgcg acgctcacac cgataccatc   8820
agcgatctct ttgatgtgct gtgcctgaac cgttattacg gatggtatgt ccaaagcggc   8880 gatttgaaa cggcagagaa ggtactgaaa aagaacttc tggcctggca ggagaaactg     8940
catcagccga ttatcatcac cgaatacggc gtggatacgt tagccgggct gcactcaatg   9000
tacaccgaca tgtggagtga agagtatcag tgtgcatggc tggatatgta tcaccgcgtc   9060
tttgatcgcg tcagcgccgt cgtcggtgaa caggtatgga atttcgccga ttttgcgacc   9120
tcgcaaggca tattgcgcgt tggcggtaac aagaaaggga tcttcactcg cgaccgcaaa   9180
ccgaagtcgg cggctttct gctgcaaaaa cgctggactg gcatgaactt cggtgaaaaa    9240
ccgcagcagg gaggcaaaca atgaatcaaa cccagctttc ttgtacaaag tgggagctcg   9300
atcgttcaaa catttggcaa taaagtttct taagattgaa tcctgttgcc ggtcttgcga   9360
tgattatcat ataatttctg ttgaattacg ttaagcatgt aataattaac atgtaatgca   9420
tgacgttatt tatgagatgg gttttatga ttagagtccc gcaattatac atttaatacg    9480
cgatagaaaa caaatatag cgcgcaaact aggataaatt atcgcgcgcg gtgtcatcta    9540
tgttactaga tcgaattcaa ctttattata catagttgat aattcactgg gccggccctg   9600
tctatcttgt tgggaaaagc cgacctaccc ggacgcgatt acttaagcaa aagatactat   9660
cgaacgaaga aagctagtag gtagactata tcaggcctga ttgtcgtttc cgccttcag    9720 tttaaactat cagtgtttga caggatatat tggcgggtaa acctaagaga aaagagcgtt   9780
tattagaata atcggatatt taaagggcg tgaaaaggtt tatccgttcg tccatttgta    9840
tgtcaatatt gggggggggg gaaagccacg ttgtgtctca aaatctctga tgttacattg   9900
cacaagataa aaatatatca tcatgaacaa taaaactgtc tgcttacata aacagtaata   9960
```

```
caagggggtgt tcgccaccat gagccatatc cagcgtgaaa cctcgtgctc ccgcccgcgc   10020
ctcaattcca atatggatgc cgacctttat ggctacaagt gggcgcgcga caacgtcggc   10080
cagtcgggcg cgaccattta tcggctttat ggcaaacccg atgccccgga actgttcctg   10140
aagcacggca aaggcagcgt cgcaaacgat gtcaccgatg agatggtccg cctgaactgg   10200
cttaccgagt tcatgccgct gccgacgatt aagcatttca tccgtacccc ggacgatgcc   10260
tggctcttga ccacggccat tccgggcaaa acggcctttc aggtccttga agagtacccg   10320
gactccggtg agaatatcgt ggacgccctc gcggtcttcc tccgccgttt gcatagcatc   10380
cccgtgtgca actgccccct caactcggac cgggttttcc gcctggcaca ggcccagtcg   10440
cgcatgaata acggcctcgt tgacgcgagc gatttcgacg atgaacggaa tggctggccg   10500
gtggaacagg tttggaagga aatgcacaaa ctgcttccgt tctcgccgga ttcggtggtc   10560
acgcatggtg atttttccct ggataatctg atctttgacg agggcaagct gatcggctgc   10620
atcgacgtgg gtcgcgtcgg tatcgccgac cgctatcagg acctggcgat cttgtggaat   10680
tgcctcggcg agttctcgcc ctcgctccag aagcgcctgt tccagaagta cggcatcgac   10740
aacccggata tgaacaagct ccagttccac ctcatgctgg acgaattttt ttgaacagaa   10800
ttggttaatt ggttgtaaca ctggcagagc attacgctga cttgacggga cggcggcttt   10860
gttgaataaa tcgaactttt gctgagttga aggatcgatg agttgaagga ccccgtagaa   10920
aagatcaaag gatcttcttg agatcctttt tttctgcgcg taatctgctg cttgcaaaca   10980
aaaaaaccac cgctaccagc ggtggtttgt ttgccggatc aagagctacc aactcttttt   11040
ccgaaggtaa ctggcttcag cagagcgcag ataccaaata ctgtccttct agtgtagccg   11100
tagttaggcc accacttcaa gaactctgta gcaccgccta catacctcgc tctgctaatc   11160
ctgttaccag tggctgctgc cagtggcgat aagtcgtgtc ttaccgggtt ggactcaaga   11220
cgatagttac cggataaggc gcagcggtcg ggctgaacgg ggggttcgtg cacacagccc   11280
agcttggagc gaacgaccta caccgaactg agatacctac agcgtgagct atgagaaagc   11340
gccacgcttc ccgaagggag aaaggcggac aggtatccgg taagcggcag gtcggaaca   11400
ggagagcgca cgagggagct tccaggggga aacgcctggt atctttatag tcctgtcggg   11460
tttcgccacc tctgacttga gcgtcgattt ttgtgatgct cgtcaggggg cggagccta   11520
tggaaaaacg ccagcaacgc ggcctttta cggttcctgg ccttttgctg gcttttgct   11580
cacatgttct ttcctgcgtt atcccctgat tctgtggata accgtattac cgcctttgag   11640
tgagctgata ccgctcgccg cagccgaacg accgagcgca gcgagtcagt gagcgaggaa   11700
gcggaagagc gcctgatgcg gtattttctc cttacgcatc tgtgcggtat ttcacaccgc   11760
ataggccgcg ataggccgac gcgaagcggc gggggcgtagg gagcgcagcg accgaagggt   11820
aggcgctttt tgcagctctt cggctgtgcg ctggccagac agttatgcac aggccaggcg   11880
ggttttaaga gttttaataa gttttaaaga gttttaggcg gaaaaatcgc cttttttctc   11940
ttttatatca gtcacttaca tgtgtgaccg gttcccaatg tacggctttg ggttcccaat   12000
gtacgggttc cggttcccaa tgtacggctt tgggttccca atgtacgtgc tatccacagg   12060
aaagagacct tttcgacctt ttccccctgc tagggcaatt tgccctagca tctgctccgt   12120
acattaggaa ccggcggatg cttcgccctc gatcaggttg cggtagcgca tgactaggat   12180
cgggccagcc tgccccgcct cctccttcaa atcgtactcc ggcaggtcat ttgacccgat   12240
cagcttgcgc acggtgaaac agaacttctt gaactctccg cgctgccac tgcgttcgta   12300
gatcgtcttg aacaaccatc tggcttctgc cttgcctgcg gcgcggcgtg ccaggcggta   12360
```

```
gagaaaacgg ccgatgccgg ggtcgatcaa aaagtaatcg gggtgaaccg tcagcacgtc    12420
cgggttcttg ccttctgtga tctcgcggta catccaatca gcaagctcga tctcgatgta    12480
ctccggccgc ccggtttcgc tctttacgat cttgtagcgg ctaatcaagg cttcaccctc    12540
ggataccgtc accaggcggc cgttcttggc cttcttggta cgctgcatgg caacgtgcgt    12600
ggtgtttaac cgaatgcagg tttctaccag gtcgtctttc tgctttccgc catcggctcg    12660
ccggcagaac ttgagtacgt ccgcaacgtg tggacggaac acgcggccgg gcttgtctcc    12720
cttcccttcc cggtatcggt tcatggattc ggttagatgg gaaaccgcca tcagtaccag    12780
gtcgtaatcc cacacactgg ccatgccggc ggggcctgcg gaaacctcta cgtgcccgtc    12840
tggaagctcg tagcggatca cctcgccagc tcgtcggtca cgcttcgaca gacggaaaac    12900
ggccacgtcc atgatgctgc gactatcgcg ggtgcccacg tcatagagca tcggaacgaa    12960
aaaatctggt tgctcgtcgc ccttgggcgg cttcctaatc gacggcgcac cggctgccgg    13020
cggttgccgg gattctttgc ggattcgatc agcggcccct tgccacgatt caccggggcg    13080
tgcttctgcc tcgatgcgtt gccgctgggc ggcctgcgcg gccttcaact tctccaccag    13140
gtcatcaccc agcgccgcgc cgatttgtac cgggccggat ggtttgcgac cgctcacgcc    13200
gattcctcgg gcttgggggt tccagtgcca ttgcagggcc ggcagacaac ccagccgctt    13260
acgcctggcc aaccgcccgt tcctccacac atggggcatt ccacggcgtc ggtgcctggt    13320
tgttcttgat tttccatgcc gcctcctta gccgctaaaa ttcatctact catttattca    13380
tttgctcatt tactctggta gctgcgcgat gtattcagat agcagctcgg taatggtctt    13440
gccttggcgt accgcgtaca tcttcagctt ggtgtgatcc tccgccggca actgaaagtt    13500
gacccgcttc atggctggcg tgtctgccag gctggccaac gttgcagcct tgctgctgcg    13560
tgcgctcgga cggccggcac ttagcgtgtt tgtgcttttg ctcattttct ctttacctca    13620
ttaactcaaa tgagttttga tttaatttca gcggccagcg cctggacctc gcgggcagcg    13680
tcgccctcgg gttctgattc aagaacggtt gtgccggcgg cggcagtgcc tgggtagctc    13740
acgcgctgcg tgatacggga ctcaagaatg ggcagctcgt acccggccag cgcctcggca    13800
acctcaccgc cgatgcgcgt gcctttgatc gcccgcgaca cgacaaaggc cgcttgtagc    13860
cttccatccg tgacctcaat gcgctgctta accagctcca ccaggtcggc ggtggcccaa    13920
atgtcgtaag ggcttggctg caccggaatc agcacgaagt cggctgcctt gatcgcggac    13980
acagccaagt ccgccgcctg gggcgctccg tcgatcacta cgaagtcgcg ccggccgatg    14040
gccttcacgt cgcggtcaat cgtcgggcgg tcgatgccga caacggttag cggttgatct    14100
tcccgcacgg ccgcccaatc gcgggcactg ccctggggat cggaatcgac taacagaaca    14160
tcggccccgg cgagttgcag ggcgcgggct agatgggttg cgatggtcgt cttgcctgac    14220
ccgcctttct ggttaagtac agcgataacc ttcatgcgtt ccccttgcgt atttgtttat    14280
ttactcatcg catcatatac gcagcgaccg catgacgcag ctgttttact caaatacaca    14340 tcacctttt agatg                                                     14355
```

<210> SEQ ID NO 8
<211> LENGTH: 1164
<212> TYPE: DNA
<213> ORGANISM: Artificial sequence
<220> FEATURE:
<223> OTHER INFORMATION: maize promoter from upstream region of
      Zm GSStuc11-12-04.13411.1 homologous to wheat WP04 promoter -continued

```
<400> SEQUENCE: 8
aatataattg cactagcaat ctatttagca tgcctaaatg ggatactatg aggttgggtg      60
ggatgtggca cctttgtata atggcccagt tccttagtgt agtcttgatc ctccccgtta     120
ggttcagact cctctaggga ttttgtagga atcatcaaat tttcataagc aatttcttgt     180
gcacaaagaa ccaaatagat tgaaaaagtt ccaaattcac tcaaacacaa aaccatggca     240
catagcttat gtgacaaaat atttggacac tagtttcata tttttttgaga tcatataagt    300 ttattatcaa actccaagga ttaaattatt ttttgaaaaa aaagaaaaa gggaaaacat      360 cataaggtga cacatggcaa cctctgaatg actagacttt taccatctct caggtgggtc    420
tggtcaacaa tcactgttgg tcggtcctta ccttgcctag acgggtcctt agtaggccta    480
ctgggttgag ttatgggata aattgtggcc tagaaacata ccagtccacc aaccttggga    540
ccacttaaaa aattgcatct tgcaccatta tactatttag atgtttttaa aaaacaataa    600
taacttttac atcgaaatca aaactagaca aatttttatac tttcacagag cagcagaaat   660
ttatacaata tgattgaata caagatgtag gacccaatgg agagaatttt tttgtctcct    720
atatgcttga atacccaaca taatatcttc gcagcatact atctatctaa tagaaaaatt    780
ataatatagt taaatactta agtagtatct agtggataga attcaatatc tcatacatgc    840
atgaggagta atatctacta gacatgcaac atattttat ctatctaata gaatatatat     900
aataaagtta atatttatat gcatcaccta ctatatataa tttgatatct tttagatgta   960
taagggacta agaataatat ctctagcaca catgcaatgc attatctatc taaatatatt   1020
atataatagt taaatattaa ttatacgtag tctaaaccta catataagcc tacccatccc   1080
cacttaaaga tctcagtgtc acacatagac catacatctc acttcgccaa aaaaatttcg  1140
tcaacagttg aagttatacc catg                                          1164

<210> SEQ ID NO 9
<211> LENGTH: 1164
<212> TYPE: DNA
<213> ORGANISM: Artificial sequence
<220> FEATURE:
<223> OTHER INFORMATION: WP04 Corn variant 3

<400> SEQUENCE: 9
aatataattg cactagcaat ctatttagcb vhcctaabvh ggatactbvh aggttgggtg     60
ggbvhtggca cctttgtata bvhgcccagt tccttagtgt agtcttgatc ctccccgtta   120
ggttcagact cctctaggga ttttgtagga atcatcaaat tttcataagc aatttcttgt   180
gcacaaagaa ccaaatagat tgaaaaagtt ccaaattcac tcaaacacaa aaccbvhgca   240
catagcttbv htgacaaaat atttggacac tagtttcata tttttttgaga tcatataagt  300 ttattatcaa actccaagga ttaaattatt ttttgaaaaa aaagaaaaa gggaaaacat    360 cataaggtga cacbvhgcaa cctctgabvh actagacttt taccatctct caggtgggtc  420
tggtcaacaa tcactgttgg tcggtcctta ccttgcctag acgggtcctt agtaggccta  480
ctgggttgag ttbvhggata aattgtggcc tagaaacata ccagtccacc aaccttggga  540
ccacttaaaa aattgcatct tgcaccatta tactatttag bvhttttttaa aaaacaataa 600 taacttttac atcgaaatca aaactagaca aatttttatac tttcacagag cagcagaaat 660
ttatacaatb vhattgaata caagbvhtag gacccbvhg agagaatttt tttgtctcct   720
atbvhcttga atacccaaca taatatcttc gcagcatact atctatctaa tagaaaaatt  780
ataatatagt taaatactta agtagtatct agtggataga attcaatatc tcatacbvhc  840
```

| | | |
|---|---|---|
| bvhaggagta atatctacta gacbvhcaac atatttttat ctatctaata gaatatatat | 900 |
| aataaagtta aatattatbv hcatcaccta ctatatataa tttgatatct tttagbvhta | 960 |
| taagggacta agaataatat ctctagcaca cbvhcabvhc attatctatc taaatatatt | 1020 |
| ataataatagt taaatattaa ttatacgtag tctaaaccta catataagcc tacccatccc | 1080 |
| cacttaaaga tctcagtgtc acacatagac catacatctc acttcgccaa aaaaatttcg | 1140 |
| tcaacagttg aagttatacc cbvh | 1164 |

<210> SEQ ID NO 10
<211> LENGTH: 1164
<212> TYPE: DNA
<213> ORGANISM: Artificial sequence
<220> FEATURE:
<223> OTHER INFORMATION: WP04 Corn variant 4

<400> SEQUENCE: 10

```
aatataattg cactagcaat ctatttagcb vhcctaabvh ggatartbvh aggtrgggtg     60
rgbvhtggca cctttgrata bvhgcccagt tccttagtgt agtcttgatc ctccccgtta    120
ggtrragact cctctaggga ttttgtagga atcatcaaat tttrataagc aatttcttgt    180
gcacaaagaa ccaaatagat tgaaaaagtt ccaaattrac tcaaacacaa aaccbvhgca    240
catagcttbv htgacaaaat atttggacac tagtttrata ttttttgaga tratataagt    300
ttattatcaa actccaagga ttaaattatt ttttgaaaaa aaaagaaaaa gggaaaacat    360
rataaggtga cacbvhgcaa cctctgabvh actagacttt taccatctct caggtgggtc    420
tggtraacaa tcactgttgg tcggtcctra ccttgcctag acgggtcctt agtaggccta    480
ctgggttgag ttbvhggata aattgtggcc tagaaacata ccagtccacc aaccttggga    540
ccacttaaaa aattgcatct tgcaccatta tactattrag bvhttttraa aaaacaataa    600
taactttrac atcgaaatra aaactagaca aattttatac tttcacagag cagcagaaat    660
ttatacaatb vhattgaata raagbvhtag gacccabvhg agagaatttt tttgrctcct    720
atbvhcttga atarccaaca taatarcttc gcagcatact atctatctaa tagaaaaatt    780
araatatagt taaatartta agtagtatct agtggataga attcaatatc tratacbvhc    840
bvhaggagta atatctarta gacbvhcaac atatttttat ctarctaata gaataratat    900
aataaagtta aatatratbv hcatcaccta ctatarataa tttgatarct ttragbvhta    960
raagggacta agaataatat ctctagcaca cbvhcabvhc attarctatc taaataratt   1020
atataatagt raaatattaa ttaracgtag tctaaaccta cataraagcc tacccatccc   1080
cactraaaga tctcagtgtc acacatagac catacatctc acttcgccaa aaaaatttcg   1140
traacagttg aagttatacc cbvh                                          1164
```

<210> SEQ ID NO 11
<211> LENGTH: 24
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(22)
<223> OTHER INFORMATION: n is a, c, g, or t

```
<400> SEQUENCE: 11
scgaynrnnn nnnnnnnnnn nnhd                                            24

<210> SEQ ID NO 12
<211> LENGTH: 10
<212> TYPE: DNA
<213> ORGANISM: Artificial Sequence
<220> FEATURE:
<223> OTHER INFORMATION: Motif

<400> SEQUENCE: 12 cwwwwwwwwg                                                            10

<210> SEQ ID NO 13
<211> LENGTH: 10
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (4)..(7)
<223> OTHER INFORMATION: n is a, c, g, or t

<400> SEQUENCE: 13 caannnnatc                                                            10

<210> SEQ ID NO 14
<211> LENGTH: 15
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (7)..(13)
<223> OTHER INFORMATION: n is a, c, g, or t

<400> SEQUENCE: 14
cctaccnnnn nnnct                                                      15

<210> SEQ ID NO 15
<211> LENGTH: 10
<212> TYPE: DNA
<213> ORGANISM: Artificial Sequence
<220> FEATURE:
<223> OTHER INFORMATION: Motif

<400> SEQUENCE: 15 ttwtwttwtt                                                            10

<210> SEQ ID NO 16
<211> LENGTH: 10
<212> TYPE: DNA
<213> ORGANISM: Artificial Sequence
<220> FEATURE:
<223> OTHER INFORMATION: Motif

<400> SEQUENCE: 16 gatgayrtgg                                                            10

<210> SEQ ID NO 17
<211> LENGTH: 11
<212> TYPE: DNA
<213> ORGANISM: Artificial Sequence
<220> FEATURE:
<223> OTHER INFORMATION: Motif
```

```
<400> SEQUENCE: 17
ycyyaccwac c                                                           11

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
ccatagtcat ggcaaaactc atgtgca                                          27

<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
ctcactattg gggtagccat gtcggct                                          27

<210> SEQ ID NO 20
<211> LENGTH: 80
<212> TYPE: DNA
<213> ORGANISM: Oryza sativa

<400> SEQUENCE: 20
gagaaggtgt ggtgcatgga gaaggtcgtc tatgtcgcca agttctgcaa gaagccgttc      60
cagcctggct accagtgcgg                                                  80

<210> SEQ ID NO 21
<211> LENGTH: 62
<212> TYPE: DNA
<213> ORGANISM: Triticum aestivum

<400> SEQUENCE: 21
tagagaaggc tctagtgtag cagatacaaa agccatagtc atggcaaaac tcatgtgctt      60
at                                                                     62

<210> SEQ ID NO 22
<211> LENGTH: 62
<212> TYPE: DNA
<213> ORGANISM: Triticum aestivum

<400> SEQUENCE: 22
tagagaaggc tctagtgtag cagatacaaa agccatagtc atggcaaaac tcatgtgctt      60
at                                                                     62

<210> SEQ ID NO 23
<211> LENGTH: 62
<212> TYPE: DNA
<213> ORGANISM: Zea mays

<400> SEQUENCE: 23
cttcgccaaa aaaatttcgt caacagttga agttataccc atggcaaaac tactcttggg      60
tt                                                                     62
```

```
<210> SEQ ID NO 24
<211> LENGTH: 62
<212> TYPE: DNA
<213> ORGANISM: Zea mays

<400> SEQUENCE: 24
cttcgccaaa aaaattccgt caacagttga agttataccc atggcaaaac tactcttggg      60
tt                                                                    62

<210> SEQ ID NO 25
<211> LENGTH: 25
<212> TYPE: DNA
<213> ORGANISM: Oryza sativa

<400> SEQUENCE: 25
atggcgagac aacaactcct aggtt                                            25

<210> SEQ ID NO 26
<211> LENGTH: 43
<212> TYPE: DNA
<213> ORGANISM: Oryza sativa

<400> SEQUENCE: 26
catctgagag aaaccaggga gatacacaca agcaatagcc atg                        43

<210> SEQ ID NO 27
<211> LENGTH: 43
<212> TYPE: DNA
<213> ORGANISM: Oryza sativa

<400> SEQUENCE: 27
catctgagag aaaccaggga gatacacaca agcaatagcc atg                        43

<210> SEQ ID NO 28
<211> LENGTH: 80
<212> TYPE: DNA
<213> ORGANISM: Zea mays

<400> SEQUENCE: 28
gagaaggtat ggtgcatgga gaaggttgtg tacgtcgcca actattgtaa gaggccgttt      60
caacctggct acaagtgcgg                                                  80

<210> SEQ ID NO 29
<211> LENGTH: 62
<212> TYPE: DNA
<213> ORGANISM: Triticum aestivum

<400> SEQUENCE: 29
tagagaaggc tctagtgtag cagatacaaa agccatagtc                            40
```